United States Patent
Bylund et al.

(10) Patent No.: US 9,145,380 B2
(45) Date of Patent: Sep. 29, 2015

(54) BIS-(SULFONYLAMINO) DERIVATIVES FOR USE IN THERAPY

(75) Inventors: Johan Bylund, Södertälje (SE); Maria E Ek, Södertälje (SE); Ylva Gravenfors, Södertälje (SE); Gunnar Nordvall, Södertälje (SE); Alexander Minidis, Södertälje (SE); Karl S. A Vallin, Södertälje (SE); Jenny Viklund, Södertälje (SE); Jörg Holenz, Södertälje (SE); Stefan Von Berg, Södertälje (SE); Daniel Sohn, Södertälje (SE)

(73) Assignee: Astrazeneca AB, Sodertalje (SE)

( * ) Notice: Subject to any disclaimer, the term of this patent is extended or adjusted under 35 U.S.C. 154(b) by 765 days.

(21) Appl. No.: 12/747,049

(22) PCT Filed: Dec. 18, 2008

(86) PCT No.: PCT/SE2008/051500
§ 371 (c)(1),
(2), (4) Date: Sep. 9, 2010

(87) PCT Pub. No.: WO2009/082347
PCT Pub. Date: Jul. 2, 2009

(65) Prior Publication Data
US 2010/0331321 A1  Dec. 30, 2010

Related U.S. Application Data

(60) Provisional application No. 61/015,287, filed on Dec. 20, 2007.

(51) Int. Cl.

| | | |
|---|---|---|
| C07C 303/00 | (2006.01) | |
| C07C 307/00 | (2006.01) | |
| C07C 309/00 | (2006.01) | |
| C07C 311/00 | (2006.01) | |
| A01N 41/06 | (2006.01) | |
| A61K 31/16 | (2006.01) | |
| C07D 307/79 | (2006.01) | |
| C07C 311/39 | (2006.01) | |
| C07C 323/67 | (2006.01) | |
| C07D 209/08 | (2006.01) | |
| C07D 209/10 | (2006.01) | |
| C07D 213/30 | (2006.01) | |
| C07D 213/61 | (2006.01) | |
| C07D 213/64 | (2006.01) | |
| C07D 239/34 | (2006.01) | |
| C07D 265/36 | (2006.01) | |
| C07D 271/10 | (2006.01) | |
| C07D 277/32 | (2006.01) | |
| C07D 307/38 | (2006.01) | |
| C07D 307/91 | (2006.01) | |
| C07D 333/34 | (2006.01) | |
| C07D 409/04 | (2006.01) | |

(52) U.S. Cl.
CPC ............ *C07D 307/79* (2013.01); *C07C 311/39* (2013.01); *C07C 323/67* (2013.01); *C07D 209/08* (2013.01); *C07D 209/10* (2013.01); *C07D 213/30* (2013.01); *C07D 213/61* (2013.01); *C07D 213/64* (2013.01); *C07D 239/34* (2013.01); *C07D 265/36* (2013.01); *C07D 271/10* (2013.01); *C07D 277/32* (2013.01); *C07D 307/38* (2013.01); *C07D 307/91* (2013.01); *C07D 333/34* (2013.01); *C07D 409/04* (2013.01); *C07C 2101/08* (2013.01); *C07C 2101/10* (2013.01); *C07C 2102/08* (2013.01); *C07C 2102/10* (2013.01)

(58) Field of Classification Search
CPC ............................ C07C 311/29; C07D 307/79
See application file for complete search history.

(56) References Cited

U.S. PATENT DOCUMENTS

| | | | |
|---|---|---|---|
| 5,529,976 A | * | 6/1996 | Kehne et al. ............... 504/213 |
| 5,886,191 A | | 3/1999 | Dominguez et al. |
| 6,297,195 B1 | | 10/2001 | Gesing et al. |
| 6,632,838 B1 | | 10/2003 | Kirsch et al. |
| 2003/0229126 A1 | | 12/2003 | Satoh et al. |
| 2009/0131468 A1 | | 5/2009 | Bylund et al. |
| 2009/0281138 A1 | | 11/2009 | Bylund et al. |
| 2010/0292279 A1 | | 11/2010 | Bylund et al. |

FOREIGN PATENT DOCUMENTS

| | | |
|---|---|---|
| DE | 941559 A1 | 3/2001 |
| WO | WO 98/03508 | 1/1998 |

(Continued)

OTHER PUBLICATIONS

Nishimoro et al. J. Med. Chem. 2006, 49, 2117-2126.*
http://www.mayoclinic.org/diseases-conditions/rheumatoid-arthritis/basics/treatment/con-20014868; retreived Nov. 17, 2014.*
Agrawal et al., "QSAR study on carbonic anhydrase inhibitors: aromatic/heterocyclic sulfonamides containing 8-quinoline-sulfonyl moieties, with topical activity as antiglaucoma agents", European Journal of Medicinal Chemistry, 2004, 39, 593-600.
Eroglu et al., "A DFT-based quantum theoretic QSAR study of aromatic and heterocyclic sulfonamides as carbonic anhydrase inhibitors against isozyme, CA-II", Journal of Molecular Graphics and Modelling, Apr. 2007, 26, 701-708.

(Continued)

*Primary Examiner* — Clinton Brooks
(74) *Attorney, Agent, or Firm* — Baker & Hostetler LLP

(57) ABSTRACT

The invention provides compounds of formula (I) wherein $R^1$, $R^3$, $L^1$, $L^2$, $G^1$, $G^2$, A and m are as defined in the specification and optical isomers, racemates and tautomers thereof, and pharmaceutically acceptable salts thereof; together with processes for their preparation, pharmaceutical compositions containing them and their use in therapy. The compounds are inhibitors of microsomal prostaglandin E synthase-1.

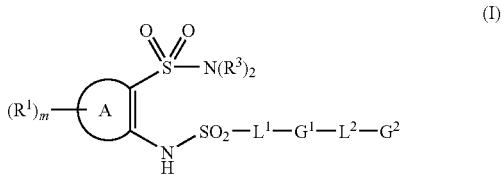

14 Claims, No Drawings

(56) References Cited

FOREIGN PATENT DOCUMENTS

| | | |
|---|---|---|
| WO | 0181312 A2 | 11/2001 |
| WO | WO 02/22595 | 3/2002 |
| WO | WO 03/018536 | 3/2003 |
| WO | 03082278 A1 | 10/2003 |
| WO | 2004026823 A1 | 4/2004 |
| WO | 2006044405 A1 | 4/2006 |
| WO | 2007042817 A1 | 4/2007 |
| WO | 2008129276 A1 | 10/2008 |
| WO | 2008129288 A2 | 10/2008 |
| WO | 2009064250 A1 | 5/2009 |
| WO | 2009064251 A1 | 5/2009 |
| WO | 2010132016 A1 | 11/2010 |

OTHER PUBLICATIONS

Nishimori et al., "Carbonic Anhydrase Inhibitors: DNA Cloning and Inhibition Studies of the a-Carbonic Anhydrase from *Helicobacter pylori*, a New Target for Developing Sulfonamide and Sulfamate Gastric Drugs", Journal of Medicinal Chemistry, 2006, vol. 49, No. 6, 2117-2126.

Vullo et al., "Carbonic Anhydrase Inhibitors: Inhibition of the Tumor-Associated Isozyme IX with Aromatic and Heterocyclic Sulfonamides", Bioorganic & Medicinal Chemistry Letters, Jan. 2003, 13, 1005-1009.

Gómez-Hernández et al., Overexpression of COX-2, Prostaglandin E Synthase-1 and Prostaglandin E Receptors in blood mononuclear cells . . . , Atherosclerosis 2006, 187, pp. 139-149.

Kojima et al., Defective Generation of a Humoral Immune Response . . . , The Journal of Immunology 2008, 180, pp. 8361-8368.

Korotkova et al., Effects of immunosuppressive treatment on microsomal prostaglandin E synthase 1 . . . , Annals of the Rheumatic Diseases 2008, 67, pp. 1596-1602.

Nakanishi et al., Genetic Deletion of mPGES-1 Suppresses Intestinal tumorigenesis, Cancer Research 2008, 68(9), pp. 3251-3259.

Wang et al., Microsomal Prostaglandin E Synthase-1 Deletion . . . , Circulation 2008, 117, pp. 1302-1309.

Wang et al., Deletion of microsomal prostaglandin E synthase-1 augments prostacyclin and retards atherogenesis, Proceedings of National Academy of Sciences 2006, 103(39), pp. 14507-14512.

Schröder et al., Journal of Lipid Research 2006, 47, 1071-80.

Scozzafava et al., Journal of Medicinal Chemistry, 2000, 43, 4542-4551.

STN International, File Registry, Compound RN 1031151-11-7, 2008.

Xu et al., The Journal of Pharmacology and Experimental Therapeutics 2008, 326(3), pp. 754-763.

PCT/ISA/210 for WO2009082347 (which corresponds to this US application).

PCT/ISA/237 for WO2009082347 (which corresponds to this US application).

\* cited by examiner

BIS-(SULFONYLAMINO) DERIVATIVES FOR USE IN THERAPY

CROSS-REFERENCE TO RELATED APPLICATIONS

This application is a US National Stage under 35 U.S.C. §371 of International Application No. PCT/SE2008/051500 (filed 18 Dec. 2008) which claims priority under 35 U.S.C. §119(e) to U.S. Application No. 61/015,287 filed on 20 Dec. 2007.

FIELD OF THE INVENTION

The present invention relates to bis-(sulfonylamino) derivatives, processes for their preparation, pharmaceutical compositions containing them and their use in therapy.

BACKGROUND OF THE INVENTION

Modulation of prostaglandin metabolism is at the center of current anti-inflammatory therapies. NSAIDs and COX-2 inhibitors block the activity of cyclooxygenases and their ability to convert arachidonic acid into prostaglandin H2 (PGH2). PGH2 can be subsequently metabolized by terminal prostaglandin synthases to the corresponding biologically active PGs, namely, PGI2, thromboxane (Tx) A2, PGD2, PGF2α, and PGE2. A combination of pharmacological, genetic and neutralizing antibody approaches demonstrates the importance of PGE2 in inflammation. The conversion of PGH2 to PGE2 by prostaglandin E synthases (PGES) may therefore represent a pivotal step in the propagation of inflammatory stimuli.

Microsomal prostaglandin E synthase-1 (mPGES-1) is an inducible PGES after exposure to pro-inflammatory stimuli. mPGES-1 is induced in the periphery and in the CNS by inflammation and represents therefore a target for acute and chronic inflammatory disorders.

PGE2 is a major prostanoid driving inflammatory processes. The Prostanoid is produced from arachidonic acid liberated by Phospholipases (PLAs). Arachidonic acid is tranformed by the action of Prostaglandin H Synthase (PGH Synthase, cycloxygenase) into PGH2 which is a substrate for mPGES-1, that is the terminal enzyme transforming PGH2 to the pro-inflammatory PGE2.

NSAIDs reduce PGE2 by inhibiting cyclooxygenase, but at the same time reducing other prostanoids, giving side effects such as ulcerations in the GI tract. mPGES-1 inhibition gives a similar effect on PGE2 production without affecteing the formation of other prostanoids, and hence a more favourable profile.

By blocking the formation of PGE2 in animal models of inflammatory pain a reduced inflammation, pain and fever response has been demonstrated (see e.g. Kojima et. al, *The Journal of Immunology* 2008, 180, 8361-6, Xu et. al., *The Journal of Pharmacology and Experimental Therapeutics* 2008, 326, 754-63).

In abdominal aortic aneurism, inflammation leads to connective tissue degradation and smooth muscle apoptosis ultimately leading to aortic dilation and rupture. In animals lacking mPGES-1 a slower disease progression and disease severity has been demonstrated (see e.g. Wang et. al. *Circulation*, 2008, 117, 1302-1309).

Several lines of evidence indicate that PGE2 is involved in malignant growth. PGE2 facilitates tumour progression by stimulation of cellular proliferation and angiogenesis and by modulation of immunosupression. In support of a role for PGE2 in carcinogenesis genetic deletion of mPGES-1 in mice supress the intestinal tumourogenesis (Nakanishi et. al. *Cancer Research* 2008, 68(9), 3251-9). In man, mPGES-1 is also upregulated in cancers such as clorectal cancer (see e.g. Schröder *Journal of Lipid Research* 2006, 47, 1071-80).

Myositis is chronic muscle disorder characterized by muscle weakness and fatigue. Proinflammatory cytokines and prostanoids have been implicated in the development of myositis. In skeletal muscle tissue from patients suffering from myositis an increase in cyclooxygenases and mPGES-1 has been demonstrated, implicating mPGES-1 as a target for treating this condition (see e.g. Korotkova *Annals of the Rheumatic Diseases* 2008, 67, 1596-1602).

In atherosclerosis inflammation of the vasculature leads to atheroma formation that eventually may progress into infarction. In patients with carotid atherosclerosis an increase in mPGES-1 in plauqe regions have been found (Gómez-Hernández *Atherosclerosis* 2006, 187, 139-49). In an animal model of atherosclerosis, mice lacking the mPGES-1 receptor was found to show a retarded atherogenesis and a concommitant reduction in macrophage—derived foam cells together with an increase in vascular smooth muscle cells (see e.g. Wang *Proceedings of National Academy of Sciences* 2006, 103(39), 14507-12).

The present invention is directed to novel compounds that are selective inhibitors of the microsomal prostaglandin E synthase-1 enzyme and would therefore be useful for the treatment of pain and inflammation in a variety of diseases or conditions.

DISCLOSURE OF THE INVENTION

In one aspect we disclose a compound of formula (I) or a pharmaceutically acceptable salt thereof

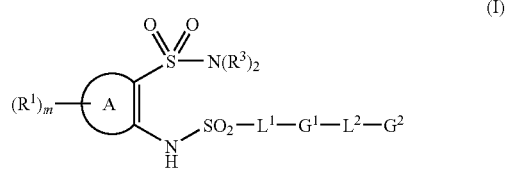

wherein:

A is selected from phenyl or a 5- or 6-membered heteroaryl or a 5- or 6-membered heterocyclenyl moiety; said phenyl or 5- or 6-membered heteroaryl or 5- or 6-membered heterocyclenyl moiety in group A being optionally fused to a phenyl, a 5- or 6-membered heteroaryl, $C_{5-6}$carbocyclyl or $C_{5-6}$heterocyclyl ring;

each $R^1$ is independently selected from halogen, nitro, $SF_5$, CN, $NR^5R^6$, OH, CHO, $CO_2C_{1-4}$alkyl, $CONR^5R^6$, $C_{1-4}$alkyl, $C_{2-4}$alkenyl, $C_{2-4}$alkynyl, $C_{1-4}$alkoxy, $G^3$, $OG^3$ or $OCH_2G^3$; said $C_{1-4}$alkyl, $C_{2-4}$alkenyl, $C_{2-4}$alkynyl or $C_{1-4}$alkoxy being optionally substituted by one or more substituents selected from OH, $NR^5R^6$, $C_{1-4}$alkyl or F;

m represents an integer 0, 1, 2, 3 or 4;

each $R^3$ is independently selected from hydrogen, CN and $C_{1-4}$alkyl; said $C_{1-4}$alkyl being optionally substituted with OH, CN, $C_{1-4}$alkoxy, $NR^7R^8$, or one or more F atoms;

$L^1$ represents a direct bond, $C_{1-4}$alkylene, $C_{2-4}$alkenylene or $C_{2-4}$alkynylene;

$L^2$ represents a direct bond, —O—, —OCH$_2$—, $C_{1-2}$alkylene, —C≡C— or —NHCONH—;

$G^1$ represents phenyl, 5- or 6-membered heteroaryl, $C_{3-10}$carbocyclyl or $C_{5-8}$heterocyclyl;

G² represents H, $C_{1-6}$alkyl, phenyl, 5- or 6-membered heteroaryl, $C_{3-10}$carbocyclyl or $C_{5-8}$heterocyclyl; said $C_{1-6}$alkyl being optionally further substituted by one or more groups selected from OH, $C_{1-6}$alkoxy and halogen;

the phenyl, heteroaryl, carbocyclyl or heterocyclyl moieties in G¹ and G² being optionally fused to one or two further rings independently selected from phenyl, a 5- or 6-membered heteroaryl, $C_{5-6}$carbocyclyl or $C_{5-6}$heterocyclyl ring;

any phenyl, heteroaryl, carbocyclyl or heterocyclyl moieties in G¹ and G² being optionally substituted by one or more substituents independently selected from halogen, OH, CN, $NO_2$, $CO_2R^9$, $C_{1-6}$alkyl, $C_{1-6}$alkoxy, $C_{1-4}$thioalkoxy, $SO_2NR^{10}R^{11}$, $NR^{12}R^{13}$, —NHCOC(OH)(CH₃)CF₃ or —CH₂OCH₂CF₂CHF₂; said $C_{1-6}$alkyl or $C_{1-6}$alkoxy being optionally substituted by OH or by one or more F atoms;

R⁹ represents $C_{1-6}$alkyl;

G³ represents phenyl or 5- or 6-membered heteroaryl; and each R⁴, R⁵, R⁶, R⁷, R⁸, R¹⁰, R¹¹, R¹² and R¹³ is independently selected from H or $C_{1-4}$alkyl;

with the proviso that the following compounds are excluded:

3-[(phenylsulfonyl)amino]pyridine-2-sulfonamide;
2-amino-N-(2-sulfamoylphenyl)benzenesulfonamide;
4-tert-butyl-N-(2-sulfamoylphenyl)benzenesulfonamide;
3-amino-4-hydroxy-N-(2-sulfamoylphenyl)benzenesulfonamide;
4-bromo-N-(2-sulfamoylphenyl)benzenesulfonamide;
4-fluoro-N-(2-sulfamoylphenyl)benzenesulfonamide;
4-methyl-N-(2-sulfamoylphenyl)benzenesulfonamide;
4-nitro-N-(2-sulfamoylphenyl)benzenesulfonamide;
2-nitro-N-(2-sulfamoylphenyl)benzenesulfonamide;
4-amino-N-(2-sulfamoylphenyl)benzenesulfonamide;
2-[(phenylsulfonyl)amino]-4-(trifluoromethyl)benzenesulfonamide;
2-{[(4-methylphenyl)sulfonyl]amino}-4-(trifluoromethyl)benzenesulfonamide;
N-(2-sulfamoylphenyl)quinoline-8-sulfonamide;
4-tert-butyl-N-(2-(N-ethylsulfamoyl)phenyl)-2,6-dimethylbenzenesulfonamide;
2,5-dibromo-N-(2-(N-ethylsulfamoyl)phenyl)benzenesulfonamide;
methyl 4-(5-fluoro-3-methylbenzo[b]thiophene-2-sulfonamido)-3-sulfamoylbenzoate;
2,3,4,5,6-pentafluoro-N-(2-sulfamoylphenyl)benzenesulfonamide;
N-(2-(N,N-dimethylsulfamoyl)phenyl)-5,7-dimethyl-[1,2,4]triazolo[1,5-a]pyrimidine-2-sulfonamide;
N-(2-(N-tert-butylsulfamoyl)phenyl)-5,7-dimethyl-[1,2,4]triazolo[1,5-a]pyrimidine-2-sulfonamide;
N-(2-(N-methoxy-N-methylsulfamoyl)phenyl)-5,7-dimethyl-[1,2,4]triazolo[1,5-a]pyrimidine-2-sulfonamide;
5,7-dimethyl-N-(2-sulfamoylphenyl)-[1,2,4]triazolo[1,5-c]pyrimidine-2-sulfonamide;
6-methyl-N-(2-sulfamoylphenyl)thiazolo[3,2-b][1,2,4]triazole-2-sulfonamide;
6-chloro-N-(2-(N,N-dimethylsulfamoyl)phenyl)-[1,2,4]triazolo[1,5-a]pyrimidine-2-sulfonamide;
6-chloro-N-(2-(N-ethyl-N-methylsulfamoyl)phenyl)-[1,2,4]triazolo[1,5-a]pyrimidine-2-sulfonamide;
N-(2-(N,N-dimethylsulfamoyl)phenyl)-5-methyl-7,8-dihydro-6H-cyclopenta[e][1,2,4]triazolo[1,5-a]pyrimidine-2-sulfonamide;
N-(2-(N,N-dimethylsulfamoyl)phenyl)-5-(trifluoromethyl)phenyl)-5,7-dimethyl-[1,2,4]triazolo[1,5-a]pyrimidine-2-sulfonamide;
N-(2-(N-ethyl-N-methylsulfamoyl)phenyl)-5,7-dimethyl-[1,2,4]triazolo[1,5-a]pyrimidine-2-sulfonamide; and
N-(2-(N,N-dimethylsulfamoyl)phenyl)-5,7-dimethyl-[1,2,4]triazolo[1,5-a]pyrimidine-2-sulfonamide.

As used herein, a $C_1$-$C_6$ alkyl moiety is a linear or branched alkyl moiety containing from 1 to 6 carbon atoms, such as a $C_1$-$C_4$ or $C_1$-$C_2$ alkyl moiety. Examples of $C_1$-$C_6$ alkyl moieties include methyl, ethyl, n-propyl, i-propyl, n-butyl, s-butyl and t-butyl, pentyl and hexyl. For the avoidance of doubt, where two alkyl moieties are present in a substituent, the alkyl moieties may be the same or different.

As used herein, a $C_1$-$C_4$ alkylene or $C_1$-$C_2$ alkylene group is any divalent linear or branched $C_1$-$C_4$ or $C_1$-$C_2$ alkyl moiety. Linear $C_1$-$C_4$ alkylene groups are methylene, ethylene, n-propylene and n-butylene groups. Branched $C_1$-$C_4$ alkylene groups include —CH(CH₃)—, —CH(CH₃)—CH₂— and —CH₂—CH(CH₃)—.

As used herein, a $C_2$-$C_4$ alkenyl moiety is a linear or branched alkyl moiety containing from 2 to 4 carbon atoms that includes a carbon-carbon double bond. As used herein, a $C_2$-$C_4$ alkenylene group is any divalent linear or branched $C_2$-$C_4$ alkylene moiety that includes a carbon-carbon double bond.

As used herein, a $C_2$-$C_4$ alkynyl moiety is a linear or branched alkyl moiety containing from 2 to 4 carbon atoms that includes a carbon-carbon triple bond. As used herein, a $C_2$-$C_4$ alkynylene group is any divalent linear or branched $C_2$-$C_4$ alkylene moiety that includes a carbon-carbon triple bond.

As used herein, a halogen is chlorine, fluorine, bromine or iodine. A halogen is typically fluorine, chlorine or bromine.

As used herein, a $C_1$-$C_6$ alkoxy moiety is a said $C_1$-$C_6$ alkyl moiety attached to an oxygen atom. Examples include methoxy and ethoxy.

As used herein, a $C_1$-$C_4$ thioalkoxy moiety is a said $C_1$-$C_4$ alkyl moiety attached to a sulphur atom. Examples include methylthio and ethylthio.

As used herein, a 5- or 6-membered heteroaryl moiety is a monocyclic 5- or 6-membered aromatic ring, containing at least one heteroatom, for example 1, 2 or 3 heteroatoms, selected from O, S and N. Examples include imidazolyl, isoxazolyl, pyrrolyl, thienyl, thiazolyl, furanyl, pyridyl, pyrazinyl, pyrimidinyl, pyridazinyl, oxadiazolyl, oxazolyl, isoxazolyl, thiazolyl, isothiazolyl, thiadiazolyl, pyrazolyl and triazolyl moieties. In one embodiment, a 5- or 6-membered heteroaryl moiety is pyrrolyl, thienyl, furanyl, pyridyl, pyrimidinyl, oxazolyl, thiazolyl or pyrazolyl moiety.

As used herein, a 5- to 8-membered heterocyclyl moiety is a monocyclic non-aromatic, saturated or unsaturated $C_5$-$C_8$ carbocyclic ring, in which at least one, for example, 1, 2 or 3, carbon atoms in the ring are replaced with a moiety selected independently from O, S, SO, $SO_2$ and N and optionally incorporating one or more carbonyl (C=O) groups. When such a ring contains a carbon-carbon double bond, it may alternatively be referred to as a heterocyclenyl moiety. Typically, a heterocyclyl moiety is a saturated $C_5$-$C_8$ ring such as a $C_5$-$C_6$ ring in which 1, 2 or 3 of the carbon atoms in the ring are replaced with a moiety selected from O, S, $SO_2$ and NH and optionally incorporating one or two CO moieties. Examples include azetidinyl, pyrazolidinyl, piperidyl, piperidin-2,6-dionyl, piperidin-2-onyl, perhydroazepinyl (hexamethylene iminyl), piperazinyl, morpholinyl, thiomorpholinyl, S-oxothiomorpholinyl, S,S-dioxothiomorpholinyl, 1,3-dioxolanyl, 1,4-dioxanyl, pyrrolidinyl, imidazolidinyl, imidazol-2-onyl, pyrrolidin-2-onyl, tetrahydrofuranyl, tetrahydrothienyl, S,S-dioxotetrahydrothienyl (tetramethylenesulfonyl), dithiolanyl, thiazolidinyl, oxazolidinyl, tetrahydropyranyl and pyrazolinyl moieties. In one embodiment, a 5- to 8-membered heterocyclyl moiety is morpholinyl, tetrahydrofuranyl or S,S-dioxotetrahydrothienyl.

For the avoidance of doubt, although the above definitions of heteroaryl and heterocyclyl groups refer to an "N" moiety which can be present in the ring, as will be evident to a skilled chemist the N atom will carry a hydrogen atom (or will carry a substituent as defined above) if it is attached to each of the adjacent ring atoms via a single bond.

As used herein, a $C_3$-$C_{10}$ carbocyclyl moiety is a monocyclic or polycyclic non-aromatic saturated or unsaturated hydrocarbon ring having from 3 to 10 carbon atoms.

In one embodiment, it is a saturated ring system (i.e. a cycloalkyl moiety) having from 3 to 7 carbon atoms. Examples include adamantyl, cyclopropyl, cyclobutyl, cyclopentyl, cyclopentenyl, cyclohexyl and cycloheptyl and bicycloheptyl.

In one embodiment, a $C_3$-$C_{10}$ carbocyclyl moiety is adamantyl, cyclopentyl, cyclohexyl or bicycloheptyl moiety.

In another embodiment, it is a $C_5$-$C_6$ cycloalkyl moiety.

Examples of bicyclic ring systems in which the two rings are fused together include naphthyl, indanyl, quinolyl, tetrahydroquinolyl, benzofuranyl, indolyl, isoindolyl, indolinyl, benzofuranyl, 2,3-dihydro-bensofuranyl, benzothienyl, indazolyl, benzimidazolyl, benzthiazolyl, benzmorpholinyl, isoquinolyl, chromanyl, indenyl, 2,3-dihydro-indenyl, quinazolyl, quinoxalyl, isocromanyl, tetrahydronaphthyl, pyrido-oxazolyl, pyridothiazolyl, dihydrobenzofuranyl, 1,3-benzodioxolyl, 2,3-dihydro-1,4-benzodioxinyl, 1,3-benzodioxinyl and 3,4-dihydro-isochromenyl.

In one embodiment, a bicyclic fused ring system is a naphthyl, indanyl, indolyl, benzofuranyl, benzothienyl, benzthiazolyl, benzmorpholinyl, pyrido-oxazolyl, pyridothiazolyl or dihydrobenzofuranyl moiety.

Examples of tricyclic ring systems in which the three rings are fused together include xanthenyl, carbazolyl, acridinyl, phenothiazinyl, phenoxazinyl, dibenzofuranyl, dibenzothienyl, S,S,-dioxodibenzothienyl, fluorenyl, phenanthrenyl and anthracenyl. In one embodiment, a tricyclic fused ring system is a dibenzofuranyl or S,S,-dioxodibenzothienyl moiety.

For the avoidance of doubt, when the phenyl, heteroaryl, carbocyclyl or heterocyclyl moieties in $G^1$ and $G^2$ are fused to one or two further rings, said fused rings may be substituted at one or more ring positions with such substituents as described above.

In one embodiment, A is selected from phenyl, pyridyl or thienyl; said phenyl or pyridyl being optionally fused to a phenyl, a 5- or 6-membered heteroaryl, $C_{5-6}$carbocyclyl or $C_{5-6}$heterocyclyl ring. Examples of fused ring systems for A include naphthyl, indanyl, quinolyl, tetrahydroquinolyl, benzofuranyl, indolyl, benzothienyl, indazolyl, benzimidazolyl, benzthiazolyl, indenyl, 2,3-dihydro-indenyl, tetrahydronaphthyl, pyrido-oxazolyl, pyridothiazolyl, dihydrobenzofuranyl, 1,3-benzodioxolyl and 2,3-dihydro-1,4-benzodioxinyl.

In one embodiment, A represents phenyl, pyridyl, thienyl or 2,3-dihydro-indenyl.

In another embodiment, A is phenyl or pyridyl.
In another embodiment, A is phenyl.
In another embodiment, A is pyridyl.
In another embodiment, A is thienyl.
In another embodiment, A is 2,3-dihydro-indenyl.

In one embodiment, $R^1$ is independently selected from halogen, nitro, $SF_5$, OH, CHO, $C_{1-4}$alkyl or $C_{1-4}$alkoxy; said $C_{1-4}$alkyl or $C_{1-4}$alkoxy being optionally substituted by OH or by one or more F atoms.

In one embodiment, $R^1$ is independently selected from halogen, CN, OH, $CONR^5R^6$, $NR^5R^6$, $C_{1-4}$alkyl, $C_{2-4}$alkynyl, $C_{1-4}$alkoxy, $G^3$, $OG^3$ or $OCH_2G^3$; said $C_{1-4}$alkyl or $C_{2-4}$alkynyl being optionally substituted by OH or by one or more F atoms.

In one embodiment, $R^1$ is independently selected from halogen, CN, OH, $CONR^5R^6$, $NR^5R^6$, $C_{1-4}$alkyl, $C_{2-4}$alkynyl, $C_{1-4}$alkoxy, $G^3$, $OG^3$ or $OCH_2G^3$; said $C_{1-4}$alkyl or $C_{2-4}$alkynyl being optionally substituted by OH.

In one embodiment, $G^3$ is phenyl, pyridyl or 2-methyl-1,3,4-oxadiazole.

In one embodiment, $R^5$ and $R^6$ is hydrogen.

In another embodiment, $R^1$ is independently selected from halogen, $C_{1-4}$alkyl or $C_{1-4}$alkoxy; said $C_{1-4}$alkyl or $C_{1-4}$alkoxy being optionally substituted by OH or by one or more F atoms.

In one embodiment, m represents an integer 0, 1 or 2.

In one embodiment, m represents an integer 0 or 1. In another embodiment, m represents an integer 0.

In one embodiment, each $R^3$ is independently selected from hydrogen, CN and $C_{1-4}$alkyl. In another embodiment, each $R^3$ represents hydrogen.

In one embodiment, $L^1$ represents a direct bond, $C_{1-3}$alkylene or $C_{2-3}$alkenylene.

In one embodiment, $L^1$ represents a direct bond, $C_{1-2}$alkylene or $C_2$alkenylene. In another embodiment, $L^1$ represents a direct bond.

In one embodiment, $L^2$ represents a direct bond, —O—, —OCH$_2$—, —NHCONH— or —C≡C—.

In one embodiment, $L^2$ represents a direct bond, —O—, —OCH$_2$—, $C_{1-2}$alkylene or —C≡C—. In another embodiment, $L^2$ represents a direct bond or —C≡C—. In another embodiment, $L^2$ represents a direct bond. In another embodiment, $L^2$ represents —C≡C—.

In one embodiment, $G^1$ represents phenyl or 5- or 6-membered heteroaryl, said phenyl or 5- or 6-membered heteroaryl being optionally fused to one or two further rings independently selected from phenyl, $C_{5-6}$carbocyclyl or $C_{5-6}$heterocyclyl ring.

In one embodiment, $G^1$ represents phenyl or 5- or 6-membered heteroaryl; optionally fused to one further ring independently selected from phenyl and 5- or 6-membered heteroaryl. In another embodiment, $G^1$ represents phenyl; optionally fused to one further ring independently selected from phenyl and 5- or 6-membered heteroaryl. In another embodiment, $G^1$ represents phenyl.

In one embodiment, $G^2$ represents H, $C_{1-6}$alkyl, phenyl or 5- or 6-membered heteroaryl; said phenyl or 5- or 6-membered heteroaryl being optionally fused to one further ring independently selected from phenyl, a 5- or 6-membered heteroaryl, $C_{5-6}$carbocyclyl or $C_{5-6}$heterocyclyl ring.

In one embodiment, $G^1$ represents phenyl, naphtyl, pyridyl, thienyl, 2,3-dihydro-indenyl tetrahydronaphtyl, 2,3-dihydro-1,4-benzodioxinyl or S,S,-dioxodibenzothienyl.

In one embodiment, $G^2$ represents hydrogen, methyl, ethyl, tert-butyl, iso-propyl, phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl or dibenzofuranyl.

In one embodiment, any phenyl, heteroaryl, carbocyclyl or heterocyclyl moieties in $G^1$ and $G^2$ are optionally substituted by one or more substituents independently selected from halogen, CN, $NO_2$, $C_{1-6}$alkyl and $C_{1-6}$alkoxy; said $C_{1-6}$alkyl or $C_{1-6}$alkoxy being optionally substituted by OH or by one or more F atoms.

In one embodiment, any phenyl, heteroaryl, carbocyclyl or heterocyclyl moieties in $G^1$ and $G^2$ are optionally substituted by one or more substituents independently selected from halogen, CN, OH, $C_{1-4}$alkyl, $C_1$thioalkoxy, $NR^{12}R^{13}$, —NH- COC(OH)(CH$_3$)CF$_3$, SO$_2$NR$^{10}$R$^{11}$, and C$_1$alkoxy; said C$_{1-4}$alkyl or C$_1$alkoxy being optionally substituted by OH or by one or more F atoms.

In one embodiment, R$^{10}$ is hydrogen.

In one embodiment, R$^{11}$, R$^{12}$ and R$^{13}$ is methyl.

In another embodiment, any phenyl, heteroaryl, carbocyclyl or heterocyclyl moieties in G$^1$ and G$^2$ are optionally substituted by one or more substituents independently selected from halogen, C$_{1-6}$alkyl and C$_{1-6}$alkoxy; said C$_{1-6}$alkyl being optionally substituted by OH or by one or more F atoms.

In one embodiment, A is phenyl, pyridyl, thienyl or 2,3-dihydro-indenyl; R$^1$ is independently selected from halogen, CN, OH, CONR$^5$R$^6$, NR$^5$R$^6$, C$_{1-4}$alkyl, C$_{2-4}$alkynyl, C$_{1-4}$alkoxy, G$^3$, OG$^3$ and OCH$_2$G$^3$; said C$_{1-4}$alkyl or C$_{2-4}$alkynyl being optionally substituted by one or more substituents selected from OH and C$_{1-4}$alkyl;

m represents an integer 0, 1 or 2;

G$^3$ is phenyl, pyridyl or 2-methyl-1,3,4-oxadiazole;

R$^3$, R$^5$, R$^6$ and R$^{10}$ represents hydrogen;

L$^1$ represents a direct bond, C$_{1-3}$alkylene or C$_{2-3}$alkenylene;

L$^2$ represents a direct bond, —O—, —OCH$_2$—, —NHCONH— or —C≡C—;

G$^1$ represents phenyl or 5- or 6-membered heteroaryl; said phenyl or 5- or 6-membered heteroaryl being optionally fused to one or two further rings independently selected from phenyl, C$_{5-6}$carbocyclyl or C$_{5-6}$heterocyclyl ring;

G$^2$ represents H, C$_{1-6}$alkyl, phenyl, 5- or 6-membered heteroaryl, C$_{3-10}$carbocyclyl or C$_{5-8}$heterocyclyl;

said phenyl or 5- or 6-membered heteroaryl being optionally fused to one further ring independently selected from phenyl, 5- or 6-membered heteroaryl, C$_{5-6}$carbocyclyl and C$_{5-6}$heterocyclyl ring;

said C$_{1-6}$alkyl being optionally further substituted by one or more groups selected from OH, C$_{1-6}$alkoxy or halogen.

any phenyl, heteroaryl, carbocyclyl or heterocyclyl moieties in G$^1$ and G$^2$ being optionally substituted by one or more substituents independently selected from halogen, CN, OH, C$_{1-4}$alkyl, C$_1$thioalkoxy, NR$^{12}$R$^{13}$, —NHCOC(OH)(CH$_3$)CF$_3$, SO$_2$NR$^{10}$R$^{11}$, and C$_1$alkoxy; said C$_{1-4}$alkyl or C$_1$alkoxy being optionally substituted by OH or by one or more F atoms; R$^{11}$ is methyl; R$^{12}$ and R$^{13}$ is methyl.

In one embodiment, A is phenyl, pyridyl, thienyl or 2,3-dihydro-indenyl;

R$^1$ is independently selected from halogen, CN, OH, CONR$^5$R$^6$, NR$^5$R$^6$, C$_{1-4}$alkyl, C$_{2-4}$alkynyl, C$_{1-4}$alkoxy, G$^3$, OG$^3$ and OCH$_2$G$^3$; said C$_{1-4}$alkyl or C$_{2-4}$alkynyl being optionally substituted by one or more substituents selected from OH and C$_{1-4}$alkyl;

m represents an integer 0, 1 or 2;

G$^3$ is phenyl, pyridyl or 2-methyl-1,3,4-oxadiazole;

R$^3$, R$^5$, R$^6$ and R$^{10}$ represents hydrogen;

L$^1$ represents a direct bond, C$_{1-3}$alkylene or C$_{2-3}$alkenylene;

L$^2$ represents a direct bond, —O—, —OCH$_2$—, —NHCONH— or —C≡C—;

G$^1$ represents phenyl, naphtyl, pyridyl, thienyl, 2,3-dihydro-indenyl tetrahydronaphtyl, 2,3-dihydro-1,4-benzodioxinyl or S,S,-dioxodibenzothienyl;

G$^2$ represents hydrogen, C$_{1-4}$alkyl, phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl and dibenzofuranyl;

any phenyl, heteroaryl, carbocyclyl or heterocyclyl moieties in G$^1$ and G$^2$ are optionally substituted by one or more substituents independently selected from halogen, CN, OH, C$_{1-4}$alkyl, C$_1$thioalkoxy, NR$^{12}$R$^{13}$, —NHCOC(OH)(CH$_3$)CF$_3$, SO$_2$NR$^{10}$R$^{11}$, and C$_1$alkoxy; said C$_{1-4}$alkyl or C$_1$alkoxy being optionally substituted by OH or by one or more F atoms;

R$^{11}$, R$^{12}$ and R$^{13}$ is methyl.

In one embodiment A is phenyl, pyridyl or thienyl or 2,3-dihydro-indenyl;

R$^1$ is independently selected from chloro, fluoro, bromo, CN, OH, CONR$^5$R$^6$, methyl, 1-butynyl, methoxy, G$^3$, OG$^3$ or OCH$_2$G$^3$; said methyl and 1-butynyl being optionally substituted by OH or methyl;

m represents an integer 0, 1 or 2;

G$^3$ is phenyl, pyridyl or 2-methyl-1,3,4-oxadiazole;

R$^3$, R$^5$, R$^6$ and R$^{10}$ represents hydrogen;

L$^1$ represents a direct bond, ethylene, 1-methylethylene, 2-methylethylene, ethenylene, —C(CH3)CH—, —CHC(CH3)- or —CH2C(CH2)-;

L$^2$ represents a direct bond, —O—, —OCH$_2$—, —NHCONH— or —C≡C—;

G$^1$ represents phenyl, naphtyl, pyridyl, thienyl, 2,3-dihydro-indenyl tetrahydronaphtyl, 2,3-dihydro-1,4-benzodioxinyl or S,S,-dioxodibenzothienyl;

G$^2$ represents hydrogen, methyl, ethyl, tert-butyl, iso-propyl phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl or dibenzofuranyl;

any methyl, ethyl, tert-butyl, iso-propyl phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl or dibenzofuranyl in G$^1$ and G$^2$ are optionally substituted by one or more substituents independently selected from bromo, chloro, fluoro, CN, OH, methyl, tert-butyl, methylthio, NR$^{12}$R$^{13}$, —NHCOC(OH)(CH$_3$)CF$_3$, SO$_2$NR$^{10}$R$^{11}$, and methoxy; said methyl, tert-butyl or methoxy being optionally substituted by OH or by one or more F atoms;

R$^{11}$, R$^{12}$ and R$^{13}$ is methyl.

In one embodiment, A is phenyl or pyridyl;

R$^1$ is independently selected from halogen, C$_{1-4}$alkyl or C$_{1-4}$alkoxy; said C$_{1-4}$alkyl or C$_{1-4}$alkoxy being optionally substituted by OH or by one or more F atoms; m represents an integer 0 or 1;

each R$^3$ represents hydrogen;

L$^1$ represents a direct bond;

L$^2$ represents a direct bond;

G$^1$ represents phenyl; optionally fused to one further ring independently selected from phenyl and 5- or 6-membered heteroaryl;

G$^2$ represents H, phenyl or 5- or 6-membered heteroaryl; optionally fused to one further ring independently selected from phenyl, a 5- or 6-membered heteroaryl, C$_{5-6}$carbocyclyl or C$_{5-6}$heterocyclyl ring; and any phenyl or heteroaryl moieties in G$^1$ and G$^2$ are optionally substituted by one or more substituents independently selected from halogen, C$_{1-6}$alkyl and C$_{1-6}$alkoxy; said C$_{1-6}$alkyl being optionally substituted by OH or by one or more F atoms.

In one embodiment, A is phenyl;

m represents an integer 0;

each R$^3$ represents hydrogen;

L$^1$ represents a direct bond;

L$^2$ represents a direct bond;

G$^1$ represents phenyl; optionally fused to one further ring independently selected from phenyl and 5- or 6-membered heteroaryl;

$G^2$ represents H, phenyl or 5- or 6-membered heteroaryl; optionally fused to one further ring independently selected from phenyl, a 5- or 6-membered heteroaryl, $C_{5-6}$carbocyclyl or $C_{5-6}$heterocyclyl ring; and any phenyl or heteroaryl moieties in $G^1$ and $G^2$ are optionally substituted by one or more substituents independently selected from halogen, $C_{1-6}$alkyl and $C_{1-6}$alkoxy; said $C_{1-6}$alkyl being optionally substituted by OH or by one or more F atoms.

In one embodiment, A is phenyl;
m represents an integer 0;
each $R^3$ represents hydrogen;
$L^1$ represents a direct bond;
$L^2$ represents —C≡C—;
$G^1$ represents phenyl; optionally fused to one further ring independently selected from phenyl and 5- or 6-membered heteroaryl;
$G^2$ represents $C_{1-6}$alkyl optionally substituted by one or more groups selected from OH, $C_{1-6}$alkoxy and halogen; and any phenyl or heteroaryl moieties in $G^1$ is optionally substituted by one or more substituents independently selected from halogen, $C_{1-6}$alkyl and $C_{1-6}$alkoxy; said $C_{1-6}$alkyl being optionally substituted by OH or by one or more F atoms.

In one aspect we disclose a compound of formula (I) or a pharmaceutically acceptable salt thereof

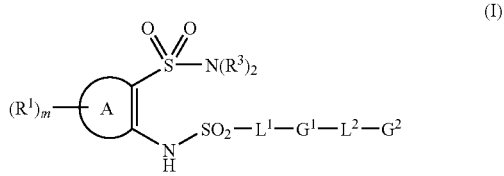

(I)

wherein:
A is selected from phenyl or a 5- or 6-membered heteroaryl or a 5- or 6-membered heterocyclenyl moiety; said phenyl or 5- or 6-membered heteroaryl or 5- or 6-membered heterocyclenyl moiety in group A being optionally fused to a phenyl, a 5- or 6-membered heteroaryl, $C_{5-6}$carbocyclyl or $C_{5-6}$heterocyclyl ring;
each $R^1$ is independently selected from halogen, nitro, $SF_5$, CN, $NR^5R^6$, OH, CHO, $CO_2C_{1-4}$alkyl, $CONR^5R^6$, $C_{1-4}$alkyl, $C_{2-4}$alkenyl, $C_{2-4}$alkynyl, $C_{1-4}$alkoxy, $G^3$, $OG^3$ or $OCH_2G^3$; said $C_{1-4}$alkyl, $C_{2-4}$alkenyl, $C_{2-4}$alkynyl or $C_{1-4}$alkoxy being optionally substituted by one or more substituents selected from OH, $NR^5R^6$, $C_{1-4}$alkyl or F;
m represents an integer 0, 1, 2, 3 or 4;
each $R^3$ is independently selected from hydrogen, CN and $C_{1-4}$alkyl; said $C_{1-4}$alkyl being optionally substituted with OH, CN, $C_{1-4}$alkoxy, $NR^7R^8$, or one or more F atoms;
$L^1$ represents a direct bond, $C_{1-4}$alkylene, $C_{2-4}$alkenylene or $C_{2-4}$alkynylene;
$L^2$ represents a direct bond, —O—, —OCH$_2$—, $C_{1-2}$alkylene, —C≡C— or —NHCONH—;
$G^1$ represents phenyl, 5- or 6-membered heteroaryl, $C_{3-10}$carbocyclyl or $C_{5-8}$heterocyclyl;
$G^2$ represents H, $C_{1-6}$alkyl, phenyl, 5- or 6-membered heteroaryl, $C_{3-10}$carbocyclyl or $C_{5-8}$heterocyclyl; said $C_{1-6}$alkyl being optionally further substituted by one or more groups selected from OH, $C_{1-6}$alkoxy and halogen;
the phenyl, heteroaryl, carbocyclyl or heterocyclyl moieties in $G^1$ and $G^2$ being optionally fused to one or two further rings independently selected from phenyl, a 5- or 6-membered heteroaryl, $C_{5-6}$carbocyclyl or $C_{5-6}$heterocyclyl ring;
any phenyl, heteroaryl, carbocyclyl or heterocyclyl moieties in $G^1$ and $G^2$ being optionally substituted by one or more substituents independently selected from halogen, OH, CN, $NO_2$, $CO_2R^9$, $C_{1-6}$alkyl, $C_{1-6}$alkoxy, $C_{1-4}$thioalkoxy, $SO_2NR^{10}R^{11}$, $NR^{12}R^{13}$, —NHCOC(OH)(CH$_3$)CF$_3$ or —CH$_2$OCH$_2$CF$_2$CHF$_2$; said $C_{1-6}$alkyl or $C_{1-6}$alkoxy being optionally substituted by OH or by one or more F atoms;
$R^9$ represents $C_{1-6}$alkyl;
$G^3$ represents phenyl or 5- or 6-membered heteroaryl; and each $R^4$, $R^5$, $R^6$, $R^7$, $R^8$, $R^{10}$, $R^{11}$, $R^{12}$ and $R^{13}$ is independently selected from H or $C_{1-4}$alkyl;
with the proviso that the following compounds are excluded:
3-[(phenylsulfonyl)amino]pyridine-2-sulfonamide;
2-amino-N-(2-sulfamoylphenyl)benzenesulfonamide;
4-tert-butyl-N-(2-sulfamoylphenyl)benzenesulfonamide;
3-amino-4-hydroxy-N-(2-sulfamoylphenyl)benzenesulfonamide;
4-bromo-N-(2-sulfamoylphenyl)benzenesulfonamide;
4-fluoro-N-(2-sulfamoylphenyl)benzenesulfonamide;
4-methyl-N-(2-sulfamoylphenyl)benzenesulfonamide;
4-nitro-N-(2-sulfamoylphenyl)benzenesulfonamide;
2-nitro-N-(2-sulfamoylphenyl)benzenesulfonamide;
4-amino-N-(2-sulfamoylphenyl)benzenesulfonamide;
2-methyl-4-[(2-sulfamoylphenyl)sulfamoyl]phenyl 2,2-dimethylpropanoate;
2-[(phenylsulfonyl)amino]-4-(trifluoromethyl)benzenesulfonamide;
2-{[(4-methylphenyl)sulfonyl]amino}-4-(trifluoromethyl)benzenesulfonamide; and
N-(2-sulfamoylphenyl)quinoline-8-sulfonamide.

In one aspect we disclose a compound of formula (I) or a pharmaceutically acceptable salt thereof

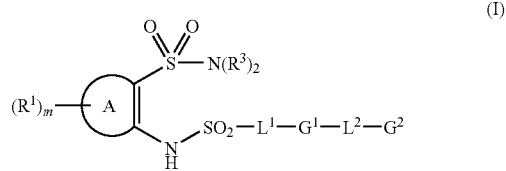

(I)

wherein:
A is selected from phenyl or a 5- or 6-membered heteroaryl or a 5- or 6-membered heterocyclenyl moiety; said phenyl or 5- or 6-membered heteroaryl or 5- or 6-membered heterocyclenyl moiety in group A being optionally fused to a phenyl, a 5- or 6-membered heteroaryl, $C_{5-6}$carbocyclyl or $C_{5-6}$heterocyclyl ring;
each $R^1$ is independently selected from halogen, nitro, $SF_5$, CN, $NR^5R^6$, OH, CHO, $CO_2C_{1-4}$alkyl, $CONR^5R^6$, $C_{1-4}$alkyl, $C_{2-4}$alkenyl, $C_{2-4}$alkynyl, $C_{1-4}$alkoxy, $G^3$, $OG^3$ or $OCH_2G^3$; said $C_{1-4}$alkyl, $C_{2-4}$alkenyl, $C_{2-4}$alkynyl or $C_{1-4}$alkoxy being optionally substituted by one or more substituents selected from OH, $NR^5R^6$, $C_{1-4}$alkyl or F;
m represents an integer 0, 1, 2, 3 or 4;
each $R^3$ is independently selected from hydrogen, CN and $C_{1-4}$alkyl; said $C_{1-4}$alkyl being optionally substituted with OH, CN, $C_{1-4}$alkoxy, $NR^7R^8$, or one or more F atoms;
$L^1$ represents a direct bond, $C_{1-4}$alkylene, $C_{2-4}$alkenylene or $C_{2-4}$alkynylene;
$L^2$ represents a direct bond, —O—, —OCH$_2$—, $C_{1-2}$alkylene, —C≡C— or —NHCONH—;
$G^1$ represents phenyl, 5- or 6-membered heteroaryl, $C_{3-10}$carbocyclyl or $C_{5-8}$heterocyclyl;
$G^2$ represents H, $C_{1-6}$alkyl, phenyl, 5- or 6-membered heteroaryl, $C_{3-10}$carbocyclyl or $C_{5-8}$heterocyclyl; said $C_{1-6}$alkyl being optionally further substituted by one or more groups selected from OH, $C_{1-6}$alkoxy and halogen;

the phenyl, heteroaryl, carbocyclyl or heterocyclyl moieties in $G^1$ and $G^2$ being optionally fused to one or two further rings independently selected from phenyl, a 5- or 6-membered heteroaryl, $C_{5-6}$carbocyclyl or $C_{5-6}$heterocyclyl ring;

any phenyl, heteroaryl, carbocyclyl or heterocyclyl moieties in $G^1$ and $G^2$ being optionally substituted by one or more substituents independently selected from halogen, OH, CN, $NO_2$, $CO_2R^9$, $C_{1-6}$alkyl, $C_{1-6}$alkoxy, $C_{1-4}$thioalkoxy, $SO_2NR^{10}R^{11}$, $NR^{12}R^{13}$, —NHCOC(OH)(CH$_3$)CF$_3$ or —CH$_2$OCH$_2$CF$_2$CHF$_2$; said $C_{1-6}$alkyl or $C_{1-6}$alkoxy being optionally substituted by OH or by one or more F atoms;

$R^9$ represents $C_{1-6}$alkyl;

$G^3$ represents phenyl or 5- or 6-membered heteroaryl; and each $R^4$, $R^5$, $R^6$, $R^7$, $R^8$, $R^{10}$, $R^{11}$, $R^{12}$ and $R^{13}$ is independently selected from H or $C_{1-4}$alkyl;

with the proviso that the following compounds are excluded:
2-amino-N-(2-sulfamoylphenyl)benzenesulfonamide;
methyl 4-(5-fluoro-3-methylbenzo[b]thiophene-2-sulfonamido)-3-sulfamoylbenzoate;
4-nitro-N-(2-sulfamoylphenyl)benzenesulfonamide;
2-nitro-N-(2-sulfamoylphenyl)benzenesulfonamide;
4-amino-N-(2-sulfamoylphenyl)benzenesulfonamide;
N-(2-sulfamoylphenyl)quinoline-8-sulfonamide;
for the use in therapy.

In one aspect we disclose a compound of formula (I) or a pharmaceutically acceptable salt thereof

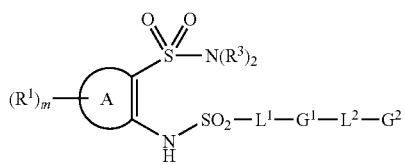

(I)

wherein:
A is selected from phenyl or a 5- or 6-membered heteroaryl or a 5- or 6-membered heterocyclenyl moiety; said phenyl or 5- or 6-membered heteroaryl or 5- or 6-membered heterocyclenyl moiety in group A being optionally fused to a phenyl, a 5- or 6-membered heteroaryl, $C_{5-6}$carbocyclyl or $C_{5-6}$heterocyclyl ring;

each $R^1$ is independently selected from halogen, nitro, $SF_5$, CN, $NR^5R^6$, OH, CHO, $CO_2C_{1-4}$alkyl, $CONR^5R^6$, $C_{1-4}$alkyl, $C_{2-4}$alkenyl, $C_{2-4}$alkynyl, $C_{1-4}$alkoxy, $G^3$, $OG^3$ or $OCH_2G^3$; said $C_{1-4}$alkyl, $C_{2-4}$alkenyl, $C_{2-4}$alkynyl or $C_{1-4}$alkoxy being optionally substituted by one or more substituents selected from OH, $NR^5R^6$, $C_{1-4}$alkyl or F;

m represents an integer 0, 1, 2, 3 or 4;

each $R^3$ is independently selected from hydrogen, CN and $C_{1-4}$alkyl; said $C_{1-4}$alkyl being optionally substituted with OH, CN, $C_{1-4}$alkoxy, $NR^7R^8$, or one or more F atoms;

$L^1$ represents a direct bond, $C_{1-4}$alkylene, $C_{2-4}$alkenylene or $C_{2-4}$alkynylene;

$L^2$ represents a direct bond, —O—, —OCH$_2$—, $C_{1-2}$alkylene, —C≡C— or —NHCONH—;

$G^1$ represents phenyl, 5- or 6-membered heteroaryl, $C_{3-10}$carbocyclyl or $C_{5-8}$heterocyclyl;

$G^2$ represents H, $C_{1-6}$alkyl, phenyl, 5- or 6-membered heteroaryl, $C_{3-10}$carbocyclyl or $C_{5-8}$heterocyclyl; said $C_{1-6}$alkyl being optionally further substituted by one or more groups selected from OH, $C_{1-6}$alkoxy and halogen;

the phenyl, heteroaryl, carbocyclyl or heterocyclyl moieties in $G^1$ and $G^2$ being optionally fused to one or two further rings independently selected from phenyl, a 5- or 6-membered heteroaryl, $C_{5-6}$carbocyclyl or $C_{5-6}$heterocyclyl ring;

any phenyl, heteroaryl, carbocyclyl or heterocyclyl moieties in $G^1$ and $G^2$ being optionally substituted by one or more substituents independently selected from halogen, OH, CN, $NO_2$, $CO_2R^9$, $C_{1-6}$alkyl, $C_{1-6}$alkoxy, $C_{1-4}$thioalkoxy, $SO_2NR^{10}R^{11}$, $NR^{12}R^{13}$, —NHCOC(OH)(CH$_3$)CF$_3$ or —CH$_2$OCH$_2$CF$_2$CHF$_2$; said $C_{1-6}$alkyl or $C_{1-6}$alkoxy being optionally substituted by OH or by one or more F atoms;

$R^9$ represents $C_{1-6}$alkyl;

$G^3$ represents phenyl or 5- or 6-membered heteroaryl; and each $R^4$, $R^5$, $R^6$, $R^7$, $R^8$, $R^{10}$, $R^{11}$, $R^{12}$ and $R^{13}$ is independently selected from H or $C_{1-4}$alkyl;

in the manufacture of a medicament for use in treating acute or chronic pain, nociceptive pain or neuropathic pain.

Examples of compounds of the invention include:
2-[2-(4-Benzofuran-2-ylphenyl)ethylsulfonylamino]benzenesulfonamide;
2-[2-[4-(2,3-Dihydrobenzofuran-2-yl)phenyl]ethylsulfonylamino]benzenesulfonamide;
2-[[(E)-2-(4-Benzofuran-2-ylphenyl)ethenyl]sulfonylamino]benzenesulfonamide;
2-[[(E)-2-(4-Benzofuran-2-ylphenyl)ethenyl]sulfonylamino]-5-fluoro-benzenesulfonamide;
2-[[(E)-2-(4-Benzofuran-2-ylphenyl)ethenyl]sulfonylamino]-4-fluoro-benzenesulfonamide;
2-[[(E)-2-(4-Benzofuran-2-ylphenyl)ethenyl]sulfonylamino]-6-fluoro-benzenesulfonamide;
2-[1-(4-Chlorophenyl)propan-2-ylsulfonylamino]benzenesulfonamide;
2-(1-Phenylpropan-2-ylsulfonylamino)benzenesulfonamide;
2-[[(E)-1-(4-Chlorophenyl)prop-1-en-2-yl]sulfonylamino]benzenesulfonamide;
2-[1-(4-Chlorophenyl)propan-2-ylsulfonylamino]-4-fluoro-benzenesulfonamide;
2-[[(E)-1-(4-chlorophenyl)prop-1-en-2-yl]sulfonylamino]-4-fluoro-benzenesulfonamide;
2-[[(E)-1-(4-Chlorophenyl)prop-1-en-2-yl]sulfonylamino]-5-fluoro-benzenesulfonamide;
2-[[(E)-1-(4-Chlorophenyl)prop-1-en-2-yl]sulfonylamino]-6-fluoro-benzenesulfonamide;
2-[[(E)-1-(4-Chlorophenyl)prop-1-en-2-yl]sulfonylamino]-3-fluoro-benzenesulfonamide;
2-[[(E)-1-(4-Chlorophenyl)prop-1-en-2-yl]sulfonylamino]-5-methyl-benzenesulfonamide;
2-[2-[4-(2-Furyl)phenyl]ethylsulfonylamino]benzenesulfonamide;
2-[2-[4-(Oxolan-2-yl)phenyl]ethylsulfonylamino]benzenesulfonamide;
2-[[(E)-2-[4-(2-Furyl)phenyl]ethenyl]sulfonylamino]benzenesulfonamide;
2-[2-[4-(Difluoromethoxy)phenyl]ethylsulfonylamino]benzenesulfonamide;
2-[[(E)-2-[4-(Difluoromethoxy)phenyl]ethenyl]sulfonylamino]-benzenesulfonamide;
2-[2-(4-Chlorophenyl)ethylsulfonylamino]-5-fluoro-benzenesulfonamide;
2-[[(E)-2-(4-Chlorophenyl)ethenyl]sulfonylamino]-5-fluoro-benzenesulfonamide;
2-[[(E)-2-(3,4-Dichlorophenyl)ethenyl]sulfonylamino]-4-fluoro-benzenesulfonamide;
2-[[(E)-2-(3,4-Dichlorophenyl)ethenyl]sulfonylamino]-5-fluoro-benzenesulfonamide;

2-[[(E)-2-(3,4-Dichlorophenyl)ethenyl]sulfonylamino]-6-fluoro-benzenesulfonamide;
2-[[(E)-2-(5-Bromo-2-methoxy-phenyl)ethenyl]sulfonylamino]-4-fluoro-benzenesulfonamide;
2-[[(E)-2-(5-Bromo-2-methoxy-phenyl)ethenyl]sulfonylamino]-5-fluoro-benzenesulfonamide;
2-[[(E)-2-(5-Bromo-2-methoxy-phenyl)ethenyl]sulfonylamino]-6-fluoro-benzenesulfonamide;
2-[[(E)-2-(5-Bromo-2-methoxy-phenyl)ethenyl]sulfonylamino]benzenesulfonamide;
2-[[(E)-2-(4-Cyanophenyl)ethenyl]sulfonylamino]-4-fluoro-benzenesulfonamide;
2-[[(E)-2-(4-Cyanophenyl)ethenyl]sulfonylamino]-5-fluoro-benzenesulfonamide;
2-[[(E)-2-(4-Cyanophenyl)ethenyl]sulfonylamino]-6-fluoro-benzenesulfonamide;
2-[[(E)-2-(4-Cyanophenyl)ethenyl]sulfonylamino]benzenesulfonamide;
4-Fluoro-2-[[(E)-2-[4-(2-furyl)phenyl]ethenyl]sulfonylamino]benzenesulfonamide;
5-Fluoro-2-[[(E)-2-[4-(2-furyl)phenyl]ethenyl]sulfonylamino]benzenesulfonamide;
2-Fluoro-6-[[(E)-2-[4-(2-furyl)phenyl]ethenyl]sulfonylamino]benzenesulfonamide;
4-Fluoro-2-[[(E)-2-(4-methylsulfanylphenyl)ethenyl]sulfonylamino]-benzenesulfonamide;
5-Fluoro-2-[[(E)-2-(4-methylsulfanylphenyl)ethenyl]sulfonylamino]-benzenesulfonamide;
2-Fluoro-6-[[(E)-2-(4-methylsulfanylphenyl)ethenyl]sulfonylamino]-benzenesulfonamide;
2-[[(E)-2-(4-Methylsulfanylphenyl)ethenyl]sulfonylamino]benzenesulfonamide;
2-[[(E)-2-[4-(Difluoromethoxy)phenyl]ethenyl]sulfonylamino]-4-fluoro-benzenesulfonamide;
2-[[(E)-2-[4-(Difluoromethoxy)phenyl]ethenyl]sulfonylamino]-5-fluoro-benzenesulfonamide;
2-[[(E)-2-[4-(Difluoromethoxy)phenyl]ethenyl]sulfonylamino]-6-fluoro-benzenesulfonamide;
2-[2-(4-Chlorophenyl)ethylsulfonylamino]-5-(hydroxymethyl)-benzenesulfonamide;
2-[2-(4-Chloro-phenyl)-ethanesulfonylamino]-5-methyl-benzenesulfonamide;
2-[2-(4-Chlorophenyl)ethylsulfonylamino]-5-(pyridin-2-ylmethoxy)benzenesulfonamide;
2-[2-(4-Chlorophenyl)ethylsulfonylamino]-5-[(5-methyl-1,3,4-oxadiazol-2-yl)methoxy]benzenesulfonamide;
2-[2-(2-Chloro-phenyl)-ethenesulfonylamino]-benzenesulfonamide;
2-[2-(4-Chloro-2-methoxy-phenyl)-ethenesulfonylamino]-benzenesulfonamide;
2-Fluoro-6-[[(E)-2-(4-phenylphenyl)ethenyl]sulfonylamino]benzenesulfonamide;
2-[[(E)-2-(3-Chlorophenyl)ethenyl]sulfonylamino]-5-fluoro-benzenesulfonamide;
5-Fluoro-2-[[(E)-2-(4-phenylphenyl)ethenyl]sulfonylamino]benzenesulfonamide;
4-Fluoro-2-[[(E)-2-(4-phenylphenyl)ethenyl]sulfonylamino]benzenesulfonamide;
5-Fluoro-2-[[(E)-2-[3-(trifluoromethyl)phenyl]ethenyl]sulfonylamino]-benzenesulfonamide;
5-Fluoro-2-[[(E)-2-(2-methoxyphenyl)ethenyl]sulfonylamino]-benzenesulfonamide;
2-[[(E)-2-(3-Chlorophenyl)ethenyl]sulfonylamino]-6-fluoro-benzenesulfonamide;
2-Fluoro-6-[[(E)-2-(2-methoxyphenyl)ethenyl]sulfonylamino]-benzenesulfonamide;
4-Fluoro-2-[[(E)-2-(2-methoxyphenyl)ethenyl]sulfonylamino]-benzenesulfonamide;
3-Fluoro-2-[[(E)-2-(4-phenylphenyl)ethenyl]sulfonylamino]benzenesulfonamide;
3-Fluoro-2-[[(E)-2-(2-methoxyphenyl)ethenyl]sulfonylamino]-benzenesulfonamide;
4-Fluoro-2-[[(E)-2-[3-(trifluoromethyl)phenyl]ethenyl]sulfonylamino]-benzenesulfonamide;
2-Fluoro-6-[[(E)-2-(2-fluorophenyl)ethenyl]sulfonylamino]benzenesulfonamide;
2-[[(E)-2-(3-Chlorophenyl)ethenyl]sulfonylamino]-5-methyl-benzenesulfonamide;
2-[[(E)-2-(3-Chlorophenyl)ethenyl]sulfonylamino]-3-fluoro-benzenesulfonamide;
3-Fluoro-2-[[(E)-2-[3-(trifluoromethyl)phenyl]ethenyl]sulfonylamino]-benzenesulfonamide;
2-Fluoro-6-[[(E)-2-[3-(trifluoromethyl)phenyl]ethenyl]sulfonylamino]-benzenesulfonamide;
4-Fluoro-2-[[(E)-2-(2-fluorophenyl)ethenyl]sulfonylamino]benzenesulfonamide;
5-Methyl-2-[[(E)-2-[3-(trifluoromethyl)phenyl]ethenyl]sulfonylamino]-benzenesulfonamide;
2-[2-(4-Cyclopentylphenyl)ethylsulfonylamino]benzenesulfonamide;
2-[2-(4-Tert-butylphenyl)ethylsulfonylamino]benzenesulfonamide;
4-Fluoro-2-[2-(4-tert-butylphenyl)ethylsulfonylamino]benzenesulfonamide;
2-[2-(4-Chlorophenyl)ethylsulfonylamino]benzenesulfonamide;
2-[[(E)-2-(4-Chlorophenyl)ethenyl]sulfonylamino]benzenesulfonamide;
2-(Phenethylsulfonylamino)benzenesulfonamide;
2-[[(E)-2-Phenylethenyl]sulfonylamino]benzenesulfonamide;
2-[2-(2-Chlorophenyl)ethylsulfonylamino]benzenesulfonamide;
2-[[(E)-2-(4-Methoxyphenyl)ethenyl]sulfonylamino]benzenesulfonamide;
2-[[(E)-2-(4-Chlorophenyl)ethenyl]sulfonylamino]-4-fluoro-benzenesulfonamide;
2-(2-Phenylpropylsulfonylamino)benzenesulfonamide;
2-[[(E)-2-(4-Chlorophenyl)ethenyl]sulfonylamino]-6-fluoro-benzenesulfonamide;
2-[[(E)-2-(2,6-Dichlorophenyl)ethenyl]sulfonylamino]benzenesulfonamide;
2-[[(E)-2-(4-Methylphenyl)ethenyl]sulfonylamino]benzenesulfonamide;
2-[[(E)-2-(2-Methoxyphenyl)ethenyl]sulfonylamino]benzenesulfonamide;
2-[[(E)-2-Naphthalen-2-ylethenyl]sulfonylamino]benzenesulfonamide;
2-[2-(4-Chlorophenyl)ethylsulfonylamino]-4-fluoro-benzenesulfonamide;
2-[[(E)-2-(4-Chlorophenyl)prop-1-enyl]sulfonylamino]benzenesulfonamide;
2-[2-(4-Chlorophenyl)prop-2-enylsulfonylamino]benzenesulfonamide;
2-Fluoro-6-[[(E)-2-naphthalen-2-ylethenyl]sulfonylamino]benzenesulfonamide;
2-Fluoro-6-[[(E)-2-[2-(trifluoromethyl)phenyl]ethenyl]sulfonylamino]-benzenesulfonamide;
2-Fluoro-6-[[(E)-2-[4-(trifluoromethyl)phenyl]ethenyl]sulfonylamino]-benzenesulfonamide;
2-[[(E)-2-(4-Bromophenyl)ethenyl]sulfonylamino]-6-fluoro-benzenesulfonamide;

4-Fluoro-2-[[(E)-2-naphthalen-2-ylethenyl]sulfonylamino]benzenesulfonamide;
4-Fluoro-2-[[(E)-2-[2-(trifluoromethyl)phenyl]ethenyl]sulfonylamino]-benzenesulfonamide;
4-Fluoro-2-[[(E)-2-[4-(trifluoromethyl)phenyl]ethenyl]sulfonylamino]-benzenesulfonamide;
2-[[(E)-2-(4-Bromophenyl)ethenyl]sulfonylamino]-4-fluoro-benzenesulfonamide;
5-Methyl-2-[[(E)-2-naphthalen-2-ylethenyl]sulfonylamino]benzenesulfonamide;
5-Methyl-2-[[(E)-2-[4-(trifluoromethyl)phenyl]ethenyl]sulfonylamino]-benzenesulfonamide;
2-[[(E)-2-(4-Bromophenyl)ethenyl]sulfonylamino]-5-methyl-benzenesulfonamide;
5-Fluoro-2-[[(E)-2-naphthalen-2-ylethenyl]sulfonylamino]benzenesulfonamide;
5-Fluoro-2-[[(E)-2-[2-(trifluoromethyl)phenyl]ethenyl]sulfonylamino]-benzenesulfonamide;
5-Fluoro-2-[[(E)-2-[4-(trifluoromethyl)phenyl]ethenyl]sulfonylamino]-benzenesulfonamide;
2-[[(E)-2-(4-Bromophenyl)ethenyl]sulfonylamino]-5-fluoro-benzenesulfonamide;
2-[[(E)-2-(2,6-Difluorophenyl)ethenyl]sulfonylamino]benzenesulfonamide;
2-[[(E)-2-[2-(Trifluoromethyl)phenyl]ethenyl]sulfonylamino]benzenesulfonamide;
2-[[(E)-2-[4-(Trifluoromethyl)phenyl]ethenyl]sulfonylamino]benzenesulfonamide;
2-[[(E)-2-(4-Bromophenyl)ethenyl]sulfonylamino]benzenesulfonamide;
2-[(E)-2-(4-Bromophenyl)ethylsulfonylamino]benzenesulfonamide;
2-[2-(4-Chlorophenyl)propylsulfonylamino]benzenesulfonamide;
2-[2-(2-Methoxyphenyl)ethylsulfonylamino]benzenesulfonamide;
2-(2-Naphthalen-2-ylethylsulfonylamino)benzenesulfonamide;
4-Fluoro-2-(2-naphthalen-2-ylethylsulfonylamino)benzenesulfonamide;
2-[(4-Chlorophenyl)methylsulfonylamino]benzenesulfonamide;
2-[[3-(2,3-Dichlorophenyl)phenyl]sulfonylamino]benzenesulfonamide;
2-[[3-(3,5-difluorophenyl)phenyl]sulfonylamino]benzenesulfonamide;
3-(5-Chloro-2-methoxy-phenyl)-N-(2-sulfamoylphenyl)benzenesulfonamide;
2-[[3-(3-Cyanophenyl)phenyl]sulfonylamino]benzenesulfonamide;
2-[[3-(4-Cyanophenyl)phenyl]sulfonylamino]benzenesulfonamide;
3-(2,4-Dimethoxypyrimidin-5-yl)-N-(2-sulfamoylphenyl)benzenesulfonamide;
2-[[3-(3-Furyl)phenyl]sulfonylamino]benzenesulfonamide;
2-[[3-(1H-Indol-5-yl)phenyl]sulfonylamino]benzenesulfonamide;
2-[[3-[3-(Trifluoromethoxy)phenyl]phenyl]sulfonylamino]benzenesulfonamide;
N-(2-Sulfamoylphenyl)-2,3-dihydro-1H-indene-5-sulfonamide;
7-Methyl-N-(2-sulfamoylphenyl)-10-oxa-7-azabicyclo[4.4.0]deca-1,3,5-triene-3-sulfonamide;
2-(3,4-Dichlorophenyl)-N-(2-sulfamoylphenyl)benzenesulfonamide;
2-[[4-[3-Chloro-5-(trifluoromethyl)pyridin-2-yl]oxyphenyl]sulfonylamino]benzenesulfonamide;
N-(2-Sulfamoylphenyl)tetralin-2-sulfonamide;
4-Phenylmethoxy-N-(2-sulfamoylphenyl)benzenesulfonamide;
2-[(4-Cyclohexylphenyl)sulfonylamino]benzenesulfonamide;
3-Phenyl-N-(2-sulfamoylphenyl)benzenesulfonamide;
5-(1-Methyl-5-trifluoromethyl-1H-pyrazol-3-yl)-thiophene-2-sulfonic acid (2-sulfamoyl-phenyl)-amide;
N-(2-Sulfamoylphenyl)-4-(trifluoromethyl)benzenesulfonamide;
2-[[3-(2,5-Dichlorophenyl)phenyl]sulfonylamino]benzenesulfonamide;
3-Dibenzofuran-4-yl-N-(2-sulfamoylphenyl)benzenesulfonamide;
2-[[3-[4-(Trifluoromethyl)phenyl]phenyl]sulfonylamino]benzenesulfonamide;
3-(3-Methoxyphenyl)-N-(2-sulfamoylphenyl)benzenesulfonamide;
3-Benzofuran-2-yl-N-(2-sulfamoylphenyl)benzenesulfonamide;
2-[[3-(2,3-Dihydrobenzofuran-5-yl)phenyl]sulfonylamino]benzenesulfonamide;
3-(6-Methoxypyridin-3-yl)-N-(2-sulfamoylphenyl)benzenesulfonamide;
2-[[3-(2,4-Dichlorophenyl)phenyl]sulfonylamino]benzenesulfonamide;
3-(1-Methylindol-2-yl)-N-(2-sulfamoylphenyl)benzenesulfonamide;
2-[[3-[3-(Trifluoromethyl)phenyl]phenyl]sulfonylamino]benzenesulfonamide;
4-Benzofuran-2-yl-N-(2-sulfamoylphenyl)benzenesulfonamide;
2-[[3-(2,4-Difluorophenyl)phenyl]sulfonylamino]benzenesulfonamide;
5-Bromo-2-[[3-(3,4-dichlorophenyl)phenyl]sulfonylamino]benzenesulfonamide;
2-[[3-(3,4-Dichlorophenyl)phenyl]sulfonylamino]-5-phenyl-benzenesulfonamide;
2,3-Difluoro-N-(2-sulfamoylphenyl)benzenesulfonamide;
2,3-Difluoro-N-(4-fluoro-2-sulfamoyl-phenyl)benzenesulfonamide;
3-Chloro-2-fluoro-N-(2-sulfamoylphenyl)benzenesulfonamide;
2,3-Dichloro-N-(2-sulfamoylphenyl)benzenesulfonamide;
2-[[3-(3,4-Dichlorophenyl)phenyl]sulfonylamino]-5-methyl-benzenesulfonamide;
4-[[3-(3,4-Dichlorophenyl)phenyl]sulfonylamino]-3-sulfamoyl-benzamide;
5-Methyl-2-[[3-[3-(trifluoromethoxy)phenyl]phenyl]sulfonylamino]-benzenesulfonamide;
2-(2,3-Dichloro-benzenesulfonylamino)-5-hydroxymethyl-benzenesulfonamide;
2-(2,3-Dichloro-benzenesulfonylamino)-5-methyl-benzenesulfonamide;
2-[[3-(3,4-Dichlorophenyl)phenyl]sulfonylamino]-5-phenoxybenzenesulfonamide;
5-Phenoxy-2-[[3-[3-(trifluoromethoxy)phenyl]phenyl]sulfonylamino]-benzenesulfonamide;
2-(2,3-Dichloro-benzenesulfonylamino)-5-hydroxy-benzenesulfonamide;
(2R)—N-[2-Chloro-4-[(2-sulfamoylphenyl)sulfamoyl]phenyl]-3,3,3-trifluoro-2-hydroxy-2-methyl-propanamide;
5-Chloro-N-(2-sulfamoylphenyl)thiophene-2-sulfonamide;
4,5-Dichloro-N-(2-sulfamoylphenyl)thiophene-2-sulfonamide;
3,4-Dichloro-N-(2-sulfamoylphenyl)benzenesulfonamide;

3-(6-Methoxypyridin-2-yl)-N-(2-sulfamoylphenyl)benzenesulfonamide;
2-[[4-[(2-Chloro1,3-thiazol-5-yl)methoxy]phenyl]sulfonylamino]-benzenesulfonamide;
3-(5-Fluoro-6-methoxy-pyridin-3-yl)-N-(2-sulfamoylphenyl)benzenesulfonamide;
3-(2-Methoxypyrimidin-5-yl)-N-(2-sulfamoylphenyl)benzenesulfonamide;
3-(4-Methylpyridin-3-yl)-N-(2-sulfamoylphenyl)benzenesulfonamide;
3-(2-Methoxypyridin-3-yl)-N-(2-sulfamoylphenyl)benzenesulfonamide;
2-[[3-(5-Mhloropyridin-3-yl)phenyl]sulfonylamino]benzenesulfonamide;
3-(5-Chloro-6-methoxy-pyridin-3-yl)-N-(2-sulfamoylphenyl)benzenesulfonamide;
3-(6-Dimethylaminopyridin-3-yl)-N-(2-sulfamoylphenyl)benzenesulfonamide;
2-[[3-[3-(Hydroxymethyl)phenyl]phenyl]sulfonylamino]benzenesulfonamide;
2-[[3-[4-(Hydroxymethyl)phenyl]phenyl]sulfonylamino]benzenesulfonamide;
2-[[4-(3,4-Dichlorophenyl)phenyl]sulfonylamino]benzenesulfonamide;
2-[[3-(3,4-Dichlorophenyl)phenyl]sulfonylamino]benzenesulfonamide;
2-[[4-(4-Chlorophenoxy)phenyl]sulfonylamino]benzenesulfonamide;
3-(4-Chlorophenyl)-1-[3-methyl-4-[(2-sulfamoylphenyl)sulfamoyl]phenyl]urea;
N-Methyl-N'-(2-sulfamoylphenyl)dibenzo[b,d]thiophene-2,8-disulfonamide 5,5-dioxide;
2,3-Dichloro-N-(4,5-difluoro-2-sulfamoylphenyl)benzenesulfonamide;
(E)-2-(2-(3,4-Dichlorophenyl)vinylsulfonamido)-5-(3-hydroxy-3-methylbut-1-ynyl)benzenesulfonamide;
4-Cyano-2-(2-(3,4-dichlorophenyl)ethylsulfonamido)benzenesulfonamide;
2-(2-(4-Chloro-2-methoxyphenyl)ethylsulfonamido)-4-cyanobenzenesulfonamide;
2-(2-(4-Chloro-2-methoxyphenyl)ethylsulfonamido)-5-cyanobenzenesulfonamide;
2-(2-(4-(3,3-dimethylbut-1-ynyl)phenyl)ethylsulfonamido)benzenesulfonamide;
2-(2-(4-(3-Hydroxy-3-methylbut-1-ynyl)phenyl)ethylsulfonamido)benzenesulfonamide;
3-(3,3-Dimethylbut-1-ynyl)-N-(2-sulfamoylphenyl)benzenesulfonamide;
2-(2-(4-Chloro-2-methoxyphenyl)ethylsulfonamido)benzenesulfonamide;
2-(2-(6-(3,3-Dimethylbut-1-ynyl)pyridin-3-yl)ethylsulfonamido)benzenesulfonamide;
2-(2-(6-(cyclohexylethynyl)pyridin-3-yl)ethylsulfonamido)benzenesulfonamide;
2-(2-(4-Bromophenyl)ethylsulfonamido)-5-methylbenzenesulfonamide;
(E)-2-(2-(4-Bromophenyl)vinylsulfonamido)-5-methylbenzenesulfonamide;
3-(2-Methylthiazol-4-yl)-N-(2-sulfamoylphenyl)benzenesulfonamide;
(E)-2-(2-(3-(Trifluoromethyl)phenyl)vinylsulfonamido)benzenesulfonamide;
(E)-2-(2-(2-Fluorophenyl)vinylsulfonamido)benzenesulfonamide;
5-Chloro-2-(2-(4-chloro-2-methoxyphenyl)ethylsulfonamido)benzenesulfonamide;
2,3-Dichloro-N-(4-chloro-2-sulfamoylphenyl)benzenesulfonamide;
2,3-Dichloro-N-(3,5-difluoro-2-sulfamoylphenyl)benzenesulfonamide;
2-(2-(3,4-Dichlorophenyl)ethylsulfonamido)-4,6-difluorobenzenesulfonamide;
2-(2-(4-Chloro-2-methoxyphenyl)ethylsulfonamido)-4,6-difluorobenzenesulfonamide;
5-Cyano-2-(2-(3,4-dichlorophenyl)ethylsulfonamido)benzenesulfonamide;
(E)-2-(2-(3,4-Dichlorophenyl)vinylsulfonamido)-4-methylbenzenesulfonamide;
2-(2-(4-Chloro-2-methoxyphenyl)ethylsulfonamido)-4-methylbenzenesulfonamide;
5-Chloro-2-(2-(3,4-dichlorophenyl)ethylsulfonamido)benzenesulfonamide;
4-(3-(5-Chloro-6-methoxypyridin-3-yl)phenylsulfonamido)pyridine-3-sulfonamide;
4-(2-(4-(Benzofuran-2-yl)phenyl)ethylsulfonamido)pyridine-3-sulfonamide;
2-(2-(4-Chloro-2-methoxyphenyl)ethylsulfonamido)-5-methylbenzenesulfonamide;
4-(2-(4-Chloro-2-methoxyphenyl)ethylsulfonamido)pyridine-3-sulfonamide;
(E)-2-(2-(4-Cyclopentenylphenyl)vinylsulfonamido)benzenesulfonamide;
(E)-2-(2-(4-(3,3-Dimethylbut-1-ynyl)phenyl)vinylsulfonamido)benzenesulfonamide;
(E)-2-(2-(4-(3-Hydroxy-3-methylbut-1-ynyl)phenyl)vinylsulfonamido)-benzenesulfonamide;
2-{2-[4-(3,3-Dimethyl-but-1-ynyl)-phenyl]-ethanesulfonylamino}-5-methyl-benzenesulfonamide;
2-{2-[4-(3,3-Dimethyl-but-1-ynyl)-phenyl]-ethanesulfonylamino}-5-hydroxymethyl-benzenesulfonamide;
2-[2-(4-Cyclopentylethynyl-phenyl)-ethanesulfonylamino]-5-hydroxymethyl-benzenesulfonamide;
2-[2-(4-Chloro-2-methoxy-phenyl)-ethanesulfonylamino]-5-hydroxymethyl-benzenesulfonamide;
3-{2-[4-(3,3-Dimethyl-but-1-ynyl)-phenyl]-ethanesulfonylamino}-thiophene-2-sulfonic acid amide;
3-[3-(5-Chloro-6-methoxy-pyridin-3-yl)-benzenesulfonylamino]-thiophene-2-sulfonic acid amide;
(E)-2-(2-(4-(1,1,2,2-tetrafluoroethoxy)phenyl)vinylsulfonamido)benzenesulfonamide;
(E)-2-(2-(2-(difluoromethoxy)phenyl)vinylsulfonamido)benzenesulfonamide;
(E)-2-(2-(4'-(trifluoromethyl)biphenyl-4-yl)vinylsulfonamido)benzenesulfonamide;
(E)-2-(2-(2-isopropoxyphenyl)vinylsulfonamido)benzenesulfonamide;
(E)-2-(2-(2-(methylthio)phenyl)vinylsulfonamido)benzenesulfonamide;
(E)-2-(2-(2-(trifluoromethoxy)phenyl)vinylsulfonamido)benzenesulfonamide;
(E)-2-(2-(2-ethoxyphenyl)vinylsulfonamido)benzenesulfonamide;
2-(2-(4-(1,1,2,2-tetrafluoroethoxy)phenyl)ethylsulfonamido)benzenesulfonamide;
2-(2-(4'-(trifluoromethyl)biphenyl-4-yl)ethylsulfonamido)benzenesulfonamide;
2-[2-(2-Hydroxy-phenyl)-ethenesulfonylamino]-benzenesulfonamide;
4-Chloro-2-(2-(4-(difluoromethoxy)phenyl)ethylsulfonamido)benzenesulfonamide;
4-Chloro-2-(2-(2-methoxyphenyl)ethylsulfonamido)benzenesulfonamide;

4-Chloro-2-(2-(4-chloro-2-methoxyphenyl)ethylsulfonamido)benzenesulfonamide;
2-(2-(3,4-Dichlorophenyl)ethylsulfonamido)-3,5-difluorobenzenesulfonamide;
2,3-Dichloro-N-(4-fluoro-5-methoxy-2-sulfamoylphenyl)benzenesulfonamide;
4-Chloro-2-(2-(3,4-dichlorophenyl)ethylsulfonamido)benzenesulfonamid;
5-Chloro-2-(2-(4-chlorophenyl)ethylsulfonamido)-4-fluorobenzenesulfonamide;
5-Chloro-2-(2-(3,4-dichlorophenyl)ethylsulfonamido)-4-fluorobenzenesulfonamide;
5-(2-(4-(Furan-2-yl)phenyl)ethylsulfonamido)-2,3-dihydro-1H-indene-4-sulfonamide;
6-(2-(4-(Furan-2-yl)phenyl)ethylsulfonamido)-2,3-dihydro-1H-indene-5-sulfonamid;
5-(2-(3,4-Dichlorophenyl)ethylsulfonamido)-2,3-dihydro-1H-indene-4-sulfonamide;
(E)-5-(2-(4-Chlorophenyl)vinylsulfonamido)-2,3-dihydro-1H-indene-4-sulfonamide;
(E)-6-(2-(4-Chlorophenyl)vinylsulfonamido)-2,3-dihydro-1H-indene-5-sulfonamide;
2-[[3-(3,4-Dichlorophenyl)phenyl]sulfonylamino]-N-methyl-benzenesulfonamide; and
2-(2-(6-((4-(Trifluoromethyl)phenyl)ethynyl)pyridin-3-yl)ethylsulfonamido)-benzenesulfonamide
and pharmaceutically acceptable salts of any one thereof.

The present invention further provides a process for the preparation of a compound of formula (I) or a pharmaceutically acceptable salt thereof as defined above which comprises, (a) reacting a compound of formula (II)

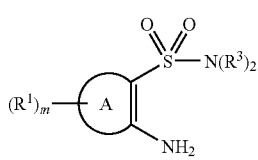

(II)

wherein $R^1$, $R^3$, A and m are as defined in formula (I), with a compound of formula (III)

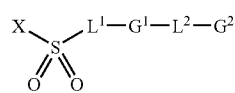

(III)

wherein $L^1$, $L^2$, $G^1$ and $G^2$ are as defined in formula (I) and X represents a leaving group such as a halogen; or (b) when $L^2$ represents a direct bond and $G^1$ and $G^2$ are both aromatic moieties, reacting a compound of formula (IV)

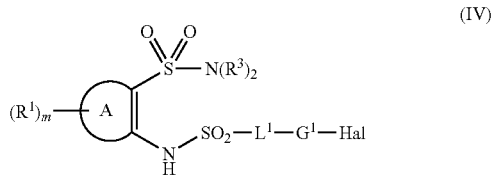

(IV)

wherein Hal represents a halogen atom and $R^1$, $R^3$, A, m and $L^1$ are as defined in formula (I), with a nucleophile $G^2$-M wherein M represents an organotin or organo boronic acid group;

and optionally after (a) or (b) carrying out one or more of the following:
 converting the compound obtained to a further compound of the invention
 forming a pharmaceutically acceptable salt of the compound.

In process (a), the reaction may conveniently be carried out in an organic solvent such as acetonitrile, dichloromethane, N,N-dimethylformamide, pyridine or N-methylpyrrolidinone at a temperature, for example, in the range from −20° C. to the boiling point of the solvent. The leaving group is a halogen such as fluorine, chlorine, bromine or iodine, preferably chlorine. If necessary or desired, a base may be added. In one embodiment, the solvent is pyridine and the aniline is reacted with a sulfonyl chloride at room temperature.

In process (b), the reaction may conveniently be carried out by reaction with an appropriate aryl boronic acid or an aryl boronic ester. The reaction may be carried out using a suitable palladium catalyst such as $Pd(PPh_3)_4$, $Pd(dppf)Cl_2$, or $Pd(OAc)_2$ or $Pd_2(dba)_3$ together with a suitable ligand such as $P(tert\text{-}butyl)_3$, 2-(dicyclohexylphosphino)biphenyl, or 2-(2',6'-dimethoxybiphenyl)-dicyclohexylphosphine, or a nickel catalyst such as nickel on charcoal or $Ni(dppe)Cl_2$ together with zinc and sodium triphenylphosphinetrimetasulfonate. A suitable base such as an alkyl amine, e.g. triethylamine, or potassium carbonate, sodium carbonate, cesium carbonate, sodium hydroxide or cesium fluoride may be used in the reaction, which can be performed in the temperature range of +20° C. to +160° C., using an oil bath or a microwave oven, in a suitable solvent or solvent mixture such as toluene, tetrahydrofuran, ethanol, dimethoxyethane/water, N,N-dimethylformamide or dioxane. The boronic acid or boronic ester may be formed in situ, by reaction of the corresponding aryl halide (e.g., the aryl bromide) with an alkyllithium reagent such as butyllithium to form an intermediate aryl lithium species, which then is reacted with a suitable boron compound, e.g., trimethyl borate, tributyl borate or triisopropyl borate.

Alternatively, the reaction may be carried out by reaction with an appropriate alkyne. The reaction may be carried out using a suitable palladium catalyst such as $Pd(PPh_3)_4$, $PdCl_2(PPh_3)_2$, $[PdCl_2(CH_3CN)_2]$ or $Pd(PPh_3)_2(OAc)_2$. The reaction may be preformed in the presence of a suitable ligand such as Xphos. The reaction may also be preformed in the presence of a suitable copper catalyst such as copper(I) iodide. A suitable base such as triethylamine, buthylamine, diisopropylamine, N,N-diisopropylethylamine or cesium carbonate may be used in the reaction, which can be performed in the temperature range of +20° C. to +160° C., using an oil bath or a microwave oven, in a suitable solvent or a mixture of solvents such as N,N-dimethylformamide, dimethyl sulfoxide, acetonitrile, toluene, tetrahydrofuran, dimethoxyethane/water or dioxane.

Specific processes for the preparation of compounds of Formula (I) are disclosed within the Examples section of the present specification. Such processes form an aspect of the present invention.

The necessary starting materials are either commercially available, are known in the literature or may be prepared using known techniques. Specific processes for the preparation of certain key starting materials are disclosed within the Examples section of the present specification and such processes form an aspect of the present invention.

Certain intermediates are novel. Such novel intermediates form another aspect of the invention.

Compounds of formula (I) can be converted into further compounds of formula (I) using standard procedures.

It will be appreciated by those skilled in the art that in the processes of the present invention certain functional groups such as hydroxyl or amino groups may need to be protected by protecting groups. Thus, the preparation of the compounds of formula (I) may involve, at an appropriate stage, the addition and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', $3^{rd}$ edition, T. W. Greene and P. G. M. Wuts, Wiley-Interscience (1999).

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) and their pharmaceutically acceptable salts have activity as pharmaceuticals, in particular as selective inhibitors of the microsomal prostaglandin E synthase-1 enzyme, and may therefore be beneficial in the treatment or prophylaxis of pain and of inflammatory diseases and conditions. Furthermore, by selectively inhibiting the pro-inflammatory PGE2, it is believed the compounds of the invention would have a reduced potential for side effects associated with the inhibition of other prostaglandins by conventional non-steroidal anti-inflammatory drugs, such as gastrointestinal and renal toxicity.

More particularly, the compounds of formula (I) and their pharmaceutically acceptable salts may be used in the treatment of osteoarthritis, rheumatoid arthritis, acute or chronic pain, neuropathic pain, apneal/SID, wound healing, cancer, benign or malignant neoplasias, stroke, atherosclerosis and Alzheimer's disease.

Even more particularly, the compounds of formula (I) and their pharmaceutically acceptable salts may be used in the treatment of osteoarthritis, rheumatoid arthritis, benign or malignant neoplasias or acute or chronic pain.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In a further aspect, the present invention provides the use of a compound of formula (I) or a pharmaceutically acceptable salt thereof as hereinbefore defined in the manufacture of a medicament for the treatment of human diseases or conditions in which modulation of microsomal prostaglandin E synthase-1 activity is beneficial.

In a further aspect, the present invention provides the use of a compound of formula (I) or a pharmaceutically acceptable salt thereof as hereinbefore defined in the manufacture of a medicament for use in the treatment of an inflammatory disease or condition.

In a further aspect, the present invention provides the use of a compound of formula (I) or a pharmaceutically acceptable salt thereof as hereinbefore defined in the manufacture of a medicament for use in treating osteoarthritis, rheumatoid arthritis, acute or chronic pain, neuropathic pain, apneal/SID, wound healing, cancer, benign or malignant neoplasias, stroke, atherosclerosis or Alzheimer's disease.

In a further aspect, the present invention provides the use of a compound of formula (I) or a pharmaceutically acceptable salt thereof as hereinbefore defined in the manufacture of a medicament for use in treating osteoarthritis, rheumatoid arthritis, benign or malignant neoplasias or acute or chronic pain.

In another aspect, the invention provides a compound of formula (I) or a pharmaceutically acceptable salt thereof as hereinbefore defined for use as a medicament.

In another aspect, the invention provides a compound of formula (I) or a pharmaceutically acceptable salt thereof as hereinbefore defined for the treatment of diseases or conditions in which modulation of microsomal prostaglandin E synthase-1 activity is beneficial.

In another aspect, the invention provides a compound of formula (I) or a pharmaceutically acceptable salt thereof as hereinbefore defined for the treatment of an inflammatory disease or condition.

In another aspect, the invention provides a compound of formula (I) or a pharmaceutically acceptable salt thereof as hereinbefore defined for the treatment of osteoarthritis, rheumatoid arthritis, acute or chronic pain, neuropathic pain, apneal/SID, wound healing, cancer, benign or malignant neoplasias, stroke, atherosclerosis or Alzheimer's disease. In another aspect, the invention provides a compound of formula (I) or a pharmaceutically acceptable salt thereof as hereinbefore defined for the treatment of osteoarthritis, rheumatoid arthritis, benign or malignant neoplasias, apnea, sudden infant death (SID), atherosclerosis, cancer, aneurysm, hyperthermia, myositis, Alzheimer's disease or arthritis. In another aspect, the invention provides a compound of formula (I) or a pharmaceutically acceptable salt thereof as hereinbefore defined for the treatment of osteoarthritis, rheumatoid arthritis, benign or malignant neoplasias or acute or chronic pain.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention also provides a method of treating, or reducing the risk of, a disease or condition in which modulation of microsomal prostaglandin E synthase-1 activity is beneficial which comprises administering to a patient in need thereof a therapeutically effective amount of a compound of formula (I) or a pharmaceutically acceptable salt thereof as hereinbefore defined.

The invention still further provides a method of treating, or reducing the risk of, an inflammatory disease or condition which comprises administering to a patient in need thereof a therapeutically effective amount of a compound of formula (I) or a pharmaceutically acceptable salt thereof as hereinbefore defined.

The invention still further provides a method of treating, or reducing the risk of, osteoarthritis, rheumatoid arthritis, acute or chronic pain, neuropathic pain, apneal/SID, wound healing, cancer, stroke, atherosclerosis or Alzheimer's disease which comprises administering to a patient in need thereof a therapeutically effective amount of a compound of formula (I) or a pharmaceutically acceptable salt thereof as hereinbefore defined. The invention still further provides a method of treating, or reducing the risk of, osteoarthritis, rheumatoid arthritis or acute or chronic pain which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin) in the form, e.g., of creams, solutions or suspensions; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

Thus, the invention further relates to combination therapies wherein a compound of formula (I) or a pharmaceutically acceptable salt thereof, or a pharmaceutical composition or formulation comprising a compound of formula (I) is administered concurrently, simultaneously, sequentially or separately with another pharmaceutically active compound or compounds selected from the following:

(i) neuropathic pain therapies including for example gabapentin, lidoderm, pregablin and equivalents and pharmaceutically active isomer(s) and metabolite(s) thereof.

(ii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof.

(iii) migraine therapies including for example almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof.

Such combination products employ the compounds of this invention within the dosage range described herein and the other pharmaceutically active compound or compounds within approved dosage ranges and/or the dosage described in their respective publication reference(s).

The present invention will now be further explained by reference to the following illustrative examples.

General Methods

All solvents used were analytical grade and commercially available anhydrous solvents were routinely used for reactions. Reactions were typically run under an inert atmosphere of nitrogen or argon.

$^1$H, $^{19}$F and $^{13}$C NMR spectra were recorded on a Varian Unity+ 400 NMR Spectrometer equipped with a 5 mm BBO probehead with Z-gradients, or a Varian Gemini 300 NMR spectrometer equipped with a 5 mm BBI probehead, or a Bruker Avance 400 NMR spectrometer equipped with a 60 µl dual inverse flow probehead with Z-gradients, or a Varian Mercury Plus 400 NMR Spectrometer equipped with a Varian 400 ATB PFG probe, or a Bruker DPX400 NMR spectrometer equipped with a 4-nucleus probehead equipped with Z-gradients, or a Bruker Avance 600 NMR spectrometer equipped with a 5 mm BBI probehead with Z-gradients, or a Bruker av400 NMR spectrometer operating at 400 MHz $^1$H and 100 MHz for $^{13}$C equipped with a 3 mm flow injection SEI $^1$H/D-$^{13}$C probehead with Z-gradients, using a BEST 215 liquid handler for sample injection, or a Bruker DRX600 NMR spectrometer, operating at 600 MHz for $^1$H, 150 MHz for $^{13}$C, and 60 MHz for $^{15}$N equipped with a 5 mm TXI probehead with Z-gradients, or equipped with a 5 mm BBO probehead with Z-gradients, or equipped with a 2.5 mm BBI probehead with Z-gradients, or a Bruker 500 MHz Avance III NMR spectrometer, operating at 500 MHz for $^1$H, 125 MHz for $^{13}$C, and 50 MHz for $^{15}$N equipped with a 5 mm TXI probehead with Z-gradients or equipped with a 5 mm TCI cryogenically cooled probehead with Z-gradients. Unless specifically noted in the examples, spectra were recorded at 400 MHz for proton, 376 MHz for fluorine-19 and 100 MHz for carbon-13.

The following reference signals were used: the middle line of DMSO-d$_6$ δ 2.50 (1H), δ 39.51 (13C); the middle line of CD$_3$OD δ 3.31 (1H) or δ 49.15 (13C); CDCl$_3$ δ 7.26 (1H) and the middle line of CDCl$_3$ δ 77.16 (13C) (unless otherwise indicated). NMR spectra are either reported from high to low field or from low to high field.

Mass spectra were recorded on a Waters LCMS consisting of an Alliance 2795 (LC), Waters PDA 2996 and a ZQ single quadrupole mass spectrometer. The mass spectrometer was equipped with an electrospray ion source (ESI) operated in a positive or negative ion mode. The capillary voltage was 3 kV and cone voltage was 30 V. The mass spectrometer was scanned between m/z 100-700 with a scan time of 0.3 s. Separations were performed on either Waters X-Terra MS C8 (3.5 μm, 50 or 100 mm×2.1 mm i.d.) or an ACE 3 AQ (100 mm×2.1 mm i.d.) obtained from ScantecLab. Flow rates were regulated to 1.0 or 0.3 mL/min, respectively. The column temperature was set to 40° C. A linear gradient was applied using a neutral or acidic mobile phase system, starting at 100% A (A: 95:5 10 mM NH$_4$OAc:MeCN, or 95:5 8 mM HCOOH:MeCN) ending at 100% B (MeCN).

Alternatively, mass spectra were recorded on a Waters LCMS consisting of an Alliance 2690 Separations Module, Waters 2487 Dual 1 Absorbance Detector (220 and 254 nm) and a Waters ZQ single quadrupole mass spectrometer. The mass spectrometer was equipped with an electrospray ion source (ESI) operated in a positive or negative ion mode. The capillary voltage was 3 kV and cone voltage was 30 V. The mass spectrometer was scanned between m/z 97-800 with a scan time of 0.3 or 0.8 s. Separations were performed on a Chromolith Performance RP-18e (100×4.6 mm). A linear gradient was applied starting at 95% A (A: 0.1% HCOOH (aq.)) ending at 100% B (MeCN) in 5 minutes. Flow rate: 2.0 mL/min.

Alternatively, LC-MS analyses were performed on a LC-MS system consisting of a Waters 5 Alliance 2795 HPLC, a Waters PDA 2996 diode array detector, a Sedex 85 ELS detector and a ZQ single quadrupole mass spectrometer. The mass spectrometer was equipped with an electrospray ion source (ES) operated in positive and negative ion mode. The capillary voltage was set to 3.3 kV and the cone voltage to 28 V, respectively. The mass spectrometer scanned between m/z 100-800 with a scan time of 0.3 s. The diode array 10 detector scanned from 200-400 nm. The temperature of the ELS detector was adjusted to 40° C. and the pressure was set to 1.9 bar. Separation was performed on an Gemini C18, 3.0 mm×50 mm, 3 μm, (Phenomenex) run at a flow rate of 1 mL/min. A linear gradient was applied starting at 100% A (A: 10 mM NH$_4$OAc in 5% CH$_3$CN) ending at 100% B (B: CH3CN) in 4.0 min followed by 100% B until 5.5 min. The column oven temperature was 15 set to 40° C.

Alternatively, LC-MS analyses were performed on a LC-MS consisting of a Waters sample manager 2777C, a Waters 1525μ binary pump, a Waters 1500 column oven, a Waters ZQ single quadrupole mass spectrometer, a Waters PDA2996 diode array detector and a Sedex 85 ELS detector. The mass spectrometer was configured with an atmospheric pressure chemical ionisation (APCI) ion source which was further equipped with atmospheric pressure photo ionisation (APPI) device. The mass spectrometer scanned in the positive mode, switching between APCI and APPI mode. The mass range was set to m/z 100-800 using a scan time of 0.1 s. The APPI repeller and the APCI corona were set to 0.58 kV and 0.70 μA, respectively. In addition, the desolvation temperature (350° C.), desolvation gas 25 (450 L/Hr) and cone gas (0 L/Hr) were constant for both APCI and APPI mode. Separation was performed using a Gemini column C18, 3.0 mm×50 mm, 3 μm, (Phenomenex) and run at a flow rate of 0.8 mL/min. A linear gradient was used starting at 100% A (A: 10 mM NH$_4$OAc in 5% MeOH) and ending at 100% B (MeOH) in 4.0 min followed by 100% B until 5.5 min. The column oven temperature was set to 55° C.

Microwave irradiation was performed in a Creator™, Initiator™ or Smith Synthesizer™ Single-mode microwave cavity producing continuous irradiation at 2450 MHz.

HPLC analyses were performed on an Agilent HP1000 system consisting of G1379A Micro Vacuum Degasser, G1312A Binary Pump, G1367A Well plate auto-sampler, G1316A Thermostatted Column Compartment and G1315B Diode Array Detector. Column: X-Terra MS, Waters, 3.0× 100 mm, 3.5 μm. The column temperature was set to 40° C. and the flow rate to 1.0 ml/min. The Diode Array Detector was scanned from 210-300 nm, step and peak width were set to 2 nm and 0.05 min, respectively. A linear gradient was applied, starting at 100% A (A: 95:5 10 mM NH$_4$OAc:MeCN) and ending at 100% B (B: MeCN), in 4 min.

Alternatively, HPLC analyses were performed on a Gynkotek P580 HPG consisting of gradient pump with a Gynkotek UVD 170S UV-vis.-detector equipped with a Chromolith Performance RP column (C18, 100 mm×4.6 mm). The column temperature was set to 25° C. A linear gradient was applied using MeCN/0.1 trifluoroacetic acid in MilliQ water, run from 10% to 100% MeCN in 5 minutes. Flow rate: 3 ml/min.

Thin layer chromatography (TLC) was performed on Merck TLC-plates (Silica gel 60 F$_{254}$) and UV visualized the spots. Column chromatography was performed on a Combi Flash® Companion™ using RediSep™ normal-phase columns or using Merck Silica gel 60 (0.040-0.063 mm). Typical solvents used for column chromatography were mixtures of chloroform/methanol, dichloromethane/methanol, heptane/ethyl acetate, chloroform/methanol/ammonia (aq.) and dichlorormethane/methanol/NH$_3$ (aq.). SCX ion exchange columns were performed on Isolute® columns. Chromatography through ion exchange columns were typically performed in solvents such a methanol.

Preparative chromatography was run on a Waters autopurification HPLC with a diode array detector. Column: XTerra MS C8, 19×300 mm, 10 μm. Narrow gradients with MeCN/(95:5 0.1M NH$_4$OAc:MeCN) were used at a flow rate of 20 ml/min. Alternatively, purification was achieved on a semi preparative Shimadzu LC-8A HPLC with a Shimadzu SPD-10A UV-vis.-detector equipped with a Waters Symmetry® column (C18, 5 μm, 100 mm×19 mm). Narrow gradients with MeCN/0.1% trifluoroacetic acid in MilliQ Water were used at a flow rate of 10 ml/min.

Alternatively, preparative chromatography was run on a Waters FractionLynx system with a Autosampler combined Automated Fraction Collector (Waters 2767), Gradient Pump (Waters 2525), Column Switch (Waters CFO) and PDA (Waters 2996). Column; XTerra® Prep MS C8 10 µm OBD™ 19×300 mm, with guard column; XTerra® Prep MS C8 10 µm 19×10 mm Cartridge. A gradient from 100% A (95% 0.1M NH₄OAc in MilliQ water and 5% MeCN) to 100% B (100% MeCN) was applied for LC-separation at flow rate 20 mL/min. The PDA was scanned from 210-350 nm. UV triggering determined the fraction collection.

Alternatively, preparative chromatography was run on a Waters FractionLynx system with a Autosampler combined Automated Fraction Collector (Waters 2767), Gradient Pump (Waters 2425), Make Up Pump (Waters 515), Waters Passive Splitter, Column Switch (Waters SFO), PDA (Waters 2996) and Waters ZQ mass spectrometer. Column; XBridge™ Prep C8 5 µm OBD™ 19×250 mm, with guard column; XTerra® Prep MS C8 10 µm 19×10 mm Cartridge. A gradient from within 100% A (95% 0.1 M NH₄OAc in MilliQ water and 5% MeCN) to 100% B (100% MeCN) was applied for LC-separation at flow rate 20 mL/min. The PDA was scanned from 210-350 nm. The ZQ mass spectrometer was run with ESI in positive or negative mode. The Capillary Voltage was 3 kV and the Cone Voltage was 30V. Mixed triggering, UV and MS signal, determined the fraction collection.

H-cube (http://thalesnano.com/H-Cube) is a system for hydrogenation under continuous flow conditions (typical settings used were full hydrogen, flow 1 ml/min, ethyl acetate/methanol 1:1 as eluent, 50° C.).

Naming was done with CambridgeSoft MedChem ELN v2.1, ChemDraw Ultra 7.0 or ACDName Abbreviations:
DCM dichloromethane
DMAP 4-(dimethylamino)pyridine
DMF N,N-dimethylformamide
DMSO dimethyl sulfoxide
TFA trifluoroacetic acid
THF tetrahydrofuran
RT room temperature
Rf retention time Example 1

2-[2-(4-Benzofuran-2-ylphenyl)ethylsulfonylamino]benzenesulfonamide

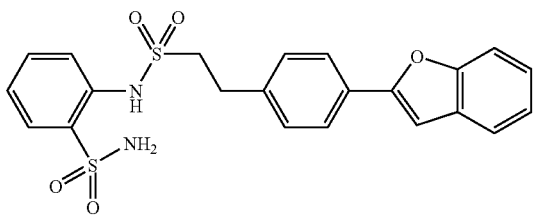 [SMILES: NS(=O)(=O)c1ccccc1NS(=O)(=O)CCc1ccc(-c2cc3ccccc3o2)cc1]

2-[[(E)-2-(4-Benzofuran-2-ylphenyl)ethenyl]sulfonylamino]benzenesulfonamide (Example 3, 43 mg, 95 µmol) was dissolved in ethyl acetate (5 ml) and subjected to the H-cube (1 ml/min, full hydrogen. 10% Pd/C). The material obtained was purified by preparative HPLC (XTerra MS C8 column, acetonitrile/ammonium acetate buffer) to give the title compound (12 mg, 28%) as a white solid. The compound of Example 2 was also obtained.

¹H NMR (400 MHz, CD₃OD) δ ppm 7.94 (dd, 1H), 7.75-7.82 (m, 3H), 7.53-7.60 (m, 2H), 7.49 (d, 1H), 7.29 (d, 2H), 7.18-7.29 (m, 3H), 7.13 (s, 1H), 3.50-3.58 (m, 2H), 3.09-3.17 (m, 2H);

ESMS: m/z [M+1] 457.0, [M−1] 455.0.

Example 2

2-[2-[4-(2,3-Dihydrobenzofuran-2-yl)phenyl]ethylsulfonylamino]benzenesulfonamide

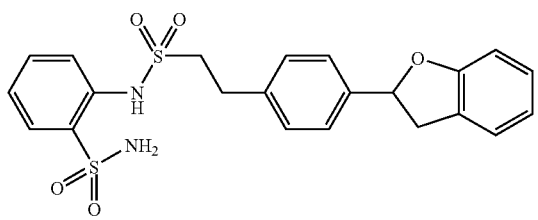 [SMILES: NS(=O)(=O)c1ccccc1NS(=O)(=O)CCc1ccc(C2Cc3ccccc3O2)cc1]

The title compound was obtained from the synthesis of Example 1 as a white solid (12 mg, 28%).

¹H NMR (400 MHz, CD₃OD) δ ppm 7.93 (dd, 1H), 7.76 (dd, 1H), 7.55 (td, 1H), 7.28 (d, 2H), 7.24 (t, 1H), 7.14-7.20 (m, 3H), 7.11 (t, 1H), 6.84 (t, 1H), 6.77 (d, 1H), 5.68 (dd, 1H), 3.60 (dd, 1H), 3.46-3.53 (m, 2H), 3.03-3.12 (m, 3H);

ESMS: m/z [M+1] 458.9, [M−1] 456.9.

Example 3

2-[[(E)-2-(4-Benzofuran-2-ylphenyl)ethenyl]sulfonylamino]benzenesulfonamide

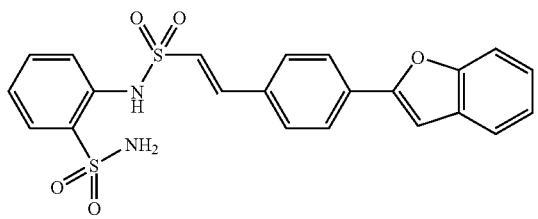 [SMILES: NS(=O)(=O)c1ccccc1NS(=O)(=O)/C=C/c1ccc(-c2cc3ccccc3o2)cc1]

2-Aminobenzenesulfonamide (38 mg, 0.22 mmol) was dissolved in pyridine (2 ml), (E)-2-(4-benzofuran-2-ylphenyl)ethenesulfonyl chloride (70 mg, 0.22 mmol) was added and the mixture stirred for 2 h. The solvent was removed in vacuo and the residue was purified by preparative HPLC (XTerra MS C8 column, acetonitrile/ammonium acetate buffer) to give the title compound (46 mg, 46%).

¹H NMR (400 MHz, CD₃OD) δ ppm 7.87-7.93 (m, 3H), 7.75 (d, 1H), 7.63 (d, 2H), 7.61 (d, 1H), 7.50-7.58 (m, 3H), 7.31 (td, 1H), 7.29 (s, 1H), 7.21-7.26 (m, 2H), 7.18 (d, 1H);

ESMS: m/z [M+1] 454.7, [M−1] 452.8.

a) (E)-2-(4-Benzofuran-2-ylphenyl)ethenesulfonyl chloride

Sulfurylchloride (0.21 mL, 2.6 mmol) was added to a solution of triphenylphosphine (0.68 g, 2.5 mmol) in CH₂Cl₂ (10 mL) at 0° C. The ice-bath was then removed and (E)-2-(4-benzofuran-2-ylphenyl)ethenesulfonic acid (0.38 g, 1.18 mmol) was added and the resulting mixture was stirred for 6 h at RT. A catalytic amount of tetrabutyl ammonium iodide was added and the reaction was stirred for an additional 12 h. The mixture was then filtered and the filtrate was concentrated in vacuo and the product was purified by column chromatography eluting with 20% EtOAc/hexanes to give the product as a yellow solid (0.27 g, 73%).

¹H NMR (400 MHz, CDCl₃) δ ppm 7.95-8.01 (m, 2H), 7.78 (d, 1H), 7.63-7.70 (m, 3H), 7.56-7.59 (m, 1H), 7.37 (ddd, 1H), 7.30 (d, 1H), 7.27-7.30 (m, 1H), 7.21 (d, 1H).

b) (E)-2-(4-Benzofuran-2-ylphenyl)ethenesulfonic acid

1-Bromo-4-[(E)-2-ethoxysulfonylethenyl]benzene (1.0 g, 3.4 mmol) and benzofuran-2-boronic acid (0.61 g, 3.7 mmol) were dissolved in DMF (20 mL). Sodium carbonate (2M, 10 mL) and tetrakis(triphenylphosphine)palladium(0) (200 mg, 0.17 mmol) were added and the resulting mixture was stirred under argon at 90° C. for 12 h. Water was added to the mixture and the resulting precipitate was collected, washed with water and dried to give the product as a sodium salt which was used in the next step without further purification (0.38 g, 35%).

¹H NMR (400 MHz, DMSO-d₆) δ ppm 7.89 (d, 2H), 7.59-7.69 (m, 4H), 7.48 (s, 1H), 7.33 (td, 1H), 7.27 (td, 1H), 6.95 (s, 2H);

ESMS: m/z [M−1] 298.9.

c) 1-Bromo-4-[(E)-2-ethoxysulfonylethenyl]benzene n-Butyllithium (59.0 mL, 1.6M solution in hexanes) was added dropwise during 25 min to a solution of ethylmethanesulfonate (9.1 mL, 86 mmol) in THF (200 mL) at −78° C. The reaction mixture was stirred for 15 min then diethyl chlorophosphate (7.2 ml, 50 mmol) was added dropwise. The solution was stirred at −78° C. for 30 min, allowed to warm to 0° C. and then cooled to −78° C. again. 4-Bromobenzaldehyde (9.2 g, 50 mmol) in THF (50 mL) was then added dropwise during 15 minutes and the resulting mixture was then allowed to slowly reach RT and stirred overnight. Water (20 mL) was added to the mixture and the reaction was concentrated in vacuo. The residue was extracted with diethyl ether and the combined organic extracts were washed with aqueous saturated sodium chloride, dried over magnesium sulfate, filtered and the solvent was evaporated in vacuo. Purification by column chromatography, using 15% ethyl acetate/hexanes as the eluent, afforded the title compound (9.3 g, 64%).

¹H NMR (600 MHz, CDCl₃) δ ppm 7.58 (d, 2H), 7.55 (d, 1H), 7.39 (d, 2H), 6.75 (d, 1H), 4.25 (q, 2H), 1.42 (t, 3H).

Example 4

2-[[(E)-2-(4-Benzofuran-2-ylphenyl)ethenyl]sulfonylamino]-5-fluoro-benzenesulfonamide

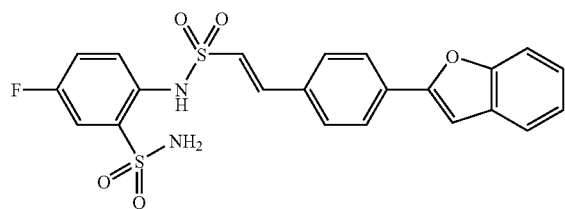 [SMILES: NS(=O)(=O)c1cc(F)ccc1NS(=O)(=O)/C=C/c1ccc(-c2cc3ccccc3o2)cc1]

The compound was synthesized using an analogous procedure to that described for Example 3 to give 23 mg, 44%.

¹H NMR (400 MHz, CD₃OD) δ ppm 7.91 (d, 2H), 7.76 (dd, 1H), 7.58-7.66 (m, 4H), 7.52 (d, 1H), 7.48 (d, 1H), 7.27-7.36 (m, 3H), 7.24 (t, 1H), 7.16 (d, 1H);

ESMS: m/z [M−1] 470.6.

Example 5

2-[[(E)-2-(4-Benzofuran-2-ylphenyl)ethenyl]sulfonylamino]-4-fluoro-benzenesulfonamide

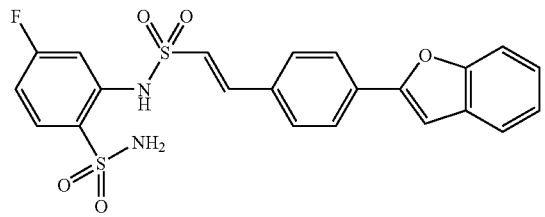 [SMILES: NS(=O)(=O)c1ccc(F)cc1NS(=O)(=O)/C=C/c1ccc(-c2cc3ccccc3o2)cc1]

The compound was synthesized using an analogous procedure to that described for Example 3 to give 31 mg, 16%.

¹H NMR (400 MHz, CD₃OD) δ ppm 7.88-7.96 (m, 3H), 7.67 (d, 2H), 7.62 (d, 1H), 7.61 (d, 1H), 7.53 (d, 1H), 7.48 (dd, 1H), 7.29-7.34 (m, 2H), 7.21-7.27 (m, 1H), 7.21 (d, 1H), 6.88-6.99 (m, 1H);

ESMS: m/z [M−1] 471.1.

Example 6

2-[[(E)-2-(4-Benzofuran-2-ylphenyl)ethenyl]sulfonylamino]-6-fluoro-benzenesulfonamide

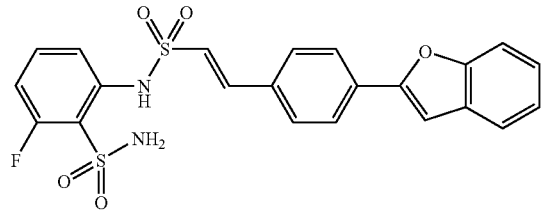

The compound was synthesized using an analogous procedure to that described for Example 3 to give 39 mg, 19%.

¹H NMR (400 MHz, CD₃OD) δ ppm 7.92 (d, 2H), 7.67 (d, 2H), 7.62 (d, 1H), 7.60 (d, 1H), 7.49-7.56 (m, 3H), 7.32 (td, 1H), 7.29 (s, 1H), 7.24 (td, 1H), 7.15 (d, 1H), 6.94-7.04 (m, 1H);

ESMS: m/z [M+1] 473.0, [M−1] 471.0.

Example 7

2-[1-(4-Chlorophenyl)propan-2-ylsulfonylamino]benzenesulfonamide

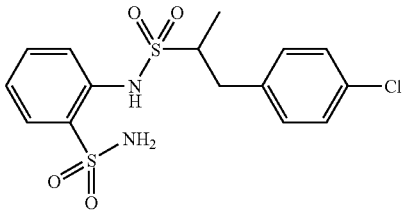

2-[[(E)-1-(4-Chlorophenyl)prop-1-en-2-yl]sulfonylamino]benzenesulfonamide (100 mg, 0.26 mmol) was dissolved in ethyl acetate (3 ml) and subjected to the H-cube (1 ml/min, full hydrogen. 10% Pd/C, 3 runs). The material obtained was purified by preparative HPLC (XTerra MS C8 column, acetonitrile/ammonium acetate buffer) to give the title compound (38 mg, 38%). The compound of Example 8 was also obtained.

$^1$H NMR (400 MHz, CD$_3$OD) δ ppm 7.94 (dd, 1H), 7.83 (dd, 1H), 7.56 (ddd, 1H), 7.19-7.30 (m, 3H), 7.14 (d, 2H), 3.50-3.63 (m, 1H), 3.38 (dd, 1H), 2.72 (dd, 1H), 1.24 (d, 3H); ESMS: m/z [M−1] 385.1, 387.0.

Example 8

2-(1-Phenylpropan-2-ylsulfonylamino)benzenesulfonamide

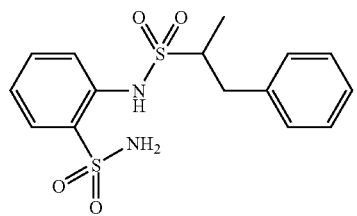 [SMILES: CC(Cc1ccccc1)S(=O)(=O)Nc1ccccc1S(N)(=O)=O]

The title compound (12 mg, 12%) was obtained from the synthesis of Example 7.

$^1$H NMR (400 MHz, CD$_3$OD) δ ppm 7.94 (dd, 1H), 7.84 (dd, 1H), 7.55 (ddd, 1H), 7.16-7.30 (m, 4H), 7.13 (d, 2H), 3.49-3.61 (m, 1H), 3.42 (dd, 1H), 2.68 (dd, 1H), 1.23 (d, 3H); ESMS: m/z [M−1] 353.

Example 9

2-[[(E)-1-(4-Chlorophenyl)prop-1-en-2-yl]sulfonylamino]benzenesulfonamide

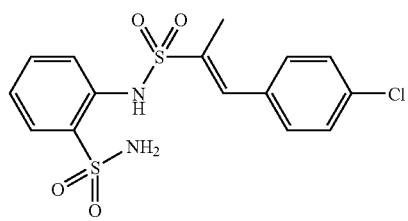 [SMILES: C/C(=C\c1ccc(Cl)cc1)S(=O)(=O)Nc1ccccc1S(N)(=O)=O]

2-Aminobenzenesulfonamide (61 mg, 0.35 mmol) was dissolved in pyridine (2 ml) and (E)-2-(4-benzofuran-2-ylphenyl)ethenesulfonyl chloride (70 mg, 0.22 mmol) was added and the reaction stirred for 2 h. The solvent was removed in vacuo and the residue was purified by preparative HPLC (XTerra MS C8 column, acetonitrile/ammonium acetate buffer) to give the title compound (46 mg, 46%).

$^1$H NMR (400 MHz, DMSO-d$_6$) δ ppm 9.14 (s, 1H), 7.88 (s, 2H), 7.85 (d, 1H), 7.54-7.63 (m, 3H), 7.49 (s, 4H), 7.21-7.31 (m, 1H), 2.13 (d, 3H);
ESMS: m/z [M+1] 386.9, 388.9, [M−1] 385.0, 387.0.

a) (E)-1-(4-Chlorophenyl)prop-1-ene-2-sulfonyl chloride

Tetrabutylammonium iodide (7.0 g, 19.0 mmol) was added to a solution of 1-chloro-4-[(E)-2-ethoxysulfonylprop-1-enyl]benzene (4.5 g, 17.3 mmol) in acetone (40 mL) at RT. The mixture was heated to reflux and stirred overnight, then cooled to RT and concentrated in vacuo. The residue was taken up in DCM then washed with water, dried over magnesium sulfate, filtered and concentrated in vacuo to give the title compound as the tetrabutylammonium salt which was used in the next step without further purification. Sulfuryl chloride (3.1 mL, 38.0 mmol) was added to a solution of triphenylphosphine (9.73 g, 37.2 mmol) in DCM (100 mL) at 0° C. The ice-bath was then removed and the reaction was stirred for 15 min. The crude (E)-1-(4-chlorophenyl)prop-1-ene-2-sulfonic acid salt (17.3 mmol) dissolved in DCM (40 mL) was then added during 15 min and the resulting mixture was stirred for 2 h at RT. The reaction was concentrated in vacuo and the product was purified by column chromatography using 10% EtOAc/hexanes as the eluent to give the product (3.3 g, 77%) as a yellow solid.

$^1$H NMR (400 MHz, CDCl$_3$) δ ppm 7.71 (br. s., 1H), 7.45-7.49 (m, 2H), 7.38-7.43 (m, 2H), 2.48 (d, 3H).

b) 1-Chloro-4-[(E)-2-ethoxysulfonylprop-1-enyl]benzene n-Butyllithium (35.0 mL, 1.6M solution in hexanes) was added dropwise during 25 min to a solution of ethyl ethanesulfonate (6.9 g, 50 mmol) (Synth. Comm. 1985, 15, 1057) in THF (100 mL) at −78° C. The reaction mixture was stirred for 15 min then diethyl chlorophosphate (4.35 ml, 30 mmol) was added dropwise. The solution was stirred at −78° C. for 30 min, allowed to warm to 0° C. and then cooled to −78° C. again. 4-Chlorobenzaldehyde (4.2 g, 30 mmol) in THF (30 mL) was then added dropwise during 15 minutes and the resulting mixture was stirred for 1 h at −78° C. and then allowed to slowly reach RT. Water (10 mL) was added to the mixture and the mixture was concentrated in vacuo. The residue was extracted with diethyl ether and the combined organic extracts were washed with aqueous saturated sodium chloride, dried over magnesium sulfate, filtered and the solvent was evaporated in vacuo. Purification by column chromatography, using a gradient of 10% ethyl acetate/hexanes to 15% ethyl acetate/hexanes as eluent, afforded the title compound (4.5 g, 58%).

$^1$H NMR (400 MHz, CDCl$_3$) δ ppm 7.56 (br. s., 1H), 7.40-7.45 (m, 2H), 7.32-7.38 (m, 2H), 4.21 (q, 2H), 2.27 (d, 3H), 1.41 (t, 3H).

Example 10

2-[1-(4-Chlorophenyl)propan-2-ylsulfonylamino]-4-fluoro-benzenesulfonamide

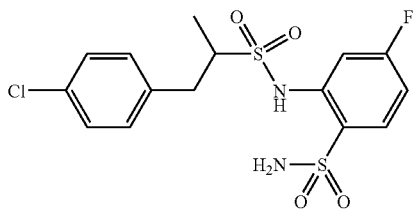 [SMILES: CC(Cc1ccc(Cl)cc1)S(=O)(=O)Nc1cc(F)ccc1S(N)(=O)=O]

2-[[(E)-1-(4-Chlorophenyl)prop-1-en-2-yl]sulfonylamino]-4-fluoro-benzenesulfonamide (60 mg, 0.15 mmol) was dissolved in ethyl acetate (3 mL) and mixture was subjected to reduction using the H-cube instrument. The reaction mixture was eluted through the Pd/C (10%) cartridge using full hydrogen (1 atm) at 1 ml/min. The mixture was subjected to the H-cube once again using the same conditions. The crude product was purified by preparative HPLC (XTerra MS C8 column, acetonitrile/ammonium acetate buffer) to give the title compound (25 mg, 38%).

$^1$H NMR (400 MHz, CD$_3$OD) δ ppm 7.87 (dd, 1H), 7.52 (dd, 1H), 7.26 (d, 2H), 7.17 (dd, 2H), 6.74 (ddd, 1H), 3.37-3.48 (m, 2H), 2.70 (dd, 1H), 1.22 (d, 3H);

ESMS: m/z [M−1] 470.0, 472.1.

Example 11

2-[[(E)-1-(4-chlorophenyl)prop-1-en-2-yl]sulfonylamino]-4-fluoro-benzenesulfonamide

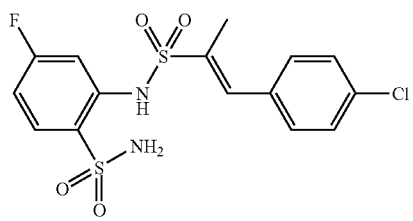 [SMILES: C/C(=C\c1ccc(Cl)cc1)S(=O)(=O)Nc1cc(F)ccc1S(N)(=O)=O]

The compound was synthesized using an analogous procedure to that described for Example 9 to give 78 mg, 55%.

$^1$H NMR (400 MHz, CD$_3$OD) δ ppm 7.95 (dd, 1H), 7.63 (s, 1H), 7.35-7.49 (m, 5H), 6.97 (t, 1H), 2.19 (d, 3H);

ESMS: m/z [M−1] 402.9, 404.8.

Example 12

2-[[(E)-1-(4-Chlorophenyl)prop-1-en-2-yl]sulfonylamino]-5-fluoro-benzenesulfonamide

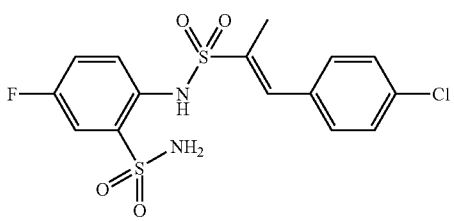 [SMILES: C/C(=C\c1ccc(Cl)cc1)S(=O)(=O)Nc1ccc(F)cc1S(N)(=O)=O]

The compound was synthesized using an analogous procedure to that described for Example 9 to give 35 mg, 71%.

$^1$H NMR (400 MHz, CD$_3$OD) δ ppm 7.74 (dd, 1H), 7.65 (dd, 1H), 7.54 (br. s., 1H), 7.39-7.44 (m, 2H), 7.35-7.38 (m, 2H), 7.32 (ddd, 1H), 2.19 (d, 3H);

ESMS: m/z [M−1] 402.9, 404.8.

Example 13

2-[[(E)-1-(4-Chlorophenyl)prop-1-en-2-yl]sulfonylamino]-6-fluoro-benzenesulfonamide

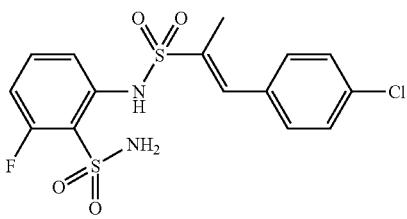 [SMILES: C/C(=C\c1ccc(Cl)cc1)S(=O)(=O)Nc1cccc(F)c1S(N)(=O)=O]

The compound was synthesized using an analogous procedure to that described for Example 9 to give 33 mg, 69%.

1H NMR (400 MHz, CD$_3$OD) δ ppm 7.56 (br s, 1H), 7.47-7.54 (m, 2H), 7.38-7.44 (m, 2H), 7.31-7.37 (m, 2H), 6.95-7.04 (m, 1H), 2.18 (d, 3H);

ESMS: m/z [M+1] 404.9, 406.9, [M−1] 402.9, 404.8.

Example 14

2-[[(E)-1-(4-Chlorophenyl)prop-1-en-2-yl]sulfonylamino]-3-fluoro-benzenesulfonamide

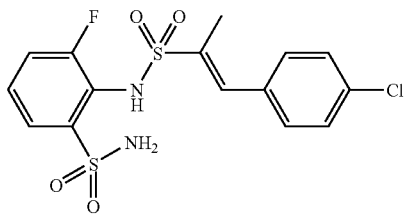 [SMILES: C/C(=C\c1ccc(Cl)cc1)S(=O)(=O)Nc1c(F)cccc1S(N)(=O)=O]

The compound was synthesized using an analogous procedure to that described for Example 9 to give 10 mg, 20%.

$^1$H NMR (400 MHz, CD$_3$OD) δ ppm 7.74-7.87 (m, 1H), 7.34-7.49 (m, 7H), 2.37 (d, 3H); ESMS: m/z [M−1] 402.5, 404.7.

Example 15

2-[[(E)-1-(4-Chlorophenyl)prop-1-en-2-yl]sulfonylamino]-5-methyl-benzenesulfonamide

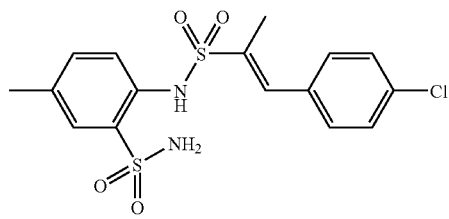 [SMILES: C/C(=C\c1ccc(Cl)cc1)S(=O)(=O)Nc1ccc(C)cc1S(N)(=O)=O]

The compound was synthesized using an analogous procedure to that described for Example 9 to give 35 mg, 73%.

$^1$H NMR (400 MHz, CD$_3$OD) δ ppm 7.72 (d, 1H), 7.59 (d, 1H), 7.53 (s, 1H), 7.37-7.43 (m, 2H), 7.31-7.37 (m, 3H), 2.33 (s, 3H), 2.17 (d, 3H);

ESMS: m/z [M+1] 398.8, 400.8, [M−1] 400.9, 402.8.

Example 16

2-[2-[4-(2-Furyl)phenyl]ethylsulfonylamino]benzenesulfonamide

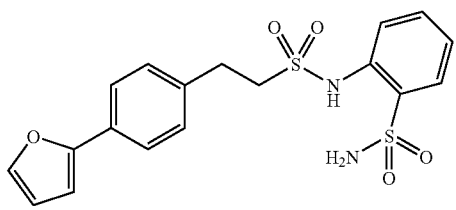 [SMILES: NS(=O)(=O)c1ccccc1NS(=O)(=O)CCc1ccc(-c2ccco2)cc1]

2-[[(E)-2-[4-(2-Furyl)phenyl]ethenyl]sulfonylamino]benzenesulfonamide (Example 18) (140 mg, 0.35 mmol) was dissolved in ethyl acetate (1.5 mL) and methanol (1.5 mL) and the mixture was subjected to reduction using the H-cube instrument. The reaction mixture was eluted through the Pd/C (10%) cartridge using full hydrogen (1 atm) at 0.5 ml/min. The solvent was then removed and the crude material was purified on semi-preparative HPLC using an X-Terra column to give the title compound (18 mg, 13%) as a white solid. The compound of Example 17 was also obtained.

$^1$H NMR (400 MHz, CD$_3$OD) δ ppm 7.95 (dd, 1H), 7.78 (dd, 1H), 7.53-7.61 (m, 3H), 7.51 (dd, 1H), 7.27 (t, 1H), 7.20 (d, 2H), 6.69 (d, 1H), 6.48 (dd, 1H), 3.46-3.56 (m, 2H), 3.03-3.12 (m, 2H);

ESMS: m/z [M−1] 404.8.

Example 17

2-[2-[4-(Oxolan-2-yl)phenyl]ethylsulfonylamino]benzenesulfonamide

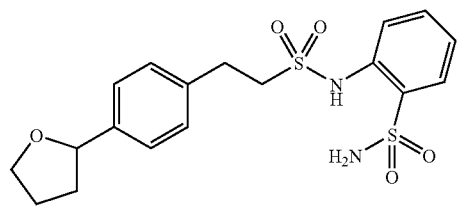 [SMILES: NS(=O)(=O)c1ccccc1NS(=O)(=O)CCc1ccc(C2CCCO2)cc1]

The title compound was obtained from the synthesis of Example 17 as a white solid (7 mg, 5%).

$^1$H NMR (400 MHz, CD$_3$OD) δ ppm 7.93 (dd, 1H), 7.75 (dd, 1H), 7.55 (td, 1H), 7.18-7.27 (m, 3H), 7.13 (d, 2H), 4.80 (t, 1H), 4.05 (dt, 1H), 3.85-3.92 (m, 1H), 3.44-3.51 (m, 2H), 3.03-3.09 (m, 2H), 2.24-2.33 (m, 1H), 1.96-2.05 (m, 2H), 1.62-1.80 (m, 1H);

ESMS: m/z [M−1] 409.0.

Example 18

2-[[(E)-2-[4-(2-Furyl)phenyl]ethenyl]sulfonylamino]benzenesulfonamide

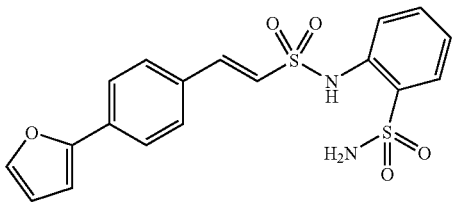 [SMILES: NS(=O)(=O)c1ccccc1NS(=O)(=O)/C=C/c1ccc(-c2ccco2)cc1]

2-Aminobenzenesulfonamide (61 mg, 0.35 mmol) was dissolved in pyridine (2.5 mL) and (E)-2-[4-(2-furyl)phenyl]ethenesulfonyl chloride) (see General procedure for synthesis of styrenyl sulfonyl chlorides) (95 mg, 0.35 mmol) was added. The reaction was stirred at RT overnight. The solvent was removed, the residue was partitioned between water and ethyl acetate, made acidic (HCl) and the mixture was extracted twice with ethyl acetate. The combined organic phases were washed with water, treated with brine, dried (MgSO$_4$), and evaporated to give the title compound (140 mg, 98%).

MS m/z M−H 403, M+H 405; Rf 3.12 min (System: Gemini column 3μ C18, 50×3.0 mm, 10 mM ammonium acetate with 5% acetonitrile/acetonitrile 0-100% during 6 min, 1 mL/min).

Example 19

2-[2-[4-(Difluoromethoxy)phenyl]ethylsulfonylamino]benzenesulfonamide

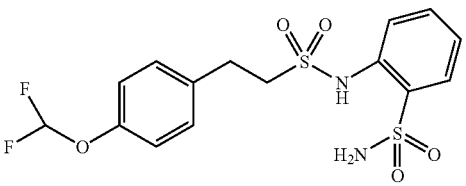 [SMILES: NS(=O)(=O)c1ccccc1NS(=O)(=O)CCc1ccc(OC(F)F)cc1]

The title compound (57 mg, 42%) was synthesized by a method analogous to that described for the preparation of Example 16.

$^1$H NMR (400 MHz, CD$_3$OD) δ ppm 7.95 (dd, 1H), 7.77 (dd, 1H), 7.57 (dd, 1H), 7.24-7.32 (m, 1H), 7.20 (d, 2H), 7.02 (d, 2H), 6.74 (t, 1H), 3.46-3.55 (m, 2H), 3.02-3.12 (m, 2H);

ESMS: m/z [M−1] 404.8.

Example 20

2-[[(E)-2-[4-(Difluoromethoxy)phenyl]ethenyl]sulfonylamino]benzenesulfonamide

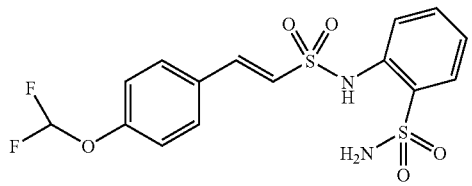 [SMILES: NS(=O)(=O)c1ccccc1NS(=O)(=O)/C=C/c1ccc(OC(F)F)cc1]

The title compound (135 mg, 94%) was synthesized by a method analogous to that described for the preparation of Example 18.

MS m/z M−H 403, M+H 405; Rf 3.12 min (System: Gemini column 3µ C18, 50×3.0 mm, 10 mM ammonium acetate with 5% acetonitrile/acetonitrile 0-100% during 6 min, 1 mL/min).

Example 21

2-[2-(4-Chlorophenyl)ethylsulfonylamino]-5-fluoro-benzenesulfonamide

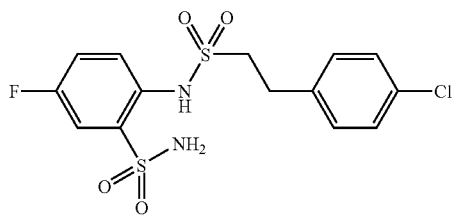 [SMILES: NS(=O)(=O)c1cc(F)ccc1NS(=O)(=O)CCc1ccc(Cl)cc1]

The title compound (74 mg, 36%) was synthesized by a method analogous to that described for the preparation of Example 16.

$^1$H NMR (400 MHz, CD$_3$OD) δ ppm 7.77 (dd, 1H), 7.69 (dd, 1H), 7.35 (ddd, 1H), 7.21-7.27 (m, 2H), 7.15-7.22 (m, 2H), 3.45-3.54 (m, 2H), 3.00-3.10 (m, 2H);

ESMS: m/z [M−1] 391.1, 393.1

Example 22

2-[[(E)-2-(4-Chlorophenyl)ethenyl]sulfonylamino]-5-fluoro-benzenesulfonamide

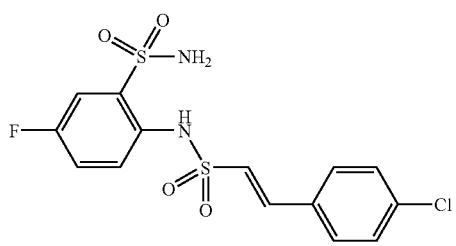 [SMILES: NS(=O)(=O)c1cc(F)ccc1NS(=O)(=O)/C=C/c1ccc(Cl)cc1]

The title compound (210 mg, 90%) was synthesized by a method analogous to that described for the preparation of Example 18.

$^1$H NMR (400 MHz, CD3CN-d$_3$) δ ppm 7.66 (dd, 1H), 7.58 (dd, 1H), 7.51-7.55 (m, 2H), 7.51 (d, 1H), 7.40-7.44 (m, 2H), 7.31 (ddd, 1H), 7.04 (d, 1H);

ESMS: m/z [M−1] 389.0.

General Procedure for Examples 23-43

Stock Solutions:

The anilines (800 µmol) were dissolved in pyridine (2 ml).

The sufonyl chlorides (prepared according to the General procedure for synthesis of styrenyl sulfonyl chlorides) (1.2 mmol) were dissolved in pyridine (6 ml).

Reaction: (24 Reactions)

The stock solution of the anilines (500 µl, 200 µmol) were mixed with the stock solutions of the sulfonyl chlorides (1.0 ml, 200 µl) in 24 wells and the reaction was put on a shaker overnight. The solvent was removed (centrifuge) and preparative chromatography was run on a Waters FractionLynx system with a Autosampler combined Automated Fraction Collector (Waters 2767), Gradient Pump (Waters 2525), Regeneration Pump (Waters 600), Make Up Pump (Waters 515), Waters Active Splitter, Column Switch (Waters CFO), PDA (Waters 2996) and Waters ZQ mass spectrometer. Column; XBridge™ Prep C8 5 µm OBD™ 19×100 mm, with guard column; XTerra® Prep MS C8 10 µm 19×10 mm Cartridge. A gradient from 100% A (95% 0.1M NH$_4$OAc in MilliQ water and 5% MeCN) to 100% B (100% MeCN) was applied for LC-separation at flow rate 25 ml/min. The PDA was scanned from 210-350 nm. The ZQ mass spectrometer was run with ESI in positive mode. The Capillary Voltage was 3 kV and the Cone Voltage was 30V. Mixed triggering, UV and MS signal, determined the fraction collection.

Purity analysis was run on a Water Acquity system with PDA (Waters 2996) and Waters ZQ mass spectrometer. Column; Acquity UPLC™ BEH C$_8$ 1.7 µm 2.1×50 mm. The column temperature was set to 65° C. A linear 2 min 15 sec gradient from 100% A (A: 95% 0.01M NH$_4$OAc in MilliQ water and 5% MeCN) to 100% B (5% 0.01M NH$_4$OAc in MilliQ water and 95% MeCN) was applied for LC-separation at flow rate 1.0 ml/min. The PDA was scanned from 210-350 nm and 254 nm was extracted for purity determination. The ZQ mass spectrometer was run with ESI in pos/neg switching mode. The Capillary Voltage was 3 kV and the Cone Voltage was 30V.

Example 23

2-[[(E)-2-(3,4-Dichlorophenyl)ethenyl]sulfonylamino]-4-fluoro-benzenesulfonamide

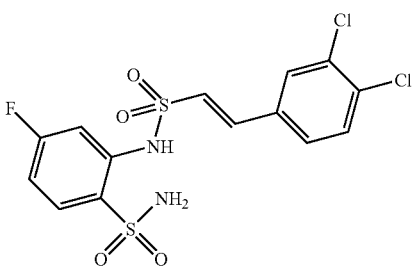 [SMILES: NS(=O)(=O)c1ccc(F)cc1NS(=O)(=O)/C=C/c1ccc(Cl)c(Cl)c1]

11 mg, 13%. ESMS: m/z [M+1] 424.8, 426.8, Rf 1.00 min.

Example 24

2-[[(E)-2-(3,4-Dichlorophenyl)ethenyl]sulfonylamino]-5-fluoro-benzenesulfonamide

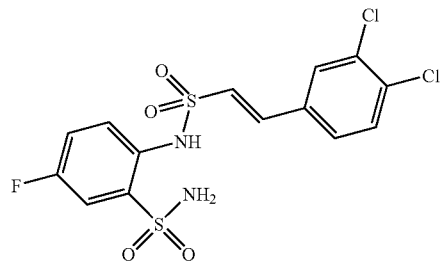 [SMILES: NS(=O)(=O)c1cc(F)ccc1NS(=O)(=O)/C=C/c1ccc(Cl)c(Cl)c1]

27 mg, 32%. ESMS: m/z [M+1] 424.8, 426.8, Rf 1.01 min.

Example 25

2-[[(E)-2-(3,4-Dichlorophenyl)ethenyl]sulfonylamino]-6-fluoro-benzenesulfonamide

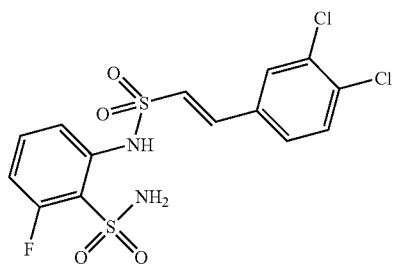 [SMILES: NS(=O)(=O)c1c(F)cccc1NS(=O)(=O)/C=C/c1ccc(Cl)c(Cl)c1]

32 mg, 37%. ESMS: m/z [M+1] 424.8, 426.8, Rf 1.03 min.

Example 26

2-[[(E)-2-(5-Bromo-2-methoxy-phenyl)ethenyl]sulfonylamino]-4-fluoro-benzenesulfonamide

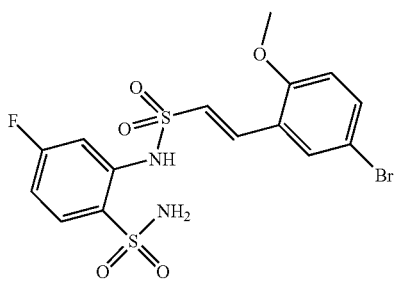 [SMILES: COc1ccc(Br)cc1/C=C/S(=O)(=O)Nc1cc(F)ccc1S(N)(=O)=O]

18 mg, 19%. ESMS: m/z [M+1] 464.8, 466.8, Rf 0.95 min.

Example 27

2-[[(E)-2-(5-Bromo-2-methoxy-phenyl)ethenyl]sulfonylamino]-5-fluoro-benzenesulfonamide

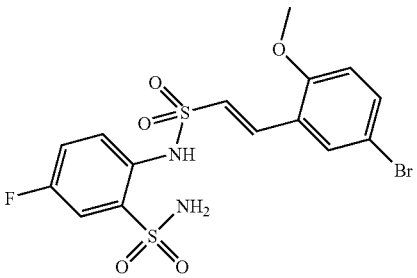 [SMILES: COc1ccc(Br)cc1/C=C/S(=O)(=O)Nc1ccc(F)cc1S(N)(=O)=O]

23 mg, 24%. ESMS: m/z [M+1] 464.8, 466.8, Rf 1.00 min.

Example 28

2-[[(E)-2-(5-Bromo-2-methoxy-phenyl)ethenyl]sulfonylamino]-6-fluoro-benzenesulfonamide

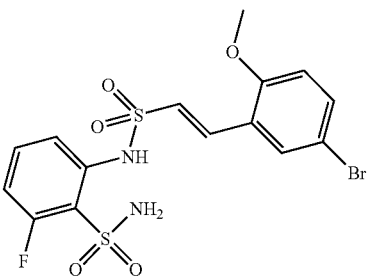 [SMILES: COc1ccc(Br)cc1/C=C/S(=O)(=O)Nc1cccc(F)c1S(N)(=O)=O]

25 mg, 27%. ESMS: m/z [M+1] 464.8, 466.8, Rf 1.03 min

Example 29

2-[[(E)-2-(5-Bromo-2-methoxy-phenyl)ethenyl]sulfonylamino]benzenesulfonamide

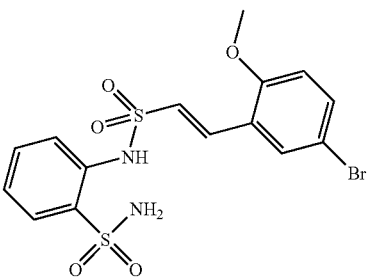 [SMILES: COc1ccc(Br)cc1/C=C/S(=O)(=O)Nc1ccccc1S(N)(=O)=O]

32 mg, 36%. ESMS: m/z [M+1] 446.8, 448.8, Rf 0.99 min.

Example 30

2-[[(E)-2-(4-Cyanophenyl)ethenyl]sulfonylamino]-4-fluoro-benzenesulfonamide

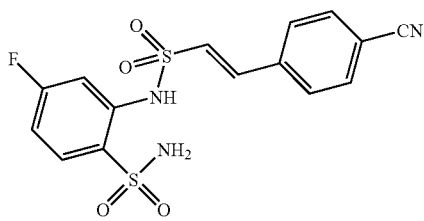 [SMILES: N#Cc1ccc(/C=C/S(=O)(=O)Nc2cc(F)ccc2S(N)(=O)=O)cc1]

22 mg, 29%. ESMS: m/z [M+1] 399.0 (ammonia adduct), Rf 0.77 min.

Example 31

2-[[(E)-2-(4-Cyanophenyl)ethenyl]sulfonylamino]-5-fluoro-benzenesulfonamide

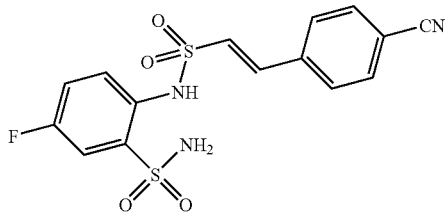 [SMILES: N#Cc1ccc(/C=C/S(=O)(=O)Nc2ccc(F)cc2S(N)(=O)=O)cc1]

32 mg, 42%. ESMS: m/z [M+1] 398.9 (ammonia adduct), Rf 0.77 min.

Example 32

2-[[(E)-2-(4-Cyanophenyl)ethenyl]sulfonylamino]-6-fluoro-benzenesulfonamide

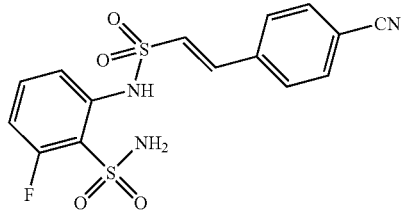 [SMILES: N#Cc1ccc(/C=C/S(=O)(=O)Nc2cccc(F)c2S(N)(=O)=O)cc1]

32 mg, 42%. ESMS: m/z [M+1] 398.9 (ammonia adduct), Rf 0.77 min.

Example 33

2-[[(E)-2-(4-Cyanophenyl)ethenyl]sulfonylamino]benzenesulfonamide

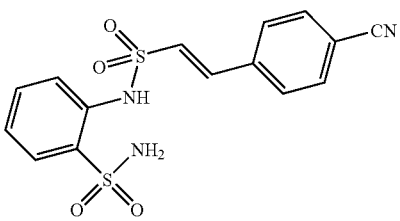 [SMILES: N#Cc1ccc(/C=C/S(=O)(=O)Nc2ccccc2S(N)(=O)=O)cc1]

27 mg, 37%. ESMS: m/z [M+1] 363.9, Rf 0.74 min.

Example 34

4-Fluoro-2-[[(E)-2-[4-(2-furyl)phenyl]ethenyl]sulfonylamino]benzenesulfonamide

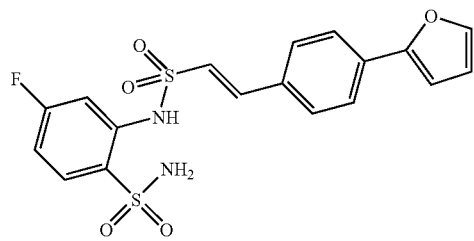 [SMILES: NS(=O)(=O)c1ccc(F)cc1NS(=O)(=O)/C=C/c1ccc(-c2ccco2)cc1]

14 mg, 17%. ESMS: m/z [M+1] 422.9, Rf 0.96 min.

Example 35

5-Fluoro-2-[[(E)-2-[4-(2-furyl)phenyl]ethenyl]sulfonylamino]benzenesulfonamide

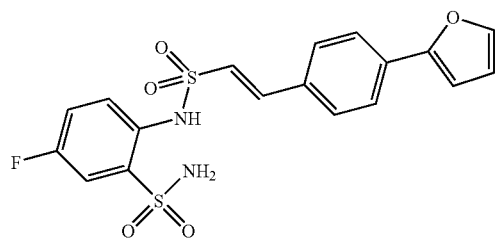 [SMILES: NS(=O)(=O)c1cc(F)ccc1NS(=O)(=O)/C=C/c1ccc(-c2ccco2)cc1]

19 mg, 22%. ESMS: m/z [M+1] 422.9, Rf 1.01 min.

Example 36

2-Fluoro-6-[[(E)-2-[4-(2-furyl)phenyl]ethenyl]sulfonylamino]benzenesulfonamide

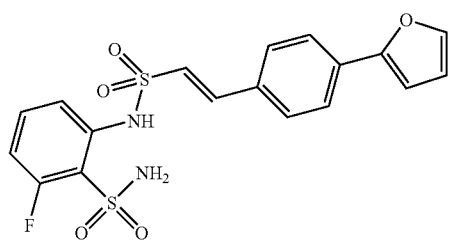 [SMILES: NS(=O)(=O)c1c(F)cccc1NS(=O)(=O)/C=C/c1ccc(-c2ccco2)cc1]

25 mg, 30%. ESMS: m/z [M+1] 422.9, Rf 1.04 min.

Example 37

4-Fluoro-2-[[(E)-2-(4-methylsulfanylphenyl)ethenyl]sulfonylamino]-benzenesulfonamide

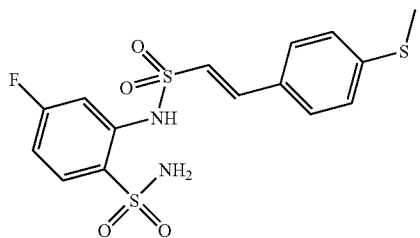 [SMILES: CSc1ccc(/C=C/S(=O)(=O)Nc2cc(F)ccc2S(N)(=O)=O)cc1]

17 mg, 21%. ESMS: m/z [M+1] 402.9, Rf 0.90 min.

Example 38

5-Fluoro-2-[[(E)-2-(4-methylsulfanylphenyl)ethenyl]sulfonylamino]-benzenesulfonamide

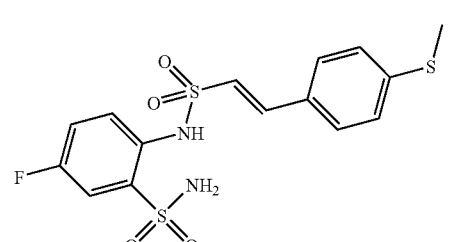

23 mg, 28%. ESMS: m/z [M+1] 402.9, Rf 0.95 min.

Example 39

2-Fluoro-6-[[(E)-2-(4-methylsulfanylphenyl)ethenyl]sulfonylamino]-benzenesulfonamide

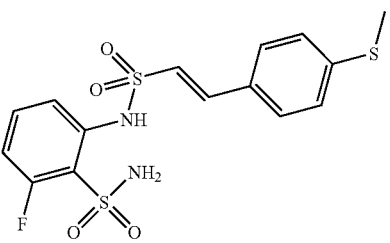 [SMILES: CSc1ccc(/C=C/S(=O)(=O)Nc2cccc(F)c2S(N)(=O)=O)cc1]

28 mg, 34%. ESMS: m/z [M+1] 402.9, Rf 0.99 min.

Example 40

2-[[(E)-2-(4-Methylsulfanylphenyl)ethenyl]sulfonylamino]benzenesulfonamide

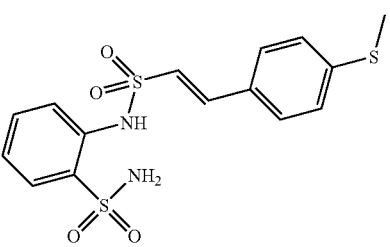 [SMILES: CSc1ccc(/C=C/S(=O)(=O)Nc2ccccc2S(N)(=O)=O)cc1]

20 mg, 26%. ESMS: m/z [M+1] 384.9, Rf 0.94 min.

Example 41

2-[[(E)-2-[4-(Difluoromethoxy)phenyl]ethenyl]sulfonylamino]-4-fluoro-benzenesulfonamide

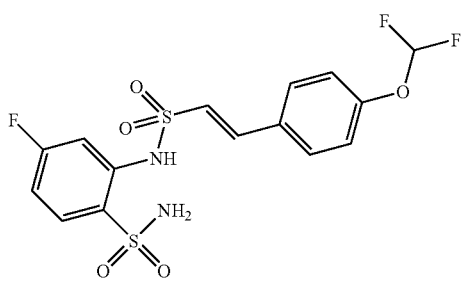 [SMILES: NS(=O)(=O)c1ccc(F)cc1NS(=O)(=O)/C=C/c1ccc(OC(F)F)cc1]

20 mg, 23%. ESMS: m/z [M+1] 422.9, Rf 0.90 min.

Example 42

2-[[(E)-2-[4-(Difluoromethoxy)phenyl]ethenyl]sulfonylamino]-5-fluoro-benzenesulfonamide

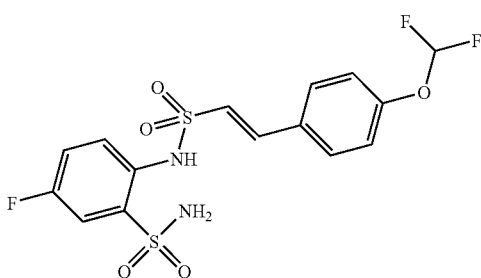 [SMILES: NS(=O)(=O)c1cc(F)ccc1NS(=O)(=O)/C=C/c1ccc(OC(F)F)cc1]

20 mg, 23%. ESMS: m/z [M+1] 422.9, Rf 0.93 min.

Example 43

2-[[(E)-2-[4-(Difluoromethoxy)phenyl]ethenyl]sulfonylamino]-6-fluoro-benzenesulfonamide

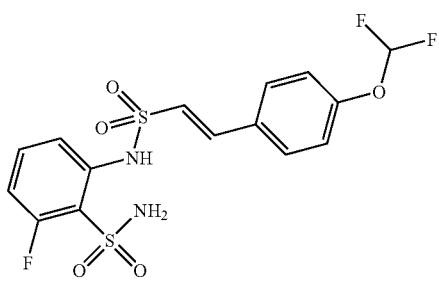 [SMILES: NS(=O)(=O)c1c(F)cccc1NS(=O)(=O)/C=C/c1ccc(OC(F)F)cc1]

28 mg, 33%. ESMS: m/z [M+1] 422.8, Rf 0.96 min.

Example 44

2-[2-(4-Chlorophenyl)ethylsulfonylamino]-5-(hydroxymethyl)benzenesulfonamide

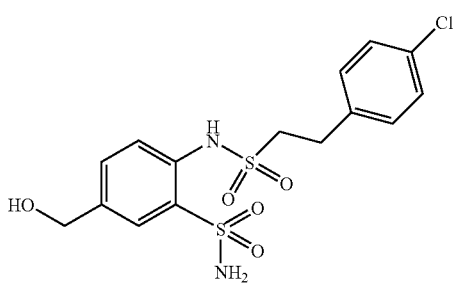 [SMILES: NS(=O)(=O)c1cc(CO)ccc1NS(=O)(=O)CCc1ccc(Cl)cc1]

To a solution of 4-[2-(4-chloro-phenyl)-ethanesulfonylamino]-3-sulfamoyl-benzoic acid (190 mg, 0.45 mmol) in dry THF (15 mL) was added LiAlH$_4$ (1M in THF, 2 mL, 2 mmol). The reaction mixture was heated at 45° C. overnight, then cooled to 0° C. and quenched by addition of water, followed by 1N HCl. The product was extracted with ethyl acetate, the combined organic phases were washed with water and brine, and dried over sodium sulfate. Volatiles were removed under reduced pressure and the crude product was purified by preparative HPLC to title compound as a white solid (51 mg, 28%).

$^1$H NMR (400 MHz, acetone-d$_6$): δ ppm 8.78 (br. s., 1H), 7.97 (d, 1H), 7.75 (d, 1H), 7.58 (dd, 1H), 7.21-7.35 (m, 4H), 7.15 (br. s., 2H), 4.66 (s, 2H), 3.49-3.66 (m, 2H), 3.03-3.16 (m, 2H);

ESMS: m/z [M−1] 402.93 and 404.82 (Cl isotopes).

a) 4-[2-(4-Chloro-phenyl)-ethanesulfonylamimo]-3-sulfamoyl-benzoic acid

A mixture of 2-[2-(4-chloro-phenyl)-ethanesulfonylamino]-5-methylbenzenesulfonamide (Example 45) (2.0 g, 5.14 mmol), 2.5N NaOH (27 mL, 6.75 mmol), water (100 mL) and KMnO$_4$ (3.35 g, 21.19 mmol) was stirred at 50° C. overnight. The reaction mixture was then filtered through Celite and the filtrate was acidified using 2N HCl. The product was extracted with ethyl acetate and the organic phase was concentrated under reduced pressure. The crude product was purified by flash column chromatography using a gradient of 5 to 10% MeOH in DCM to afford the title compound (490 mg, 23%).

$^1$H NMR (400 MHz, CD$_3$OD): δ ppm 8.59 (s, 1H), 8.16 (d, J=8.61 Hz, 1H), 7.84 (d, J=8.61 Hz, 1H), 7.23 (m, 2H), 7.17 (m, 2H), 4.87 (br. S, 4H), 3.66-3.54 (m, 2H), 3.10 (d, J=8.22 Hz, 2H);

ESMS: m/z [M−1] 416.92.

Example 45

2-[2-(4-Chloro-phenyl)-ethanesulfonylamimo]-5-methylbenzenesulfonamide

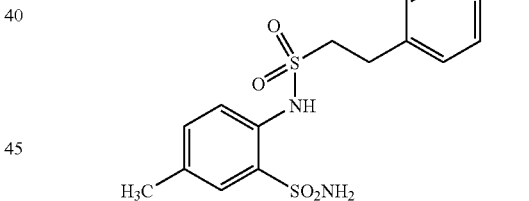

A mixture of 2-amino-5-methyl-benzenesulfonamide (5.0 g, 26.84 mmol), 2-(4-chloro-phenyl)-ethanesulfonyl chloride (8.0 g, 33.56 mmol) and pyridine (100 mL) was stirred at RT overnight. The reaction mixture was concentrated under reduced pressure and the residue was partitioned between ethyl acetate and 1N HCl. The organic phase was concentrated in vacuo and the crude product was purified by flash column chromatography to afford the title compound (8.0 g, 51%).

$^1$H NMR (400 MHz, CDCl$_3$): δ ppm 8.13 (br. s, 1H), 7.79 (br. s, 1H), 7.56-7.44 (m, 1H), 7.40 (d, 1H), 7.32-7.19 (m, 3H), 7.15 (d, 2H), 5.26 (br., s, 2H), 3.56-3.43 (m, 2H), 3.19 (dd, 2H), 2.40 (br, s, 3H);

ESMS: [M−1] 386.86 and 388.82 (Cl isotopes).

a) 2-Amino-5-methyl-benzenesulfonamide

A mixture of 7-methyl-1,1-dioxo-1,4-dihydro-2-H-benzo[1,2,4]thiadiazin-3-one (7.20 g, 36.36 mmol) in aqueous H₂SO₄ (50% v/v, 200 mL) was heated at 105° C. for 16 h. The clear solution was then cooled to 0° C. and neutralized using 5N NaOH. The product was extracted with ethyl acetate. The combined extracts were washed with water and concentrated under reduced pressure. The crude product was purified by flash column chromatography using ethyl acetate/hexane (1:1) to afford 4.5 g (85%) of the title compound.

$^1$H NMR (400 MHz, DMSO-$d_6$): δ ppm 7.33 (s, 1H), 7.16 (s, 2H), 7.05 (d, 1H), 6.70 (d, 1H), 5.65 (s, 2H), 2.19 (s, 3H).

b) 7-Methyl-1,1-dioxo-1,4-dihydro-2-H-benzo[1,2,4]thiadiazin-3-one p-Toluidine (11.00 g, 102.65 mmol) dissolved in nitromethane (50 mL) was added slowly over 20 minutes to a solution of chlorosulfonyl isocyanate (16.89 g, 119.40 mmol) in nitromethane (160 mL) at −5° C. The suspension was stirred at −5° C. for an additional 15 minutes and AlCl₃ (17.00 g, 129.00 mmol) was added portionwise. The reaction mixture was then heated at 105° C. for 30 minutes. The hot solution was poured onto ice (1 L) and the resulting precipitate was filtered off and washed with water (300 mL). The solid was then dissolved in a hot aqueous sodium bicarbonate solution (10 g/200 mL), treated with charcoal, and filtered. The cooled solution was neutralized using 6N HCl and the resulting white precipitate was filtered off, washed with water and dried to afford the title compound (14 g, 64%).

$^1$H NMR (400 MHz, DMSO-$d_6$): δ ppm 11.19 (s, 1H), 7.60 (s, 1H), 7.42 (d, 1H), 7.09 (d, 1H), 2.38 (s, 3H).

Example 46

2-[2-(4-Chlorophenyl)ethylsulfonylamino]-5-(pyridin-2-ylmethoxy)benzenesulfonamide

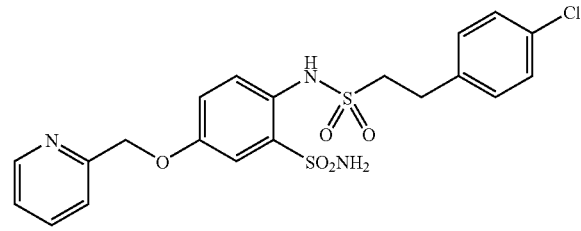 [SMILES: NS(=O)(=O)c1cc(OCc2ccccn2)ccc1NS(=O)(=O)CCc1ccc(Cl)cc1]

To a solution of NaH (57%, 56 mg, 1.33 mmol) in dry DMSO (10 mL) was added N-Boc-2-[2-(4-chloro-phenyl)-ethanesulfonylamino]-5-hydroxy-benzenesulfonamide (Example 46b) (220 mg, 0.44 mmol). The reaction mixture was stirred at RT for 2 h (solution turned brown). Toluene-4-sulfonic acid pyridine-2-ylmethyl ester (141 mg, 0.53 mmol) was then added and stirring was continued for 4 h at RT. The reaction mixture was quenched by addition of saturated NH₄Cl and the product was extracted with EtOAc (3×30 mL). The combined extracts were dried over anhydrous MgSO₄ and concentrated in vacuo to give a yellow oil (182 mg) which was then dissolved in DCM (2 mL). The resulting solution was cooled to 0° C., TFA (1 mL) was added and the reaction mixture was allowed to warm to RT over 3 h. Volatiles were removed under reduced pressure and the residue was purified by preparative HPLC to give the title compound as a white solid (TFA salt, 90 mg, 60%).

$^1$H NMR (400 MHz, CD₃OD): δ ppm 8.63 (d, 1H), 8.09 (t, 1H), 7.76 (d, 1H) 7.70 ((d, 1H), 7.63 (d, 1H), 7.57 (t, 1H), 7.29 (m, 1H), 7.24 (d, 2H), 7.18 (d, 2H), 5.30 (s, 2H), 3.47 (m, 2H), 3.05 (m, 2H); $^{19}$F NMR (400 MHz, CDCl₃): δ(ppm) −77.57; ESMS: m/z [M⁺+1] 481.89.

a) Toluene-4-sulfonic acid pyridine-2-ylmethyl ester

Powdered KOH (1.74 g, 30.65 mmol) was added to a vigorously stirred solution of pyridin-2-yl-methanol (2 mL, 20.72 mmol) in THF (100 mL) at 0° C. The reaction mixture was stirred for 15 minutes and tosyl chloride (5.13 g, 26.90 mmol) was then added. The reaction mixture was allowed to warm to RT and stirring was continued overnight. The reaction mixture was quenched with saturated NaHCO₃ and the product was extracted with EtOAc (3×50 mL). The combined extracts were dried over MgSO₄ and concentrated in vacuo to give a yellow oil. The residue was purified by flash column chromatography using EtOAc: hexane (1:4) to yield the title compound (4.6 g, 85%) as a yellowish solid.

$^1$H NMR (400 MHz, CDCl₃): δ ppm 8.53 (m, 1H), 7.85 (d, 2H), 7.73 (t, 1H), 7.44 (d, 1H), 7.35 (d, 2H), 7.25 (m, 1H), 5.14 (s, 2H), 2.44 (s, 3H);
ESMS: m/z [M⁺+1] 263.31.

b) N-Boc-2-[2-(4-chloro-phenyl)-ethanesulfonylamino]-5-hydroxy-benzenesulfonamide To a solution of 2-[2-(4-chloro-phenyl)-ethanesulfonylamino]-5-hydroxy-benzenesulfonamide (2.50 g, 6.41 mmol) in DCM (150 mL) at 0° C. was added Et₃N (4.46 mL, 14.07 mmol) followed by Boc₂O (3.07 g, 14.07 mmol). The resulting mixture was stirred for 15 minutes at 0° C. and then DMAP (0.78 g, 6.41 mmol) was added in one portion (reaction became exothermic). The reaction mixture was stirred at 0° C. for another hour, allowed to warm to RT and stirred overnight. The organic phase was washed with 2N HCl (3×50 mL), water (3×30 mL) and dried over MgSO₄. Removal of solvent under reduced pressure afforded 3.5 g (94%) of the di-Boc intermediate which was used in the next step without purification. In the $^1$H NMR spectrum, two singlets were observed at 1.42 ppm and 1.34 ppm, which correspond to O-Boc and N-Boc groups respectively. To a solution of the di-Boc intermediate (1.20 g, 2.03 mmol) in EtOH (150 mL) was added LiOH (10% aqueous solution, 40 mL) at RT. The reaction mixture was stirred at 55° C. for 14 h. The progress of the reaction was monitored by $^1$H NMR. The singlet at 1.42 ppm for the O-Boc group was not observed upon completion of the reaction. The reaction mixture was concentrated to approximately half volume and acidified by the addition of 5N HCl to a pH of 4-5. The product was extracted with EtOAc (3×50 mL) and the combined extracts were dried over MgSO₄ and concentrated in vacuo. The residue was purified by column chromatography using 1% MeOH/DCM to afford the product as a yellow solid (747 mg, 75%).

$^1$H NMR (400 MHz, CD₃OD): δ ppm 7.64 (d, 1H), 7.37 (s, 1H), 7.26 (d, 2H), 7.18 (d, 2H), 7.09 (m, 1H), 3.44 (m, 2H), 3.05 (m, 2H), 1.34 (s, 9H);
ESMS: m/z [M−1] 489.25.

c) 2-[2-(4-Chloro-phenyl)-ethanesulfonylamino]-5-hydroxy-benzenesulfonamide

To a solution of 2-[2-(4-chloro-phenyl)-ethanesulfonylamino]-5-methoxy-benzenesulfonamide (4.0 g, 9.90 mmol) in DCM (250 mL) at −78° C., BBr₃ (1M in DCM, 70 mL, 70 mmol) was added dropwise over 20 minutes. The reaction mixture was allowed to warm to RT and the stirring was continued overnight. The reaction mixture was then cooled to −78° C., quenched by addition of methanol (20 mL) and water (50 mL), and the product was extracted with ethyl acetate. The organic extracts were washed with water, dried over sodium sulfate and concentrated under reduced pressure. The crude product was recrystallized from methanol to the title compound (3.45 g, 92%).

$^1$H NMR (400 MHz, DMSO-D$_6$): δ ppm 10.04 (s, 1H), 8.66 (s, 1H), 7.65 (s, 2H), 7.45 (d, 1H), 7.35 (m, 3H), 7.27 (d, 2H), 6.99 (dd, 1H), 3.53 (m, 2H), 2.97 (m, 2H);
ESMS: m/z [M−1] 389.

d) 2-[2-(4-Chloro-phenyl)-ethanesulfonylamino]-5-methoxy-benzenesulfonamide

To a solution of 2-amino-5-methoxy-benzenesulfonamide (4.0 g, 19.80 mmol) in pyridine (60 mL), 2-(4-chloro-phenyl)-ethanesulfonyl chloride (4.73 g, 19.79 mmol) was added slowly at 0° C. The reaction mixture was stirred at RT for 16 h and then concentrated under reduced pressure at 35° C. The residue was then partitioned between ethyl acetate and 1N HCl. The organic layer was separated, dried over sodium sulfate and concentrated in vacuo. The crude product was purified by flash column chromatography using ethyl acetate/hexane (1:1) to give the title compound (7.1 g, 88%).

$^1$H NMR (400 MHz, CD$_3$OD) δ ppm 7.65 (d, 1H), 7.49 (d, 1H), 7.21-7.27 (m, 2H), 7.15-7.19 (m, 2H), 7.12-7.15 (m, 1H), 3.83 (s, 3H), 3.42-3.47 (m, 2H), 3.02 (dd, 2H).

Example 47

2-[2-(4-Chlorophenyl)ethylsulfonylamino]-5-[(5-methyl-1,3,4-oxadiazol-2-yl)methoxy]benzene-sulfonamide

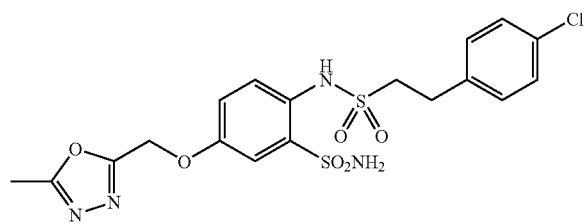 [SMILES: Cc1nnc(COc2ccc(NS(=O)(=O)CCc3ccc(Cl)cc3)c(S(N)(=O)=O)c2)o1]

Following the general procedure as described in Example 46, sodium phenolate generated from N-Boc-2-[2-(4-chloro-phenyl)-ethanesulfonylamino]-5-hydroxy-benzenesulfonamide (210 mg, 0.43 mmol) was reacted with toluene-4-sulfonic acid 5-methyl-[1,3,4]oxadiazol-2-ylmethyl ester to afford 178 mg of the crude alkylation product. After deprotection of the sulfonamide group, the crude product was purified by preparative HPLC to give the title compound as a white solid (TFA salt, 95 mg, 65%).

$^1$H NMR (400 MHz, CD$_3$OD) δ ppm 7.71 (d, 1H), 7.61 (d, 1H), 7.30 (m, 1H), 7.25 (d, 2H), 7.18 (d, 2H), 5.35 (s, 2H), 3.48 (m, 2H), 3.05 (m, 2H), 2.54 (s, 3H);
ESMS: m/z [M−1] 484.85.

a) Toluene-4-sulfonic acid 5-methyl-[1,3,4]oxadiazol-2-ylmethyl ester

Following the general procedure as described in Example 46a, the title compound was prepared from commercially available 5-methyl-[1,3,4]oxadiazol-2-yl)-methanol (1.0 g, 80%).

$^1$H NMR (400 MHz, CD$_3$OD): δ ppm 7.80 (d, 2H), 7.41 (d, 2H), 5.30 (s, 2H), 2.50 (s, 3H), 2.30 (s, 3H);
ESMS: m/z [M$^+$+1] 268.89.

Example 48

2-[2-(2-Chloro-phenyl)-ethenesulfonylamino]-benzenesulfonamide

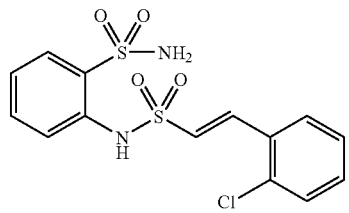 [SMILES: NS(=O)(=O)c1ccccc1NS(=O)(=O)/C=C/c1ccccc1Cl]

2-Aminobenzene sulfonamide (153 mg, 0.89 mmol) was added in one portion to a solution of 2-(2-chloro-phenyl)-ethenesulfonyl chloride (150 mg, 0.63 mmol) in pyridine (2 mL) at RT. After 30 minutes of stirring, no more starting material was detected by tlc. The reaction mixture was concentrated under reduced pressure and the residue was taken up in ethyl acetate and a small amount of methanol. The organic phase was washed with 1N HCl, saturated sodium bicarbonate, dried over MgSO$_4$, and concentrated under reduced pressure. Purification by preparative tlc afforded the target compound, which was then recrystallized from ethyl acetate/pentane/diethyl ether to afford the title compound (85 mg, 36%) as a white solid.

$^1$H NMR (400 MHz, DMSO-d$_6$): δ ppm 9.19 (s, 1H), 7.89-7.83 (m, 2H), 7.81 (d, 1H), 7.71 (d, 1H), 7.66-7.59 (m, 2H), 7.57-7.50 (m, 1H), 7.50-7.43 (m, 1H), 7.43-7.36 (m, 1H), 7.35-7.27 (m, 1H);
ESMS: m/z [M−1] 371.09;
CHN for C$_{14}$H$_{13}$ClN$_2$O$_4$S$_2$. Calc.: C, 45.10; H, 3.51; N, 7.51. Found: C, 44.89; H, 3.71; N, 7.54.

Example 49

2-[2-(4-Chloro-2-methoxy-phenyl)-ethenesulfonylamino]-benzenesulfonamide

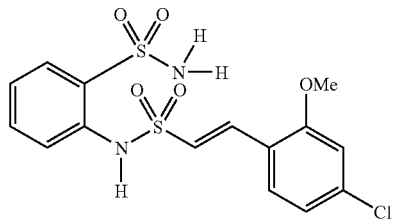 [SMILES: COc1cc(Cl)ccc1/C=C/S(=O)(=O)Nc1ccccc1S(N)(=O)=O]

2-Aminobenzene sulfonamide (194 mg, 1.13 mmol) was added in one portion to a solution of 2-(4-chloro-2-methoxyphenyl)-ethenesulfonyl chloride (300 mg, 1.13 mmol) in pyridine (3 mL) at RT. After 1 h stirring, no more starting material was detected by tlc. The reaction mixture was concentrated and the residue was taken up in ethyl acetate with a small amount of methanol. The organic phase was washed with 1N HCl, saturated sodium bicarbonate, dried over MgSO$_4$ and concentrated under reduced pressure. The crude product was purified on silica gel using DCM/methanol, 99:1 to afford material which was further purified by recrystallization from methanol to give the title compound (184 mg, 41%) as a white solid.

$^1$H NMR (400 MHz, DMSO-d$_6$): δ ppm 9.05 (s, 1H), 7.86-7.78 (m, 3H), 7.66-7.55 (m, 4H), 7.40 (d, 1H), 7.31-7.23 (m, 1H), 7.18 (d, 1H), 7.05 (dd, 1H), 3.88 (s, 3H);

ESMS: m/z [M−1] 401.12;

CHN for C$_{15}$H$_{15}$ClN$_2$O$_5$S$_2$, 0.6MeOH. Calc.: C, 44.39; H, 4.15; N, 6.64. Found: C, 44.42; H, 4.29; N, 6.72.

a) 2-(4-Chloro-2-methoxy-phenyl)-ethenesulfonyl chloride

Thionyl chloride (8.1 mL, 111.19 mmol) was added dropwise at 0° C. to a solution of 2-(4-chloro-2-methoxy-phenyl)-ethenesulfonic acid (5.53 g, 22.24 mmol) in DMF (10 mL). The reaction mixture was stirred at RT for 3 h and then was poured onto crushed ice. Ethyl acetate (50 mL) was added to the mixture. The organic phase was separated, washed with brine (3×20 mL), dried over MgSO$_4$ and concentrated under reduced pressure. The oily residue was purified on silica gel using hexane/ethyl acetate, 4:1 to give the target compound which was then recrystallized from pentane/diethyl ether to afford the title compound (2.30 g, 61% over 3 steps) as a white solid.

$^1$H NMR (400 MHz, CDCl$_3$): δ ppm 7.78 (d, 1H), 7.52 (d, 1H), 7.38 (d, 1H), 7.04 (dd, 1H), 6.99 (d, 1H), 3.97 (s, 3H);

ESMS: m/z [M−1] 247.05 (corresponding sulfonic acid M=248);

CHN for C$_9$H$_8$Cl$_2$O$_3$S. Calc.: C, 40.47; H, 3.02. Found: C, 40.67; H, 3.11.

b) 2-(4-Chloro-2-methoxy-phenyl)-ethenesulfonic acid

Tetrabutyl-ammonium iodide (6.25 g, 16.91 mmol) was added to a solution of 2-(4-chloro-2-methoxy-phenyl)-ethenesulfonic acid ethyl ester (3.90 g, 14.09 mmol) in acetone (300 mL). The reaction mixture was heated at reflux overnight, then was cooled to RT and concentrated under reduced pressure. The residue was purified on silica gel using hexane/ethyl acetate, 1:1 to elute the impurities, then DCM/methanol, 95:5 to afford crude material which contained tetrabutyl-ammonium iodide. The oily residue was triturated with diethyl ether to afford a beige solid (9.15 g) which was used in the next step without further purification.

To a stirred solution of the solid (9.15 g crude from preceding step) in water (100 mL) and methanol (20 mL) was added dropwise 3N HCl until the pH of the solution was approximately 1. The reaction mixture was concentrated under reduced pressure to afford an oily residue which was purified on silica gel using DCM/methanol, 95:5 to 90:10 to afford the title compound (5.53 g) contaminated with some tetrabutyl-ammonium chloride and which was used in the next step without further purification.

$^1$H NMR (400 MHz, CDCl$_3$): δ ppm 7.52 (d, 1H), 7.13-7.08 (m, 2H), 6.97 (dd, 1H), 6.83 (d, 1H), 3.86 (s, 3H).

c) 2-(4-Chloro-2-methoxy-phenyl)-ethenesulfonic acid ethyl ester

A 2.5M solution of n-butyllithium in hexanes (6.15 mL, 15.37 mmol) was added dropwise to a stirred solution of (diethoxy-phosphoryl)-methanesulfonic acid ethyl ester (4.0 g, 15.37 mmol) in THF (200 mL) at −78° C. The reaction mixture was stirred at −78° C. for 15 minutes. A solution of 4-chloro-2-methoxy-benzaldehyde (2.41 g, 14.10 mmol) in THF (20 mL) was then added dropwise. After the addition was complete the reaction mixture was warmed to RT, stirred for 1 h and quenched with brine. The reaction mixture was concentrated under reduced pressure and DCM (200 mL) was added. The organic layer was separated, washed with brine (3×100 mL) and dried over MgSO$_4$. Removal of solvent under reduced pressure, followed by purification on silica gel using hexane/ethyl acetate, 4:1 to 2:1 afforded the title compound (3.90 g, quantitative) as a white solid.

$^1$H NMR (400 MHz, CDCl$_3$): δ ppm 7.70 (d, 1H), 7.36 (d, 1H), 6.99 (d, 1H), 6.97-6.92 (m, 2H), 4.22 (q, 2H), 3.92 (s, 3H), 1.40 (t, 3H); ESMS: m/z [M$^+$+1] 277.04.

Example 50

2-Fluoro-6-[[(E)-2-(4-phenylphenyl)ethenyl]sulfonylamino]benzenesulfonamide

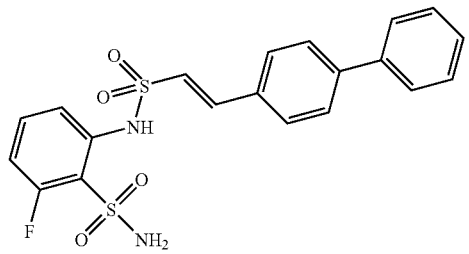 [SMILES: NS(=O)(=O)c1c(F)cccc1NS(=O)(=O)/C=C/c1ccc(-c2ccccc2)cc1]

2-Amino-6-fluoro-benzenesulfonamide (38 mg, 200 µmol) and (E)-2-(4-phenylphenyl)ethenesulfonyl chloride (56 mg, 200 µmol) were dissolved in pyridine (1.5 mL) and the reaction mixture was shaken for 12 h. The solvent was removed in vacuum and the residues were purified by HPLC to give the product (16.6 mg, 19%).

MS m/z M−H 431, Rf 1.1 min (see above system in General procedure for Examples 23 to 43).

The compounds of Examples 51 to 68 were prepared using the general procedure described for Example 50.

Example 51

2-[[(E)-2-(3-Chlorophenyl)ethenyl]sulfonylamino]-5-fluoro-benzenesulfonamide

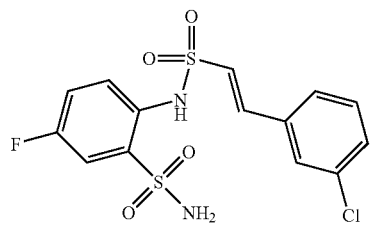 [SMILES: NS(=O)(=O)c1cc(F)ccc1NS(=O)(=O)/C=C/c1cccc(Cl)c1]

35 mg, 45%.

$^1$H NMR (400 MHz, DMSO-d$_6$) δ ppm 9.06 (br. s., 1H), 7.90 (br. s., 2H), 7.80 (br. s., 1H), 7.56-7.72 (m, 3H), 7.38-7.56 (m, 5H); MS m/z M−H 389.

Example 52

5-Fluoro-2-[[(E)-2-(4-phenylphenyl)ethenyl]sulfonylamino]benzenesulfonamide

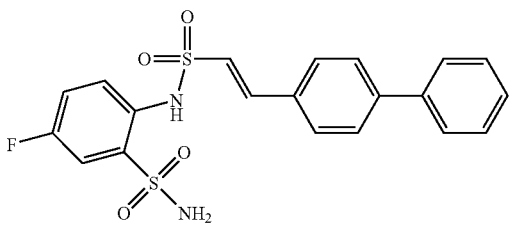 [SMILES: NS(=O)(=O)c1cc(F)ccc1NS(=O)(=O)/C=C/c1ccc(-c2ccccc2)cc1]

30 mg, 35%.
$^1$H NMR (400 MHz, DMSO-d$_6$) δ ppm 9.03 (br. s., 1H), 7.92 (br. s., 2H), 7.44-7.76 (m, 12H), 7.35-7.44 (m, 2H); MS m/z M−H 431.

Example 53

4-Fluoro-2-[[(E)-2-(4-phenylphenyl)ethenyl]sulfonylamino]benzenesulfonamide

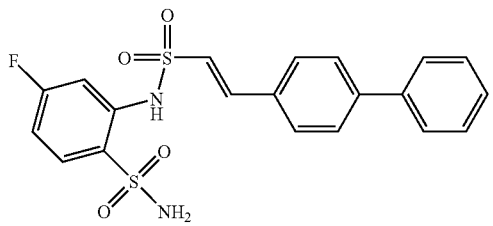 [SMILES: NS(=O)(=O)c1ccc(F)cc1NS(=O)(=O)/C=C/c1ccc(-c2ccccc2)cc1]

10 mg, 12%.
$^1$H NMR (400 MHz, DMSO-d$_6$) δ ppm 9.23 (br. s., 1H), 7.64-7.95 (m, 10H), 7.35-7.57 (m, 5H), 7.14 (br. s., 1H); MS m/z M−H 431.

Example 54

5-Fluoro-2-[[(E)-2-[3-(trifluoromethyl)phenyl]ethenyl]sulfonylamino]-benzenesulfonamide

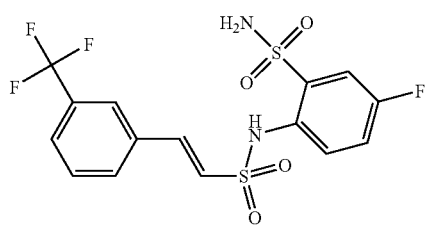 [SMILES: NS(=O)(=O)c1cc(F)ccc1NS(=O)(=O)/C=C/c1cccc(C(F)(F)F)c1]

10 mg, 11%.

$^1$H NMR (400 MHz, DMSO-d$_6$) δ ppm 9.09 (br. s., 1H), 8.09 (s, 1H), 7.97 (d, 1H), 7.89 (br. s., 2H), 7.78 (d, 1H), 7.44-7.71 (m, 6H); MS m/z M−H 423.

Example 55

5-Fluoro-2-[[(E)-2-(2-methoxyphenyl)ethenyl]sulfonylamino]benzenesulfonamide

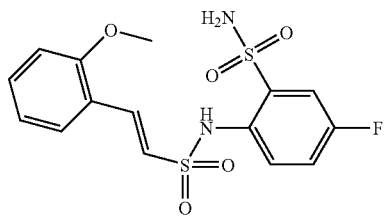 [SMILES: COc1ccccc1/C=C/S(=O)(=O)Nc1ccc(F)cc1S(N)(=O)=O]

13 mg, 16%.
$^1$H NMR (400 MHz, DMSO-d$_6$) δ ppm 8.95 (s, 1H), 7.91 (br. s., 2H), 7.55-7.68 (m, 4H), 7.47-7.55 (m, 1H), 7.43 (t, 1H), 7.32 (d, 1H), 7.08 (d, 1H), 6.97 (t, 1H), 3.84 (s, 3H); MS m/z M−H 385.

Example 56

2-[[(E)-2-(3-Chlorophenyl)ethenyl]sulfonylamino]-6-fluoro-benzenesulfonamide

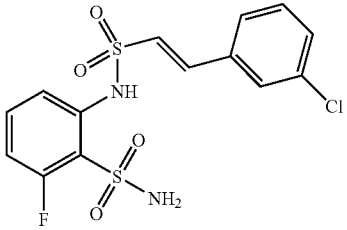 [SMILES: NS(=O)(=O)c1c(F)cccc1NS(=O)(=O)/C=C/c1cccc(Cl)c1]

25 mg, 32%.
$^1$H NMR (400 MHz, DMSO-d$_6$) δ ppm 9.86 (s, 1H), 8.15 (br. s., 2H), 7.88 (br. s., 1H), 7.34-7.77 (m, 7H), 7.12 (t, 1H); MS m/z M+H 391, M−H 389.

Example 57

2-Fluoro-6-[[(E)-2-(2-methoxyphenyl)ethenyl]sulfonylamino]benzenesulfonamide

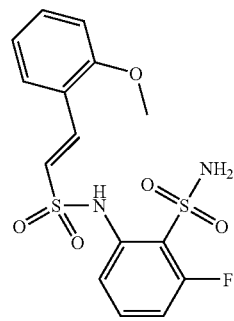 [SMILES: COc1ccccc1/C=C/S(=O)(=O)Nc1cccc(F)c1S(N)(=O)=O]

11 mg, 14%.

$^1$H NMR (400 MHz, DMSO-d$_6$) δ ppm 9.78 (s, 1H), 8.15 (s, 2H), 7.75 (d, 1H), 7.66 (d, 1H), 7.56-7.64 (m, 1H), 7.42-7.49 (m, 1H), 7.31-7.40 (m, 2H), 7.05-7.16 (m, 2H), 6.98 (t, 1H), 3.87 (s, 3H); MS m/z M+H 387, M−H 385.

Example 58

4-Fluoro-2-[[(E)-2-(2-methoxyphenyl)ethenyl]sulfonylamino]benzenesulfonamide

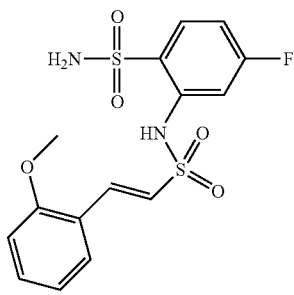 [SMILES: COc1ccccc1/C=C/S(=O)(=O)Nc1cc(F)ccc1S(N)(=O)=O]

12 mg, 16%.

$^1$H NMR (400 MHz, DMSO-d$_6$) δ ppm 9.15 (br. s., 1H), 6.91-7.96 (m, 11H), 3.86 (s, 3H); MS m/z M+H 387, M−H 385.

Example 59

3-Fluoro-2-[[(E)-2-(4-phenylphenyl)ethenyl]sulfonylamino]benzenesulfonamide

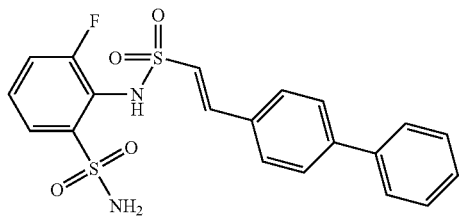 [SMILES: NS(=O)(=O)c1cccc(F)c1NS(=O)(=O)/C=C/c1ccc(-c2ccccc2)cc1]

22 mg, 25%.

$^1$H NMR (400 MHz, DMSO-d$_6$) δ ppm 9.25 (br. s., 1H), 7.67-7.82 (m, 7H), 7.34-7.63 (m, 9H); MS m/z M−H 431.

Example 60

3-Fluoro-2-[[(E)-2-(2-methoxyphenyl)ethenyl]sulfonylamino]benzenesulfonamide

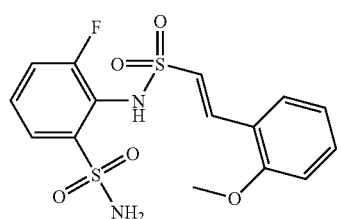

31 mg, 40%.

$^1$H NMR (400 MHz, DMSO-d$_6$) δ ppm 9.17 (br. s., 1H), 7.74 (d, 1H), 7.63 (d, 1H), 7.41-7.61 (m, 6H), 7.37 (d, 1H), 7.11 (d, 1H), 7.02 (t, 1H), 3.87 (s, 3H); MS m/z M+H 387, M−H 385.

Example 61

4-Fluoro-2-[[(E)-2-[3-(trifluoromethyl)phenyl]ethenyl]sulfonylamino]benzenesulfonamide

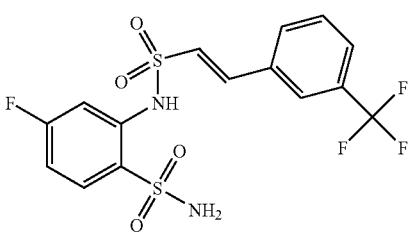 [SMILES: NS(=O)(=O)c1ccc(F)cc1NS(=O)(=O)/C=C/c1cccc(C(F)(F)F)c1]

9 mg, 10%.

$^1$H NMR (400 MHz, DMSO-d$_6$) δ ppm 9.28 (br. s., 1H), 8.14 (br. s., 1H), 8.01 (d, 1H), 7.61-7.93 (m, 7H), 7.39 (d, 1H), 7.15 (br. s., 1H); MS m/z M−H 423.

Example 62

2-Fluoro-6-[[(E)-2-(2-fluorophenyl)ethenyl]sulfonylamino]benzenesulfonamide

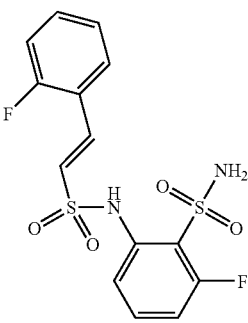 [SMILES: NS(=O)(=O)c1c(F)cccc1NS(=O)(=O)/C=C/c1ccccc1F]

36 mg, 48%.

$^1$H NMR (400 MHz, DMSO-d$_6$) δ ppm 9.83 (s, 1H), 8.14 (br. s., 2H), 7.83 (t, 1H), 7.57-7.68 (m, 2H), 7.44-7.57 (m, 2H), 7.39 (d, 1H), 7.23-7.35 (m, 2H), 7.14 (t, 1H); MS m/z M+H 375, M−H 373.

Example 63

2-[[(E)-2-(3-Chlorophenyl)ethenyl]sulfonylamino]-5-methyl-benzenesulfonamide

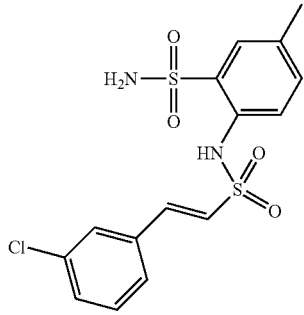 [SMILES: Cc1ccc(NS(=O)(=O)/C=C/c2cccc(Cl)c2)c(S(N)(=O)=O)c1]

31 mg, 41%.
¹H NMR (400 MHz, DMSO-d₆) δ ppm 9.04 (s, 1H), 7.80 (br. s., 1H), 7.74 (br. s., 2H), 7.59-7.66 (m, 2H), 7.37-7.55 (m, 6H), 2.29 (s, 3H); MS m/z M+H 387, M−H 385.

Example 64

2-[[(E)-2-(3-Chlorophenyl)ethenyl]sulfonylamino]-3-fluoro-benzenesulfonamide

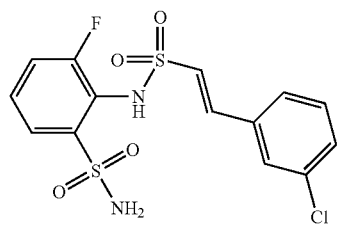 [SMILES: NS(=O)(=O)c1cccc(F)c1NS(=O)(=O)/C=C/c1cccc(Cl)c1]

40 mg, 51%. MS m/z M+H 391, M−H 389, Rf 0.8 min (see above system in General procedure for Examples 23-43).

Example 65

3-Fluoro-2-[[(E)-2-[3-(trifluoromethyl)phenyl]ethenyl]sulfonylamino]benzenesulfonamide

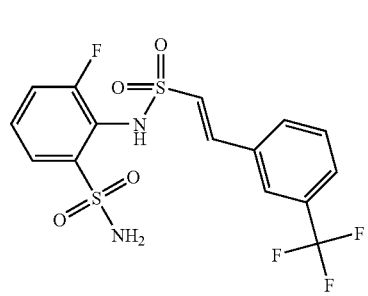 [SMILES: NS(=O)(=O)c1cccc(F)c1NS(=O)(=O)/C=C/c1cccc(C(F)(F)F)c1]

14 mg, 16%.

¹H NMR (400 MHz, DMSO-d₆) δ ppm 9.32 (br. s., 1H), 8.09 (s, 1H), 8.00 (d, 1H), 7.79 (d, 1H), 7.74 (d, 1H), 7.68 (t, 1H), 7.45-7.63 (m, 6H); MS m/z M+H 425, M−H 423.

Example 66

2-Fluoro-6-[[(E)-2-[3-(trifluoromethyl)phenyl]ethenyl]sulfonylamino]benzenesulfonamide

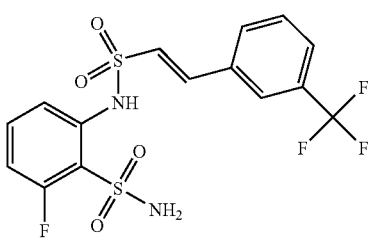 [SMILES: NS(=O)(=O)c1c(F)cccc1NS(=O)(=O)/C=C/c1cccc(C(F)(F)F)c1]

9 mg, 10%.
¹H NMR (400 MHz, DMSO-d₆) δ ppm 9.87 (s, 1H), 8.11-8.21 (m, 3H), 8.03 (d, 1H), 7.55-7.84 (m, 5H), 7.41 (d, 1H), 7.12 (t, 1H); MS m/z M+H 425, M−H 423.

Example 67

4-Fluoro-2-[[(E)-2-(2-fluorophenyl)ethenyl]sulfonylamino]benzenesulfonamide

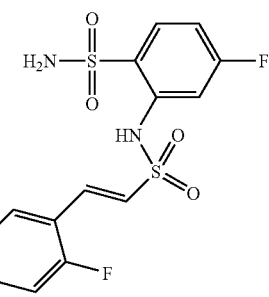

27 mg, 37%. MS m/z M+H 375, M−H 373, 0.8 min (see above system in General procedure for Examples 23-43).

Example 68

5-Methyl-2-[[(E)-2-[3-(trifluoromethyl)phenyl]ethenyl]sulfonylamino]benzenesulfonamide

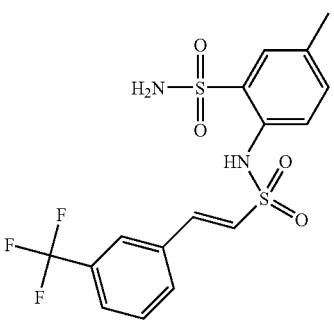 [SMILES: Cc1ccc(NS(=O)(=O)/C=C/c2cccc(C(F)(F)F)c2)c(S(N)(=O)=O)c1]

9 mg, 10%.

¹H NMR (400 MHz, DMSO-d₆) δ ppm 9.06 (s, 1H), 8.09 (s, 1H), 7.96 (d, 1H), 7.71-7.82 (m, 3H), 7.49-7.69 (m, 5H), 7.40 (d, 1H), 2.29 (s, 3H); MS m/z M−H 419.

Example 69

2-[2-(4-Cyclopentylphenyl)ethylsulfonylamino]benzenesulfonamide

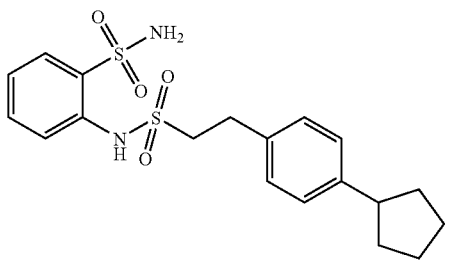 [SMILES: NS(=O)(=O)c1ccccc1NS(=O)(=O)CCc1ccc(C2CCCC2)cc1]

(E)-2-(2-(4-Cyclopentenylphenyl)vinylsulfonamido)benzenesulfonamide (25.00 mg, 0.06 mmol) was dissolved in EtOAc (1.6 mL) and MeOH (1.6 mL) and hydrogenated under continuous flow hydrogenation conditions (full hydrogen, flow 1 ml/min, ethyl acetate/methanol 1:1 as eluent) at 50° C. using an H-Cube system. The solvent was removed in vacuo and the residue was purified by column chromatography on silica using heptane/ethyl acetate gradient mixtures as eluent (0-100% ethyl acetate) to give the product as a solid (14 mg, 55%).
¹H NMR (400 MHz, DMSO-d₆) δ ppm 8.93 (s, 1H), 7.81-7.91 (m, 3H), 7.68 (d, 1H), 7.61 (t, 1H), 7.33 (t, 1H), 7.06-7.16 (m, 4H), 3.51-3.60 (m, 2H), 2.83-2.99 (m, 3H), 1.90-2.00 (m, 2H), 1.67-1.79 (m, 2H), 1.55-1.68 (m, 2H), 1.39-1.52 (m, 2H); MS m/z M−H 407.

Example 70

2-[2-(4-Tert-butylphenyl)ethylsulfonylamino]benzenesulfonamide

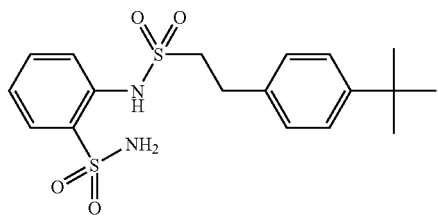 [SMILES: CC(C)(C)c1ccc(CCS(=O)(=O)Nc2ccccc2S(N)(=O)=O)cc1]

2-Aminobenzenesulfonamide (0.057 g, 0.33 mmol) was dissolved in pyridine (2.5 mL) followed by addition of (E)-2-(4-tert-butylphenyl)ethenesulfonyl chloride (0.078 g, 0.30 mmol) and the reaction was stirred at RT overnight. The solvent was then removed under reduced pressure and the pale yellow oily residue was used in the next step without further purification. The crude material (0.118 g, 0.3 mmol) was dissolved in MeOH (5 mL) with a few drops of EtOAc and was subjected to reduction using the H-cube instrument. The reaction mixture was eluted through the Pd/C (10%) cartridge using full hydrogen (1 atm) at 1 ml/min. The mixture was subjected to the H-cube once again using the same conditions for full conversion of the starting material and purified by preparative HPLC (XTerra MS C8 column, acetonitrile/ammonium acetate buffer) to give the title compound (56 mg, 47%) as a white solid.
¹H NMR (400 MHz, CDCl₃) δ ppm 7.97 (dd, 1H), 7.56-7.66 (m, 2H), 7.27-7.35 (m, 3H), 7.13 (d, 2H), 3.52-3.58 (m, 2H), 3.17-3.23 (m, 2H), 1.30 (s, 9H). MS m/z M−H 395.

a) (E)-2-(4-tert-Butylphenyl)ethenesulfonyl chloride

The title compound (0.65 g, 16%) was synthesized by an analogous method to that described for the preparation of Example 9a.
¹H NMR (400 MHz, CDCl₃) δ ppm 7.73 (d, 1H), 7.50 (s, 4H), 7.21 (d, 1H), 1.35 (s, 9H); (GC) MS m/z M+H 259.

b) 1-[(E)-2-Ethoxysulfonylethenyl]-4-tert-butyl-benzene

The title compound (4.12 g, 62%) was synthesized by an analogous method to that described for the preparation of Example 9b.
¹H NMR (400 MHz, CDCl₃) δ ppm 7.60 (d, 1H), 7.46 (s, 4H), 6.71 (d, 1H), 4.22 (q, 2H), 1.40 (t, 3H), 1.34 (s, 9H). (GC) MS m/z M+H 269.

Example 71

4-Fluoro-2-[2-(4-tert-butylphenyl)ethylsulfonylamino]benzenesulfonamide

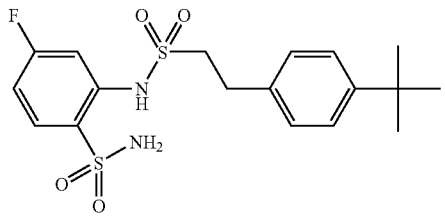 [SMILES: CC(C)(C)c1ccc(CCS(=O)(=O)Nc2cc(F)ccc2S(N)(=O)=O)cc1]

The title compound (31 mg, 25%) was synthesized by the analogous method to that described for Example 70.
¹H NMR (400 MHz, CDCl₃) δ ppm 8.42 (s, 1H), 7.97 (dd, 1H), 7.41 (dd, 1H), 7.30-7.36 (m, 2H), 7.11-7.16 (m, 2H), 6.93-6.99 (m, 1H), 5.07 (s, 2H), 3.49-3.58 (m, 2H), 3.15-3.22 (m, 2H), 1.30 (s, 9H). MS m/z M−H 413.

Example 72

2-[2-(4-Chlorophenyl)ethylsulfonylamino]benzenesulfonamide

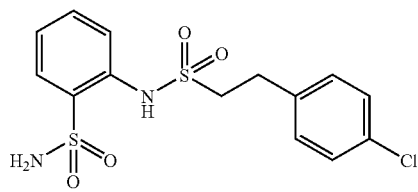 [SMILES: NS(=O)(=O)c1ccccc1NS(=O)(=O)CCc1ccc(Cl)cc1]

2-Aminobenzenesulfonamide (0.52 g, 3 mmol) was dissolved in pyridine (20 mL) followed by addition of 2-(4- chlorophenyl)ethanesulfonyl chloride (0.80 g, 3.3 mmol) and the reaction was stirred at RT overnight. The solvent was then removed under reduced pressure and the crude material was purified by preparative HPLC (XTerra MS C8 column, acetonitrile/ammonium acetate buffer) to give the title compound (87 mg, 8%) as a white solid.

¹H NMR (400 MHz, DMSO-d₆) δ ppm 8.95 (br. s., 1H), 7.81-7.90 (m, 3H), 7.67 (d, 1H), 7.60 (t, 1H), 7.28-7.35 (m, 3H), 7.21-7.27 (m, 2H), 3.55-3.63 (m, 2H), 2.95-3.02 (m, 2H); MS m/z M−H 373.

The compounds of Examples 73, 75 to 78, 80 to 84 and 88 to 106 were prepared using the general method described for Example 72.

Example 73

2-[[(E)-2-(4-Chlorophenyl)ethenyl]sulfonylamino]benzenesulfonamide

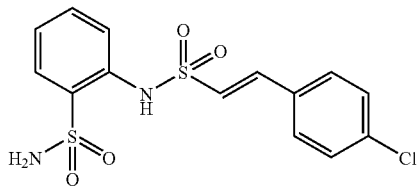 [SMILES: NS(=O)(=O)c1ccccc1NS(=O)(=O)/C=C/c1ccc(Cl)cc1]

283 mg, 76%.

¹H NMR (400 MHz, DMSO-d₆) δ ppm 9.13 (s, 1H), 7.84 (s, 2H), 7.79-7.85 (m, 1H), 7.70 (d, 2H), 7.54-7.64 (m, 3H), 7.49 (d, 2H), 7.46 (d, 1H), 7.28 (t, 1H). MS m/z M−H 372.

Example 74

2-(Phenethylsulfonylamino)benzenesulfonamide

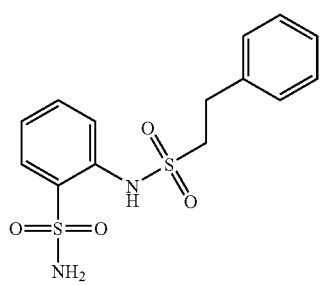 [SMILES: NS(=O)(=O)c1ccccc1NS(=O)(=O)CCc1ccccc1]

2-[[(E)-2-Phenylethenyl]sulfonylamino]benzenesulfonamide (0.052 g, 0.15 mmol) was dissolved in MeOH (5 mL) followed by the addition of 10% Pd/C (30 mg). The solution was subjected to hydrogen overnight at 40° C. After filtration, the crude product was purified by preparative HPLC (XTerra MS C8 column, acetonitrile/ammonium acetate buffer) to give the title compound (4 mg, 8%) as a white solid.

¹H NMR (400 MHz, CDCl₃) δ ppm 8.26 (br. s, 1H), 7.98 (dd, 1H), 7.56-7.68 (m, 2H), 7.24-7.35 (m, 4H), 7.16-7.24 (m, 2H), 5.14 (br. s., 2H), 3.52-3.60 (m, 2H), 3.19-3.27 (m, 2H). MS m/z M−H 339.

Example 75

2-[[(E)-2-Phenylethenyl]sulfonylamino]benzenesulfonamide

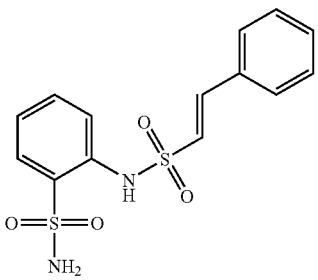 [SMILES: NS(=O)(=O)c1ccccc1NS(=O)(=O)/C=C/c1ccccc1]

90 mg, 42%.

¹H NMR (400 MHz, DMSO-d₆) δ ppm 9.12 (s, 1H), 7.85 (s, 2H), 7.82 (d, 1H), 7.52-7.70 (m, 5H), 7.36-7.47 (m, 4H), 7.26 (t, 1H). LC-MS, m/z, M−H 337, M+H, 339, Rf 2.99 min.

Example 76

2-[2-(2-Chlorophenyl)ethylsulfonylamino]benzenesulfonamide

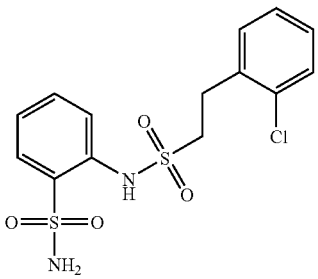 [SMILES: NS(=O)(=O)c1ccccc1NS(=O)(=O)CCc1ccccc1Cl]

104 mg, 23%.

¹H NMR (400 MHz, CD₃CN) δ ppm 7.89 (dd, 1H), 7.69-7.73 (m, 1H), 7.56-7.61 (m, 1H), 7.29-7.37 (m, 2H), 7.19-7.28 (m, 3H), 3.49-3.56 (m, 2H), 3.17-3.24 (m, 2H). MS m/z M+H 375.

Example 77

2-[[(E)-2-(4-Methoxyphenyl)ethenyl]sulfonylamino]benzenesulfonamide

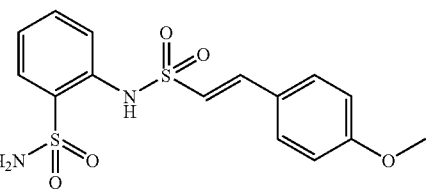

19 mg, 30%.

¹H NMR (400 MHz, CDCl₃) δ ppm 8.35 (s, 1H), 7.89-8.02 (m, 1H), 7.52-7.69 (m, 3H), 7.41-7.52 (m, 2H), 6.89-6.98 (m, 2H), 6.73-6.86 (m, 2H), 5.10 (s, 2H), 3.79-3.94 (m, 3H). MS m/z M−H 367.

Example 78

2-[[(E)-2-(4-Chlorophenyl)ethenyl]sulfonylamino]-4-fluoro-benzenesulfonamide

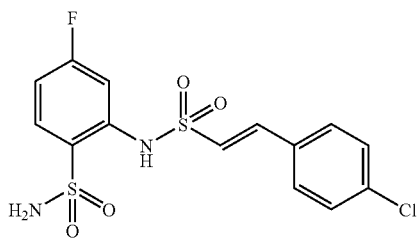 [SMILES: NS(=O)(=O)c1ccc(F)cc1NS(=O)(=O)/C=C/c1ccc(Cl)cc1]

164 mg, 45%.
¹H NMR (400 MHz, CD₃CN) δ ppm 7.79 (dd, 1H), 7.52-7.56 (m, 2H), 7.49 (d, 1H), 7.37-7.42 (m, 2H), 7.32 (dd, 1H), 7.03 (d, 1H), 6.70 (ddd, 1H). MS m/z M−H 389.

Example 79

2-(2-Phenylpropylsulfonylamino)benzenesulfonamide

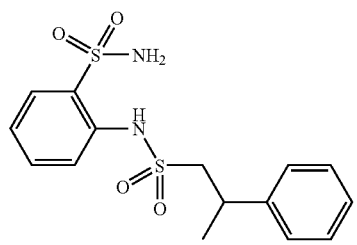 [SMILES: CC(CS(=O)(=O)Nc1ccccc1S(N)(=O)=O)c1ccccc1]

A mixture of 2-[[(E)-2-(4-chlorophenyl)prop-1-enyl]sulfonylamino]benzenesulfonamide and 2-[2-(4-chlorophenyl)prop-2-enylsulfonylamino]benzenesulfonamide (40 mg, 0.11 mmol) was dissolved in methanol (3 ml) and subjected to the H-cube (1 ml/min, full hydrogen. 10% Pd/C, 2 runs). The product obtained was purified by preparative HPLC (XTerra MS C8 column, acetonitrile/ammonium acetate buffer) to give the title compound (13 mg, 32%) as a white solid.
¹H NMR (400 MHz, CDCl₃) δ ppm 7.93 (ddd, 1H), 7.51-7.60 (m, 2H), 7.18-7.34 (m, 6H), 3.58-3.68 (m, 1H), 3.45-3.57 (m, 2H), 1.51 (d, 3H). MS m/z M−H 353.

Example 80

2-[[(E)-2-(4-Chlorophenyl)ethenyl]sulfonylamino]-6-fluoro-benzenesulfonamide

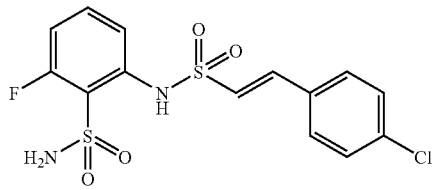 [SMILES: NS(=O)(=O)c1c(F)cccc1NS(=O)(=O)/C=C/c1ccc(Cl)cc1]

147 mg, 89%.
¹H NMR (400 MHz, CD₃CN) δ ppm 7.53-7.59 (m, 3H), 7.48-7.52 (m, 1H), 7.44-7.47 (m, 1H), 7.40-7.44 (m, 2H), 7.04 (d, 1H), 6.91-6.98 (m, 1H). MS m/z M−H 389.

Example 81

2-[[(E)-2-(2,6-Dichlorophenyl)ethenyl]sulfonylamino]benzenesulfonamide

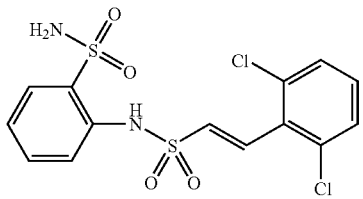 [SMILES: NS(=O)(=O)c1ccccc1NS(=O)(=O)/C=C/c1c(Cl)cccc1Cl]

140 mg, 69%.
¹H NMR (400 MHz, CD₃CN) δ ppm 7.88 (dd, 1H), 7.74 (dd, 1H), 7.64 (d, 1H), 7.60 (ddd, 1H), 7.40-7.45 (m, 2H), 7.32 (ddd, 1H), 7.27 (ddd, 1H), 7.11 (d, 1H).). MS m/z M−H 405.

Example 82

2-[[(E)-2-(4-Methylphenyl)ethenyl]sulfonylamino]benzenesulfonamide

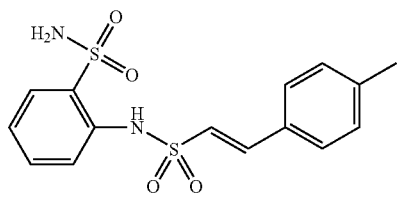 [SMILES: Cc1ccc(/C=C/S(=O)(=O)Nc2ccccc2S(N)(=O)=O)cc1]

143 mg, 81%.
¹H NMR (400 MHz, CD₃CN) δ ppm 7.85 (dd, 1H), 7.67 (dd, 1H), 7.58 (d, 1H), 7.56 (ddd, 1H), 7.41-7.47 (m, 2H), 7.18-7.26 (m, 3H), 7.00 (d, 1H), 2.34 (s, 3H). MS m/z M−H 351.

Example 83

2-[[(E)-2-(2-Methoxyphenyl)ethenyl]sulfonylamino]benzenesulfonamide

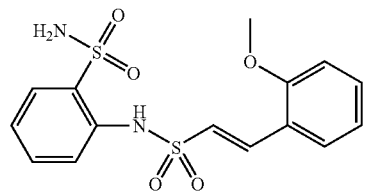 [SMILES: COc1ccccc1/C=C/S(=O)(=O)Nc1ccccc1S(N)(=O)=O]

158 mg, 86%.
$^1$H NMR (400 MHz, CD$_3$CN) δ ppm 7.86 (dd, 1H), 7.73 (d, 1H), 7.68 (dd, 1H), 7.57 (ddd, 1H), 7.48 (dd, 1H), 7.42 (ddd, 1H), 7.23 (ddd, 1H), 7.21 (d, 1H), 7.03 (d, 1H), 6.97 (td, 1H), 3.87 (s, 3H). MS m/z M−H 367.

Example 84

2-[[(E)-2-Naphthalen-2-ylethenyl]sulfonylamino]benzenesulfonamide

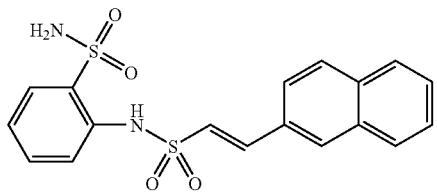 [SMILES: NS(=O)(=O)c1ccccc1NS(=O)(=O)/C=C/c1ccc2ccccc2c1]

111 mg, 57%.
$^1$H NMR (400 MHz, CD$_3$CN) δ ppm 8.05-8.09 (m, 1H), 7.87-7.93 (m, 3H), 7.86 (dd, 1H), 7.77 (d, 1H), 7.72 (dd, 1H), 7.66 (dd, 1H), 7.53-7.61 (m, 3H), 7.22 (ddd, 1H), 7.18 (d, 1H). MS m/z M−H 387.

Example 85

2-[2-(4-Chlorophenyl)ethylsulfonylamino]-4-fluoro-benzenesulfonamide

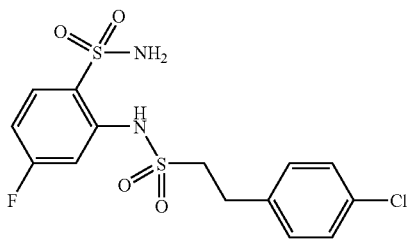 [SMILES: NS(=O)(=O)c1ccc(F)cc1NS(=O)(=O)CCc1ccc(Cl)cc1]

2-[[(E)-2-(4-Chlorophenyl)ethenyl]sulfonylamino]-4-fluoro-benzenesulfonamide (120 mg, 0.31 mmol) was dissolved in ethyl acetate (5 ml) and subjected to the H-cube (1 ml/min, full hydrogen. 10% Pd/C). The product obtained was purified by preparative HPLC (XTerra MS C8 column, acetonitrile/ammonium acetate buffer) to give the title compound (60 mg, 49%) as a white solid.

$^1$H NMR (400 MHz, CD$_3$CN) δ ppm 7.92 (dd, 1H), 7.44 (dd, 1H), 7.25-7.31 (m, 2H), 7.16-7.24 (m, 2H), 6.98 (ddd, 1H), 3.54-3.61 (m, 2H), 3.07-3.13 (m, 2H). MS m/z M−H 391.

Example 86

2-[[(E)-2-(4-Chlorophenyl)prop-1-enyl]sulfonylamino]benzenesulfonamide

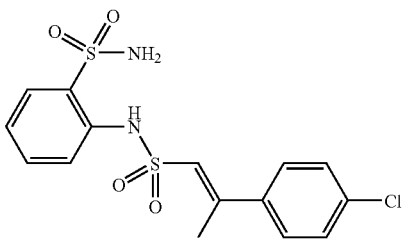 [SMILES: C/C(=C\S(=O)(=O)Nc1ccccc1S(N)(=O)=O)c1ccc(Cl)cc1]

Sulfuryl chloride (60 mmol) was added dropwise to stirred anhydrous DMF (4.6 mL) cooled to 0° C. under nitrogen. After the addition was completed, the mixture was warmed to RT and stirred further for 0.5 h. 4-Chloro-α-methylstyrene (0.25 mol) was then slowly added and the reaction mixture was run overnight at 45° C. The reaction mixture was cooled and then poured onto crushed ice and then extracted with Et$_2$O, washed with brine and dried over Na$_2$SO$_4$. After solvent removal, the residue was purified by chromatography (silica gel, eluents: ethyl acetate/heptane) to furnish a mixture of 2-(4-chlorophenyl)prop-2-ene-1-sulfonyl chloride and 2-(4-chlorophenyl)prop-1-ene-1-sulfonyl chloride (2.17 g, 29%) as a white solid.

The title compound (72 mg, 14%) and the compound of Example 87 were then prepared using the general method described for Example 72.

$^1$H NMR (400 MHz, CD$_3$CN) δ ppm 7.87 (ddd, 1H), 7.65 (ddd, 1H), 7.56 (ddd, 1H), 7.36-7.45 (m, 4H), 7.23 (ddd, 1H), 6.73 (q, 1H), 2.45 (d, 3H). MS m/z M−H 385.

Example 87

2-[2-(4-Chlorophenyl)prop-2-enylsulfonylamino]benzenesulfonamide

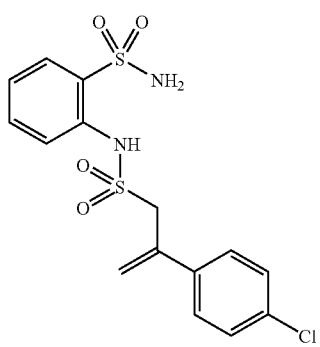 [SMILES: C=C(CS(=O)(=O)Nc1ccccc1S(N)(=O)=O)c1ccc(Cl)cc1]

The title compound (26 mg, 5%) was obtained from the synthesis in Example 86.

1H NMR (400 MHz, CD$_3$CN) δ ppm 7.84 (ddd, 1H), 7.66 (dd, 1H), 7.58 (ddd, 1H), 7.39-7.43 (m, 2H), 7.27-7.31 (m, 2H), 7.24 (ddd, 1H), 5.70 (s, 1H), 5.39 (s, 1H), 4.50 (d, 2H). MS m/z M−H 385.

Example 88

2-Fluoro-6-[[(E)-2-naphthalen-2-ylethenyl]sulfonylamino]benzenesulfonamide

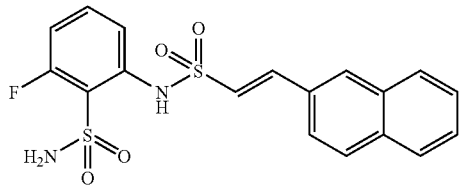 [SMILES: NS(=O)(=O)c1c(F)cccc1NS(=O)(=O)/C=C/c1ccc2ccccc2c1]

31 mg, 38%.
$^1$H NMR (400 MHz, DMSO-d$_6$) δ ppm 9.88 (s, 1H), 8.27 (s, 1H), 8.16 (s, 2H), 7.90-7.98 (m, 3H), 7.6 (d, 1H), 7.81 (d, 1H), 7.53-7.65 (m, 4H), 7.44 (d, 1H), 7.10 (t, 1H). MS m/z M−H 405.

Example 89

2-Fluoro-6-[[(E)-2-[2-(trifluoromethyl)phenyl]ethenyl]sulfonylamino]benzenesulfonamide

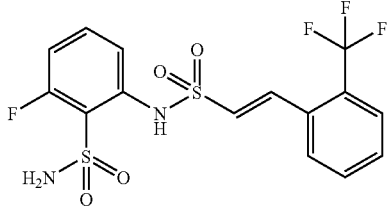 [SMILES: NS(=O)(=O)c1c(F)cccc1NS(=O)(=O)/C=C/c1ccccc1C(F)(F)F]

35 mg, 41%.
$^1$H NMR (400 MHz, DMSO-d$_6$) δ ppm 9.85 (br. s., 1H), 8.14 (br. s., 2H), 7.95 (d, 1H), 7.82 (d, 1H), 7.53-7.77 (m, 5H), 7.37 (d, 1H), 7.16 (t, 1H). MS m/z M−H 423.

Example 90

2-Fluoro-6-[[(E)-2-[4-(trifluoromethyl)phenyl]ethenyl]sulfonylamino]benzenesulfonamide

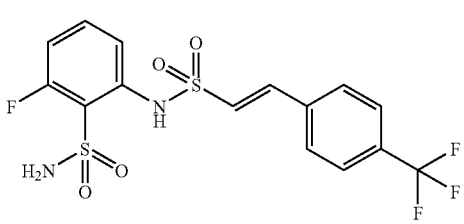 [SMILES: NS(=O)(=O)c1c(F)cccc1NS(=O)(=O)/C=C/c1ccc(C(F)(F)F)cc1]

34 mg, 40%.

$^1$H NMR (400 MHz, DMSO-d$_6$) δ ppm 9.85 (br. s., 1H), 8.15 (s, 2H), 7.95 (d, 2H), 7.79 (d, 2H), 7.76 (d, 1H), 7.52-7.69 (m, 2H), 7.41 (d, 1H), 7.13 (t, 1H). MS m/z M−H 423.

Example 91

2-[[(E)-2-(4-Bromophenyl)ethenyl]sulfonylamino]-6-fluoro-benzenesulfonamide

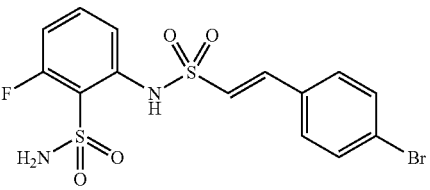 [SMILES: NS(=O)(=O)c1c(F)cccc1NS(=O)(=O)/C=C/c1ccc(Br)cc1]

31 mg, 36%.
$^1$H NMR (400 MHz, DMSO-d$_6$) δ ppm 9.83 (s, 1H), 8.15 (s, 2H), 7.55-7.71 (m, 6H), 7.51 (d, 1H), 7.39 (d, 1H), 7.11 (t, 1H). MS m/z M−H 433/435.

Example 92

4-Fluoro-2-[[(E)-2-naphthalen-2-ylethenyl]sulfonylamino]benzenesulfonamide

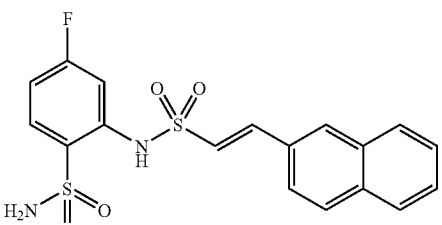

30 mg, 37%.
$^1$H NMR (400 MHz, DMSO-d$_6$) δ ppm 9.26 (br. s., 1H), 8.25 (s, 1H), 7.75-8.00 (m, 8H), 7.52-7.67 (m, 3H), 7.42 (dd, 1H), 7.02-7.20 (m, 1H). MS m/z M−H 405.

Example 93

4-Fluoro-2-[[(E)-2-[2-(trifluoromethyl)phenyl]ethenyl]sulfonylamino]benzenesulfonamide

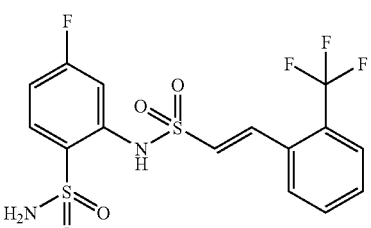

16 mg, 19%.

¹H NMR (400 MHz, DMSO-d₆) δ ppm 9.33 (br. s., 1H), 7.93 (d, 1H), 7.82-7.92 (m, 1H), 7.81 (d, 2H), 7.62-7.77 (m, 4H), 7.49-7.59 (m, 1H), 7.34 (d, 1H), 7.10-7.22 (m, 1H). MS m/z M−H 423.

Example 94

4-Fluoro-2-[[(E)-2-[4-(trifluoromethyl)phenyl]ethenyl]sulfonylamino]benzenesulfonamide

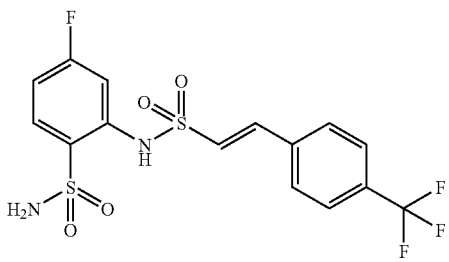 [SMILES: NS(=O)(=O)c1ccc(F)cc1NS(=O)(=O)/C=C/c1ccc(C(F)(F)F)cc1]

23 mg, 27%.
ESMS: m/z [M−1] 423, [M+1] 425, Rf 0.96 min according to the general MS procedure described for Examples 23-43.

Example 95

2-[[(E)-2-(4-Bromophenyl)ethenyl]sulfonylamino]-4-fluoro-benzenesulfonamide

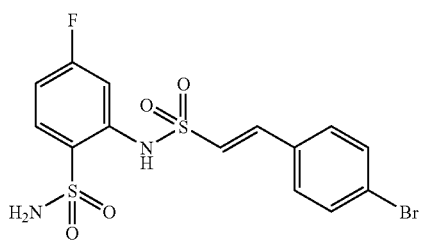 [SMILES: NS(=O)(=O)c1ccc(F)cc1NS(=O)(=O)/C=C/c1ccc(Br)cc1]

26 mg, 30%.
¹H NMR (400 MHz, DMSO-d₆) δ ppm 9.23 (br. s., 1H), 7.77-7.94 (m, 3H), 7.59-7.73 (m, 5H), 7.52 (d, 1H), 7.37 (d, 1H), 7.01-7.22 (m, 1H). MS m/z M−H 433/435.

Example 96

5-Methyl-2-[[(E)-2-naphthalen-2-ylethenyl]sulfonylamino]benzenesulfonamide

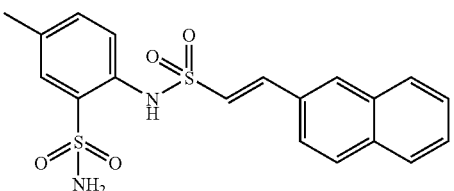

40 mg, 49%.
¹H NMR (400 MHz, DMSO-d₆) δ ppm 9.04 (s, 1H), 8.19 (s, 1H), 7.89-7.96 (m, 3H), 7.77 (d, 1H), 7.76 (s, 2H), 7.67 (d, 1H), 7.63 (s, 1H), 7.53-7.61 (m, 3H), 7.48 (d, 1H), 7.40 (d, 1H), 2.27 (s, 3H). MS m/z M−H 401.

Example 97

5-Methyl-2-[[(E)-2-[4-(trifluoromethyl)phenyl]ethenyl]sulfonylamino]benzenesulfonamide

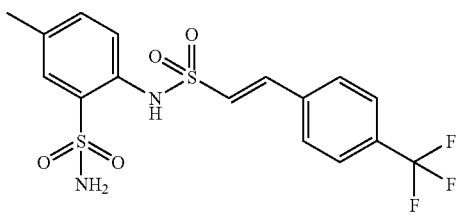 [SMILES: Cc1ccc(NS(=O)(=O)/C=C/c2ccc(C(F)(F)F)cc2)c(S(N)(=O)=O)c1]

42 mg, 50%.
¹H NMR (400 MHz, DMSO-d₆) δ ppm 9.06 (s, 1H), 7.87 (d, 2H), 7.77 (d, 2H), 7.73 (s, 2H), 7.65 (s, 1H), 7.60 (d, 1H), 7.48-7.56 (m, 2H), 7.40 (d, 1H), 2.28 (s, 3H). MS m/z M−H 419.

Example 98

2-[[(E)-2-(4-Bromophenyl)ethenyl]sulfonylamino]-5-methyl-benzenesulfonamide

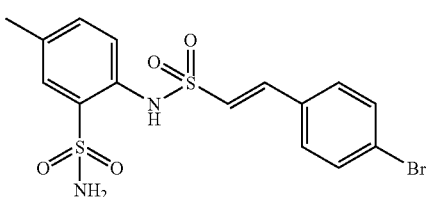

40 mg, 46%.
¹H NMR (400 MHz, DMSO-d₆) δ ppm 9.01 (s, 1H), 7.74 (s, 2H), 7.64 (s, 1H), 7.57-7.63 (m, 4H), 7.51 (d, 1H), 7.50 (d, 1H), 7.39 (d, 1H), 7.40 (d, 1H), 2.29 (s, 3H). MS m/z M−H 429/431.

Example 99

5-Fluoro-2-[[(E)-2-naphthalen-2-ylethenyl]sulfonylamino]benzenesulfonamide

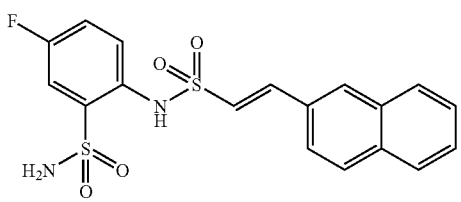 [SMILES: NS(=O)(=O)c1cc(F)ccc1NS(=O)(=O)/C=C/c1ccc2ccccc2c1]

34 mg, 41%.

¹H NMR (400 MHz, DMSO-d₆) δ ppm 9.06 (s, 1H), 8.19 (s, 1H), 7.88-7.99 (m, 5H), 7.78 (d, 1H), 7.43-7.72 (m, 7H). MS m/z M−H 405.

Example 100

5-Fluoro-2-[[(E)-2-[2-(trifluoromethyl)phenyl]ethenyl]sulfonylamino]benzenesulfonamide

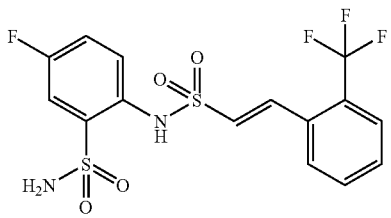 [SMILES: NS(=O)(=O)c1cc(F)ccc1NS(=O)(=O)/C=C/c1ccccc1C(F)(F)F]

31 mg, 36%.
¹H NMR (400 MHz, DMSO-d₆) δ ppm 9.15 (br. s., 1H), 7.90 (d, 1H), 7.86 (br. s., 2H), 7.80 (d, 1H), 7.73 (t, 1H), 7.58-7.68 (m, 3H), 7.49-7.57 (m, 2H), 7.42 (d, 1H). MS m/z M−H 423.

Example 101

5-Fluoro-2-[[(E)-2-[4-(trifluoromethyl)phenyl]ethenyl]sulfonylamino]benzenesulfonamide

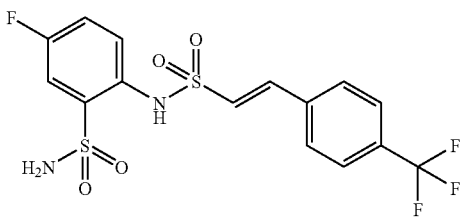 [SMILES: NS(=O)(=O)c1cc(F)ccc1NS(=O)(=O)/C=C/c1ccc(C(F)(F)F)cc1]

31 mg, 37%.
¹H NMR (400 MHz, DMSO-d₆) δ ppm 9.11 (br. s., 1H), 7.83-7.95 (m, 4H), 7.74-7.81 (m, 2H), 7.45-7.69 (m, 5H). MS m/z M−H 423.

Example 102

2-[[(E)-2-(4-Bromophenyl)ethenyl]sulfonylamino]-5-fluoro-benzenesulfonamide

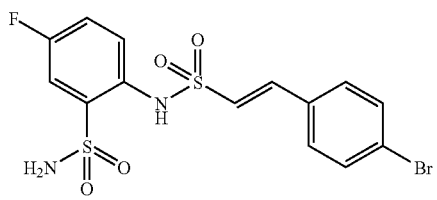 [SMILES: NS(=O)(=O)c1cc(F)ccc1NS(=O)(=O)/C=C/c1ccc(Br)cc1]

32 mg, 36%.

¹H NMR (400 MHz, DMSO-d₆) δ ppm 9.04 (s, 1H), 7.89 (br. s., 2H), 7.58-7.68 (m, 6H), 7.48 (d, 1H), 7.44-7.53 (m, 1H), 7.40 (d, 1H). MS m/z M−H 433/435.

Example 103

2-[[(E)-2-(2,6-Difluorophenyl)ethenyl]sulfonylamino]benzenesulfonamide

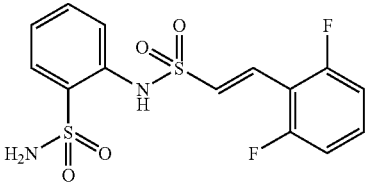 [SMILES: NS(=O)(=O)c1ccccc1NS(=O)(=O)/C=C/c1c(F)cccc1F]

18 mg, 24%.
¹H NMR (400 MHz, DMSO-d₆) δ ppm 9.11 (s, 1H), 7.84 (d, 1H), 7.78 (br. s., 2H), 7.59-7.64 (m, 2H), 7.51-7.59 (m, 1H), 7.42 (d, 1H), 7.39 (d, 1H), 7.28-7.35 (m, 1H), 7.18-7.26 (m, 2H). MS m/z M−H 373.

Example 104

2-[[(E)-2-[2-(Trifluoromethyl)phenyl]ethenyl]sulfonylamino]benzenesulfonamide

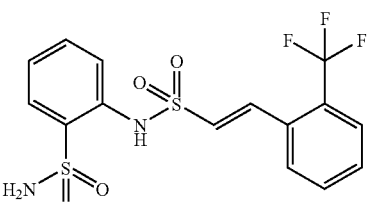

31 mg, 38%.
¹H NMR (400 MHz, DMSO-d₆) δ ppm 9.19 (br. s., 1H), 7.89 (d, 1H), 7.83 (d, 1H), 7.76-7.82 (m, 3H), 7.73 (t, 1H), 7.56-7.67 (m, 4H), 7.49 (d, 1H), 7.28-7.35 (m, 1H). MS m/z M−H 405.

Example 105

2-[[(E)-2-[4-(Trifluoromethyl)phenyl]ethenyl]sulfonylamino]benzenesulfonamide

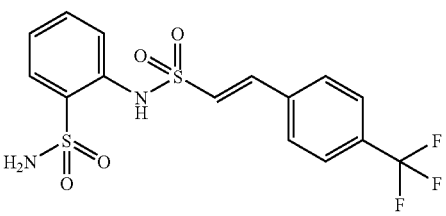 [SMILES: NS(=O)(=O)c1ccccc1NS(=O)(=O)/C=C/c1ccc(C(F)(F)F)cc1]

35 mg, 43%.

ESMS: m/z [M−1] 405, [M+1] 407, Rf 1.00 min. according to the general MS procedure for Examples 23-43.

Example 106

2-[[(E)-2-(4-Bromophenyl)ethenyl]sulfonylamino]benzenesulfonamide

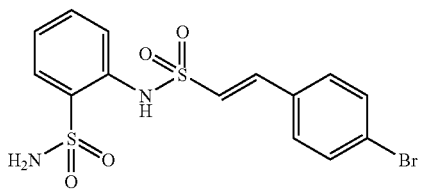 [SMILES: NS(=O)(=O)c1ccccc1NS(=O)(=O)/C=C/c1ccc(Br)cc1]

36 mg, 43%.

¹H NMR (400 MHz, DMSO-d₆) δ ppm 9.12 (s, 1H), 7.83 (d, 1H), 7.81 (s, 2H), 7.53-7.64 (m, 7H), 7.45 (d, 1H), 7.27 (t, 1H). MS m/z M−H 415/417.

Example 107

2-[(E)-2-(4-Bromophenyl)ethylsulfonylamino]benzenesulfonamide

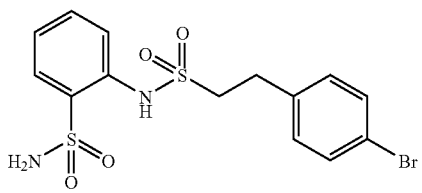 [SMILES: NS(=O)(=O)c1ccccc1NS(=O)(=O)CCc1ccc(Br)cc1]

To a solution of (E)-2-(2-(4-bromophenyl)vinylsulfonamido)benzenesulfonamide (0.063 g, 0.15 mmol) in THF (10 mL) were added 4-methylbenzenesulfonohydrazide (1.676 g, 9.00 mmol) and sodium acetate (0.738 g, 9.00 mmol). (J. Org. Chem. 2006, 5870). The mixture was heated at reflux under argon overnight, quenched with water (5 mL), and extracted three times with ethyl acetate. The combined organic phases were extracted with 1M HCl, washed with water, brine and followed by organic solvent removal. The brine phase was then extracted three times with ethyl acetate. The combined organic solvent was then removed under reduced pressure and the crude product was purified by preparative HPLC (XTerra MS C8 column, acetonitrile/ammonium acetate buffer) to give the title compound (25 mg, 40%) as a white solid.

¹H NMR (400 MHz, DMSO-d₆) δ ppm 8.94 (s, 1H), 7.79-7.94 (m, 3H), 7.56-7.72 (m, 2H), 7.39-7.50 (m, 2H), 7.26-7.38 (m, 1H), 7.15-7.24 (m, 2H), 3.53-3.67 (m, 2H), 2.90-3.02 (m, 2H). MS m/z M−H 417/419.

Example 108

2-[2-(4-Chlorophenyl)propylsulfonylamino]benzenesulfonamide

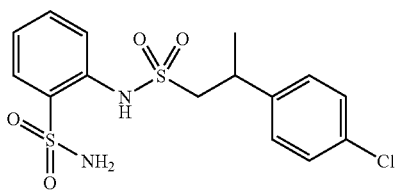 [SMILES: CC(CS(=O)(=O)Nc1ccccc1S(N)(=O)=O)c1ccc(Cl)cc1]

A mixture of (E)-2-(2-(4-chlorophenyl)prop-1-enylsulfonamido)benzenesulfonamide and 2-[2-(4-chlorophenyl)prop-2-enylsulfonylamino]benzenesulfonamide (100 mg, 0.26 mmol) was dissolved in EtOAc in a 5 mL syringe. The solution was filtered and injected into the H-cube (1 ml/min, full hydrogen. 10% Pd/C). The solvent was then removed under reduced pressure and the crude material was purified by preparative HPLC (XTerra MS C8 column, acetonitrile/ammonium acetate buffer) to give the title compound (56 mg, 56%).

¹H NMR (400 MHz, CDCl₃) δ ppm 8.20 (s, 1H), 7.94 (dd, 1H), 7.48-7.62 (m, 2H), 7.21-7.32 (m, 3H), 7.08-7.18 (m, 2H), 5.07 (s, 2H), 3.53-3.64 (m, 1H), 3.42-3.54 (m, 2H), 1.48 (d, 3H). MS m/z M−H 387.

Example 109

2-[2-(2-Methoxyphenyl)ethylsulfonylamino]benzenesulfonamide

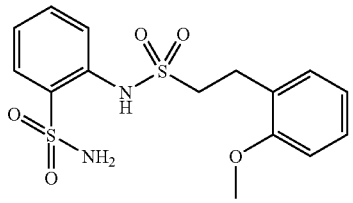 [SMILES: COc1ccccc1CCS(=O)(=O)Nc1ccccc1S(N)(=O)=O]

(E)-2-(2-(2-Methoxyphenyl)vinylsulfonamido)benzenesulfonamide (94 mg, 0.26 mmol) was dissolved in methanol (5 mL) in a 5 mL syringe. The solution was injected to the H-cube (1 ml/min, full hydrogen; 10% Pd/C). The solvent was then removed under reduced pressure and the crude material was purified by preparative HPLC (XTerra MS C8 column, acetonitrile/ammonium acetate buffer) to give the title compound (69 mg, 73%).

¹H NMR (400 MHz, CDCl₃) δ ppm 8.28 (s, 1H), 7.98 (dd, 1H), 7.66 (dd, 1H), 7.56-7.62 (m, 1H), 7.27-7.32 (m, 1H), 7.21-7.27 (m, 1H), 7.16 (dd, 1H), 6.90 (td, 1H), 6.84 (dd, 1H), 5.23 (s, 2H), 3.75 (s, 3H), 3.53-3.63 (m, 2H), 3.15-3.25 (m, 2H). MS m/z M−H 369.

Example 110

2-(2-Naphthalen-2-ylethylsulfonylamino)benzenesulfonamide

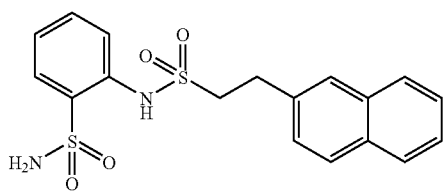 [SMILES: NS(=O)(=O)c1ccccc1NS(=O)(=O)CCc1ccc2ccccc2c1]

The title compound (45 mg, 50%) was synthesized using the general method described for Example 108.

$^1$H NMR (400 MHz, CD$_3$CN) δ ppm 7.85 (dd, 1H), 7.66-7.76 (m, 4H), 7.63 (s, 1H), 7.50 (ddd, 1H), 7.30-7.39 (m, 2H), 7.28 (dd, 1H), 7.17 (ddd, 1H), 3.54-3.64 (m, 2H), 3.12-3.23 (m, 2H). MS m/z M−H 389.

Example 111

4-Fluoro-2-(2-naphthalen-2-ylethylsulfonylamino)benzenesulfonamide

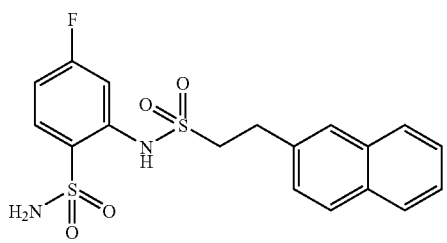 [SMILES: NS(=O)(=O)c1ccc(F)cc1NS(=O)(=O)CCc1ccc2ccccc2c1]

The title compound (13 mg, 27%) was synthesized using the general method described for Example 70.

$^1$H NMR (400 MHz, CD$_3$CN) δ ppm 7.89 (dd, 1H), 7.67-7.77 (m, 3H), 7.66 (s, 1H), 7.48 (dd, 1H), 7.27-7.40 (m, 3H), 6.92 (ddd, 1H), 3.64-3.73 (m, 2H), 3.14-3.27 (m, 2H). MS m/z M−H 407.

Example 112

2-[(4-Chlorophenyl)methylsulfonylamino]benzenesulfonamide

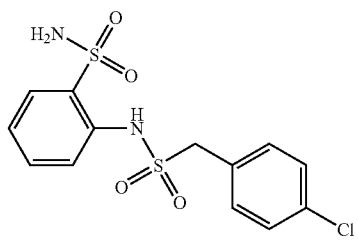 [SMILES: NS(=O)(=O)c1ccccc1NS(=O)(=O)Cc1ccc(Cl)cc1]

The title compound (89 mg, 49%) was synthesized using the general procedure described for Example 72.

$^1$H NMR (400 MHz, CD$_3$CN) δ ppm 7.86-7.90 (m, 1H), 7.51-7.56 (m, 2H), 7.29-7.36 (m, 4H), 7.24-7.28 (m, 1H), 4.57 (s, 2H). MS m/z M−H 359.

Example 113

2-[[3-(2,3-Dichlorophenyl)phenyl]sulfonylamino]benzenesulfonamide

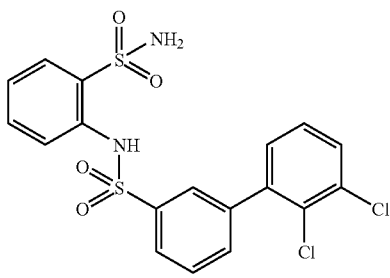 [SMILES: NS(=O)(=O)c1ccccc1NS(=O)(=O)c1cccc(-c2cccc(Cl)c2Cl)c1]

Tetrakis(triphenylphosphine)palladium(0) (14 mg, 0.012 mmol), was added to a solution of 2,3-dichlorophenylboronic acid (57 mg, 0.30 mmol) and 2-[(3-bromophenyl)-sulfonylamino]benzenesulfonamide (97 mg, 0.25 mmol) in DMF (1 mL). The reaction mixture was stirred at RT under argon for 15 minutes before addition of 2M Na$_2$CO$_3$ (0.5 mL). The reaction was stirred overnight at 90° C., filtered and purified by preparative HPLC (XTerra MS C8 column, acetonitrile/ammonium acetate buffer) to give the title compound (61 mg, 53%) as a white solid.

$^1$H NMR (400 MHz, Acetone-d$_6$) δ ppm 7.97-8.01 (m, 2H), 7.80-7.89 (m, 1H), 7.60-7.74 (m, 4H), 7.47-7.52 (m, 2H), 7.42 (d, 1H), 7.15 (t, 1H). MS m/z M−H 455/457/459.

a) 2-[(3-Bromophenyl)sulfonylamino]benzenesulfonamide

3-Bromo-benzenesulfonyl chloride (8.34 mL, 57.9 mmol) was added to a solution of 2-amino-benzenesulfonamide (9.965 g, 57.9 mmol) dissolved in pyridine (90 mL). The reaction was stirred for 4 h followed by solvent removal under vacuo. The reaction mixture was added to water and the product was extracted three times with EtOAc. The combined organic extracts were washed with brine, dried (MgSO$_4$), filtered and evaporated to furnish a dark yellow oil. The oil was dissolved in EtOAc and precipitated by addition of heptane. The solid was finally recrystallized from EtOH to give the title compound (10.784 g, 48%) as a white solid.

$^1$H NMR (400 MHz, DMSO-d$_6$) δ ppm 9.39 (br. s., 1H), 8.04 (t, 1H), 7.84-7.91 (m, 2H), 7.80 (dd, 1H), 7.76 (s, 2H), 7.51-7.58 (m, 2H), 7.49 (dd, 1H), 7.27 (t, 1H). MS m/z M−H 389/391.

The compounds of Examples 114 to 121 were prepared using the general method described for Example 113.

Example 114

2-[[3-(3,5-difluorophenyl)phenyl]sulfonylamino]benzenesulfonamide

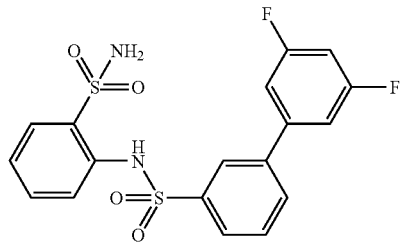 [SMILES: NS(=O)(=O)c1ccccc1NS(=O)(=O)c1cccc(-c2cc(F)cc(F)c2)c1]

33 mg, 31%.
¹H NMR (400 MHz, CD₃CN) δ ppm 8.07-8.11 (m, 1H), 7.82-7.89 (m, 2H), 7.73 (dd, 1H), 7.65-7.68 (m, 1H), 7.55-7.61 (m, 3H), 7.48-7.53 (m, 1H), 7.40-7.46 (m, 3H), 7.22-7.28 (m, 1H), 7.04-7.11 (m, 1H). MS m/z M−H 423.

Example 115

3-(5-Chloro-2-methoxy-phenyl)-N-(2-sulfamoylphenyl)benzenesulfonamide

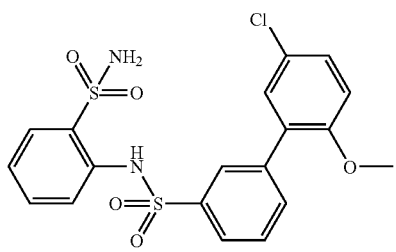 [SMILES: COc1ccc(Cl)cc1-c1cccc(S(=O)(=O)Nc2ccccc2S(N)(=O)=O)c1]

36 mg, 32%.
¹H NMR (400 MHz, CD₃CN) δ ppm 7.96-8.00 (m, 1H), 7.81 (ddd, 1H), 7.74 (dd, 1H), 7.68 (ddd, 1H), 7.65 (dd, 1H), 7.51 (dt, 1H), 7.45 (ddd, 1H), 7.28 (dd, 1H), 7.20 (d, 1H), 7.06-7.12 (m, 1H), 7.04 (d, 1H), 1.85 (s, 3H). MS m/z M−H 451.

Example 116

2-[[3-(3-Cyanophenyl)phenyl]sulfonylamino]benzenesulfonamide

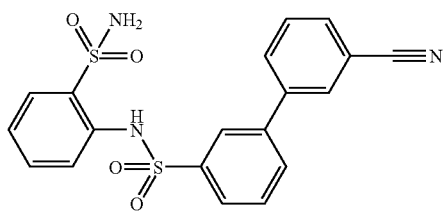 [SMILES: N#Cc1cccc(-c2cccc(S(=O)(=O)Nc3ccccc3S(N)(=O)=O)c2)c1]

48 mg, 46%.
¹H NMR (400 MHz, Acetone-d₆) δ ppm 8.25 (t, 1H), 8.07-8.09 (m, 1H), 8.03 (ddd, 1H), 7.97-8.01 (m, 2H), 7.80-7.85 (m, 2H), 7.77 (dd, 1H), 7.65-7.74 (m, 2H), 7.53 (ddd, 1H), 7.16 (ddd, 1H). MS m/z M−H 412.

Example 117

2-[[3-(4-Cyanophenyl)phenyl]sulfonylamino]benzenesulfonamide

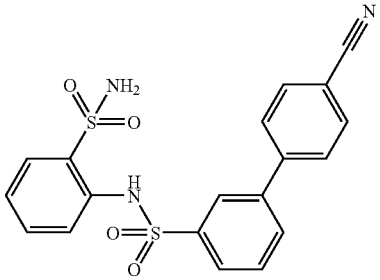 [SMILES: N#Cc1ccc(-c2cccc(S(=O)(=O)Nc3ccccc3S(N)(=O)=O)c2)cc1]

43 mg, 42%.
¹H NMR (400 MHz, Acetone-d₆) δ ppm 8.24-8.25 (m, 1H), 7.96-8.03 (m, 2H), 7.86-7.92 (m, 4H), 7.83 (dd, 1H), 7.77 (dd, 1H), 7.70 (t, 1H), 7.53 (ddd, 1H), 7.13-7.20 (m, 1H). MS m/z M−H 412.

Example 118

3-(2,4-Dimethoxypyrimidin-5-yl)-N-(2-sulfamoylphenyl)benzenesulfonamide

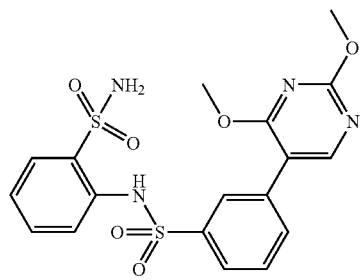 [SMILES: COc1ncc(-c2cccc(S(=O)(=O)Nc3ccccc3S(N)(=O)=O)c2)c(OC)n1]

16 mg, 17%.
¹H NMR (400 MHz, CD₃OD) δ ppm 8.25 (s, 1H), 8.02 (s, 1H), 7.85 (d, 1H), 7.82 (d, 1H), 7.68-7.77 (m, 2H), 7.55 (t, 1H), 7.49 (t, 1H), 7.18 (t, 1H), 4.04 (s, 3H), 4.03 (s, 3H). MS m/z M−H 449.

Example 119

2-[[3-(3-Furyl)phenyl]sulfonylamino]benzenesulfonamide

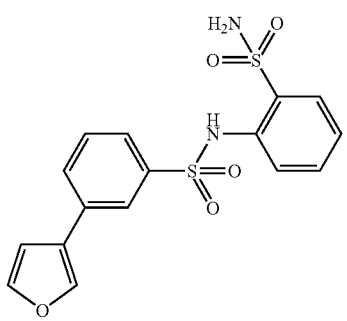 [SMILES: NS(=O)(=O)c1ccccc1NS(=O)(=O)c1cccc(-c2ccoc2)c1]

68 mg, 72%.

$^1$H NMR (400 MHz, Acetone-d$_6$) δ ppm 8.09-8.17 (m, 2H), 7.78-7.89 (m, 3H), 7.72 (dd, 1H), 7.67 (t, 1H), 7.57 (dt, 1H), 7.52 (ddd, 1H), 7.16 (ddd, 1H), 6.94 (dd, 1H).). MS m/z M−H 377.

Example 120

2-[[3-(1H-Indol-5-yl)phenyl]sulfonylamino]benzenesulfonamide

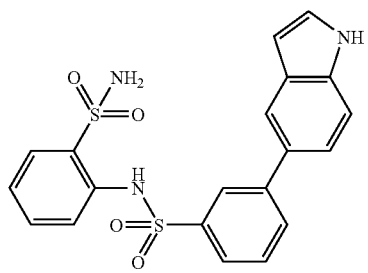 [SMILES: NS(=O)(=O)c1ccccc1NS(=O)(=O)c1cccc(-c2ccc3[nH]ccc3c2)c1]

78 mg, 73%.
$^1$H NMR (400 MHz, CD$_3$OD) δ ppm 8.10 (t, 1H), 7.77-7.88 (m, 3H), 7.76 (d, 1H), 7.71 (d, 1H), 7.53 (t, 1H), 7.47 (d, 1H), 7.45 (d, 1H), 7.33 (dd, 1H), 7.27 (d, 1H), 7.14 (t, 1H), 6.52 (dd, 1H). MS m/z M−H 426.

Example 121

2-[[3-[3-(Trifluoromethoxy)phenyl]phenyl]sulfonylamino]benzenesulfonamide

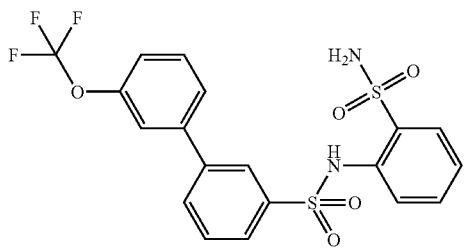 [SMILES: NS(=O)(=O)c1ccccc1NS(=O)(=O)c1cccc(-c2cccc(OC(F)(F)F)c2)c1]

65 mg, 55%.
$^1$H NMR (400 MHz, CD$_3$OD) δ ppm 8.06 (t, 1H), 7.89 (dd, 1H), 7.79-7.85 (m, 2H), 7.74 (d, 1H), 7.42-7.62 (m, 5H), 7.31 (d, 1H), 7.15 (t, 1H). MS m/z M−H 471.

Example 122

N-(2-Sulfamoylphenyl)-2,3-dihydro-1H-indene-5-sulfonamide

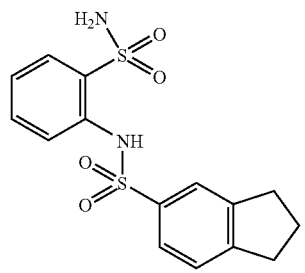 [SMILES: NS(=O)(=O)c1ccccc1NS(=O)(=O)c1ccc2c(c1)CCC2]

Indan-5-sulfonyl chloride (43 mg, 0.2 mmol) was added to a pyridine stock solution of 1.34M 2-amino-benzenesulfonamide (0.150 mL, 0.2 mmol). The reaction mixture was shaken overnight followed by solvent removal under vacuo. The crude mixture was dissolved in DMSO and purified by preparative HPLC (XTerra MS C8 column, acetonitrile/ammonium acetate buffer) to give the title compound (22 mg, 32%) as a white solid. MS m/z M−H 351. Rf 0.91 min (see above system in General procedure for Examples 23-43).

The compounds of Examples 123 to 131 were prepared using the general method described for Example 122.

Example 123

7-Methyl-N-(2-sulfamoylphenyl)-10-oxa-7-azabicyclo[4.4.0]deca-1,3,5-triene-3-sulfonamide

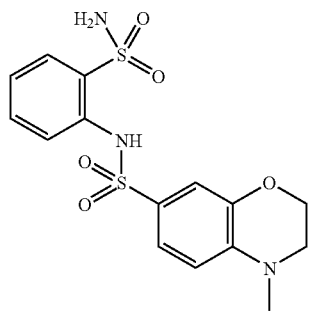 [SMILES: CN1CCOc2cc(S(=O)(=O)Nc3ccccc3S(N)(=O)=O)ccc21]

31 mg, 41%.
$^1$H NMR (400 MHz, DMSO-d$_6$) δ ppm 9.14 (s, 1H), 7.82 (s, 2H), 7.77 (d, 1H), 7.45-7.56 (m, 2H), 7.18 (ddd, 1H), 7.14 (dd, 1H), 7.10 (d, 1H), 6.77 (d, 1H), 4.20-4.28 (m, 4H), 2.82 (s, 3H). MS m/z M−H 382.

Example 124

2-(3,4-Dichlorophenyl)-N-(2-sulfamoylphenyl)benzenesulfonamide

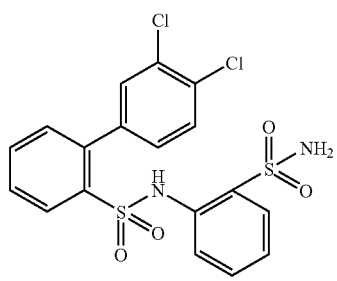 [SMILES: NS(=O)(=O)c1ccccc1NS(=O)(=O)c1ccccc1-c1ccc(Cl)c(Cl)c1]

27 mg, 30%.
$^1$H NMR (400 MHz, DMSO-d$_6$) δ ppm 9.40 (br. s., 1H), 7.90-8.05 (m, 5H), 7.76-7.86 (m, 3H), 7.74 (s, 2H), 7.54 (br. s., 2H), 7.16-7.28 (m, 1H). MS m/z M−H 455.

Example 125

2-[[4-[3-Chloro-5-(trifluoromethyl)pyridin-2-yl]oxyphenyl]sulfonylamino]benzenesulfonamide

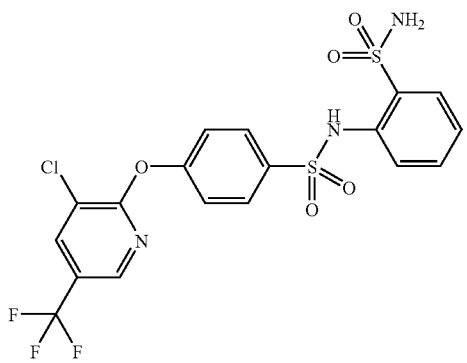 [SMILES: NS(=O)(=O)c1ccccc1NS(=O)(=O)c1ccc(Oc2ncc(C(F)(F)F)cc2Cl)cc1]

67 mg, 66%.
$^1$H NMR (400 MHz, DMSO-d$_6$) δ ppm 9.40 (br. s., 1H), 8.62 (d, 1H), 8.53-8.55 (m, 1H), 8.02 (d, 2H), 7.83 (br. s., 3H), 7.53-7.60 (m, 2H), 7.48 (d, 2H), 7.22-7.32 (m, 1H). MS m/z M−H 506.

Example 126

N-(2-Sulfamoylphenyl)tetralin-2-sulfonamide

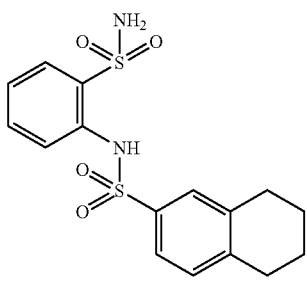 [SMILES: NS(=O)(=O)c1ccccc1NS(=O)(=O)c1ccc2c(c1)CCCC2]

48 mg, 65%.
$^1$H NMR (400 MHz, DMSO-d$_6$) δ ppm 9.28 (s, 1H), 7.82 (s, 2H), 7.77 (d, 1H), 7.65 (s, 1H), 7.60 (dd, 1H), 7.47-7.52 (m, 2H), 7.24 (d, 1H), 7.16-7.22 (m, 1H), 2.72-2.77 (m, 4H), 1.68-1.73 (m, 4H). MS m/z M−H 365.

Example 127

4-Phenylmethoxy-N-(2-sulfamoylphenyl)benzenesulfonamide

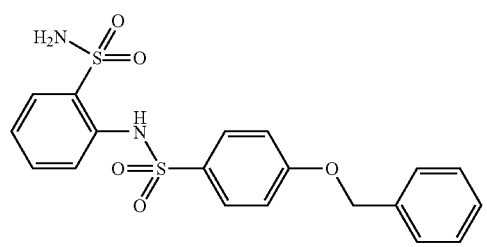 [SMILES: NS(=O)(=O)c1ccccc1NS(=O)(=O)c1ccc(OCc2ccccc2)cc1]

45 mg, 54%.

MS m/z M−H 417. Rf 1.1 min (see above system in General procedure for Examples 23 to 43).

Example 128

2-[(4-Cyclohexylphenyl)sulfonylamino]benzenesulfonamide

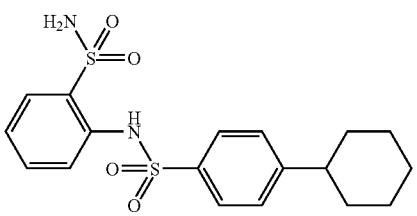 [SMILES: NS(=O)(=O)c1ccccc1NS(=O)(=O)c1ccc(C2CCCCC2)cc1]

45 mg, 57%.
MS m/z M−H 393. RF 1.12 min (see above system in General procedure for Examples 23 to 43).

Example 129

3-Phenyl-N-(2-sulfamoylphenyl)benzenesulfonamide

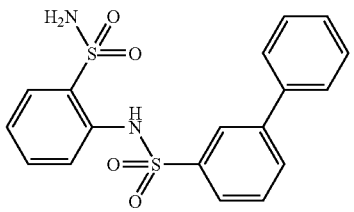 [SMILES: NS(=O)(=O)c1ccccc1NS(=O)(=O)c1cccc(-c2ccccc2)c1]

35 mg, 46%.
$^1$H NMR (400 MHz, DMSO-d$_6$) δ ppm 9.36 (br. s., 1H), 8.12 (s, 1H), 7.95 (d, 1H), 7.89 (d, 1H), 7.81 (br. s., 2H), 7.78 (d, 1H), 7.63-7.70 (m, 3H), 7.47-7.60 (m, 4H), 7.39-7.45 (m, 1H), 7.19-7.27 (m, 1H). MS m/z M−H 387.

Example 130

5-(1-Methyl-5-trifluoromethyl-1H-pyrazol-3-yl)-thiophene-2-sulfonic acid (2-sulfamoyl-phenyl)-amide

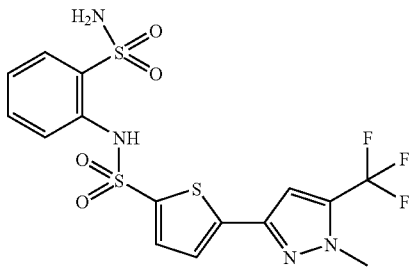 [SMILES: Cn1nc(-c2ccc(S(=O)(=O)Nc3ccccc3S(N)(=O)=O)s2)cc1C(F)(F)F]

50 mg, 53%.
MS m/z M−H 465. Rf 0.41 min (see above system in General procedure for Examples 23 to 43).

Example 131

N-(2-Sulfamoylphenyl)-4-(trifluoromethyl)benzene-sulfonamide

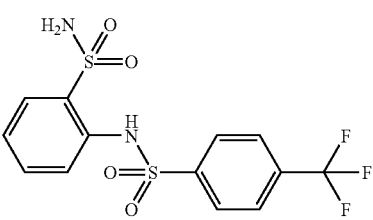 [SMILES: NS(=O)(=O)c1ccccc1NS(=O)(=O)c1ccc(C(F)(F)F)cc1]

16 mg, 22%.
$^1$H NMR (400 MHz, DMSO-d$_6$) δ ppm 9.48 (br. s., 1H), 8.07 (d, 2H), 7.92-8.02 (m, 2H), 7.67-7.85 (m, 3H), 7.47-7.60 (m, 2H), 7.22-7.35 (m, 1H). MS m/z M−H 379.

Example 132

2-[[3-(2,5-Dichlorophenyl)phenyl]sulfonylamino]benzenesulfonamide

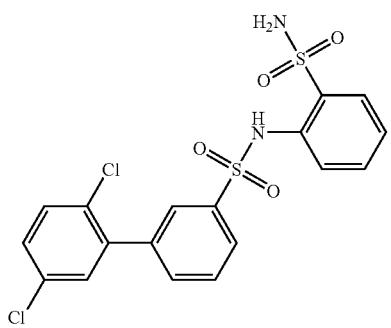 [SMILES: NS(=O)(=O)c1ccccc1NS(=O)(=O)c1cccc(-c2cc(Cl)ccc2Cl)c1]

Tetrakis(triphenylphosphine)palladium(0) (14 mg, 0.012 mmol) was added to 2,5-dichlorophenylboronic acid (57 mg, 0.30 mmol) in DMF (0.25 mL) and a DMF stock solution of 0.5M 2-[(3-bromophenyl)sulfonylamino]benzenesulfonamide (0.5 mL, 0.25 mmol). The reaction mixture was stirred at RT under argon for 15 minutes before addition of 2M Na$_2$CO$_3$ (0.5 mL). The reaction was stirred overnight at 90° C., filtered and purified by preparative HPLC (XTerra MS C8 column, acetonitrile/ammonium acetate buffer) to give the title compound (15 mg, 13%) as a white solid.

$^1$H NMR (400 MHz, DMSO-d$_6$) δ ppm 9.37 (br. s., 1H), 7.95 (d, 1H), 7.91 (s, 1H), 7.65-7.86 (m, 5H), 7.62 (d, 1H), 7.50-7.59 (m, 3H), 7.48 (d, 1H), 7.25 (t, 1H). MS m/z M−H 455.

The compounds of Examples 133 to 143 were prepared using the general method described for Example 132.

Example 133

3-Dibenzofuran-4-yl-N-(2-sulfamoylphenyl)benzene-nesulfonamide

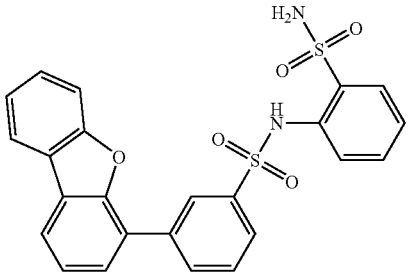 [SMILES: NS(=O)(=O)c1ccccc1NS(=O)(=O)c1cccc(-c2cccc3c2oc2ccccc23)c1]

38 mg, 32%.
$^1$H NMR (400 MHz, DMSO-d$_6$) δ ppm 9.45 (br. s., 1H), 8.43 (s, 1H), 8.20-8.27 (m, 3H), 8.00 (d, 1H), 7.76-7.87 (m, 4H), 7.70-7.75 (m, 2H), 7.64 (d, 1H), 7.52-7.60 (m, 3H), 7.46 (t, 1H), 7.24 (t, 1H) MS m/z M−H 477.

Example 134

2-[[3-[4-(Trifluoromethyl)phenyl]phenyl]sulfonylamino]benzenesulfonamide

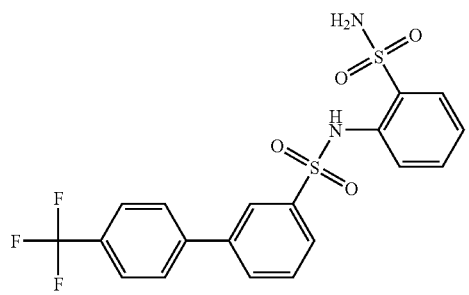 [SMILES: NS(=O)(=O)c1ccccc1NS(=O)(=O)c1cccc(-c2ccc(C(F)(F)F)cc2)c1]

36 mg, 32%.
$^1$H NMR (400 MHz, DMSO-d$_6$) δ ppm 9.37 (br. s., 1H), 8.20 (s, 1H), 8.03 (d, 1H), 7.95 (d, 1H), 7.90 (d, 2H), 7.85 (d, 2H), 7.75-7.82 (m, 3H), 7.71 (t, 1H), 7.50-7.62 (m, 2H), 7.24 (t, 1H). MS m/z M−H 455.

Example 135

3-(3-Methoxyphenyl)-N-(2-sulfamoylphenyl)benzene-nesulfonamide

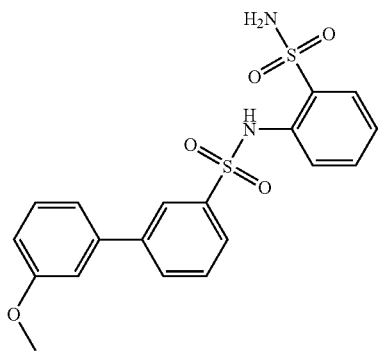

36 mg, 34%.

$^1$H NMR (400 MHz, DMSO-d$_6$) δ ppm 9.35 (s, 1H), 8.12 (s, 1H), 7.96 (d, 1H), 7.89 (d, 1H), 7.81 (s, 2H), 7.78 (d, 1H), 7.51-7.69 (m, 3H), 7.40 (t, 1H), 7.16-7.26 (m, 3H), 6.99 (dd, 1H), 3.83 (s, 3H). MS m/z M−H 417.

Example 136

3-Benzofuran-2-yl-N-(2-sulfamoylphenyl)benzenesulfonamide

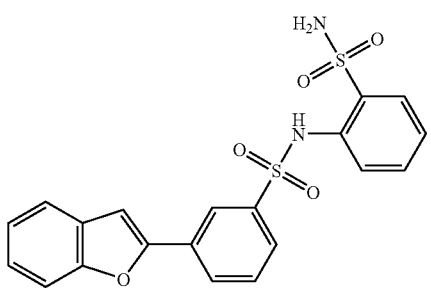

25 mg, 24%.

$^1$H NMR (400 MHz, DMSO-d$_6$) δ ppm 9.42 (br. s., 1H), 8.38 (s, 1H), 8.19 (d, 1H), 7.89 (d, 1H), 7.75-7.84 (m, 3H), 7.65-7.74 (m, 3H), 7.51-7.65 (m, 3H), 7.37 (t, 1H), 7.29 (t, 1H), 7.20-7.27 (m, 1H). MS m/z M−H 427.

Example 137

2-[[3-(2,3-Dihydrobenzofuran-5-yl)phenyl]sulfonylamino]benzenesulfonamide

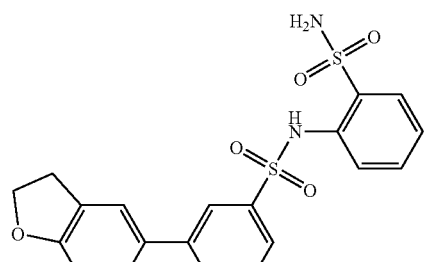

42 mg, 39%.

$^1$H NMR (400 MHz, DMSO-d$_6$) δ ppm 9.35 (s, 1H), 8.06 (s, 1H), 7.87 (d, 1H), 7.81 (br. s., 2H), 7.78 (d, 1H), 7.52-7.66 (m, 5H), 7.39 (dd, 1H), 7.23 (t, 1H), 6.86 (d, 1H), 4.58 (t, 2H), 3.23 (t, 2H). MS m/z M−H 429.

Example 138

3-(6-Methoxypyridin-3-yl)-N-(2-sulfamoylphenyl)benzenesulfonamide

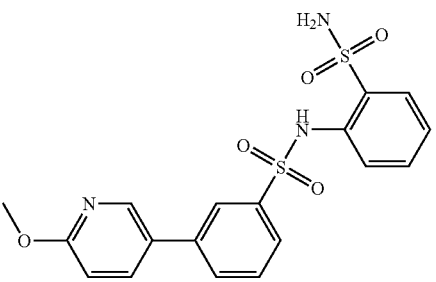

32 mg, 30%.

$^1$H NMR (400 MHz, DMSO-d$_6$) δ ppm 9.35 (br. s., 1H), 8.48 (d, 1H), 8.13 (br. s., 1H), 8.01 (dd, 1H), 7.95 (d, 1H), 7.88 (d, 1H), 7.82 (br. s., 2H), 7.77 (d, 1H), 7.66 (t, 1H), 7.50-7.61 (m, 2H), 7.23 (t, 1H), 6.94 (d, 1H), 3.91 (s, 3H). MS m/z M−H 418.

Example 139

2-[[3-(2,4-Dichlorophenyl)phenyl]sulfonylamino]benzenesulfonamide

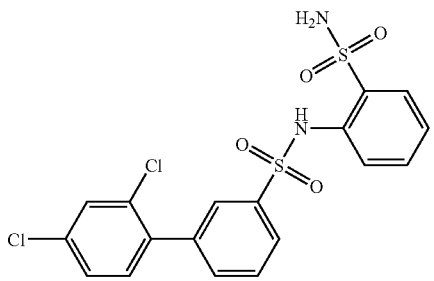

22 mg, 19%.
MS m/z M−H 455. Rf 0.55 min (see above system in General procedure for Examples 23 to 43).

Example 140

3-(1-Methylindol-2-yl)-N-(2-sulfamoylphenyl)benzenesulfonamide

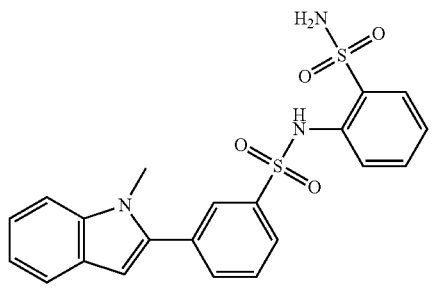

18 mg, 16%.

¹H NMR (400 MHz, DMSO-d₆) δ ppm 9.38 (br. s., 1H), 7.99 (s, 1H), 7.92 (d, 1H), 7.88 (d, 1H), 7.77-7.83 (m, 3H), 7.71 (t, 1H), 7.58 (d, 1H), 7.54-7.65 (m, 2H), 7.50 (d, 1H), 7.26 (t, 1H), 7.21 (t, 1H), 7.08 (t, 1H), 6.62 (s, 1H), 3.64 (s, 3H). MS m/z M−H 440.

Example 141

2-[[3-[3-(Trifluoromethyl)phenyl]phenyl]sulfonylamino]benzenesulfonamide

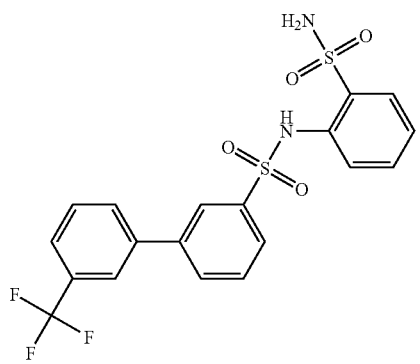

40 mg, 36%.

¹H NMR (400 MHz, DMSO-d₆) δ ppm 9.35 (br. s., 1H), 8.19 (s, 1H), 8.04 (d, 1H), 7.90-8.00 (m, 3H), 7.65-7.83 (m, 6H), 7.57-7.63 (m, 1H), 7.53 (t, 1H), 7.23 (t, 1H). MS m/z M−H 455.

Example 142

4-Benzofuran-2-yl-N-(2-sulfamoylphenyl)benzenesulfonamide

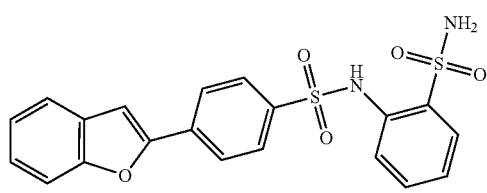 [SMILES: NS(=O)(=O)c1ccccc1NS(=O)(=O)c1ccc(-c2cc3ccccc3o2)cc1]

13 mg, 12%.

¹H NMR (400 MHz, DMSO-d₆) δ ppm 9.39 (br. s., 1H), 8.09 (d, 2H), 8.00 (d, 2H), 7.75-7.84 (m, 3H), 7.71 (d, 1H), 7.62-7.67 (m, 2H), 7.55 (br. s., 2H), 7.37 (t, 1H), 7.29 (t, 1H), 7.21-7.26 (m, 1H). MS m/z M−H 427.

Example 143

2-[[3-(2,4-Difluorophenyl)phenyl]sulfonylamino]benzenesulfonamide

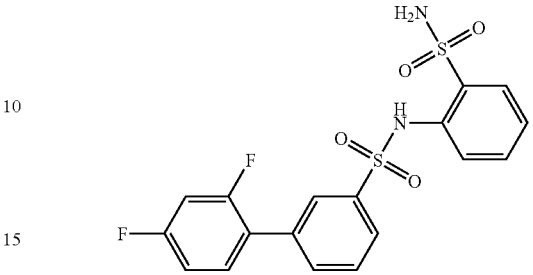

12 mg, 11%.
MS m/z M−H 423. Rf 0.59 min (see above system in General procedure for Examples 23 to 43).

Example 144

5-Bromo-2-[[3-(3,4-dichlorophenyl)phenyl]sulfonylamino]benzenesulfonamide

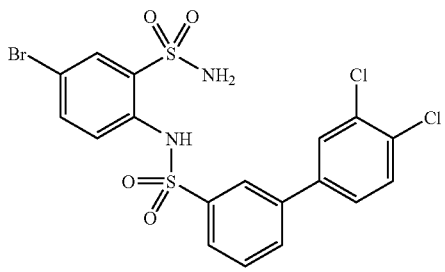 [SMILES: NS(=O)(=O)c1cc(Br)ccc1NS(=O)(=O)c1cccc(-c2ccc(Cl)c(Cl)c2)c1]

2-Amino-5-bromobenzenesulfonamide (0.60 g, 2.39 mmol) was dissolved in pyridine (6 ml) and 3-(3,4-dichlorophenyl)-phenylsulfonyl chloride (0.82 g, 2.51 mmol) was added and the reaction stirred overnight. The solvent was removed in vacuo and the residue was purified by preparative HPLC (XTerra MS C8 column, acetonitrile/ammonium acetate buffer) to give the title compound (0.70 g, 55% yield).

¹H NMR (400 MHz, DMSO-d₆) δ ppm 9.35 (br. s., 1H), 8.19 (t, 1H), 8.03 (d, 1H), 7.97 (d, 1H), 7.92 (s, 2H), 7.85-7.91 (m, 2H), 7.77 (d, 1H), 7.65-7.76 (m, 3H), 7.54 (d, 1H); MS m/z M−H 533, 535, 537.

Example 145

2-[[3-(3,4-Dichlorophenyl)phenyl]sulfonylamino]-5-phenyl-benzenesulfonamide

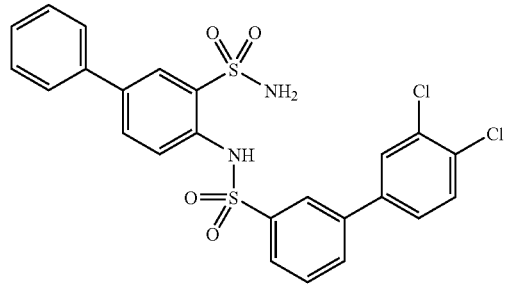 [SMILES: NS(=O)(=O)c1cc(-c2ccccc2)ccc1NS(=O)(=O)c1cccc(-c2ccc(Cl)c(Cl)c2)c1]

5-Bromo-2-[[3-(3,4-dichlorophenyl)phenyl]sulfonylamino]benzenesulfonamide (70 mg, 0.13 mmol) was dissolved in DMF (700 μl), then phenylboronic acid (20 mg, 0.16 mmol) was added followed by the addition of 2M sodium carbonate solution (260 μl). The mixture was subjected to vacuum/argon (×3), tetrakis(triphenylphosphine)palladium (8 mg, 0.05 mol %) was added and the reaction was allowed to stir at 80° C. overnight. The cooled reaction mixture was filtered and was then purified by preparative HPLC (XTerra MS C8 column, acetonitrile/ammonium acetate buffer) to give the title compound (23 mg, 32%).

$^1$H NMR (400 MHz, CD$_3$OD) δ ppm 8.07 (d, 1H), 8.04 (t, 1H), 7.91 (ddd, 1H), 7.85 (d, 1H), 7.81 (ddd, 1H), 7.76-7.79 (m, 1H), 7.72 (d, 1H), 7.59 (d, 1H), 7.53-7.58 (m, 3H), 7.48 (dd, 1H), 7.38-7.44 (m, 2H), 7.31-7.36 (m, 1H); MS m/z M−H 531, 533.

Example 146

2,3-Difluoro-N-(2-sulfamoylphenyl)benzenesulfonamide

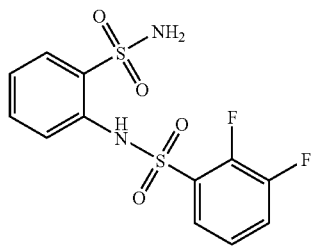

2-Aminobenzenesulfonamide (26 mg, 0.15 mmol) was dissolved in pyridine (1 ml) and 2,3-difluorophenylsulfonyl chloride (19 μl, 0.15 mmol) was added and the reaction stirred overnight. The solvent was removed in vacuo and the residue was purified by preparative HPLC (XTerra MS C8 column, acetonitrile/ammonium acetate buffer) to give the title compound (30 mg, 58%).

$^1$H NMR (400 MHz, CD$_3$OD) δ ppm 6.77-6.85 (m, 1H) 7.12-7.27 (m, 2H) 7.31-7.45 (m, 2H) 7.64-7.78 (m, 2H); MS m/z M−H 347.

Example 147

2,3-Difluoro-N-(4-fluoro-2-sulfamoyl-phenyl)benzenesulfonamide

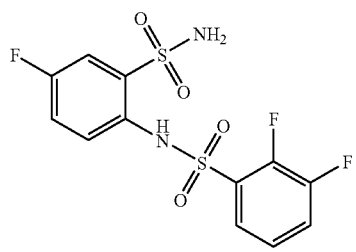

2-Amino-5-fluorobenzenesulfonamide (29 mg, 0.15 mmol) was dissolved in pyridine (1 ml) and 2,3-difluorophenylsulfonyl chloride (19 μl, 0.15 mmol) was added and the reaction stirred overnight. The solvent was removed in vacuo and the residue was purified by preparative HPLC (XTerra MS C8 column, acetonitrile/ammonium acetate buffer) to give the title compound (25 mg, 46%).

$^1$H NMR (400 MHz, CD$_3$OD) δ ppm 6.98-7.07 (m, 1H) 7.12-7.22 (m, 1H) 7.30-7.41 (m, 1H) 7.42-7.49 (m, 2H) 7.63-7.71 (m, 1H); MS m/z M−H 364.

Example 148

3-Chloro-2-fluoro-N-(2-sulfamoylphenyl)benzenesulfonamide

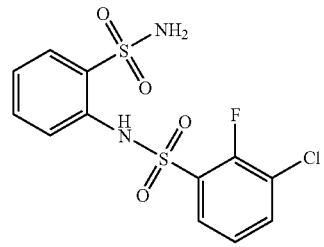

2-Aminobenzenesulfonamide (54 mg, 0.31 mmol) and 3-chloro-2-fluoro-benzenesulfonyl chloride (47 mg, 0.21 mmol) were dissolved in pyridine (1 ml) and the reaction mixture was stirred for 12 h. The solvent was removed in vacuo and the residue was purified by HPLC to give the product (15 mg, 19%).

$^1$H NMR (400 MHz, DMSO-d$_6$) δ ppm 9.72 (br. s., 1H), 7.90 (t, 1H), 7.78-7.86 (m, 2H), 7.73 (br. s., 2H), 7.51-7.58 (m, 1H), 7.46-7.51 (m, 1H), 7.39 (t, 1H), 7.26-7.34 (m, 1H); MS m/z M−H 363.

Example 149

2,3-Dichloro-N-(2-sulfamoylphenyl)benzenesulfonamide

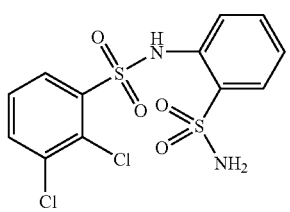 [SMILES: NS(=O)(=O)c1ccccc1NS(=O)(=O)c1cccc(Cl)c1Cl]

The title compound (56%) was synthesized using the general method described for Example 148.

$^1$H NMR (400 MHz, DMSO-d$_6$) δ ppm 9.88 (br. s., 1H), 8.19 (d, 1H), 7.99 (d, 1H), 7.80-7.92 (m, 3H), 7.63 (t, 1H), 7.48 (t, 1H), 7.31 (d, 1H), 7.24 (t, 1H); MS m/z M−H 379, 381.

Example 150

2-[[3-(3,4-Dichlorophenyl)phenyl]sulfonylamino]-5-methyl-benzenesulfonamide

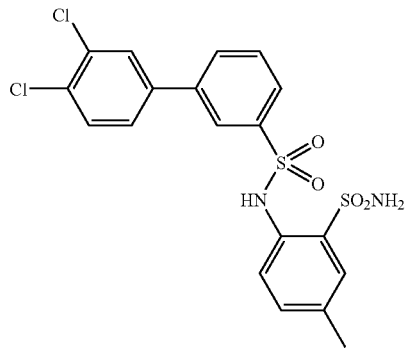 [SMILES: Cc1ccc(NS(=O)(=O)c2cccc(-c3ccc(Cl)c(Cl)c3)c2)c(S(N)(=O)=O)c1]

To a solution of 2-(3-bromobenzenesulfonylamino)-5-methyl-benzensulfonamide (1.50 g, 3.70 mmol), 3,4-dichlorobenzeneboronic acid (0.84 g, 4.44 mmol), tricyclohexyl phosphine (0.45 g, 1.60 mmol) and potassium phosphate (3 g, 14.15 mmol) in DMF (10 mL), was added Pd(OAc)$_2$ (0.17 g, 0.74 mmol). The reaction mixture was stirred at 80° C. for 10 h, diluted with 1N HCl and the product was extracted with ethyl acetate. The organic phase was separated, dried over sodium sulfate and concentrated in vacuo. The crude product was purified by flash column chromatography using ethyl acetate/hexane (1:3) to afford the title compound (0.9 g, 51%).

$^1$H NMR (400 MHz, DMSO-d$_6$): δ ppm 9.23 (s, 1H), 8.15 (s, 1H), 8.02 (d, 1H), 7.95 (d, 1H), 7.89 (d, 1H), 7.78-7.72 (m, 3H), 7.70-7.65 (m, 2H), 7.60 (d, 1H), 7.50 (d, 1H), 7.36 (d, 1H), 2.22 (s, 3H);

ESMS: m/z [M−1] 468.91 and 470.86 (Cl isotopes).

a) 2-(3-Bromobenzenesulfonylamino)-5-methyl-benzensulfonamide

To a solution of 2-amino-5-methyl-benzenesulfonamide (Example 45a) (6.0 g, 32.3 mmol) in pyridine (20 mL), 3-bromobenzenesulphonyl chloride (8.24 g, 32.3 mmol) was added portionwise at 0° C. The reaction was stirred at RT for 10 h. The pyridine was removed in vacuo at 35° C. and the residue was dissolved in ethyl acetate. The organic phase was washed with aqueous 1N HCl, water and brine, dried over sodium sulfate, and concentrated under reduced pressure. The crude product was purified by flash column chromatography using ethyl acetate/hexane (1:1) as eluent to give the title compound (8 g, 63%).

$^1$H NMR (400 MHz, DMSO-d$_6$): δ ppm 9.31 (s, 1H), 8.01 (s, 1H), 7.89-7.81 (m, 2H), 7.70 (s, 2H), 7.61 (s, 1H), 7.58-7.50 (m, 1H), 7.41-7.34 (m, 2H), 2.22 (s, 3H);

ESMS: m/z [M−1] 402.93 and 404.95 (Br isotopes).

Example 151

4-[[3-(3,4-Dichlorophenyl)phenyl]sulfonylamino]-3-sulfamoyl-benzamide

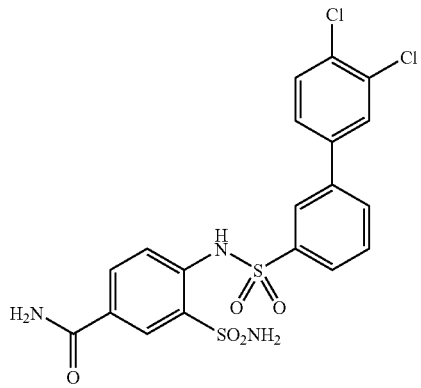 [SMILES: NC(=O)c1ccc(NS(=O)(=O)c2cccc(-c3ccc(Cl)c(Cl)c3)c2)c(S(N)(=O)=O)c1]

2-[[3-(3,4-Dichlorophenyl)phenyl]sulfonylamino]-5-methylbenzene sulfonamide (Example 150) (0.5 g, 1.06 mmol) was dissolved in 1N NaOH (50 mL). KMnO$_4$ (1 g, 6.33 mmol) was added and the reaction mixture was stirred at 80° C. for 4 h, cooled to RT and filtered through Celite. The filtrate was treated with sodium bisulphite (3 g) until a colourless solution was obtained. The reaction mixture was then acidified to pH 3 by addition of 3N HCl. The resulting white precipitate was filtered off and washed with water to give a crude product which was used in the next step without further purification.

To a solution of 4-[[3-(3,4-dichlorophenyl)phenyl]sulfonylamino]-3-sulfamoylbenzoic acid (0.20 g, 0.39 mmol) in DMF (5 mL) was added carbonyldiimidazole (0.06 g, 0.39 mmol). The reaction mixture was heated at 80° C. for 2 h, then aqueous ammonia solution (30%, 2 mL) was added and the resulting solution was stirred at RT for 2 h. The pH of the reaction mixture was then adjusted to pH 5 using 6N HCl and the resulting white precipitate was collected by filtration. The crude product was purified by preparative HPLC to afford the title compound (13 mg, 7%).

$^1$H NMR (400 MHz, acetone-D$_6$): δ ppm 9.47 (br, 1H), 8.38 (d, 1H), 8.27 (s, 1H), 8.08-8.00 (m, 3H), 7.93 (s, 1H), 7.82 (d, 1H), 7.74-7.70 (m, 3H), 7.65 (s, 1H), 7.26 (s, 2H), 6.79 (s, 1H);

ESMS: m/z [M−1] 499.72.

Example 152

5-Methyl-2-[[3-[3-(trifluoromethoxy)phenyl]phenyl]sulfonylamino]benzenesulfonamide

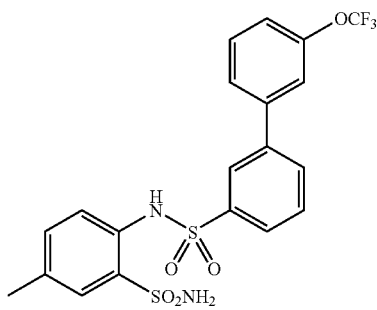 [SMILES: Cc1ccc(NS(=O)(=O)c2cccc(-c3cccc(OC(F)(F)F)c3)c2)c(S(N)(=O)=O)c1]

Pd(OAc)$_2$ (44 mg, 0.19 mmol) was added to a solution of 2-(3-bromobenzenesulfonylamino)-5-methyl-benzensulfonamide (Example 150a) (0.40 g, 0.98 mmol), 3-(trifluoromethoxy)benzeneboronic acid (0.61 g, 2.96 mmol), tricyclohexyl phosphine (82 mg, 0.29 mmol) and potassium phosphate (0.42 g, 1.19 mmol) in toluene (10 mL). A few drops of water were added and the reaction mixture was stirred at 110° C. overnight. The reaction mixture was then diluted with 1N HCl and the product was extracted with ethyl acetate. The organic phase was separated, dried over sodium sulfate and concentrated in vacuo. The crude product was purified by flash column chromatography using ethyl acetate/hexane (1:3) to afford the title compound (140 mg, 30%).

$^1$H NMR (400 MHz, DMSO-d$_6$): δ ppm 9.25 (s, 1H), 8.10 (s, 1H), 7.98 (d, 1H), 7.87 (d, 1H), 7.54-7.81 (m, 7H), 7.49 (d, 1H) 7.42 (d, 1H), 7.34 (d, 1H), 2.23 (s, 3H);

$^{19}$F NMR (400 MHz, DMSO-d$_6$): δ ppm −57.12;

ESMS: m/z 484.79 [M−1].

Example 153

2-(2,3-Dichloro-benzenesulfonylamino)-5-hydroxymethyl-benzenesulfonamide

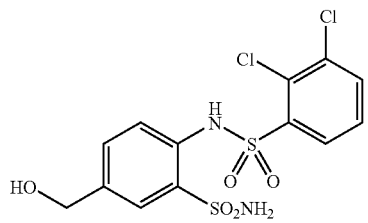 [SMILES: NS(=O)(=O)c1cc(CO)ccc1NS(=O)(=O)c1cccc(Cl)c1Cl]

Lithium aluminum hydride (1M in THF, 6.6 mL, 6.6 mmol) was added slowly to a stirred solution of 4-(2,3-dichloro-benzenesulfonylamino)-3-sulfamoyl-benzoic acid ethyl ester (600 mg, 1.32 mmol) in dry THF (15 mL) at −10° C. The reaction mixture was allowed to warm to RT and stirring was continued for 4 h. The reaction mixture was then cooled to 0° C. and quenched by addition of water, followed by 1N HCl. The product was extracted with ethyl acetate, the combined organic phases were washed with water and brine, and dried over sodium sulfate. Volatiles were removed under reduced pressure and the crude product was purified by preparative HPLC to afford the title compound (60 mg, 11%).

$^1$H NMR (400 MHz, DMSO-D$_6$): δ ppm 9.86 (br. s., 1H), 8.10-8.30 (m, 1H), 7.99 (d, 1H), 7.84 (m, 3H), 7.62 (dd, 1H), 7.39 (d, 1H), 7.28 (d, 1H), 4.44 (s, 2H), 1.84-2.22 (m, 1H);

ESMS: m/z [M−1] 408.79 and 410.75 (Cl isotopes).

a) 4-(2,3-Dichloro-benzenesulfonylamino)-3-sulfamoyl-benzoic acid ethyl ester

A solution of 4-(2,3-dichloro-benzenesulfonylamino)-3-sulfamoyl-benzoic acid (1.3 g, 3.05 mmol) in ethanol (20 mL) was stirred at RT and a few drops of thionyl chloride were added. The reaction mixture was heated at reflux for 7 h, cooled to RT and concentrated under reduced pressure. The residue was purified by flash column chromatography using ethyl acetate/hexane (1:1) as eluent to afford the title compound (1.4 g, 100%).

$^1$H NMR (400 MHz, DMSO-d$_6$): δ ppm 8.41 (d, 1H), 8.19-8.31 (m, 1H), 8.00-8.17 (m, 4H), 7.66 (dd, 1H), 7.48 (d, 1H), 4.30 (q, 2H), 1.29 (t, 3H).

b) 4-(2,3-Dichloro-benzenesulfonylamino)-3-sulfamoyl-benzoic acid 2-(2,3-Dichloro-benzenesulfonylamino)-5-methyl-benzenesulfonamide (Example 154) (186.1 mg, 0.47 mmol) was dissolved in 1N NaOH (2 mL) and water (10 mL). KMnO$_4$ (0.24 g, 1.52 mmol) was added and the reaction mixture was stirred at 70° C. for 3 h, cooled to RT and filtered through Celite. The filtrate was treated with sodium bisulphite until a colourless solution was obtained and the mixture was then acidified to pH 3 by addition of 3N HCl. The product was extracted with ethyl acetate and the organic phase was concentrated under reduced pressure. The crude product was purified by preparative HPLC to afford the title compound (124 mg, 62%).

$^1$H NMR (400 MHz, DMSO-D$_6$): δ ppm 8.41 (d, 1H), 8.24 (d, 1H), 7.93-8.11 (m, 4H), 7.66 (dd, 1H), 7.45 (d, 1H);

ESMS: m/z [M−1]: 422.72 and 424.67.

Example 154

2-(2,3-Dichloro-benzenesulfonylamino)-5-methyl-benzenesulfonamide

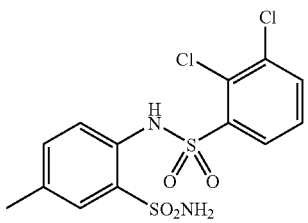 [SMILES: Cc1ccc(NS(=O)(=O)c2cccc(Cl)c2Cl)c(S(N)(=O)=O)c1]

To a solution of 2-amino-5-methyl-benzenesulfonamide (1.86 g, 1 mmol) in pyridine (20 mL), 2,3-dichlorobenzenesulphonyl chloride (3.0 g, 1.25 mmol) was added at 0° C. The reaction was stirred at RT for 17 h. The pyridine was removed in vacuo and the residue was dissolved in ethyl acetate. The organic phase was washed with aqueous 1N HCl, water and brine, dried over sodium sulfate, and concentrated under reduced pressure. The crude product was purified by flash column chromatography using ethyl acetate/hexane (1:1) as eluent to give the title compound (2.4 g, 60%).

$^1$H NMR (400 MHz, DMSO-D$_6$): δ ppm 9.77 (br. s., 1H), 8.02-8.25 (m, 1H), 7.95 (dd, 1H), 7.77 (s, 2H), 7.47-7.73 (m, 2H), 7.04-7.36 (m, 2H), 2.23 (s, 3H);

ESMS: m/z [M−1]: 392.85 and 394.67 (Cl isotopes).

Example 155

2-[[3-(3,4-Dichlorophenyl)phenyl]sulfonylamino]-5-phenoxybenzenesulfonamide

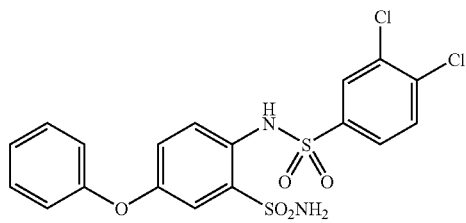 [SMILES: NS(=O)(=O)c1cc(Oc2ccccc2)ccc1NS(=O)(=O)c1ccc(Cl)c(Cl)c1]

To a solution of 2-(3-bromophenylsulfonamido)-5-phenoxybenzenesulfonamide (241.5 mg, 0.5 mmol), 3,4-dichlorobenzeneboronic acid (190.8 mg, 1.0 mmol), tricyclohexyl phosphine (50 mg, 0.18 mmol) and potassium phosphate (340 mg, 1.6 mmol) in DMF (10 mL), was added Pd(OAc)$_2$ (20 mg, 0.09 mmol). The reaction mixture was stirred at 80° C. for 7 h, diluted with 1N HCl and the product was extracted with ethyl acetate. The organic phase was separated, dried over sodium sulfate and concentrated in vacuo. The crude product was purified by flash column chromatography using ethyl acetate/hexane (1:1) to afford the title compound (42 mg, 15%).

$^1$H NMR (400 MHz, DMSO-d$_6$): δ ppm 9.26 (s, 1H), 8.14 (s, 1H), 8.02 (s, 1H), 7.97 (d, 1H), 7.88 (d, 1H), 7.73-7.81 (m, 3H), 7.64-7.73 (m, 2H), 7.56 (d, 1H), 7.39 (dd, 2H), 7.34 (d, 1H), 7.13-7.26 (m, 2H), 6.99 (d, 2H);

ESMS: m/z [M−1] 546.80 and 548.69 (Cl isotopes).

a) 2-(3-Bromophenylsulfonamido)-5-phenoxybenzenesulfonamide

To a solution of 2-amino-5-phenoxybenzenesulfonamide (528 mg, 2 mmol) in pyridine (15 mL), 3-bromobenzenesulphonyl chloride (669.3 mg, 2.3 mmol) was added portionwise at 0° C. The reaction was stirred at RT overnight. The pyridine was removed in vacuo and the residue was dissolved in ethyl acetate. The organic phase was washed with aqueous 1N HCl, water and brine, dried over sodium sulfate, and concentrated under reduced pressure. The crude product was purified by flash column chromatography using ethyl acetate/hexane (1:3) as eluent to give the title compound (700 mg, 72%).

$^1$H NMR (400 MHz, DMSO-d$_6$): δ (ppm 9.30 (br s, 1H), 7.94 (s, 1H), 7.76-7.91 (m, 2H), 7.71 (s, 2H), 7.52 (dd, 1H), 7.48 (d, 1H), 7.41 (dd, 2H), 7.35 (d, 1H), 7.13-7.27 (m, 2H), 7.01 (d, 2H); ESMS: m/z [M−1] 480.88 and 482.83 (Br isotopes).

b) 2-Amino-5-phenoxybenzenesulfonamide

A mixture of 7-phenoxy-1,1-dioxo-1,4-dihydro-2-H-benzo[1,2,4]thiadiazin-3-one (18.0 g, 61.8 mmol) in aqueous H$_2$SO$_4$ (50% v/v, 1 L) was heated at 105° C. for 7 h. The clear solution was then cooled to 0° C. and neutralized using 5N NaOH. The product was extracted with ethyl acetate. The combined extracts were washed with water and concentrated under reduced pressure. The crude product was purified by flash column chromatography using ethyl acetate/hexane (1:1) to afford the title compound (4.0 g, 24%).

$^1$H NMR (400 MHz, DMSO-d$_6$): δ ppm 7.27-7.41 (m, 4H), 7.21 (d, 1H), 7.07 (m, 2H), 6.91 (d, 2H), 6.85 (d, 1H), 5.76 (s, 2H).

c) 7-Phenoxy-1,1-dioxo-1,4-dihydro-2-H-benzo[1,2,4]thiadiazin-3-one

4-Phenoxybenzenamine (18.4 g, 101.1 mmol) dissolved in nitromethane (30 mL) was added slowly over 25 minutes to a solution of chlorosulfonyl isocyanate (16.4 g, 115.8 mmol) in nitromethane (100 mL) at −5° C. The suspension was stirred at −5° C. for an additional 15 minutes and AlCl$_3$ (16.8 g, 125.9 mmol) was added portionwise. The reaction mixture was then heated at 105° C. for 30 minutes. The hot solution was poured onto ice (1 L) and the resulting precipitate was filtered off and washed with water (300 mL). The solid was then dissolved in hot aqueous sodium bicarbonate solution (10 g/200 mL), treated with charcoal, and filtered. The cooled solution was neutralized using 6N HCl and the resulting white precipitate was filtered off, washed with water and dried to afford the title compound (18 g, 62%).

$^1$H NMR (400 MHz, DMSO-d$_6$): δ ppm 11.21 (s, 1H), 7.40-7.47 (m, 2H), 7.38 (dd, 1H), 7.26-7.31 (m, 2H), 7.17-7.25 (m, 2H), 7.07 (d, 2H).

Example 156

5-Phenoxy-2-[[3-[3-(trifluoromethoxy)phenyl]phenyl]sulfonylamino]benzenesulfonamide

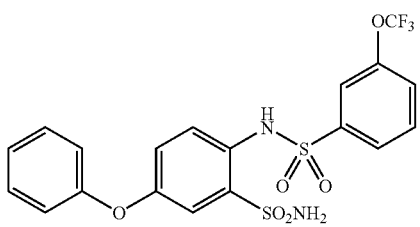 [SMILES: NS(=O)(=O)c1cc(Oc2ccccc2)ccc1NS(=O)(=O)c1cccc(OC(F)(F)F)c1]

To a solution of 2-(3-bromophenylsulfonamido)-5-phenoxybenzenesulfonamide (Example 155a) (150.0 mg, 0.31 mmol), 3-(trifluoromethoxy)benzeneboronic acid (192 mg, 0.93 mmol), tricyclohexyl phosphine (25 mg, 0.09 mmol) and potassium phosphate (131 mg, 0.62 mmol) in DMF (10 mL), was added Pd(OAc)$_2$ (14 mg, 0.06 mmol). The reaction mixture was stirred at 80° C. overnight, diluted with 1N HCl and the product was extracted with ethyl acetate. The organic phase was separated, dried over sodium sulfate and concentrated in vacuo. The crude product was purified by flash column chromatography using methanol/DCM (1:99) to afford the title compound (92 mg, 53%).

$^1$H NMR (400 MHz, CD$_3$OD) δ ppm 8.00 (s, 1H), 7.82-7.88 (m, 2H), 7.75 (d, 1H), 7.52-7.64 (m, 3H), 7.49 (s, 1H), 7.41 (d, 1H), 7.33 (dd, 3H), 7.09-7.18 (m, 2H), 6.93 (d, 2H);

$^{19}$F NMR (400 MHz, CD$_3$OD) δ ppm −59.72; ESMS: m/z [M−1] 562.92.

Example 157

2-(2,3-Dichloro-benzenesulfonylamino)-5-hydroxy-benzenesulfonamide

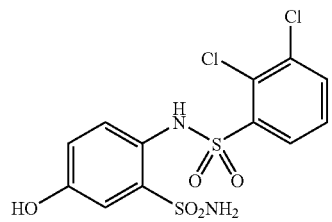 [SMILES: NS(=O)(=O)c1cc(O)ccc1NS(=O)(=O)c1cccc(Cl)c1Cl]

To a solution of 2-(2,3-dichloro-benzenesulfonylamino)-5-methoxy-benzenesulfonamide (4.8 g, 11.68 mmol) in DCM (200 mL) at −20° C., BBr$_3$ (1M in DCM, 60 mL, 60 mmol) was added dropwise over 30 minutes. The reaction mixture was allowed to warm to RT and the stirring was continued overnight. The reaction mixture was then cooled to −20° C., quenched by addition of methanol (20 mL) and volatiles were removed under reduced pressure. The residue was partitioned between water (50 mL) and ethyl acetate (100 mL). The organic phase was washed with water, dried over sodium sulfate and concentrated under reduced pressure. The crude product was recrystallized from methanol to afford the title compound (4.6 g, 65%).

$^1$H NMR (400 MHz, DMSO-d$_6$): δ ppm 10.04 (s, 1H), 9.52 (s, 1H), 7.86-8.12 (m, 2H), 7.41-7.70 (m, 3H), 7.25 (d, 1H), 7.08 (d, 1H), 6.88 (dd, 1H);

ESMS: m/z [M−1] 394.80 and 396.76 (Cl isotopes).

a) 2-(2,3-Dichloro-benzenesulfonylamino)-5-methoxy-benzenesulfonamide

To a solution of 2-amino-5-methoxy-benzenesulfonamide (2.73 g, 13.43 mmol) in pyridine (25 mL), 2,3-dichlorobenzenesulfonyl chloride (3.68 g, 15.0 mmol) was added slowly at 0° C. The reaction mixture was stirred at RT overnight and then concentrated under reduced pressure. The residue was then partitioned between ethyl acetate and 1N HCl. The organic layer was separated, dried over sodium sulfate and concentrated in vacuo. The crude product was purified by flash column chromatography using ethyl acetate/hexane (1:1) to afford the title compound (4.8 g, 87%).

$^1$H NMR (400 MHz, DMSO-d$_6$) δ ppm 9.64 (br. s., 1H), 8.03 (d, 1H), 7.94 (d, 1H), 7.71 (s, 2H) 7.55 (dd, 1H), 7.35 (d, 1H), 7.21 (d, 1H), 7.01-7.17 (m, 1H), 3.73 (s, 3H).

Example 158

(2R)—N-[2-Chloro-4-[(2-sulfamoylphenyl)sulfamoyl]phenyl]-3,3,3-trifluoro-2-hydroxy-2-methyl-propanamide

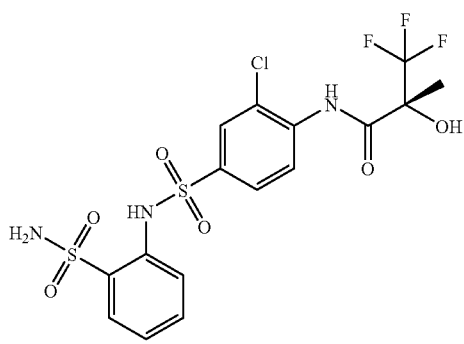 [SMILES: C[C@@](O)(C(=O)Nc1ccc(S(=O)(=O)Nc2ccccc2S(N)(=O)=O)cc1Cl)C(F)(F)F]

To a solution of 3-chloro-4-[[(2R)-3,3,3-trifluoro-2-hydroxy-2-methyl-propanoyl]amino]benzenesulfonyl chloride (110 mg, 0.3 mmol) in DCM (5 ml) and pyridine (30 µl, 0.33 mmol) was added DMAP (~2 mg) followed by 2-aminobenzenesulfonamide (52 mg, 0.3 mmol). The resulting mixture was stirred at RT for 18 h. The solution was concentrated and partitioned between ethyl acetate (6 ml) and 1M HCl (5 ml). The organic layer was separated, washed with saturated NaHCO$_3$, dried (MgSO$_4$) and evaporated to give a gum which was dissolved in a small amount of ethyl acetate and then iso-hexane was added to precipitate the title compound as a solid. LCMS 502.2 (M+H), Rf 7.64 min. [Column: HYPERSIL ODS; Flow Rate: 1.5 ml/min; Detector Wavelength: 254 nm; Solvent A: 0.1% Formic Acid in Water; Solvent B: 0.1% Formic Acid in Acetonitrile; Gradient: 5-95% B]

Example 159

5-Chloro-N-(2-sulfamoylphenyl)thiophene-2-sulfonamide

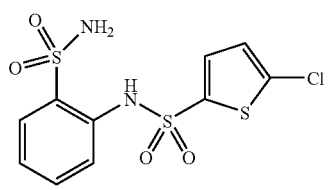 [SMILES: NS(=O)(=O)c1ccccc1NS(=O)(=O)c1ccc(Cl)s1]

To a solution of 2-aminobenzenesulfonamide (172 mg) in pyridine (3 ml) was added 5-chlorothiophene-2-sulfonyl chloride (217 mg) and the resulting mixture was heated at 60° C. for 18 h. The mixture was concentrated and then partitioned between DCM (20 ml) and 2N HCl (10 ml). The organics were separated, dried (MgSO$_4$) and evaporated to a gum which was purified by silica chromatography eluting with a gradient of ethyl acetate/hexane to give the title compound as a solid (201 mg).

LCMS 351, 353 (M−H, Cl pattern); $^1$H NMR (400 MHz, DMSO-d$_6$) δ 7.35 (d, 1H), 7.35 (m, 2H), 7.6 (m, 2H), 7.75 (s, 2H), 7.85 (d, 1H, 9.5 (bs, 1H).

Example 160

4,5-Dichloro-N-(2-sulfamoylphenyl)thiophene-2-sulfonamide

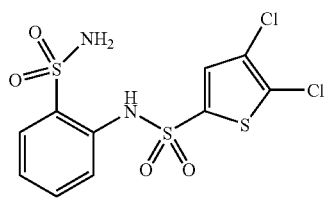 [SMILES: NS(=O)(=O)c1ccccc1NS(=O)(=O)c1cc(Cl)c(Cl)s1]

The title compound was prepared using the general method described in Example 159 but using 4,5-dichlorothiophene-2-sulfonyl chloride.

LCMS 386, 388, 390 (M−H, Cl$_2$ pattern); $^1$H NMR (400 MHz, DMSO-d$_6$) δ 7.35 (m, 1H), 7.55-7.9 (m, 6H), 9.6 (bs, 1H).

Example 161

3,4-Dichloro-N-(2-sulfamoylphenyl)benzenesulfonamide

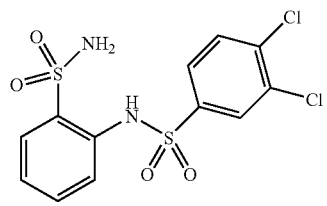 [SMILES: NS(=O)(=O)c1ccccc1NS(=O)(=O)c1ccc(Cl)c(Cl)c1]

The title compound was prepared using the general method described in Example 159 but using 3,4-dichlorophenylsulfonyl chloride.

LCMS 380, 382, 384 (M−H, Cl$_2$ pattern); $^1$H NMR (400 MHz, DMSO-d$_6$) δ 7.3 (t, 1H), 7.55 (m, 2H), 7.70 (s, 2H), 7.82 (m, 3H), 8.09 (s, 1H), 9.5 (bs, 1H).

Example 162

3-(6-Methoxypyridin-2-yl)-N-(2-sulfamoylphenyl)benzenesulfonamide

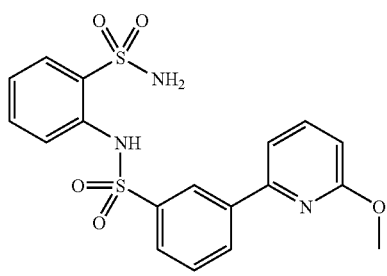 [SMILES: COc1cccc(-c2cccc(S(=O)(=O)Nc3ccccc3S(N)(=O)=O)c2)n1]

1,1'-Bis(diphenylphosphino)ferrocene palladium dichloride methylene chloride adduct (14 mg, 0.02 mmol) was added to a solution of 6-methoxy pyridine-2-boronic acid pinacol ester (135 mg, 0.57 mmol), 2-[(3-bromophenyl)sulfonylamino]benzenesulfonamide (150 mg, 0.38 mmol) (see Example 113a) and Na$_2$CO$_3$ (0.18 mg, 1.72 mmol) in THF:water, 10:1 (4 mL). The reaction mixture was heated in a microwave reactor at 120° C. for 20 min. Some DCM was added followed by brine and the aqueous layer was extracted twice with DCM. The combined organic layers were dried with Na$_2$SO$_4$ and after filtration and evaporation the crude was purified by preparative HPLC (XTerra MS C8 column, acetonitrile/ammonium acetate buffer) to give the title compound (30 mg, 19%) as a yellow oil.

$^1$H NMR (400 MHz, CD$_3$OD) δ ppm 8.57 (t, 1H), 8.22 (ddd, 1H), 7.92 (ddd, 1H), 7.79 (dd, 1H), 7.69 (dd, 1H), 7.67 (dd, 1H), 7.56 (t, 1H), 7.43 (dd, 1H), 7.40 (ddd, 1H), 7.00-7.10 (m, 1H), 6.73 (d, 1H), 4.95 (br. s., 2H), 1.94 (s, 3H). MS m/z M+H 420, M−H 418.

Example 163

2-[[4-[(2-Chloro1,3-thiazol-5-yl)methoxy]phenyl]sulfonylamino]benzenesulfonamide

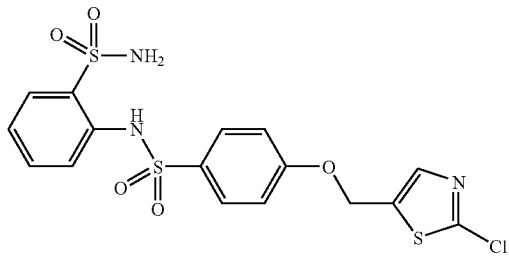 [SMILES: NS(=O)(=O)c1ccccc1NS(=O)(=O)c1ccc(OCc2cnc(Cl)s2)cc1]

To 2-aminobenzenesulfonamide (53 mg, 0.308 mmol) in pyridine (1 mL) was added 4-(2-Chloro-thiazol-5-ylmethoxy)-benzenesulfonyl chloride (100 mg, 0.308 mmol). The reaction mixture was stirred for 40 h. Some conversion was observed but much solid was formed. More 2-aminobenzenesulfonamide (53 mg, 0.308 mmol) and DCM (1 mL) were added. The reaction mixture was stirred overnight. After removal of the pyridine by blowing with nitrogen gas, the residue was purified by preparative HPLC (XTerra MS C8 column, acetonitrile/ammonium acetate buffer) to give the title compound (30 mg, 21%) as an off-white solid.

$^1$H NMR (400 MHz, CD$_3$OD) δ ppm 7.81-7.87 (m, 2H), 7.80 (dd, 1H), 7.60-7.67 (m, 2H), 7.43 (ddd, 1H), 7.12 (t, 1H), 7.05-7.09 (m, 2H), 5.30 (s, 2H).

MS m/z M+H 460/462, M−H 458/460.

The compounds of Examples 164 to 172 were prepared using the general method described for Example 113.

Example 164

3-(5-Fluoro-6-methoxy-pyridin-3-yl)-N-(2-sulfamoylphenyl)benzenesulfonamide

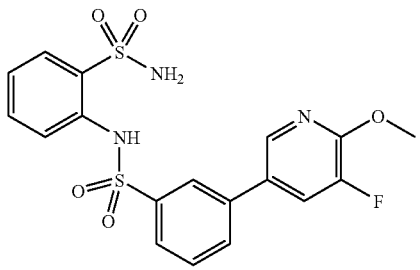 [SMILES: COc1ncc(-c2cccc(S(=O)(=O)Nc3ccccc3S(N)(=O)=O)c2)cc1F]

33 mg, 31%.

$^1$H NMR (400 MHz, CD$_3$OD) δ ppm 8.15 (d, 1H), 8.04 (t, 1H), 7.85 (ddd, 1H), 7.79-7.83 (m, 2H), 7.76 (d, 1H), 7.75 (dd, 1H), 7.57 (t, 1H), 7.46-7.53 (m, 1H), 7.18 (t, 1H), 4.04 (s, 3H). MS m/z M+H 438, M−H 436.

Example 165

3-(2-Methoxypyrimidin-5-yl)-N-(2-sulfamoylphenyl)benzenesulfonamide

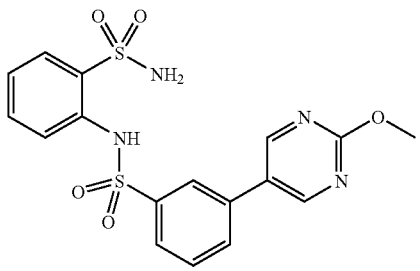 [SMILES: COc1ncc(-c2cccc(S(=O)(=O)Nc3ccccc3S(N)(=O)=O)c2)cn1]

35.1 mg, 83%.

$^1$H NMR (400 MHz, DMSO-d$_6$) δ ppm 9.37 (br s, 1H), 8.93 (s, 2H), 8.23 (br s, 1H), 7.45-8.08 (m, 8H), 7.23 (br s, 1H), 3.98 (s, 3H). MS m/z M+H 421, M−H 419.

Example 166

3-(4-Methylpyridin-3-yl)-N-(2-sulfamoylphenyl)benzenesulfonamide

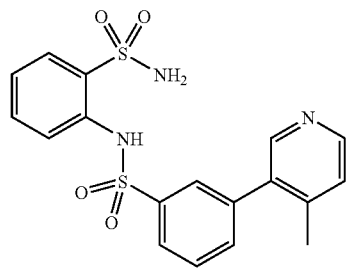 [SMILES: Cc1ccncc1-c1cccc(S(=O)(=O)Nc2ccccc2S(N)(=O)=O)c1]

32.8 mg, 43%.
$^1$H NMR (400 MHz, DMSO-d$_6$) δ ppm 9.40 (br s, 1H), 8.50 (br s, 1H), 8.35 (br s, 1H), 7.92 (ddd, 1H), 7.72-7.83 (m, 4H), 7.65-7.71 (m, 2H), 7.59 (dd, 1H), 7.53 (ddd, 1H), 7.35 (d, 1H), 7.23 (t, 1H), 2.10 (s, 3H). MS m/z M+H 404, M–H 402.

Example 167

3-(2-Methoxypyridin-3-yl)-N-(2-sulfamoylphenyl)benzenesulfonamide

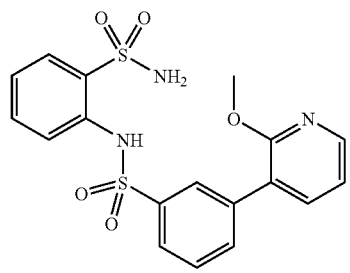 [SMILES: COc1ncccc1-c1cccc(S(=O)(=O)Nc2ccccc2S(N)(=O)=O)c1]

7 mg, 9%.
$^1$H NMR (400 MHz, CD$_3$OD) δ ppm 8.15 (dd, 1H), 8.06 (t, 1H), 7.85 (ddd, 1H), 7.83 (dd, 1H), 7.77 (ddd, 1H), 7.66-7.73 (m, 2H), 7.54 (t, 1H), 7.48 (ddd, 1H), 7.13-7.19 (m, 1H), 7.05 (dd, 1H), 3.91 (s, 3H). MS m/z M+H 420, M–H 418.

Example 168

2-[[3-(5-Chloropyridin-3-yl)phenyl]sulfonylamino]benzenesulfonamide

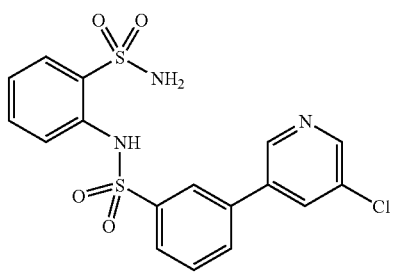 [SMILES: NS(=O)(=O)c1ccccc1NS(=O)(=O)c1cccc(-c2cncc(Cl)c2)c1]

30 mg, 37%.
$^1$H NMR (400 MHz, CD$_3$OD) δ ppm 8.70 (s, 1H), 8.57 (s, 1H), 8.06-8.16 (m, 2H), 7.93 (d, 1H), 7.86 (d, 1H), 7.80 (dd, 1H), 7.73 (d, 1H), 7.60 (t, 1H), 7.46 (dt, 1H), 7.12 (t, 1H).
MS m/z M+H 423/425, M–H 421/423.

Example 169

3-(5-Chloro-6-methoxy-pyridin-3-yl)-N-(2-sulfamoylphenyl)benzenesulfonamide

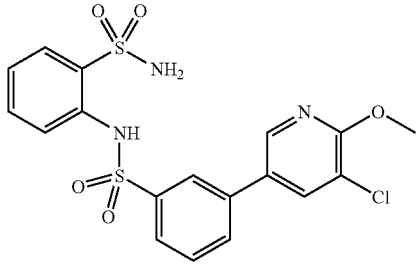 [SMILES: COc1ncc(-c2cccc(S(=O)(=O)Nc3ccccc3S(N)(=O)=O)c2)cc1Cl]

39 mg, 45%.
$^1$H NMR (600 MHz, DMSO-d$_6$) δ ppm 9.35 (br. s., 1H), 8.46 (d, 1H), 8.25 (d, 1H), 8.19 (br. s., 1H), 7.99 (dd, 1H), 7.91 (d, 1H), 7.83 (br. s., 2H), 7.77 (d, 1H), 7.66 (t, 1H), 7.57-7.60 (m, 1H), 7.51-7.56 (m, 1H), 7.15-7.28 (m, 1H), 3.98 (s, 3H).
MS m/z M+H 454/456, M–H 452/454.

Example 170

3-(6-Dimethylaminopyridin-3-yl)-N-(2-sulfamoylphenyl)benzenesulfonamide

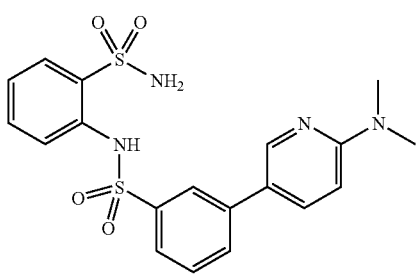 [SMILES: CN(C)c1ccc(-c2cccc(S(=O)(=O)Nc3ccccc3S(N)(=O)=O)c2)cn1]

33 mg, 40%.
$^1$H NMR (400 MHz, DMSO-d$_6$) δ ppm 9.35 (br. s., 1H), 8.42 (d, 1H), 8.06 (s, 1H), 7.87 (d, 1H), 7.82 (dd, 1H), 7.72-7.82 (m, 4H), 7.46-7.63 (m, 3H), 7.09-7.28 (m, 1H), 6.73 (d, 1H), 3.07 (s, 6H). MS m/z M+H 433, M–H 431.

Example 171

2-[[3-[3-(Hydroxymethyl)phenyl]phenyl]sulfonylamino]benzenesulfonamide

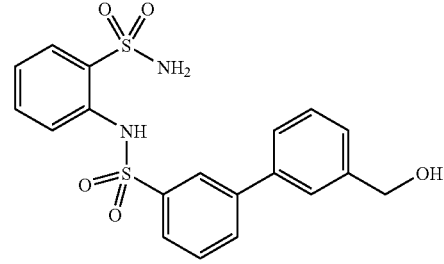 [SMILES: NS(=O)(=O)c1ccccc1NS(=O)(=O)c1cccc(-c2cccc(CO)c2)c1]

35 mg, 44%.

$^1$H NMR (400 MHz, CD$_3$OD) δ ppm 8.09 (t, 1H), 7.86 (d, 1H), 7.78-7.83 (m, 2H), 7.71 (d, 1H), 7.51-7.58 (m, 2H), 7.35-7.50 (m, 4H), 7.12 (t, 1H), 4.67 (s, 2H).

MS m/z M−H 417.

Example 172

2-[[3-[4-(Hydroxymethyl)phenyl]phenyl]sulfonylamino]benzenesulfonamide

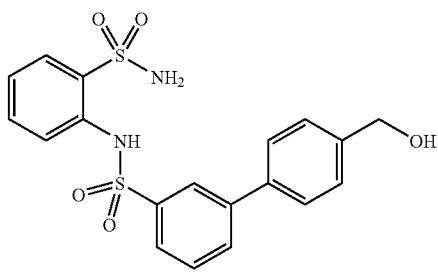 [SMILES: NS(=O)(=O)c1ccccc1NS(=O)(=O)c1cccc(-c2ccc(CO)cc2)c1]

28 mg, 35%.

$^1$H NMR (400 MHz, DMSO-d$_6$) δ ppm 9.38 (br. s, 1H), 8.13 (br. s., 1H), 7.96 (d, 1H), 7.89 (d, 1H), 7.83 (br. s., 2H), 7.79 (d, 1H), 7.63 (d, 2H), 7.51-7.69 (m, 3H), 7.44 (d, 2H), 7.24 (t, 1H), 5.27 (t, 1H), 4.56 (d, 2H). MS m/z M−H 417.

The compounds of Examples 173 to 176 were prepared using the general method described for Example 163.

Example 173

2-[[4-(3,4-Dichlorophenyl)phenyl]sulfonylamino]benzenesulfonamide

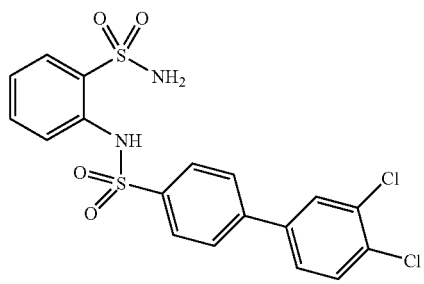 [SMILES: NS(=O)(=O)c1ccccc1NS(=O)(=O)c1ccc(-c2ccc(Cl)c(Cl)c2)cc1]

117 mg, 64%.

$^1$H NMR (400 MHz, DMSO-d$_6$) δ ppm 9.41 (s, 1H), 7.97-8.05 (m, 3H), 7.91-7.97 (m, 2H), 7.75-7.86 (m, 3H), 7.74 (s, 2H), 7.48-7.59 (m, 2H), 7.18-7.28 (m, 1H).

MS m/z M−H 455/457/459.

Example 174

2-[[3-(3,4-Dichlorophenyl)phenyl]sulfonylamino]benzenesulfonamide

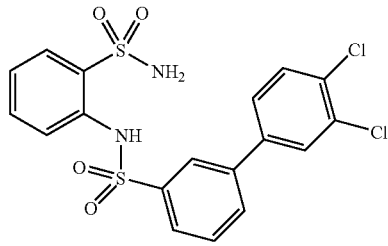 [SMILES: NS(=O)(=O)c1ccccc1NS(=O)(=O)c1cccc(-c2ccc(Cl)c(Cl)c2)c1]

135 mg, 74%.

$^1$H NMR (400 MHz, DMSO-d$_6$) δ ppm 9.35 (s, 1H), 8.19 (t, 1H), 8.01 (d, 1H), 7.96 (d, 1H), 7.93 (d, 1H), 7.81 (s, 2H), 7.77 (d, 1H), 7.76 (d, 1H), 7.64-7.70 (m, 2H), 7.50-7.60 (m, 2H), 7.24 (t, 1H). MS m/z M−H 455/457/459.

Example 175

2-[[4-(4-Chlorophenoxy)phenyl]sulfonylamino]benzenesulfonamide

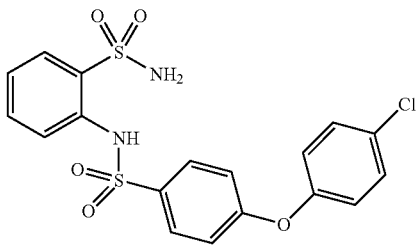 [SMILES: NS(=O)(=O)c1ccccc1NS(=O)(=O)c1ccc(Oc2ccc(Cl)cc2)cc1]

154 mg, 88%.

$^1$H NMR (400 MHz, DMSO-d$_6$) δ ppm 9.29 (s, 1H), 7.90 (d, 2H), 7.80 (s, 2H), 7.79 (d, 1H), 7.45-7.57 (m, 4H), 7.24 (ddd, 1H), 7.13-7.19 (m, 2H), 7.10 (d, 2H). M−H 437/439.

Example 176

3-(4-Chlorophenyl)-1-[3-methyl-4-[(2-sulfamoylphenyl)sulfamoyl]phenyl]urea

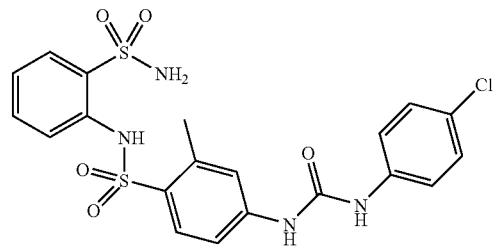 [SMILES: Cc1cc(NC(=O)Nc2ccc(Cl)cc2)ccc1S(=O)(=O)Nc1ccccc1S(N)(=O)=O]

131 mg, 66%.

¹H NMR (400 MHz, DMSO-d₆) δ ppm 9.44 (s, 1H), 9.12 (s, 1H), 8.96 (s, 1H), 7.96 (d, 1H), 7.90 (s, 2H), 7.80 (dd, 1H), 7.52 (dd, 1H), 7.44-7.50 (m, 3H), 7.37-7.43 (m, 2H), 7.30-7.36 (m, 2H), 7.17 (ddd, 1H), 2.55 (s, 3H). M+H 495/497 M−H 493/495.

Example 177

N-Methyl-N'-(2-sulfamoylphenyl)dibenzo[b,d]thiophene-2,8-disulfonamide 5,5-dioxide

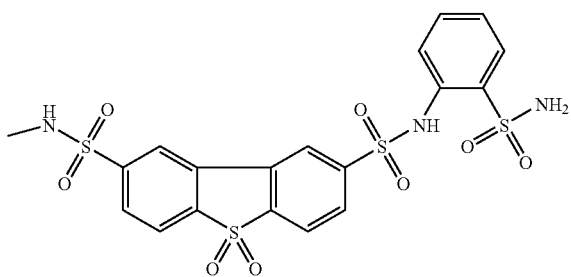 [SMILES: CNS(=O)(=O)c1ccc2c(c1)-c1cc(S(=O)(=O)Nc3ccccc3S(N)(=O)=O)ccc1S2(=O)=O]

Hydrogen peroxide (35%, 1.2 ml) was added to a suspension of N-methyl-N'-(2-sulfamoylphenyl)dibenzo[b,d]thiophene-2,8-disulfonamide (160 mg) in acetic acid (1.8 ml) and the mixture was heated at 100° C. for 1 h. The mixture was diluted with water (5 ml), the solid was recovered by filtration, washed with water and dried to give the title compound (86 mg, 51%).

¹H NMR (400 MHz), DMSO-d₆) δ 2.47 (s, 3H), 7.27 (brs, 1H), 7.53 (m, 2H), 7.73 (m, 4H), 8.03 (d, 1H), 8.12 (d, 1H), 8.29 (m, 2H), 8.7 (s, 1H), 8.93 (s, 1H), 9.5 (brs, 1H).

Mass spectrum: EI 542.8.

a) N-Methyl-N'-(2-sulfamoylphenyl)dibenzo[b,d]thiophene-2,8-disulfonamide 8-(Methylsulfamoyl)dibenzo[b,d]thiophene-2-sulfonyl chloride (200 mg) was added to a solution of 2-aminobenzenesulfonamide (191 mg) in sulfolane (2 ml). The mixture was stirred at RT for 20 h then diluted with 1N hydrochloric acid. The solid was recovered, washed with 1N hydrochloric acid and dried to give the title compound (196 mg, 72%).

Mass spectrum: EI 511.1.

b) 8-(Methylsulfamoyl)dibenzo[b,d]thiophene-2-sulfonyl chloride

N-Methyldibenzo[b,d]thiophene-2-sulfonamide (1.56 g) was added to chlorosulfonic acid (3.27 g) and the mixture was stirred at RT for 5 h. The mixture was then treated with ice cold water, the precipitate was filtered off, washed with cold water and dried to give the title compound (1.6 g, 76%).

¹H NMR (400 MHz, DMSO-d₆) δ 2.49 (s, 3H), 7.53 (brs, 1H), 7.84 (d, 1H), 7.9 (d, 2H), 8.1 (d, 1H), 8.3 (d, 1H), 8.59 (s, 1H), 8.77 (s, 1H).

c) N-Methyldibenzo[b,d]thiophene-2-sulfonamide

A large excess of aqueous methylamine was added to a suspension of dibenzo[b,d]thiophene-2-sulfonyl chloride (2.83 g) in sulfolane (15 ml) and the mixture was stirred at RT for 3 h. The reaction mixture was diluted with water, and the precipitate was recovered, washed with water, dried and purified by silica gel chromatography eluting with a gradient of ethyl acetate:DCM of 0:100 to 10:90 to give the title compound (1.79 g, 64%).

¹H NMR (400 MHz, DMSO-d₆) δ 2.48 (s, 3H), 7.52 (brs, 1H), 7.61 (m, 2H), 7.89 (d, 1H), 8.13 (d, 1H), 8.31 (d, 1H), 8.52 (d, 1H), 8.75 (s, 1H).

d) Dibenzo[b,d]thiophene-2-sulfonyl chloride

BuLi (2.5M, 10 ml) was added dropwise to a suspension of 2-bromodibenzo[b,d]thiophene (6.31 g) (N. M. Cullinane, J. Chem. Soc. 1936, 1435) in dry ether (80 ml) under argon at −5° C., and the mixture was stirred at this temperature for 15 minutes. This solution was added to a stirred solution of sulfur dioxide (80 ml) in ether (80 ml) at −50° C. over 5 minutes, the mixture was stirred for 15 minutes at −50° C. and the temperature of the reaction mixture was then allowed to reach RT over 1 h. The solvent was evaporated and the residue was dried under vacuum overnight. The lithium salt was suspended in ether (150 ml), sulfuryl chloride (3.24 g) was added at 0° C. and the mixture was stirred at RT for 1 h. The mixture was concentrated to dryness to give the title compound (6.8 g, 100%).

¹H NMR (400 MHz, DMSO-d₆) 7.53 (m, 2H), 7.78 (m, 1H), 8.0 (d, 1H), 8.04 (m, 1H), 8.36 (m, 1H), 8.52 (s, 1H).

General Procedure for Synthesis of Styrenyl Sulfonyl Chlorides

Method A

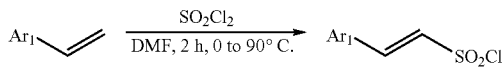

Sulfuryl chloride (360 mmol) was added dropwise to vigorously stirred anhydrous DMF (30 mL) at 0° C. while maintaining the temperature below 10° C. The reaction mixture was allowed to warm to RT and stirring was continued for 30 minutes. The appropriate styrene derivative (36 mmol) was then added in one portion and the resulting solution was heated at 90° C. for 2 h. The reaction mixture was cooled, poured onto crushed ice and the product was extracted with ethyl acetate. The organic phase was washed with cold water, dried over sodium sulfate and concentrated under reduced pressure. The crude product was purified by flash column chromatography using 2% ethyl acetate/hexane as eluent, followed by recrystallization from ether/pentane to afford the pure sample.

The compounds listed in Table 1 were synthesized following this method.

TABLE 1

| Structure | Yield | Analytical data |
|---|---|---|
| (2-OMe-phenyl)-CH=CH-SO2Cl | 5% | ¹H NMR (400 MHz, CDCl₃) δ ppm 7.88 (d, 1H), 7.56 (d, 1H), 7.52-7.45 (m, 2H), 7.05-6.98 (m, 2H), 3.98 (s, 3H). ESMS m/z [M − 1] 213 for corresponding sulfonic acid (M = 214). CHN for C₉H₉ClO₃S Calc.: C, 46.46; H, 3.90. Found: C, 46.91; H, 4.01. |
| (naphth-2-yl)-CH=CH-SO2Cl | 17% | ¹H NMR (400 MHz, CDCl₃) δ ppm 8.05 (s, 1H), 7.95-7.85 (m, 4H), 7.66-7.57 (m, 3H), 7.37 (d, 1H). ESMS m/z [M − 1] 233 for corresponding sulfonic acid (M = 234). CHN for C₁₂H₉ClO₂S Calc.: C, 57.03; H, 3.59. Found: C, 57.20; H, 3.64. |
| (2,6-difluorophenyl)-CH=CH-SO2Cl | 40% | ¹H NMR (400 MHz, CDCl₃) δ ppm 7.90 (d, 1H), 7.59 (d, 1H), 7.55-7.48 (m, 1H), 7.06-7.01 (m, 2 H). ESMS m/z [M − 1] 219 for corresponding sulfonic acid (M = 220). CHN for C₈H₅ClF₂O₂S Calc.: C, 40.26; H, 2.11. Found: C, 40.27; H, 2.28. |
| (2-CF3-phenyl)-CH=CH-SO2Cl | 39% | ¹H NMR (400 MHz, CDCl₃) δ ppm 8.13 (d, 1H), 8.10 (m, 1H), 7.82-7.62 (m, 3H), 7.23 (d, 1H). ESMS m/z [M − 1] 251 for corresponding sulfonic acid (M = 252). CHN for C₉H₆ClF₃O₂S Calc.: C, 39.94; H, 2.23. Found: C, 40.30; H, 2.44. |
| (biphenyl-4-yl)-CH=CH-SO2Cl | 15% | ¹H NMR (400 MHz, CDCl₃) δ ppm 7.78 (d, 1H), 7.72 (m, 2H), 7.62 (m, 4H), 7.55-7.42 (m, 3H), 7 27 (d, 1H). ESMS m/z [M − 1] 259 for corresponding sulfonic acid (M = 260). CHN for C₁₄H₁₁ClO₂S Calc.: C, 60.32; H, 3.98. Found: C, 60.79; H, 3.60. |
| (3-CF3-phenyl)-CH=CH-SO2Cl | 54% | ¹H NMR (400 MHz, CDCl₃) δ ppm 7.85-7.72 (m, 4H) 7.64 (t, J = 7.83 Hz, 1H) 7.32 (d, J = 15.26 Hz, 1H). ESMS m/z [M − 1] 250 for corresponding sulfonic acid, (M = 252.21) CHN for C₉H₆ClF₃O₂S, Calc: C, 39.94; H, 2.23; Found: C, 40.12; H, 2.39; |
| (2-F-phenyl)-CH=CH-SO2Cl | 7% | ¹H NMR (400 MHz, CDCl₃) δ ppm 7.78 (d, J = 15.26 Hz, 1H) 7.57-7.47 (m, 2H) 7.41 (d, J = 15.26 Hz, 1H) 7.26 (d, 1H) 7.23-7.15 (m, 1H). ESMS m/z [M − 1] 200.89 for corresponding sulfonic acid, (M = 202.20) CHN for C₈H₆ClFO₂S, Calc: C, 43.55; H, 2.74; Found: C, 43.72; H, 2.82; |

Method B

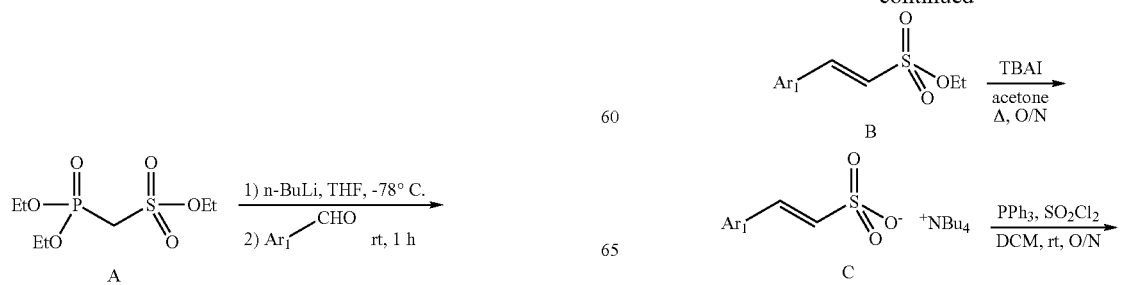

Method B.2 Synthesis of Arylethenesulfonyl Chloride D
Step i) Arylethenesulfonatetetrabutyl-Ammonium C

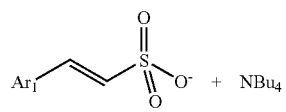

Tetrabutyl-ammonium iodide (18.10 mmol) was added to a solution of arylethenesulfonic acid ethyl ester B (15.08 mmol) in acetone (500 mL) and the reaction mixture was heated at reflux overnight. The reaction mixture was then cooled to RT and concentrated under reduced pressure. The residue was purified on silica gel using DCM/methanol (95:5) to afford a mixture of C and tetrabutyl-ammonium iodide. The oily residue was then triturated with diethyl ether to afford C (contaminated with tetrabutylammonium iodide) which was used in the next step without further purification.

Step ii) Arylethenesulfonyl Chloride D

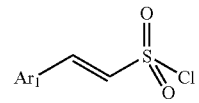

Sulfuryl chloride (1.72 g, 12.7 mmol) was added to a solution of triphenylphosphine (3.09 g, 11.8 mmol) in dry DCM (50 mL) at 0° C. The mixture was stirred at 0° C. for 15 minutes and the crude ammonium salt (5.8 mmol, prepared as described in step i) dissolved in DCM (20 mL) was added. The resulting solution was allowed to warm to RT and stirring was continued overnight. The reaction mixture was then concentrated under reduced pressure and the crude product was purified by flash column chromatography using 1-5% ethyl acetate/hexane to give sulfonyl chloride D.

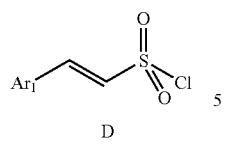

D

Method B.1 Synthesis of Arylethenesulfonic Acid Ethyl Esters

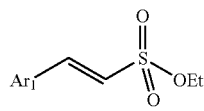

A 2.5M solution of n-butyllithium in hexanes (15.40 mmol) was added dropwise to a stirred solution of (diethoxyphosphoryl)methanesulfonic acid ethyl ester A (15.40 mmol) in THF (160 mL) at −78° C. The reaction mixture was stirred at −78° C. for 15 minutes, then a solution of the appropriate aldehyde (14.10 mmol) in THF (5 mL) was added dropwise. After the addition was complete, the reaction mixture was warmed to RT, stirred for 1 h, and quenched with brine. Most of the THF was then removed in vacuo and DCM (200 mL) was added. The organic layer was separated, washed with brine (3×100 mL), dried over MgSO$_4$ and concentrated under reduced pressure. The crude product was purified on silica gel using hexane/ethyl acetate (2:1) to afford the ester B.

The compounds listed in Table 2 were synthesized following this procedure.

TABLE 2

| Structure | Yield | Analytical data |
|---|---|---|
| Br-, OMe aryl vinyl SO$_2$OEt | 99% | $^1$H NMR (400 MHz, CDCl$_3$) δ ppm 7.71 (d, 1H), 7.58-7.48 (m, 2H), 6.95 (d, 1H), 6.82 (d, 1H), 4.21 (q, 2H), 3.92 (s, 3H), 1.40 (t, 3H). ESMS m/z [M +1] 320 and 322 (Br isotopes). |
| MeS-aryl vinyl SO$_3$Et | 91% | $^1$H NMR (400 MHz, CDCl$_3$) δ ppm 7.54 (d, J = 15.60 Hz, 1H) 7.42 (d, J = 8.58 Hz, 2H) 7.24 (s, 2H) 6.68 (d, J = 15.60 Hz, 1H) 4.22 (q, J = 7.15 Hz, 2H) 2.51 (s, 3H) 1.40 (t, J = 7.22 Hz, 3H). |
| NC-aryl vinyl SO$_3$Et | 77% | $^1$H NMR (400 MHz, CDCl$_3$) δ ppm 7.74 (d, J = 8.19 Hz, 2H) 7.66-7.56 (m, 3H) 6.87 (d, J = 15.60 Hz, 1H) 4.28 (q, J = 7.02 Hz, 2H) 1.43 (t, J = 7.22 Hz, 3H). |
| CHF$_2$O-aryl vinyl SO$_3$Et | 99% | $^1$H NMR (400 MHz, CDCl$_3$) δ ppm 7.620-7.50 (m, 3H) 7.18 (d, J = 8.22 Hz, 2H) 6.77-6.63 (m, 1H) 6.57 (t, 1H) 4.24 (q, J = 7.04 Hz, 2H) 1.41 (t, J = 7.24 Hz, 3H). |
| furyl-phenyl vinyl SO$_3$Et | 81% | $^1$H NMR (400 MHz, CDCl$_3$) δ ppm 7.72 (d, J = 8.61 Hz, 2H) 7.59 (d, J = 15.65 Hz, 1H) 7.53 (d, J = 8.61 Hz, 3H) 6.77 (d, J = 3.52 Hz, 1H) 6.73 (d, J = 15.26 Hz, 1H) 6.52 (dd, J = 3.52, 1.96 Hz, 1H) 4.24 (q, J = 7.04 Hz, 2H) 1.41 (t, J = 7.04 Hz, 3H). |

The compounds listed in Table 3 were synthesized following this method.

TABLE 3

| Structure | Yield[a] | Analytical data |
|---|---|---|
| Br-C6H3(OMe)-CH=CH-SO2Cl | 44% | $^1$H NMR (400 MHz, CDCl$_3$) δ ppm 7.78 (d, 1H), 7.58-7.54 (m, 3H), 7.51 (d, 1H), 6.88 (d, 1H), 3.95 (s, 3H). ESMS m/z [M − 1] 290 and 292 (Br isotopes) for corresponding sulfonic acid (M = 293). CHN for C$_9$H$_8$BrClO$_3$S Calc.: C, 34.69; H, 2.59. Found: C, 34.39; H, 2.70. |
| NC-C6H4-CH=CH-SO2Cl | 56% | $^1$H NMR (400 MHz, CDCl$_3$) δ ppm 7.77 (t, J = 8.22 Hz, 2H) 7.74-7.63 (m, 3H) 7.33 (d, J = 14.87 Hz, 1H). ESMS m/z [M − 1] 207.88 for corresponding sulfonic acid, (M = 209.22). CHN for C$_9$H$_6$ClNO$_2$S, Calc: C, 47.48; H, 2.66; N, 6.15 Found: C, 47.48; H, 2.76; N, 6.20 |
| MeS-C6H4-CH=CH-SO2Cl | 34% | $^1$H NMR (400 MHz, CDCl$_3$) δ ppm 7.68 (d, J = 15.26 Hz, 1H) 7.45 (d, J = 8.22 Hz, 2H) 7.30-7.24 (m, 2H) 7.17 (d, J = 15.26 Hz, 1H) 2.53 (s, 3H). ESMS m/z [M − 1] 228.93 for corresponding sulfonic acid, (M = 230.30) CHN for C$_9$H$_9$ClO$_2$S$_2$, Calc: C, 43.46; H, 3.65; Found: C, 43.71; H, 3.96. |
| F2HCO-C6H4-CH=CH-SO2Cl | 49.5% | $^1$H NMR (400 MHz, CDCl$_3$) δ ppm 7.71 (d, J = 14.87 Hz, 1H) 7.58 (d, J = 8.61 Hz, 2H) 7.28-7.14 (m, 3H) 6.80-6.39 (m, 1H). ESMS m/z [M − 1] 248.98 for corresponding sulfonic acid, (M = 250.22). CHN for C$_9$H$_7$ClF2O$_3$S, Calc: C, 40.23; H, 2.63; Found: C, 40.60; H, 2.79. |
| furan-C6H4-CH=CH-SO2Cl | 33% | $^1$H NMR (400 MHz, CDCl$_3$) δ ppm 7.80-7.60 (m, 3H) 7.61-7.51 (m, 3H) 7.22 (d, J = 15.26 Hz, 1H) 6.81 (d, J = 3.52 Hz, 1H) 6.53 (d, J = 1.56 Hz, 1H). ESMS m/z [M − 1] 248.91 for corresponding sulfonic acid, (M = 250.27). CHN for C$_9$H$_7$ClF2O$_3$S, Calc: C, 53.64; H, 3.38; Found: C, 53.58; H, 3.49. |

[a] yield calculated over 2 steps

Example 178

2,3-Dichloro-N-(4,5-difluoro-2-sulfamoylphenyl)benzenesulfonamide

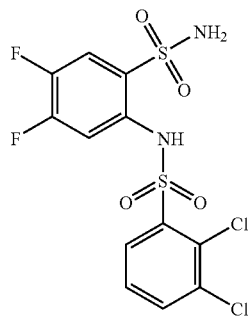 [SMILES: NS(=O)(=O)c1cc(F)c(F)cc1NS(=O)(=O)c1cccc(Cl)c1Cl]

2-Amino-4,5-difluorobenzenesulfonamide (99 mg, 0.48 mmol) and dichlorobenzenesulfonyl chloride (152 mg, 0.62 mmol) were dissolved in anhydrous pyridine (2 mL). The mixture was stirred at ambient temperature under an atmosphere of argon for 24 h. The solvent was evaporated in vacuo, water was added and the product was extracted with ethyl acetate. The combined organic phases were washed with brine, dried over magnesium sulfate and concentrated. Purification by preparative HPLC gave 107 mg (54% yield) of the title compound.

$^1$H NMR (400 MHz, (CD$_3$)$_2$CO) δ ppm 8.30 (dd, 1H) 7.88 (dd, 1H) 7.76 (dd, 1H) 7.62 (t, 1H) 7.42 (dd, 6.95 Hz, 1H); MS (ESI) m/z 415, 417 [M−1]$^-$.

Example 179

(E)-2-(2-(3,4-Dichlorophenyl)vinylsulfonamido)-5-(3-hydroxy-3-methylbut-1-ynyl)benzenesulfonamide

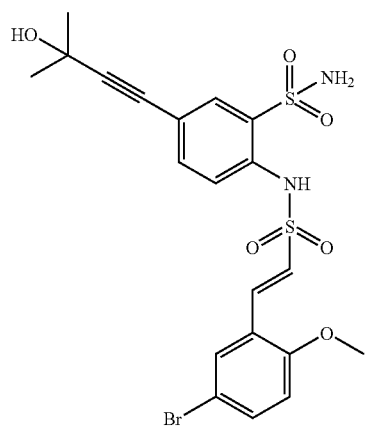 [SMILES: COc1ccc(Br)cc1/C=C/S(=O)(=O)Nc1ccc(C#CC(C)(C)O)cc1S(N)(=O)=O]

The title compound was synthesized as described for Example 178 in 16% yield, starting from 2-amino-5-(3-hydroxy-3-methylbut-1-ynyl)benzenesulfonamide and (E)-2-(5-bromo-2-methoxyphenyl)ethenesulfonyl chloride (93 mg, 0.30 mmol). Purification by preparative HPLC.

MS (ESI) m/z 527, 529 [M−1]⁻.

a) 2-amino-5-(3-hydroxy-3-methylbut-1-ynyl)benzenesulfonamide

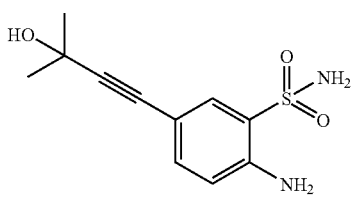 [SMILES: CC(C)(O)C#Cc1ccc(N)c(S(N)(=O)=O)c1]

2-Amino-5-bromobenzenesulfonamide (2 g, 7.96 mmol), copper(I) iodide (0.076 g, 0.40 mmol) and bis(triphenylphosphine)palladium(II) chloride (0.280 g, 0.40 mmol) were slurried in anhydrous N,N-dimethylformamide (6 mL) in a microwave vial. 2-Methyl-3-butyn-2-ol (2.316 mL, 23.89 mmol) followed by diisopropylamine (3.37 mL, 23.89 mmol) were added, the vial was capped, purged with argon and the mixture was heated in a microwave at 100° C. for 30 min. The mixture was filtered and the solvent was evaporated in vacuo. Purification by column chromatography, using a gradient of 60-70% ethyl acetate in heptane as the eluent, gave 0.92 g (46% yield) of the title compound.

¹H NMR (400 MHz, DMSO-d₆) δ ppm 7.55 (d, 1H) 7.30 (s, 2H) 7.20 (dd, 1H) 6.74 (d, 1H) 6.13 (s, 2H) 5.33 (s, 1H) 1.43 (s, 6H); MS (ESI) m/z 253 [M−1]⁻.

Example 180

4-Cyano-2-(2-(3,4-dichlorophenyl)ethylsulfonamido)benzenesulfonamide

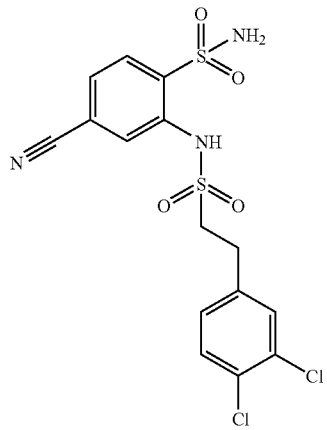 [SMILES: N#Cc1ccc(S(N)(=O)=O)c(NS(=O)(=O)CCc2ccc(Cl)c(Cl)c2)c1]

(E)-4-Cyano-2-(2-(3,4-dichlorophenyl)vinylsulfonamido)benzenesulfonamide (123 mg, 0.28 mmol), sodium acetate (93 mg, 1.14 mmol) and para-toluenesulfonhydrazide (212 mg, 1.14 mmol) were dissolved in anhydrous tetrahydrofuran (3 mL) in a microwave vial. The vial was capped and evacuated two times with argon. The mixture was heated in a microwave at 180° C. for 15 min. The mixture was filtered and the solvent was evaporated in vacuo. Purification twice by preparative HPLC gave 4.8 mg (4% yield) of the title compound.

¹H NMR (400 MHz, CD₃OD) δ ppm 8.02-8.06 (m, 2H) 7.54 (d, 1H) 7.42 (d, 1H) 7.39 (d, 1H) 7.17 (dd, 1H) 3.56-3.62 (m, 2H) 3.07-3.13 (m, 2H); MS (ESI) m/z 432, 434 [M−1]⁻.

a) (E)-4-cyano-2-(2-(3,4-dichlorophenyl)vinylsulfonamido)benzenesulfonamide

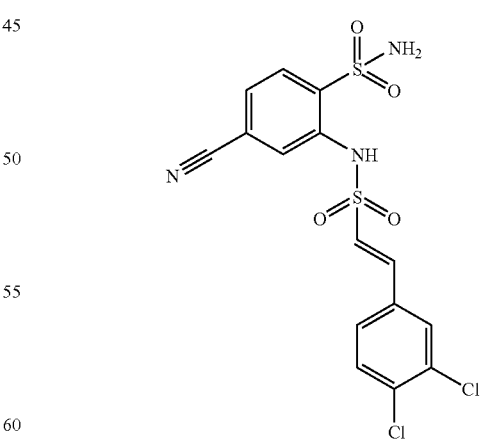

The title compound was synthesized as described for Example 178 in 57% yield, starting from 2-amino-4-cyanobenzenesulfonamide and (E)-2-(3,4-dichlorophenyl)ethenesulfonyl chloride.

MS (ESI) m/z 430, 432 [M−1]⁻.

Example 181

2-(2-(4-Chloro-2-methoxyphenyl)ethylsulfonamido)-4-cyanobenzenesulfonamide

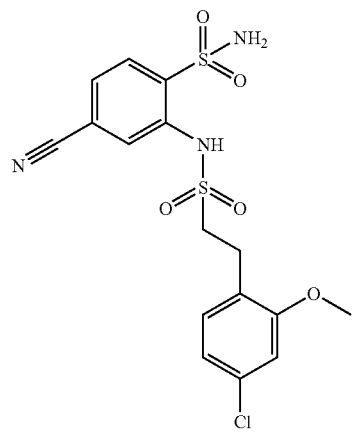 [SMILES: COc1cc(Cl)ccc1CCS(=O)(=O)Nc1cc(C#N)ccc1S(N)(=O)=O]

The title compound was synthesized as described for Example 180 in 6% yield, starting from (E)-2-(2-(4-chloro-2-methoxyphenyl)vinylsulfonamido)-4-cyanobenzenesulfonamide.

$^1$H NMR (400 MHz, CDCl$_3$) δ ppm 8.05 (d, 1H) 7.86 (d, 1H) 7.49 (dd, 1H) 7.09 (d, 1H) 6.88 (dd, 1H) 6.82 (d, 1H) 3.78 (s, 3H) 3.53-3.58 (m, 2H) 3.12-3.18 (m, 2H); MS (ESI) m/z 428, 430 [M−1]$^−$.

a) (E)-2-(2-(4-Chloro-2-methoxyphenyl)vinylsulfonamido)-4-cyanobenzenesulfonamide

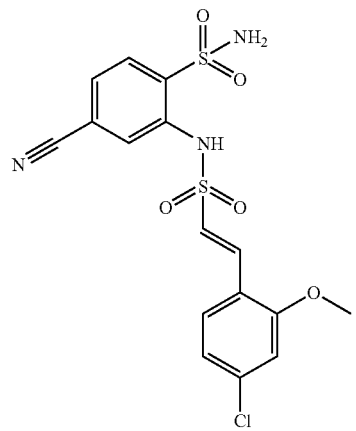 [SMILES: COc1cc(Cl)ccc1/C=C/S(=O)(=O)Nc1cc(C#N)ccc1S(N)(=O)=O]

The title compound was synthesized as described for Example 178 in 36% yield, starting from 2-amino-4-cyanobenzenesulfonamide and 2-(4-chloro-2-methoxyphenyl)-ethenesulfonyl chloride.

MS (ESI) m/z 426, 428 [M−1]$^−$.

Example 182

2-(2-(4-Chloro-2-methoxyphenyl)ethylsulfonamido)-5-cyanobenzenesulfonamide

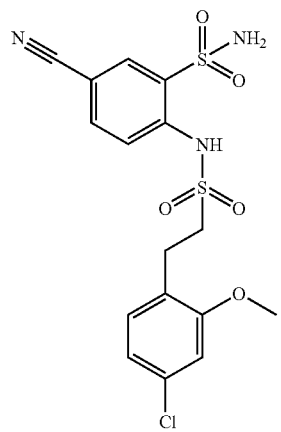 [SMILES: COc1cc(Cl)ccc1CCS(=O)(=O)Nc1ccc(C#N)cc1S(N)(=O)=O]

The title compound was synthesized as described for Example 180 in 88% yield, starting from (E)-2-(2-(4-chloro-2-methoxyphenyl)vinylsulfonamido)-5-cyanobenzenesulfonamide (26 mg, 0.06 mmol). The reaction was run at 120° C.

$^1$H NMR (400 MHz, DMSO-d$_6$) δ ppm 7.80 (d, 1H) 7.51 (dd, 1H) 7.44 (d, 1H) 7.15 (d, 1H) 6.98 (d, 1H) 6.89 (dd, 1H) 3.76 (s, 3H) 2.97-3.03 (m, 2H) 2.90-2.96 (m, 2H); MS (ESI) m/z 428, 430 [M−1]$^−$.

a) (E)-2-(2-(4-Chloro-2-methoxyphenyl)vinylsulfonamido)-5-cyanobenzenesulfonamide The title compound was synthesized as described for Example 178 in 27% yield, starting from 2-amino-5-cyanobenzenesulfonamide and 2-(4-chloro-2-methoxyphenyl)-ethenesulfonyl chloride.

MS (ESI) m/z 426, 428 [M−1]$^−$.

Example 183

2-(2-(4-(3,3-dimethylbut-1-ynyl)phenyl)ethylsulfonamido)benzenesulfonamide

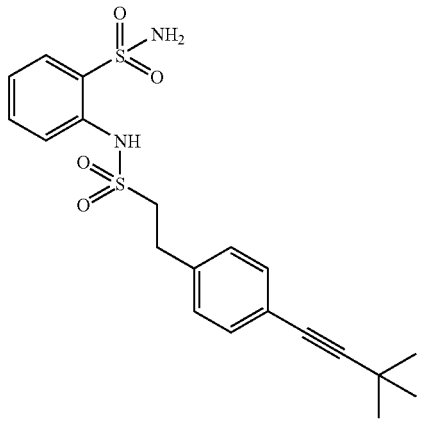 [SMILES: CC(C)(C)C#Cc1ccc(CCS(=O)(=O)Nc2ccccc2S(N)(=O)=O)cc1]

The title compound was synthesized as described for Example 179a) in 16% yield, starting from 2-(2-(4-bromophenyl)ethylsulfonamido)benzenesulfonamide and 3,3-dimethyl-1-butyne.

$^1$H NMR (400 MHz, DMSO-d$_6$) δ ppm 8.94 (s, 1H) 7.80-7.91 (m, 3H) 7.65-7.71 (m, 1H) 7.61 (t, 1H) 7.33 (t, 1H) 7.20-7.27 (m, 2H) 7.14-7.20 (m, 2H) 3.54-3.63 (m, 2H) 2.95-3.03 (m, 2H) 1.27 (s, 9H); MS (ESI) m/z 419 [M−1]$^−$.

Example 184

2-(2-(4-(3-Hydroxy-3-methylbut-1-ynyl)phenyl)ethylsulfonamido)benzenesulfonamide

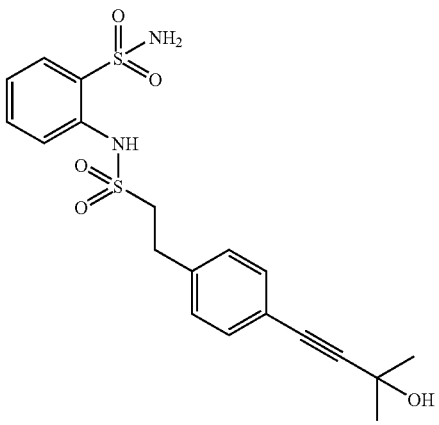 [SMILES: CC(C)(O)C#Cc1ccc(CCS(=O)(=O)Nc2ccccc2S(N)(=O)=O)cc1]

The title compound was synthesized as described for Example 179 a) in 42% yield, starting from 2-[2-(4-bromophenyl)ethylsulfonylamino]benzenesulfonamide and 2-methyl-3-butyn-2-ol.

$^1$H NMR (400 MHz, DMSO-d$_6$) δ ppm 8.94 (s, 1H) 7.81-7.90 (m, 3H) 7.66-7.71 (m, 1H) 7.61 (t, 1H) 7.33 (t, 1H) 7.25-7.30 (m, 2H) 7.18-7.23 (m, 2H) 5.43 (s, 1H) 3.57-3.64 (m, 2H) 2.97-3.04 (m, 2H) 1.44 (s, 6H); MS (ESI) m/z 421 [M−1]$^−$.

Example 185

3-(3,3-Dimethylbut-1-ynyl)-N-(2-sulfamoylphenyl)benzenesulfonamide

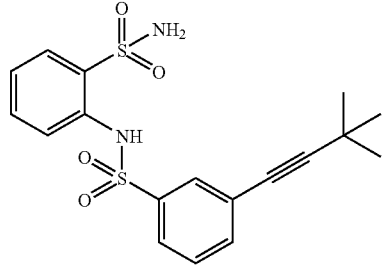 [SMILES: CC(C)(C)C#Cc1cccc(S(=O)(=O)Nc2ccccc2S(N)(=O)=O)c1]

The title compound was synthesized as described for Example 179a) in 27% yield, starting from 3-bromo-N-(2-sulfamoylphenyl)benzenesulfonamide and 3,3-dimethyl-1-butyne.

$^1$H NMR (400 MHz, DMSO-d$_6$) δ ppm 9.37 (br. s., 1H) 7.75-7.86 (m, 5H) 7.61 (d, 1H) 7.54 (t, 2H) 7.45 (d, 1H) 7.22-7.30 (m, 1H) 1.29 (s, 9H); MS (ESI) m/z 391 [M−1]$^−$ a)
3-Bromo-N-(2-sulfamoylphenyl)benzenesulfonamide

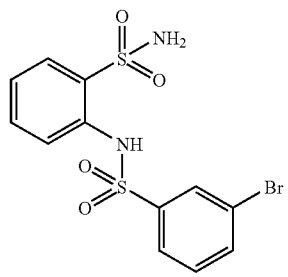 [SMILES: NS(=O)(=O)c1ccccc1NS(=O)(=O)c1cccc(Br)c1]

The title compound was synthesized as described for Example 178 in 48% yield, starting from 2-aminobenzenesulfonamide and 3-bromobenzenesulfonyl chloride. The product solidified after the extractive work up. Diethyl ether (25 mL) was added and the crystals were crushed with a glass stick. The mixture was filtered and the solid was rinsed with diethyl ether and dried in vacuo at ambient temperature.

MS (ESI) m/z 389, 391 [M−1]$^−$.

Example 186

2-(2-(4-Chloro-2-methoxyphenyl)ethylsulfonamido)benzenesulfonamide

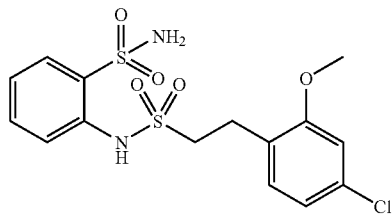 [SMILES: COc1cc(Cl)ccc1CCS(=O)(=O)Nc1ccccc1S(N)(=O)=O]

The title compound was synthesized as described for Example 180 in 47% yield, starting from 2-[2-(4-chloro-2-methoxy-phenyl)-ethanesulfonylamino]-benzenesulfonamide. The starting material was divided into two microwave vials and the reactions were run at 130° C. The reaction mixtures were pooled and then filtered. The solvent was evaporated in vacuo, water was added and the product was extracted with ethyl acetate. The organic phase was washed with brine, dried over magnesium sulfate and concentrated. Purification by recrystallization in methanol.

$^1$H NMR (400 MHz, DMSO-d$_6$) δ ppm 8.95 (s, 1H) 7.88 (dd, 1H) 7.83 (s, 2H) 7.59-7.68 (m, 2H) 7.30-7.36 (m, 1H) 7.17 (d, 1H) 6.98 (d, 1H) 6.90 (dd, 1H) 3.66 (s, 3H) 3.45-3.52 (m, 2H) 2.90-2.97 (m, 2H); MS (ESI) m/z 403, 405 [M−1]$^-$.

Example 187

2-(2-(6-(3,3-Dimethylbut-1-ynyl)pyridin-3-yl)ethyl-sulfonamido)benzenesulfonamide

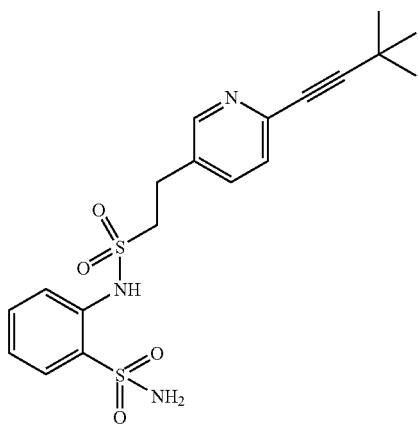 [SMILES: CC(C)(C)C#Cc1ccc(CCS(=O)(=O)Nc2ccccc2S(N)(=O)=O)cn1]

The title compound was synthesized as described for Example 179 a) in 34% yield, starting from 2-(2-(6-bromopyridin-3-yl)ethylsulfonamido)benzenesulfonamide and 3,3-dimethyl-1-butyne. Purification by column chromatography, using 10 to 60% ethyl acetate in heptane as the eluent.

$^1$H NMR (400 MHz, DMSO-d$_6$) δ ppm 8.96 (s, 1H) 8.36 (d, 1H) 7.78-7.92 (m, 3H) 7.57-7.70 (m, 3H) 7.29-7.38 (m, 2H) 3.59-3.71 (m, 2H) 2.99-3.07 (m, 2H) 1.29 (s, 9H);

MS (ESI) m/z 420 [M−1]$^-$ a) 2-(2-(6-Bromopyridin-3-yl)ethylsulfonamido) benzenesulfonamide

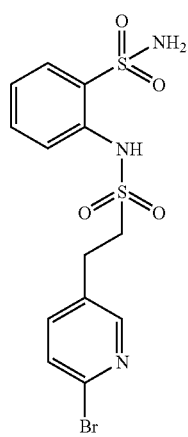 [SMILES: NS(=O)(=O)c1ccccc1NS(=O)(=O)CCc1ccc(Br)nc1]

The title compound was synthesized as described for Example 180 in 62% yield, starting from (E)-2-(2-(6-bromopyridin-3-yl)vinylsulfonamido)benzenesulfonamide. The reaction was run at 110° C. for 30 min. Purification by column chromatography using 5% methanol in chloroform as the eluent.

b) (E)-2-(2-(6-Bromopyridin-3-yl)vinylsulfonamido) benzenesulfonamide

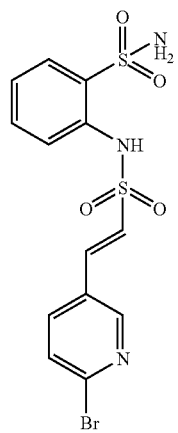 [SMILES: NS(=O)(=O)c1ccccc1NS(=O)(=O)/C=C/c1ccc(Br)nc1]

The title compound was synthesized as described for Example 178 in 69% yield, starting from 2-aminobenzenesulfonamide and (E)-2-(6-bromopyridin-3-yl)ethenesulfonyl chloride. Purification by column chromatography, using ammonium hydroxide/methanol/chloroform (1:10:89) as the eluent.

$^1$H NMR (400 MHz, DMSO-d$_6$) δ ppm 8.60 (d, 1H) 8.12 (dd, 1H) 7.57 (d, 1H) 7.50 (d, 1H) 7.40 (d, 1H) 6.98-7.33 (m, 6H) 6.67 (br. s., 1H).

c) (E)-2-(6-Bromopyridin-3-yl)ethenesulfonyl chloride

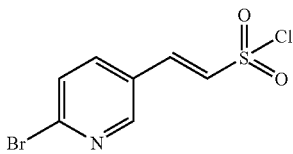 [SMILES: O=S(=O)(Cl)/C=C/c1ccc(Br)nc1]

Triphenylphosphine (2.74 g, 10.44 mmol) was dissolved in anhydrous dichloromethane (30 mL) under an atmosphere of argon and the mixture was cooled to 0° C. with an ice bath. Sulfuryl chloride (0.87 mL, 10.68 mmol) was added dropwise and the cooling bath was removed. The solution was stirred at ambient temperature for 15 min. A solution of (E)-2-(6-bromopyridin-3-yl)ethenesulfonic acid tetrabutylammonium (2.46 g, 4.86 mmol) in anhydrous dichloromethane (10 mL) was added dropwise over 10 min. The reaction was stirred at ambient temperature for 1.5 h and the mixture was concentrated. Purification by column chromatography, using a gradient of 5-30% ethyl acetate in heptane as the eluent, gave 0.51 g of the title compound.

¹H NMR (400 MHz, DMSO-d₆) δ ppm 8.54 (d, 1H) 8.07 (dd, 1H) 7.47 (d, 1H) 7.09 (d, 1H) 6.92 (d, 1H).

d) (E)-2-(6-Bromopyridin-3-yl)ethenesulfonic acid tetrabutylammonium

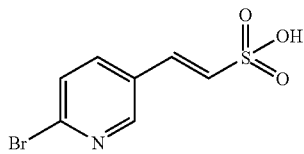 [SMILES: O=S(=O)(O)/C=C/c1ccc(Br)nc1]

(E)-Ethyl 2-(6-bromopyridin-3-yl)ethenesulfonate (1.42 g, 4.86 mmol) and tetrabutylammonium iodide (1.98 g, 5.35 mmol) were dissolved in anhydrous acetone and the mixture was heated at 85° C. over night. The mixture was filtered and the solvent was evaporated to give 2.99 g of the title compound.

MS (ESI) m/z 262, 264 [M−1]⁻.

e) (E)-Ethyl 2-(6-bromopyridin-3-yl)ethenesulfonate

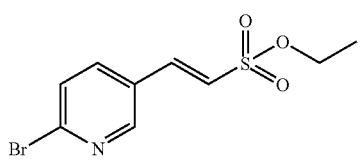

Ethyl methanesulfonate (1.00 mL, 9.34 mmol) was dissolved in anhydrous tetrahydrofuran (20 mL) in an oven dried round bottle under an atmosphere of argon. The solution was cooled to −78° C. and 2.5 M n-butyllithium in hexane (4.09 mL, 10.23 mmol) was added dropwise over 15 min. The mixture was stirred at −78° C. for 15 min and diethyl chlorophosphate (0.78 mL, 5.38 mmol) was added dropwise. The reaction was stirred at −78° C. for 1 h and then the temperature was allowed to reach 0° C. before recooling to −78° C. A solution of 2-bromo-5-formylpyridine (1.0 g, 5.38 mmol) in anhydrous tetrahydrofuran (5 mL) was added dropwise over 15 min and the resulting mixture was stirred for 15 min and then allowed to reach ambient temperature. Water (3 mL) was added and the solvent was evaporated in vacuo. The residue was partitioned between diethyl ether and water. The aqueous phase was extracted with diethyl ether and the formed precipitate was filtered off and rinsed with diethyl ether. This was pure product which was pooled with the rest of the material after purification. The aqueous phase was extracted once more with diethyl ether and the combined organic phases were dried over magnesium sulfate and concentrated. Purification by column chromatography, using a gradient of 10-60% ethyl acetate in heptane as the eluent, gave 0.77 g pooled with the material from the extractive work up to give 1.42 g (90% yield) of the title compound.

¹H NMR (400 MHz, DMSO-d₆) δ ppm 8.77 (d, 1H) 8.19 (dd, 1H) 7.79 (d, 1H) 7.67 (d, 2H) 4.22 (q, 2H) 1.30 (t, 3H); MS (ESI) m/z 262, 264 [M−1]⁻ (M-ethyl).

Example 188

2-(2-(6-(cyclohexylethynyl)pyridin-3-yl)ethylsulfonamido)benzenesulfonamide

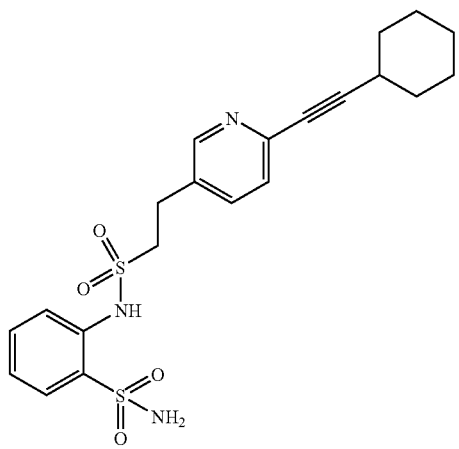 [SMILES: NS(=O)(=O)c1ccccc1NS(=O)(=O)CCc1ccc(C#CC2CCCCC2)nc1]

The title compound was synthesized as described for Example 179 a) in 25% yield, starting from 2-(2-(6-bromopyridin-3-yl)ethylsulfonamido)benzenesulfonamide and cyclohexylacetylene. Purification by column chromatography using a gradient of 10-60% ethyl acetate in heptane as the eluent.

¹H NMR (400 MHz, DMSO-d₆) δ ppm 8.96 (s, 1H) 8.37 (d, 1H) 7.78-7.92 (m, 3H) 7.57-7.70 (m, 3H) 7.29-7.39 (m, 2H) 3.65 (t, 2H) 2.98-3.07 (m, 2H) 2.60-2.70 (m, 1H) 1.77-1.87 (m, 2H) 1.61-1.73 (m, 2H) 1.41-1.55 (m, 3H) 1.29-1.40 (m, 3H); MS (ESI) m/z 446 [M−1]⁻.

Example 189

2-(2-(4-Bromophenyl)ethylsulfonamido)-5-methylbenzenesulfonamide

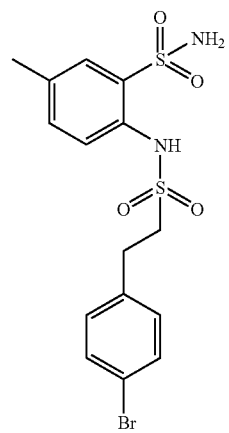 [SMILES: Cc1ccc(NS(=O)(=O)CCc2ccc(Br)cc2)c(S(N)(=O)=O)c1]

The title compound was synthesized as described for Example 180 in 62% yield, starting from (E)-2-(2-(4-bromophenyl)vinylsulfonamido)-5-methylbenzenesulfonamide. The reaction was run at 120° C. for 30 min. Purification by column chromatography using 10 to 50% ethyl acetate in heptane as the eluent.

¹H NMR (400 MHz, DMSO-d₆) δ ppm 8.84 (br. s., 1H) 7.76 (br. s., 2H) 7.69 (br. s., 1H) 7.55 (d, 1H) 7.39-7.48 (m, 3H) 7.15-7.21 (m, 2H) 3.50-3.58 (m, 2H) 2.92-2.99 (m, 2H) 2.33 (s, 3H); MS (ESI) m/z 431, 433 [M−1]⁻.

Example 190

(E)-2-(2-(4-Bromophenyl)vinylsulfonamido)-5-methylbenzenesulfonamide

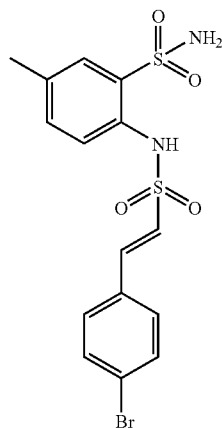 [SMILES: Cc1ccc(NS(=O)(=O)/C=C/c2ccc(Br)cc2)c(S(N)(=O)=O)c1]

The title compound was synthesized as described for Example 178 in 96% yield, starting from 2-amino-5-methylbenzenesulfonamide and (E)-2-(4-bromophenyl)ethenesulfonyl chloride (US20040186134 A1). Purification by column chromatography using a gradient of 10-50% ethyl acetate in heptane as the eluent.

MS (ESI) m/z 429, 431 [M−1]⁻.

Example 191

3-(2-Methylthiazol-4-yl)-N-(2-sulfamoylphenyl)benzenesulfonamide

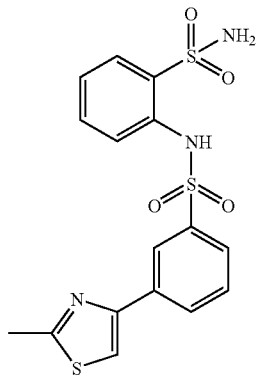 [SMILES: Cc1nc(-c2cccc(S(=O)(=O)Nc3ccccc3S(N)(=O)=O)c2)cs1]

The title compound was synthesized as described for Example 178 in 5% yield, starting from 2-aminobenzenesulfonamide and 3-(2-methylthiazol-4-yl)benzene-1-sulfonyl chloride.

¹H NMR (600 MHz, DMSO-d₆) δ ppm 9.40 (s, 1H) 8.47 (s, 1H) 8.20 (d, 1H) 8.11 (s, 1H) 7.74-7.87 (m, 4H) 7.64 (t, 1H) 7.52 (br. s., 2H) 7.19-7.26 (m, 1H) 2.73 (s, 3H);

MS (ESI) m/z 408 [M−1]⁻.

Example 192

(E)-2-(2-(3-(Trifluoromethyl)phenyl)vinylsulfonamido)benzenesulfonamide

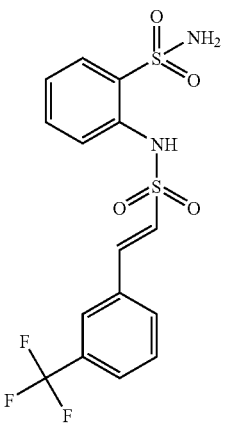 [SMILES: NS(=O)(=O)c1ccccc1NS(=O)(=O)/C=C/c1cccc(C(F)(F)F)c1]

The title compound was synthesized as described for Example 178 in 37% yield, starting from 2-aminobenzenesulfonamide and (E)-2-(3-(trifluoromethyl)phenyl)ethenesulfonyl chloride.

¹H NMR (600 MHz, DMSO-d₆) δ ppm 9.17 (s, 1H) 8.12 (s, 1H) 7.99 (d, 1H) 7.81-7.85 (m, 3H) 7.79 (d, 1H) 7.61-7.73 (m, 4H) 7.59 (t, 1H) 7.28 (t, 1H); MS (ESI) m/z 405 [M−1]⁻.

Example 193

(E)-2-(2-(2-Fluorophenyl)vinylsulfonamido)benzenesulfonamide

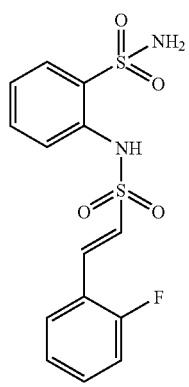 [SMILES: NS(=O)(=O)c1ccccc1NS(=O)(=O)/C=C/c1ccccc1F]

The title compound was synthesized as described for Example 178 in 31% yield, starting from 2-aminobenzenesulfonamide and (E)-2-(2-fluorophenyl)ethenesulfonyl chloride.

¹H NMR (600 MHz, DMSO-d₆) δ ppm 9.12 (s, 1H) 7.79-7.87 (m, 3H) 7.77 (t, 1H) 7.41-7.65 (m, 5H) 7.23-7.33 (m, 3H); MS (ESI) m/z 355 [M−1]⁻.

Example 194

5-Chloro-2-(2-(4-chloro-2-methoxyphenyl)ethylsulfonamido)benzenesulfonamide

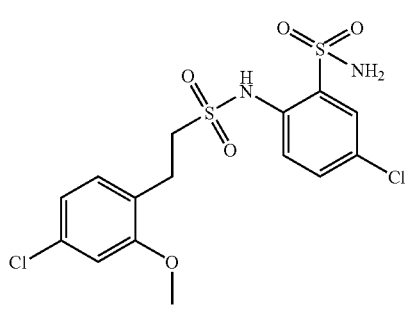 [SMILES: COc1cc(Cl)ccc1CCS(=O)(=O)Nc1ccc(Cl)cc1S(N)(=O)=O]

Sodium acetate (64 mg, 0.78 mmol) and para-toluenesulfonhydrazide (145 mg, 0.78 mmol) was added to a solution of (E)-5-chloro-2-(2-(4-chloro-2-methoxyphenyl)vinylsulfonamido)benzenesulfonamide (85 mg, 0.19 mmol) in tetrahydrofuran (3 mL). The reaction mixture was heated at 180° C. for 15 min in a microwave reactor. The solids were removed by filtration, washed with tetrahydrofuran and the combined filtrates were evaporated. Purification by preparative HPLC gave 0.037 g (43% yield) of the title compound.

$^1$H NMR (DMSO-d$_6$) δ ppm 8.99 (br s, 1H) 8.15-7.75 (m, 3H) 7.62 (br s, 2H) 7.17 (d, 1H) 7.00 (d, 1H) 6.91 (dd, 1H) 3.70 (s, 3H) 3.46 (br s., 2H) 2.88-3.03 (m, 2H); MS (ESI) m/z 437 [M−1]$^-$.

a) (E)-5-Chloro-2-(2-(4-chloro-2-methoxyphenyl)vinylsulfonamido)benzenesulfonamide

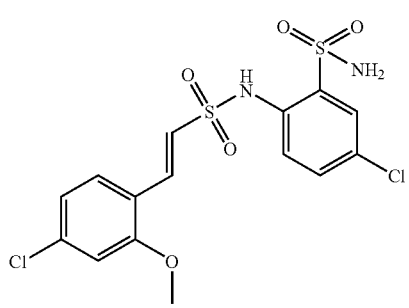 [SMILES: COc1cc(Cl)ccc1/C=C/S(=O)(=O)Nc1ccc(Cl)cc1S(N)(=O)=O]

A solution of 2-amino-5-chlorobenzenesulfonamide (0.041 g, 0.20 mmol) and (E)-2-(4-chloro-2-methoxyphenyl)ethenesulfonyl chloride (0.053 g, 0.20 mmol) in pyridine (2 mL) was stirred at room temperature over night. The reaction mixture was concentrated, 1 M hydrochloric acid was added and the mixture was extracted with dichloromethane. The organic phase was dried over magnesium sulfate and the solvent was evaporated to give 0.087 g (99% yield) of the title compound.

MS (ESI) m/z 435 [M−1]$^-$.

Example 195

2,3-Dichloro-N-(4-chloro-2-sulfamoylphenyl)benzenesulfonamide

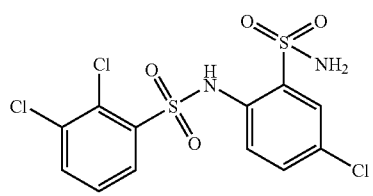 [SMILES: NS(=O)(=O)c1cc(Cl)ccc1NS(=O)(=O)c1cccc(Cl)c1Cl]

The title compound was synthesized as described for Example 194 a) in 21% yield, using 2,3-dichlorobenzene-1-sulfonyl chloride (1.5 equiv.). Purification by preparative HPLC.

$^1$H NMR (DMSO-d$_6$) δ ppm 8.15 (dd, 1H) 7.88-8.07 (m, 3H) 7.84 (d, 1H) 7.54-7.67 (m, 2H) 7.36 (d, 1H); MS (ESI) m/z 413, 415 [M−1]$^-$.

Example 196

2,3-Dichloro-N-(3,5-difluoro-2-sulfamoylphenyl)benzenesulfonamide

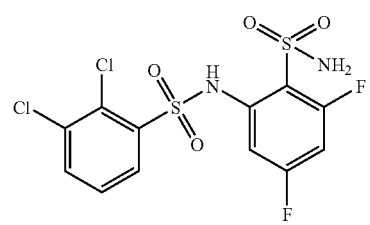 [SMILES: NS(=O)(=O)c1c(F)cc(F)cc1NS(=O)(=O)c1cccc(Cl)c1Cl]

The title compound was synthesized as described for Example 194 a) in 7% yield, starting from 2-amino-4,6-difluorobenzenesulfonamide and 2,3-dichlorobenzene-1-sulfonyl chloride (1.5 equiv.). Purification by preparative HPLC.

$^1$H NMR (DMSO-d$_6$) δ ppm 8.27 (d, 2H) 8.03 (d, 1H) 7.65 (t, 1H) 6.96 (d, 1H); MS (ESI) m/z 415, 417 [M−1]$^-$.

Example 197

2-(2-(3,4-Dichlorophenyl)ethylsulfonamido)-4,6-difluorobenzenesulfonamide

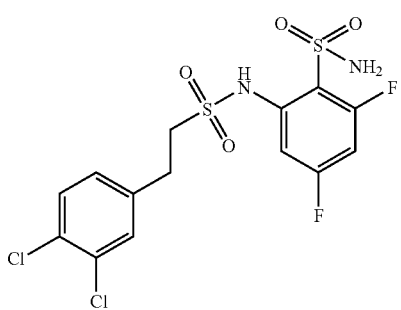 [SMILES: NS(=O)(=O)c1c(F)cc(F)cc1NS(=O)(=O)CCc1ccc(Cl)c(Cl)c1]

The title compound was synthesized as described for Example 194 in 28% yield, starting from (E)-2-(2-(3,4-dichlorophenyl)vinylsulfonamido)-4,6-difluorobenzenesulfonamide. The reaction was run at 140° C. Purification by preparative HPLC.

$^{1}$H NMR (DMSO-d$_{6}$) δ ppm 9.60 (br s, 1H) 8.05 (br s, 2H) 7.43 (d, 1H) 7.36 (d, 1H) 7.02-7.18 (m, 3H) 3.67 (t, 2H) 2.80-2.94 (m, 2H); MS (ESI) m/z 443, 445 [M−1]$^{−}$.

a) (E)-2-(2-(3,4-Dichlorophenyl)vinylsulfonamido)-4,6-difluorobenzenesulfonamide

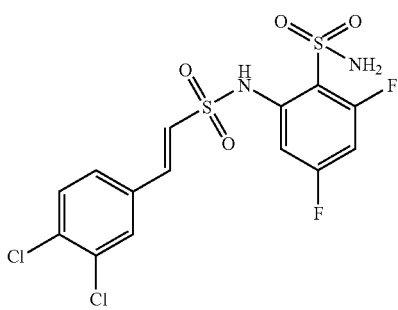 [SMILES: NS(=O)(=O)c1c(F)cc(F)cc1NS(=O)(=O)/C=C/c1ccc(Cl)c(Cl)c1]

The title compound was synthesized as described for Example 194 a) in 49% yield, starting from 2-amino-4,6-difluorobenzenesulfonamide and (E)-2-(3,4-dichlorophenyl)ethenesulfonyl chloride (1.5 equiv.). Purification by column chromatography, using chloroform/methanol (95:5) as the eluent.

$^{1}$H NMR (DMSO-d$_{6}$) δ ppm 10.01 (br s, 1H) 8.25 (br s., 2H) 8.14 (s, 1H) 7.66-7.83 (m, 4H) 7.12-7.39 (m, 2H); MS (ESI) m/z 441, 443 [M−1]$^{−}$.

Example 198

2-(2-(4-Chloro-2-methoxyphenyl)ethylsulfonamido)-4,6-difluorobenzenesulfonamide

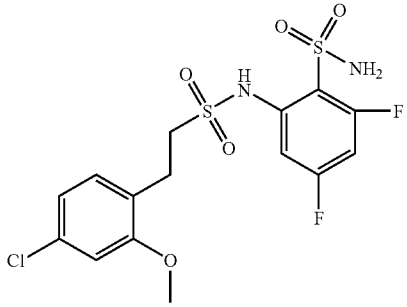 [SMILES: COc1cc(Cl)ccc1CCS(=O)(=O)Nc1cc(F)cc(F)c1S(N)(=O)=O]

The title compound was synthesized as described for Example 197 in 44% yield, starting from (E)-2-(2-(4-chloro-2-methoxyphenyl)vinylsulfonamido)-4,6-difluorobenzenesulfonamide. Purification by preparative HPLC.

$^{1}$H NMR (DMSO-d$_{6}$) δ ppm 9.82 (br s, 1H) 8.24 (s, 2H) 7.19-7.35 (m, 3H) 7.00 (d, 1H) 6.92 (dd, 1H) 3.58-3.74 (m, 5H) 2.92-3.01 (m, 2H); MS (ESI) m/z 439 [M−1]$^{−}$.

a) (E)-2-(2-(4-Chloro-2-methoxyphenyl)vinylsulfonamido)-4,6-difluorobenzenesulfonamide

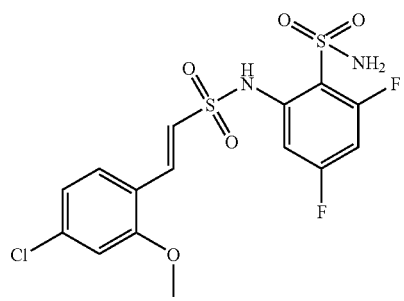 [SMILES: COc1cc(Cl)ccc1/C=C/S(=O)(=O)Nc1cc(F)cc(F)c1S(N)(=O)=O]

The title compound was synthesized as described for Example 197 a) in 48% yield, using (E)-2-(4-chloro-2-methoxyphenyl)ethenesulfonyl chloride (1.5 equiv.). Purification by column chromatography, using chloroform/methanol (95:5) as the eluent.

$^{1}$H NMR (DMSO-d$_{6}$) δ ppm 9.95 (br s, 1H) 8.24 (br s, 2H) 7.68-7.80 (m, 2H) 7.51 (d, 1H) 7.04-7.34 (m, 4H) 3.91 (s, 3H); MS (ESI) m/z 437 [M−1]$^{−}$.

Example 199

5-Cyano-2-(2-(3,4-dichlorophenyl)ethylsulfonamido)benzenesulfonamide

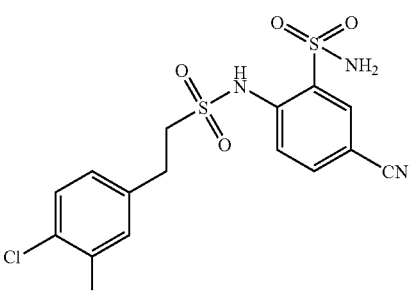

The title compound was synthesized as described for Example 194 in 26% yield, starting from (E)-5-cyano-2-(2-(3,4-dichlorophenyl)vinylsulfonamido)benzenesulfonamide. The reaction was run at 120° C. Purification by preparative HPLC.

¹H NMR (DMSO-d₆) δ ppm 9.00 (br s, 1H) 7.99 (br s, 1H) 7.74-7.93 (m, 3H) 7.58 (d, 1H) 7.29-7.40 (m, 2H) 7.06 (dd, 1H) 3.62 (br s, 2H) 2.82-2.91 (m, 2H); MS (ESI) m/z 432, 434 [M−1]⁻.

a) (E)-5-Cyano-2-(2-(3,4-dichlorophenyl)vinylsulfonamido)benzenesulfonamide

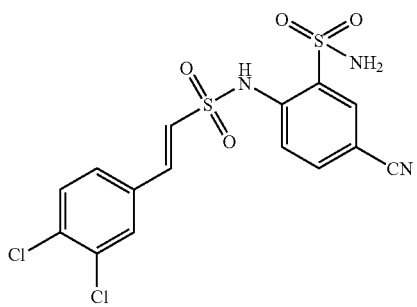 [SMILES: N#Cc1ccc(NS(=O)(=O)/C=C/c2ccc(Cl)c(Cl)c2)c(S(N)(=O)=O)c1]

The title compound was synthesized as described for Example 194 a), starting from 2-amino-5-cyanobenzenesulfonamide and (E)-2-(3,4-dichlorophenyl)ethenesulfonyl chloride (1.5 equiv.). Purification by column chromatography, using chloroform/methanol (95:5-9:1) as the eluent.

MS (ESI) m/z 430, 432 [M−1]⁻.

Example 200

(E)-2-(2-(3,4-Dichlorophenyl)vinylsulfonamido)-4-methylbenzenesulfonamide

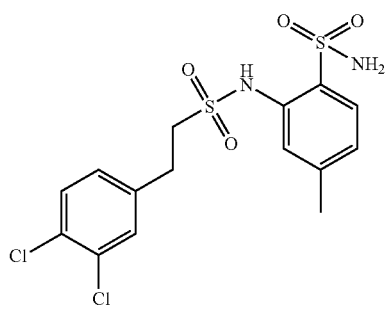 [SMILES: Cc1ccc(S(N)(=O)=O)c(NS(=O)(=O)CCc2ccc(Cl)c(Cl)c2)c1]

The title compound was synthesized as described for Example 197 in 32% yield, starting from (E)-2-(2-(3,4-dichlorophenyl)vinylsulfonamido)-4-methylbenzenesulfonamide. Purification by preparative HPLC.

¹H NMR (DMSO-d₆) δ ppm 8.81 (s, 1H) 7.58-7.75 (m, 3H) 7.40-7.49 (m, 2H) 7.34 (s, 1H) 7.14 (dd, 1H) 7.04 (d, 1H) 3.48-3.65 (m, 2H) 2.87-3.00 (m, 2H) 2.27 (s, 3H);

MS (ESI) m/z 421, 423 [M−1]⁻.

a) (E)-2-(2-(3,4-Dichlorophenyl)vinylsulfonamido)-4-methylbenzenesulfonamide

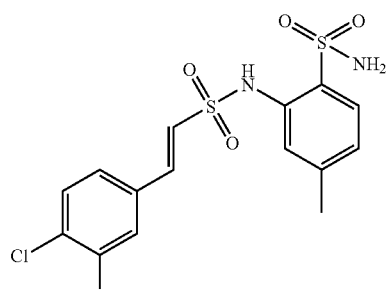

The title compound was synthesized as described for Example 194 a) in 54% yield, starting from 2-amino-4-methylbenzenesulfonamide and (E)-2-(3,4-dichlorophenyl)ethenesulfonyl chloride (1.5 equiv.). Purification by column chromatography, using chloroform/methanol (95:5) as the eluent.

¹H NMR (DMSO-d₆) δ ppm 9.13 (s, 1H) 8.06 (s, 1H) 7.76 (s, 2H) 7.67-7.74 (m, 3H) 7.52-7.66 (m, 2H) 7.41 (s, 1H) 7.11 (d, 1H) 2.35 (s, 3H); MS (ESI) m/z 419, 421 [M−1]⁻

Example 201

2-(2-(4-Chloro-2-methoxyphenyl)ethylsulfonamido)-4-methylbenzenesulfonamide

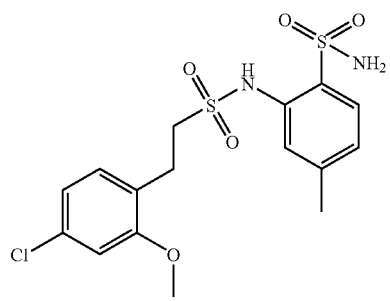 [SMILES: COc1cc(Cl)ccc1CCS(=O)(=O)Nc1cc(C)ccc1S(N)(=O)=O]

The title compound was synthesized as described for Example 197 in 66% yield, starting from (E)-2-(2-(4-chloro-2-methoxyphenyl)vinylsulfonamido)-4-methylbenzenesulfonamide. Purification by preparative HPLC.

¹H NMR (DMSO-d₆) δ ppm 8.91 (s, 1H) 7.72-7.82 (m, 3H) 7.44 (d, 1H) 7.10-7.21 (m, 2H) 7.00 (d, 1H) 6.91 (dd, 1H) 3.68 (s, 3H) 3.45-3.55 (m, 2H) 2.91-2.99 (m, 2H) 2.37 (s, 3H); MS (ESI) m/z 417 [M−1]⁻.

a) (E)-2-(2-(4-Chloro-2-methoxyphenyl)vinylsulfonamido)-4-methylbenzenesulfonamide

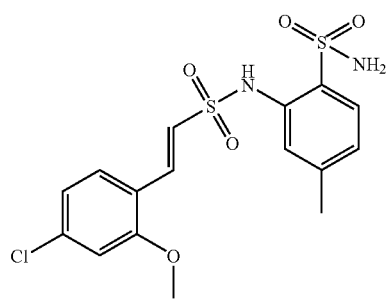 [SMILES: COc1cc(Cl)ccc1/C=C/S(=O)(=O)Nc1cc(C)ccc1S(N)(=O)=O]

The title compound was synthesized as described for Example 194 a) in 69% yield, starting from 2-amino-4-methylbenzenesulfonamide and (E)-2-(4-chloro-2-methoxyphenyl)ethenesulfonyl chloride (1.5 equiv.). Purification by column chromatography, using chloroform/methanol (95:5) as the eluent.

¹H NMR (DMSO-d₆) δ ppm 9.03 (s, 1H) 7.75 (s, 2H) 7.59-7.73 (m, 3H) 7.35-7.46 (m, 2H) 7.20 (d, 1H) 7.08 (td, 2H) 3.89 (s, 3H) 2.34 (s, 3H); MS (ESI) m/z 415 [M−1]⁻.

Example 202

5-Chloro-2-(2-(3,4-dichlorophenyl)ethylsulfonamido)benzenesulfonamide

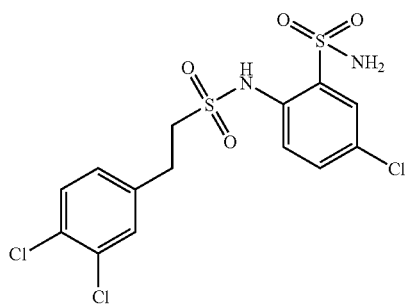 [SMILES: NS(=O)(=O)c1cc(Cl)ccc1NS(=O)(=O)CCc1ccc(Cl)c(Cl)c1]

The title compound was synthesized as described for Example 197 in 59% yield, starting from (E)-5-chloro-2-(2-(3,4-dichlorophenyl)vinylsulfonamido)benzenesulfonamide. Purification by preparative HPLC.

¹H NMR (DMSO-d₆) δ ppm 8.97 (s, 1H) 7.96 (br s, 2H) 7.86 (s, 1H) 7.64-7.74 (m, 2H) 7.49-7.59 (m, 2H) 7.25 (dd, 1H) 3.62-3.74 (m, 2H) 2.97-3.09 (m, 2H); MS (ESI) m/z 441, 443 [M−1]⁻.

a) (E)-5-Chloro-2-(2-(3,4-dichlorophenyl)vinylsulfonamido)benzenesulfonamide

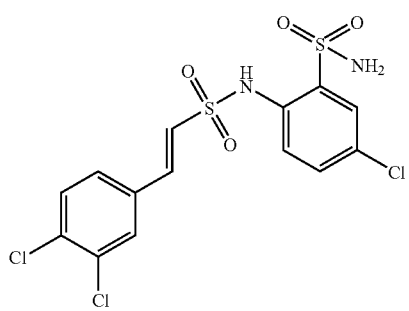 [SMILES: NS(=O)(=O)c1cc(Cl)ccc1NS(=O)(=O)/C=C/c1ccc(Cl)c(Cl)c1]

The title compound was synthesized as described for Example 194 a) in 49% yield, starting from 2-amino-5-chlorobenzenesulfonamide and (E)-2-(3,4-dichlorophenyl)ethenesulfonyl chloride (1.5 equiv.). Purification by column chromatography, using chloroform/methanol (95:5) as the eluent.

¹H NMR (DMSO-d₆) δ ppm 9.18 (br s, 1H) 8.06 (d, 1H) 7.96 (br s, 2H) 7.83 (s, 1H) 7.51-7.77 (m, 6H); MS (ESI) m/z 439, 441 [M−1]⁻.

Example 203

4-(3-(5-Chloro-6-methoxypyridin-3-yl)phenylsulfonamido)pyridine-3-sulfonamide

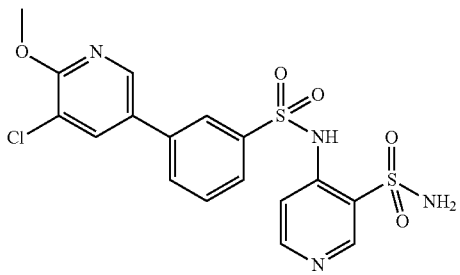 [SMILES: COc1ncc(-c2cccc(S(=O)(=O)Nc3ccncc3S(N)(=O)=O)c2)cc1Cl]

A solution of N,N-diallyl-4-(3-(5-chloro-6-methoxypyridin-3-yl)phenylsulfonamido)pyridine-3-sulfonamide (0.19 g, 0.36 mmol) in dichloromethane (5 mL) was added to tetrakis(triphenylphosphine)palladium(0) (0.021 g, 0.022 mmol) and 1,3-dimethylbarbituric acid (0.336 g, 2.15 mmol) under an atmosphere of argon. The reaction was heated at 100° C. for 15 min in a microwave reactor and the reaction mixture was concentrated. Purification by column chromatography, using chloroform/methanol (95:5-9:1) as the eluent, gave the title compound in 49% yield.

¹H NMR (DMSO-d₆) δ ppm 13.01 (br s, 1H) 8.39 (dd, 2H) 8.18 (d, 1H) 8.09 (t, 1H) 7.94 (dd, 1H) 7.73-7.79 (m, 2H) 7.48 (t, 1H) 7.33 (d, 1H) 6.89 (s, 2H) 3.88 (s, 3H); MS (ESI) m/z 453 [M−1]⁻.

a) N,N-Diallyl-4-(3-(5-chloro-6-methoxypyridin-3-yl)phenylsulfonamido)pyridine-3-sulfonamide

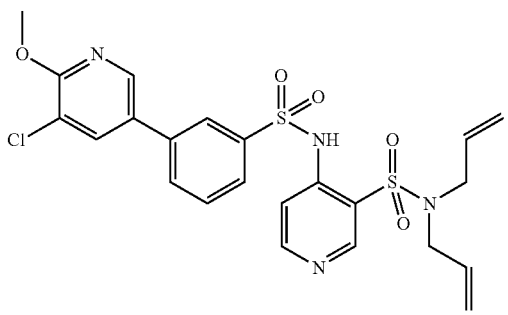 [SMILES: C=CCN(CC=C)S(=O)(=O)c1cnccc1NS(=O)(=O)c1cccc(-c2cnc(OC)c(Cl)c2)c1]

A mixture of N,N-diallyl-4-(3-bromophenylsulfonamido)pyridine-3-sulfonamide (0.29 g, 0.62 mmol), 5-chloro-6-methoxypyridin-3-ylboronic acid (0.15 g, 0.81 mmol), (1,1'-bis(diphenylphosphino)ferrocene)-dichloropalladium(II) (0.026 g, 0.030 mmol), cesium carbonate (0.30 g, 0.93 mmol), 1,2-dimethoxyethane (4.5 mL) and water (0.5 mL) under an atmosphere of argon was heated at 100° C. for 15 min in a microwave reactor. The reaction mixture was partitioned between ethyl acetate and diluted hydrochloric acid, the organic phase was dried over magnesium sulfate and the solvent was evaporated. Purification by column chromatography, using chloroform/methanol (98:2) as the eluent, gave the title compound in 58% yield.

MS (ESI) m/z 533 [M−1]⁻.

b) N,N-Diallyl-4-(3-bromophenylsulfonamido)pyridine-3-sulfonamide

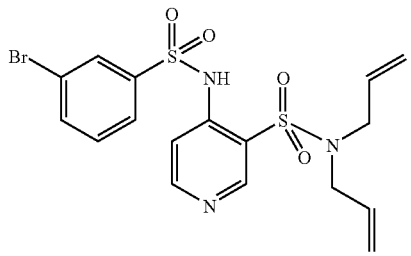 [SMILES: C=CCN(CC=C)S(=O)(=O)c1cnccc1NS(=O)(=O)c1cccc(Br)c1]

A mixture of N,N-diallyl-4-aminopyridine-3-sulfonamide (0.25 g, 1.0 mmol) and cesium carbonate (0.82 g, 2.5 mmol) in tetrahydrofuran (10 mL) was stirred for 5 min, 3-bromobenzenesulfonyl chloride (0.17 mL, 1.2 mmol) was added and the reaction was stirred at room temperature over night. Diluted hydrochloric acid was added and the mixture was extracted with ethyl acetate. The organic phase was dried over magnesium sulfate and the solvent was evaporated. Purification by column chromatography, using chloroform/methanol (95:5) as the eluent, gave the title compound in 72% yield.

¹H NMR (DMSO-d₆) δ ppm 13.19 (br s, 1H) 8.54 (d, 1H) 8.07 (dd, 1H) 7.95 (t, 1H) 7.82-7.88 (m, 1H) 7.79 (ddd, 1H) 7.52 (t, 1H) 7.44 (d, 1H) 5.47-5.60 (m, 2H) 5.02-5.11 (m, 4H) 3.74 (d, 4H); MS (ESI) m/z 470, 472 [M−1]⁻.

c) N,N-Diallyl-4-aminopyridine-3-sulfonamide

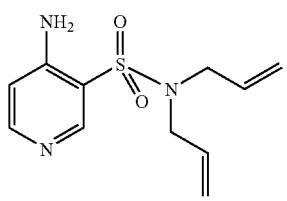 [SMILES: C=CCN(CC=C)S(=O)(=O)c1cnccc1N]

A mixture of N,N-diallyl-4-chloropyridine-3-sulfonamide (1.5 g, 5.5 mmol), lithium iodide (0.74 g, 5.5 mmol) and ammonia (7 M in methanol, 14 mL, 5.5 mmol) under an atmosphere of argon was heated at 120° C. for 2 h in a microwave reactor. Silica was added and the solvent was evaporated. Purification by column chromatography, using chloroform/methanol (95:5) as the eluent, gave the title compound in 59% yield.

¹H NMR (DMSO-d₆) δ ppm 8.43 (s, 1H) 8.12 (d, 1H) 6.67-6.97 (m, 3H) 5.57-5.69 (m, 2H) 5.12-5.23 (m, 4H) 3.80 (d, 4H); MS (ESI) m/z 254 [M−1]⁻.

d) N,N-Diallyl-4-chloropyridine-3-sulfonamide

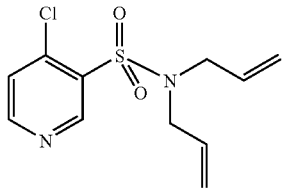 [SMILES: C=CCN(CC=C)S(=O)(=O)c1cnccc1Cl]

4-Chloropyridine-3-sulfonamide (1.93 g, 10.0 mmol) was added in portions to a solution of sodium hydride (60% in mineral oil, 0.88 g, 22.0 mmol) in N,N-dimethylformamide (50 mL). The reaction mixture was stirred at room temperature for 1 h, cooled to 0° C. and allyl bromide (1.90 mL, 22.0 mmol) was added. After 3 h at room temperature methanol was added and the reaction was partitioned between chloroform and water, the organic phase was dried over magnesium sulfate and the solvent was evaporated. Purification by column chromatography, using chloroform/methanol (99:1) as the eluent, gave the title compound in 87% yield.

¹H NMR (DMSO-d₆) δ ppm 9.06 (s, 1H) 8.79 (d, 1H) 7.83 (d, 1H) 5.59-5.73 (m, 2H) 5.12-5.24 (m, 4H) 3.93 (d, 4H).

Example 204

4-(2-(4-(Benzofuran-2-yl)phenyl)ethylsulfonamido)pyridine-3-sulfonamide

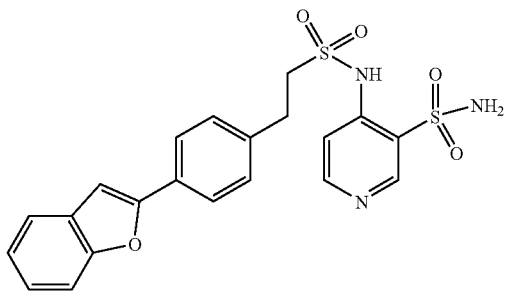 [SMILES: NS(=O)(=O)c1cnccc1NS(=O)(=O)CCc1ccc(-c2cc3ccccc3o2)cc1]

The title compound was synthesized as described for Example 197 in 36% yield, starting from (E)-4-(2-(4-(benzofuran-2-yl)phenyl)vinylsulfonamido)pyridine-3-sulfonamide. Purification by preparative HPLC.

¹H NMR (DMSO-d₆) δ ppm 12.82 (br s, 1H) 8.48 (s, 1H) 8.02 (d, 1H) 7.84-7.90 (m, 2H) 7.59-7.68 (m, 2H) 7.37-7.48 (m, 4H) 7.23-7.35 (m, 2H) 6.99 (br s, 2H) 3.42-3.50 (m, 2H) 3.07-3.20 (m, 2H); MS (ESI) m/z 456 [M−1]⁻.

a) (E)-4-(2-(4-(Benzofuran-2-yl)phenyl)vinylsulfonamido)pyridine-3-sulfonamide

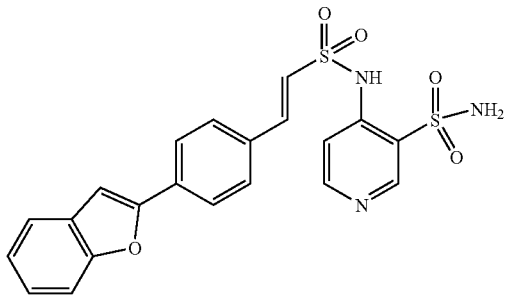 [SMILES: NS(=O)(=O)c1cnccc1NS(=O)(=O)/C=C/c1ccc(-c2cc3ccccc3o2)cc1]

The title compound was synthesized as described for Example 203 in 12% yield, starting from (E)-N,N-diallyl-4-(2-(4-(benzofuran-2-yl)phenyl)vinylsulfonamido)pyridine-3-sulfonamide and heated at 120° C. for 1 h 15 min. Purification by column chromatography, using chloroform/methanol (97:3-9:1) as the eluent.

$^1$H NMR (DMSO-d$_6$) δ ppm 13.01 (br s, 1H) 8.51 (s, 1H) 8.09 (d, 1H) 7.96 (d, 2H) 7.80 (d, 2H) 7.67 (ddd, 2H) 7.55 (d, 1H) 7.43 (dd, 2H) 7.23-7.40 (m, 3H) 6.98 (br s, 2H); MS (ESI) m/z 454 [M−1]$^-$.

b) (E)-N,N-Diallyl-4-(2-(4-(benzofuran-2-yl)phenyl) vinylsulfonamido)pyridine-3-sulfonamide

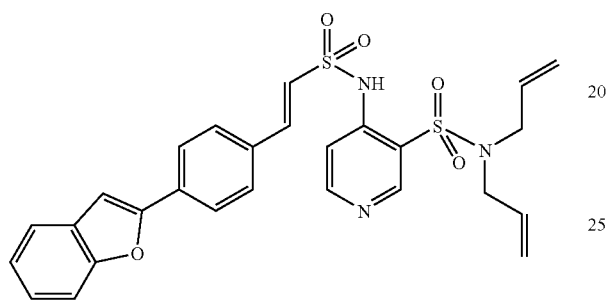

A mixture of (E)-N,N-diallyl-4-(2-(4-bromophenyl)vinylsulfonamido)pyridine-3-sulfonamide (0.47 g, 0.94 mmol), 2-benzofuranboronic acid (0.20 g, 1.23 mmol), (1,1'-bis(diphenylphosphino)ferrocene)-dichloropalladium(II) (0.039 g, 0.050 mmol), cesium carbonate (0.46 g, 1.41 mmol), 1,2-dimethoxyethane (9 mL) and water (1 mL) under an atmosphere of argon was heated at 120° C. for 15 min in a microwave. The reaction mixture was partitioned between ethyl acetate and diluted hydrochloric acid, the organic phase was dried over magnesium sulfate and the solvent was evaporated. Purification by column chromatography, using chloroform/methanol (98:2) as the eluent, gave the title compound in 38% yield.

$^1$H NMR (DMSO-d$_6$) δ ppm 13.03 (br s, 1H) 8.52 (d, 1H) 8.04 (dd, 1H) 7.96 (d, 2H) 7.83 (d, 2H) 7.67 (ddd, 2H) 7.57 (d, 1H) 7.43-7.51 (m, 2H) 7.25-7.41 (m, 3H) 5.60-5.73 (m, 2H) 5.00-5.15 (m, 4H) 3.87-3.96 (m, 4H); MS (ESI) m/z 534 [M−1]$^-$.

c) (E)-N,N-Diallyl-4-(2-(4-bromophenyl)vinylsulfonamido)pyridine-3-sulfonamide

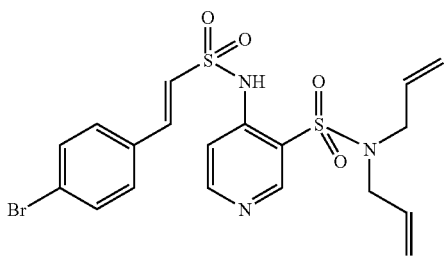 [SMILES: C=CCN(CC=C)S(=O)(=O)c1cnccc1NS(=O)(=O)/C=C/c1ccc(Br)cc1]

Triethylamine (0.440 mL, 3.16 mmol) added was to a solution of N,N-diallyl-4-aminopyridine-3-sulfonamide (0.40 g, 1.58 mmol) in pyridine (10 mL), the mixture was stirred for 5 min and (E)-2-(4-bromophenyl)ethenesulfonyl chloride (0.53 g, 1.89 mmol) was added. After stirring over night the pyridine was evaporated, diluted hydrochloric acid was added and the mixture was extracted with ethyl acetate. The organic phase was dried over magnesium sulfate and the solvent was evaporated. Purification by column chromatography, using chloroform/methanol (97:3) as the eluent, gave the title compound in 60% yield.

$^1$H NMR (DMSO-d$_6$) δ ppm 13.03 (br s, 1H) 8.52 (d, 1H) 8.03 (dd, 1H) 7.58-7.72 (m, 4H) 7.30-7.47 (m, 3H) 5.57-5.74 (m, 2H) 4.99-5.15 (m, 4H) 3.89 (d, 4H).

Example 205

2-(2-(4-Chloro-2-methoxyphenyl)ethylsulfonamido)-5-methylbenzenesulfonamide

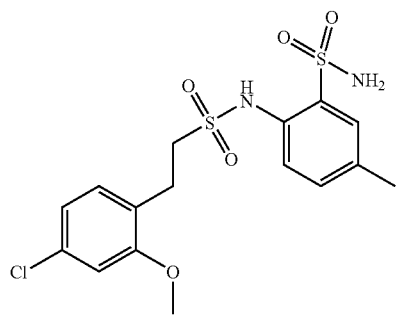 [SMILES: COc1cc(Cl)ccc1CCS(=O)(=O)Nc1ccc(C)cc1S(N)(=O)=O]

The title compound was synthesized as described for Example 194 in 37% yield, starting from (E)-2-(2-(4-chloro-2-methoxyphenyl)vinylsulfonamido)-5-methylbenzenesulfonamide. The reaction was run at 180° C. Purification by preparative HPLC.

$^1$H NMR (DMSO-d$_6$) δ ppm 8.85 (s, 1H) 7.75 (s, 2H) 7.69 (d, 1H) 7.54 (d, 1H) 7.44 (dd, 1H) 7.16 (d, 1H) 6.99 (d, 1H) 6.90 (dd, 1H) 3.68 (s, 3H) 3.39-3.47 (m, 2H) 2.88-2.96 (m, 2H) 2.33 (s, 3H); MS (ESI) m/z 417 [M−1]$^-$.

a) E)-2-(2-(4-Chloro-2-methoxyphenyl)vinylsulfonamido)-5-methylbenzenesulfonamide

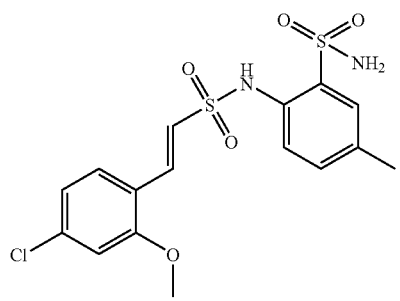 [SMILES: COc1cc(Cl)ccc1/C=C/S(=O)(=O)Nc1ccc(C)cc1S(N)(=O)=O]

The title compound was synthesized as described for Example 194 a) in 81% yield, starting from 2-amino-5-methylbenzenesulfonamide and (E)-2-(4-chloro-2-methoxyphenyl)ethenesulfonyl chloride (1 equiv.).

¹H NMR (DMSO-d₆) δ ppm 8.95 (s, 1H) 7.76 (s, 2H) 7.60-7.66 (m, 2H) 7.48-7.59 (m, 2H) 7.34-7.44 (m, 2H) 7.19 (d, 1H) 7.06 (dd, 1H) 3.88 (s, 3H) 2.29 (s, 3H); MS (ESI) m/z 415 [M−1]⁻.

Example 206

4-(2-(4-Chloro-2-methoxyphenyl)ethylsulfonamido)pyridine-3-sulfonamide

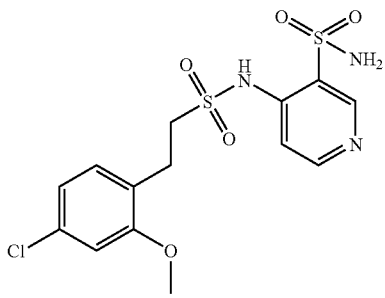 [SMILES: COc1cc(Cl)ccc1CCS(=O)(=O)Nc1ccncc1S(N)(=O)=O]

The title compound was synthesized as described for Example 194 in 38% yield, starting from (E)-4-(2-(4-chloro-2-methoxyphenyl)vinylsulfonamido)pyridine-3-sulfonamide. The reaction was run at 180° C. Purification by preparative HPLC.

¹H NMR (DMSO-d₆) δ ppm 12.83 (br s, 1H) 8.48 (s, 1H) 8.01 (d, 1H) 7.36 (d, 1H) 7.22 (d, 1H) 7.04 (d, 1H) 6.87-7.01 (m, 3H) 3.82 (s, 3H) 3.23-3.30 (m, 2H) 2.94-3.04 (m, 2H); MS (ESI) m/z 404 [M−1]⁻.

a) (E)-4-(2-(4-Chloro-2-methoxyphenyl)vinylsulfonamido)pyridine-3-sulfonamide

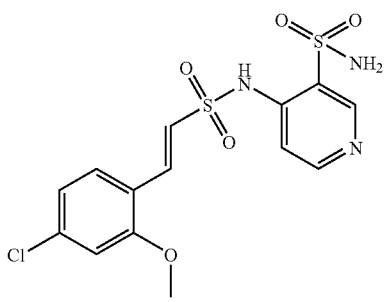 [SMILES: COc1cc(Cl)ccc1/C=C/S(=O)(=O)Nc1ccncc1S(N)(=O)=O]

The title compound was synthesized as described for Example 203 in 65% yield, starting from (E)-N,N-diallyl-4-(2-(4-chloro-2-methoxyphenyl)vinylsulfonamido)pyridine-3-sulfonamide and heating at 100° C. for 1 h. The reaction mixture was evaporated and subsequent purification by column chromatography, using chloroform/methanol (98:2-9:1) as the eluent.

¹H NMR (DMSO-d₆) δ ppm 13.04 (br s, 1H) 8.52 (s, 1H) 8.09 (d, 1H) 7.68 (d, 1H) 7.51-7.59 (m, 1H) 7.37-7.47 (m, 2H) 7.19 (d, 1H) 7.06 (dd, 1H) 6.96 (br s, 2H) 3.90 (s, 3H); MS (ESI) m/z 402 [M−1]⁻.

b) (E)-N,N-Diallyl-4-(2-(4-chloro-2-methoxyphenyl)vinylsulfonamido)pyridine-3-sulfonamide

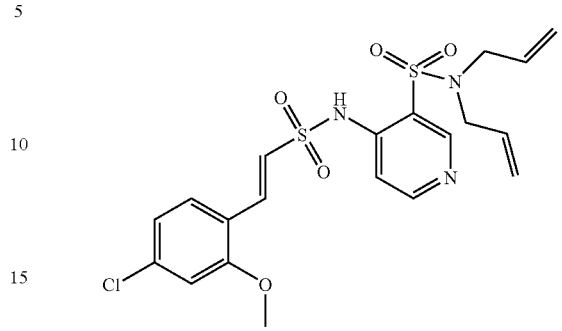

The title compound was synthesized as described for Example 204 c) in 50% yield, starting from N,N-diallyl-4-aminopyridine-3-sulfonamide and (E)-2-(4-chloro-2-methoxyphenyl)ethenesulfonyl chloride. Purification by column chromatography, using chloroform/methanol (98:2) as the eluent.

¹H NMR (CDCl₃) δ ppm 9.27 (br s, 1H) 8.88 (s, 1H) 8.56 (d, 1H) 7.82 (d, 1H) 7.54 (d, 1H) 7.37 (d, 1H) 7.10 (d, 1H) 7.01 (dd, 1H) 6.96 (d, 1H) 5.59-5.73 (m, 2H) 5.18-5.29 (m, 4H) 3.88-3.97 (m, 7H); MS (ESI) m/z 482 [M−1]⁻.

Example 207

(E)-2-(2-(4-Cyclopentenylphenyl)vinylsulfonamido)benzenesulfonamide

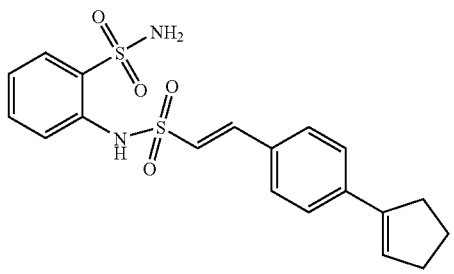 [SMILES: NS(=O)(=O)c1ccccc1NS(=O)(=O)/C=C/c1ccc(C2=CCCC2)cc1]

2-[[(E)-2-(4-Bromophenyl)ethenylsulfonylamino]benzenesulfonamide (75 mg, 0.18 mmol), cyclopenten-1-ylboronic acid (40.2 mg, 0.36 mmol), (1,1'-bis(diphenylphosphino)ferrocene)-dichloropalladium(II) (14.79 mg, 0.02 mmol) and sodium carbonate (38.1 mg, 0.36 mmol) were suspended in N,N-dimethylformamide (2 mL) and the reaction mixture was stirred under an atmosphere of argon at 90° C. for 16 hours. The reaction mixture was diluted with tetrahydrofuran and filtered through Celite. The solvent was removed in vacuo and the residue was purified by preparative HPLC. The residue was purified a second time by column chromatography, using gradient mixtures of ethyl acetate/heptane as eluent (0%-100% ethyl acetate) to give 50 mg (69% yield) of the title compound.

¹H NMR (DMSO-d₆) δ ppm 7.84 (m, 3H), 7.62 (m, 2H), 7.56 (m, 2H), 7.49 (m, 2H), 7.49 (m, 2H), 7.39 (m, 1H), 7.25 (m, 1H), 2.65 (m, 2H), 2.49 (m, 2H), 1.49 (m, 2H); MS (ESI) m/z 403 [M−1]⁻.

Example 208

(E)-2-(2-(4-(3,3-Dimethylbut-1-ynyl)phenyl)vinyl-sulfonamido)benzenesulfonamide

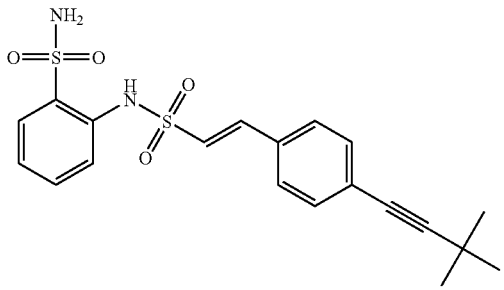 [SMILES: CC(C)(C)C#Cc1ccc(/C=C/S(=O)(=O)Nc2ccccc2S(N)(=O)=O)cc1]

2-[[(E)-2-(4-Bromophenyl)ethenylsulfonylamino]benzenesulfonamide (79 mg, 0.19 mmol), (2-tert-butyl-1-ethynyl) diisopropoxyborane (80 mg, 0.38 mmol), (1,1'-bis(diphenylphosphino)ferrocene)-dichloropalladium(II) (7.79 mg, 9.47 μmol) and sodium carbonate (40.1 mg, 0.38 mmol) were suspended in N,N-dimethylformamide (2.5 mL) and water (0.2 mL) and the reaction mixture was stirred vigorously under an atmosphere of argon at 90° C. for 3 hours. The mixture was filtered through a pad of Celite, the solvent was removed in vacuo and the residue was purified by preparative HPLC to give 10 mg (23% yield) of the title compound.

$^1$H NMR (CD$_3$OD) δ ppm 7.88 (m, 1H), 7.72 (m, 1H), 7.50 (m, 4H), 7.33 (m, 2H), 7.20 (br.s., 1H), 7.10 (m, 1H), 1.30 (s, 9H); MS (ESI) m/z 417 [M−1]$^-$.

Example 209

(E)-2-(2-(4-(3-Hydroxy-3-methylbut-1-ynyl)phenyl) vinylsulfonamido)benzenesulfonamide

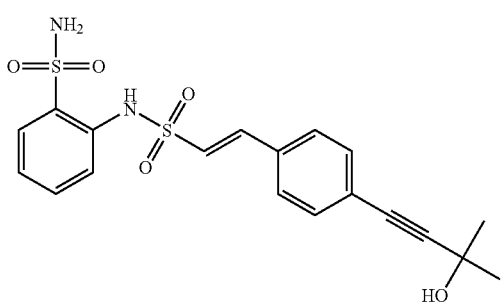 [SMILES: CC(C)(O)C#Cc1ccc(/C=C/S(=O)(=O)Nc2ccccc2S(N)(=O)=O)cc1]

2-[[(E)-2-(4-Bromophenyl)ethenylsulfonylamino]henzenesulfonamide (79 mg, 0.19 mmol), 2-methyl-3-butyn-2-ol (18 μL, 0.19 mmol), copper(I) iodide (9.00 mg, 0.05 mmol), tetrakis(triphenylphosphine)palladium(0) (30.0 mg, 0.03 mmol) and triethylamine (79 μL, 0.57 mmol) were dissolved in tetrahydrofuran (2 mL), the reaction mixture was stirred at 50° C. under an atmosphere of argon for 4 hours and subsequently stirred at room temperature for 10 hours. The reaction mixture was filtered, the solvent was removed in vacuo and the residue was purified by preparative HPLC to give 4 mg (5% yield) of the title compound.

$^1$H NMR (CD$_3$OD) δ ppm 7.78 (m, 1H), 7.73 (m, 1H), 7.5 (m, 4H), 7.38 (m, 2H), 7.23 (m, 1H), 7.15 (m, 1H), 1.54 (s, 6H); MS (ESI) m/z 419 [M−1]$^-$.

Example 210

2-{2-[4-(3,3-Dimethyl-but-1-ynyl)-phenyl]-ethane-sulfonylamino}-5-methyl-benzenesulfonamide

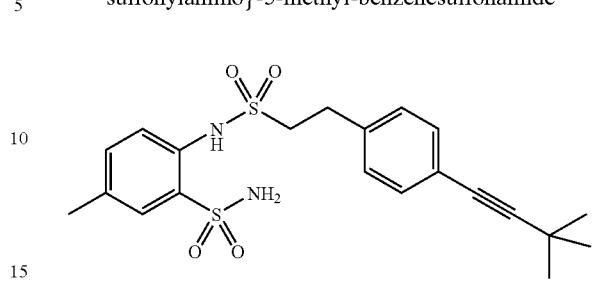

A mixture of 2-[2-(4-bromo-phenyl)-ethanesulfonylamino]-5-methyl-benzenesulfonamide (0.08 g, 0.18 mmol), N,N-diisopropylethylamine (0.1 mL, 0.55 mmol), and copper (I) iodide (7 mg, 0.04 mmol) in anhydrous N,N-dimethylformamide (2 mL) was degassed with nitrogen for 30 min. (1,1'-Bis(diphenylphosphino)ferrocene)-dichloropalladium (II) (14 mg, 0.02 mmol) and 3,3-dimethyl-1-butyne (0.045 mL, 0.37 mmol) were added and the reaction mixture was heated in a sealed tube at 80° C. overnight. The reaction mixture was diluted with ethyl acetate (20 mL), washed with water and brine, dried over sodium sulfate and concentrated under reduced pressure. The residue was purified by preparative TLC, using 5% methanol in dichloromethane as the eluent, to give 20 mg (25% yield) of the title compound.

$^1$H NMR (400 MHz, CD$_3$OD) δ ppm 7.77 (s, 1H), 7.65 (d, 1H), 7.40 (d, 1H), 7.22 (d, 2H), 7.20 (d, 2H), 3.48 (m, 2H), 3.45 (m, 2H), 2.37 (m, 3H), 1.28 (s, 9H); MS (ESI) m/z 433 [M−1]$^-$.

a) 2-[2-(4-Bromo-phenyl)-ethanesulfonylamino]-5-methyl-benzenesulfonamide

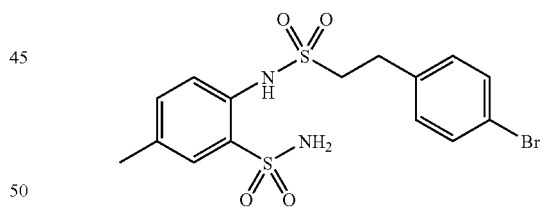

A mixture of 2-amino-5-methyl-benzenesulfonamide (0.1 g, 0.53 mmol) and 2-(4-bromo-phenyl)-ethanesulfonyl chloride (0.14 g, 0.49 mmol) in anhydrous pyridine (4 mL) was stirred at room temperature overnight. The reaction mixture was diluted with ethyl acetate (20 mL) and the organic phase was washed with aqueous hydrochloric acid (1 M, 20 mL), saturated sodium bicarbonate (20 mL) and brine, dried over magnesium sulfate and concentrated under reduced pressure. The residue was purified by preparative TLC, using 5% methanol in dichloromethane as the eluent, to give 80 mg (38% yield) of title compound.

$^1$H NMR (400 MHz, CD$_3$OD) δ ppm 7.77 (s, 1H), 7.64 (d, 1H), 7.40-7.37 (m, 3H), 7.11 (d, 2H), 3.49-3.45 (m, 2H), 3.04-3.02 (m, 2H), 2.37 (s, 3H)

b) 2-(4-Bromo-phenyl)-ethanesulfonyl chloride

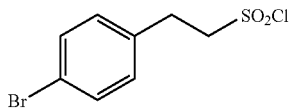 [SMILES: O=S(=O)(Cl)CCc1ccc(Br)cc1]

Thionyl chloride (1.51 mL, 20.8 mmol) was added dropwise at 0° C. to a suspension of sodium 2-(4-bromo-phenyl)-ethanesulfonate (4.33 g, 15.08 mmol) in a mixture of anhydrous benzene (50 mL) and N,N-dimethylformamide (1 mL). The reaction mixture was allowed to warm to room temperature and was then heated at 80° C. for 18 hours. The reaction mixture was cooled to room temperature and filtered through a pad of Celite. The solids were washed with benzene and the combined filtrates were concentrated in vacuo. The residue was taken up in hexane (30 mL) and the resulting suspension was heated at 50° C. for 30 min. After cooling to room temperature, the formed precipitate was collected by filtration to give 4.06 g (95% yield) of the title compound.

$^1$H NMR (400 MHz, DMSO-$d_6$) δ ppm 7.42 (d, 2H), 7.17 (d, 2H), 2.89-2.79 (m, 2H), 2.80-2.68 (m, 2H); MS (ESI) m/z 263 [M−1]$^-$ (corresponding sulfonic acid MW=265)

c) Sodium 2-(4-bromo-phenyl)-ethanesulfonate

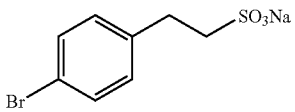

Sodium sulfite (4.75 g, 37.68 mmol) was added to a suspension of 1-bromo-4-(2-bromo-ethyl)-benzene (5.00 g, 18.94 mmol) in water (60 mL). The reaction mixture was heated at 105-107° C. for 18 hours and then cooled to −5° C. The formed precipitate was removed by filtration, washed with water (50 mL) and dried under vacuum to give 4.33 g (86% yield) of the title compound.

$^1$H NMR (400 MHz, DMSO-$d_6$) δppm 7.44 (d, 2H), 7.18 (d, 2H), 2.88-2.80 (m, 2H), 2.68-2.61 (m, 2H); MS (ESI) m/z 263 [M−1]$^-$ (corresponding sulfonic acid, MW=265).

Example 211

2-{2-[4-(3,3-Dimethyl-but-1-ynyl)-phenyl]-ethanesulfonylamino}-5-hydroxymethyl-benzenesulfonamide

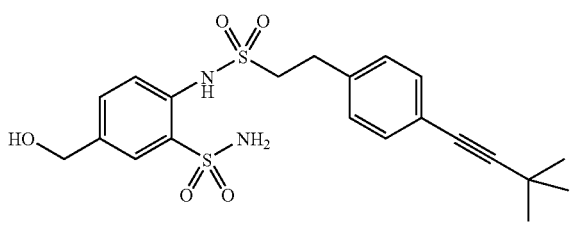 [SMILES: CC(C)(C)C#Cc1ccc(CCS(=O)(=O)Nc2ccc(CO)cc2S(N)(=O)=O)cc1]

The title compound was synthesized as described for Example 210 in 5% yield, starting from 2-[2-(4-bromo-phenyl)-ethanesulfonylamino]-5-hydroxymethyl-benzenesulfonamide and 3,3-dimethyl-1-butyne. Purification by preparative HPLC.

$^1$H NMR (400 MHz, CD$_3$OD) δ ppm 7.97 (s, 1H), 7.74 (d, 1H), 7.54 (d, 1H), 7.20 (d, 2H), 7.09 (d, 2H), 4.60 (s, 2H), 3.46 (m, 2H), 3.02 (m, 2H), 1.28 (s, 9H); MS (ESI) m/z 449 [M−1]$^-$.

a) 2-[2-(4-Bromo-phenyl)-ethanesulfonylamino]-5-hydroxymethyl-benzenesulfonamide (3)

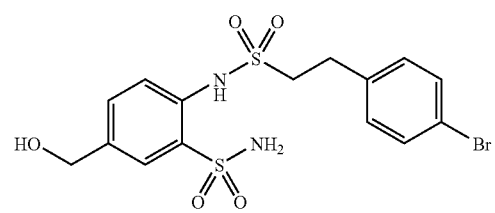 [SMILES: NS(=O)(=O)c1cc(CO)ccc1NS(=O)(=O)CCc1ccc(Br)cc1]

Lithium aluminum hydride (1 M in tetrahydrofuran, 1.9 mL, 1.9 mmol) was added dropwise to a solution of 4-[2-(4-bromo-phenyl)-ethanesulfonylamino]-3-sulfamoyl-benzoic acid (0.22 g, 0.47 mmol) in anhydrous tetrahydrofuran (20 mL) at 0° C. The reaction mixture was stirred at room temperature for 5 hours, cooled to 0° C. and quenched by addition of saturated sodium sulfate solution (20 mL). The precipitate was removed by filtration and the filtrate was extracted with ethyl acetate. The organic phase was washed with brine, dried over sodium sulfate and concentrated under reduced pressure to give 0.15 g (71% yield) of the title compound.

$^1$H NMR (400 MHz, CD$_3$OD) δ ppm 7.82 (s, 1H), 7.49 (d, 2H), 7.39 (d, 1H), 7.28 (d, 1H), 7.13 (d, 2H), 4.56 (s, 2H), 3.45 (m, 2H), 3.06 (m, 2H); MS (ESI) m/z 447, 449 [M−1]$^-$.

b) 4-[2-(4-Bromo-phenyl)-ethanesulfonylamino]-3-sulfamoyl-benzoic acid

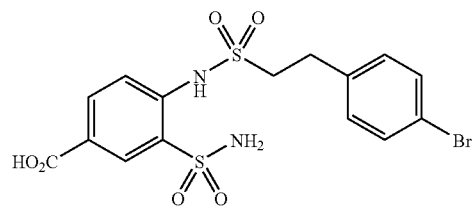 [SMILES: NS(=O)(=O)c1cc(C(=O)O)ccc1NS(=O)(=O)CCc1ccc(Br)cc1]

To a suspension of 2-[2-(4-bromo-phenyl)-ethanesulfonylamino]-5-methyl-benzenesulfonamide (0.3 g, 0.69 mmol) in water (12 mL) was added 2.5 M sodium hydroxide until a clear solution was obtained (~12 mL). Potassium permanganate (0.55 g, 3.46 mmol) was added and the resulting reaction mixture was heated at 70° C. for 3 hours. The hot solution was filtered through a pad of Celite and the solids were washed with water. Solid sodium bisulfate was added to the filtrate until the pink color disappeared. The aqueous solution was treated with charcoal, filtered, and the pH was adjusted to pH~1 using 6 M hydrochloric acid. The formed precipitate was collected by filtration, washed with water, and dried to give 0.22 g (69% yield) of the title compound.

¹H NMR (400 MHz, CD₃OD) δ ppm 8.58 (s, 1H), 8.18 (d, 1H), 7.85 (d, 1H), 7.39 (d, 2H), 7.13 (d, 2H), 3.63-3.59 (m, 2H), 3.10-3.06 (m, 2H); MS (ESI) m/z 461, 463 [M−1]⁻.

Example 212

2-[2-(4-Cyclopentylethynyl-phenyl)-ethanesulfonylamino]-5-hydroxymethyl-benzenesulfonamide

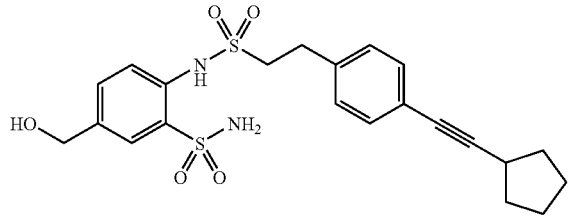 [SMILES: NS(=O)(=O)c1cc(CO)ccc1NS(=O)(=O)CCc1ccc(C#CC2CCCC2)cc1]

The title compound was synthesized as described for Example 210 in 11% yield, starting from 2-[2-(4-bromophenyl)-ethanesulfonylamino]-5-hydroxymethyl-benzenesulfonamide and ethynyl-cyclopentane. Purification by preparative HPLC.

¹H NMR (400 MHz, CD₃OD) δ ppm 7.96 (s, 1H), 7.75 (d, 1H), 7.55 (d, 1H), 7.21 (d, 2H), 7.09 (d, 2H), 4.62 (s, 2H), 3.40-3.53 (m, 2H), 2.98-3.10 (m, 2H), 2.68-2.85 (m, 1H), 1.89-2.06 (m, 2H), 1.54-1.83 (m, 6H); MS (ESI) m/z 461 [M−1]⁻.

Example 213

2-[2-(4-Chloro-2-methoxy-phenyl)-ethanesulfonylamino]-5-hydroxymethyl-benzenesulfonamide

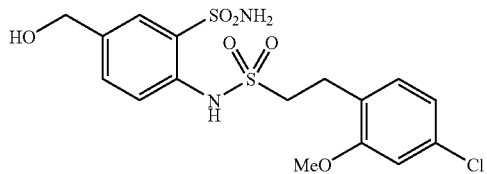 [SMILES: COc1cc(Cl)ccc1CCS(=O)(=O)Nc1ccc(CO)cc1S(N)(=O)=O]

To a solution of methyl ester 4-[2-(4-chloro-2-methoxy-phenyl)-ethanesulfonylamino]-3-sulfamoyl-benzoic acid methyl ester (0.18 g, 0.39 mmol) in anhydrous tetrahydrofuran (30 mL) lithium aluminum hydride (0.20 g, 5.27 mmol) was added in small portions at −10° C. The reaction mixture was allowed to warm to room temperature and stirred for 14 hours. The mixture was cooled to −10° C., quenched by the addition of saturated aqueous sodium sulfate, acidified using 2 M hydrochloric acid and extracted with ethyl acetate. The combined extracts were washed with water and brine, dried over sodium sulfate and concentrated under reduced pressure. Purification by preparative HPLC gave 12.8 mg (7.5% yield) of the title compound.

¹H NMR (400 MHz, (CD₃)₂O) δ ppm 8.84 (s, 1H), 7.98 (s, 1H), 7.74 (d, 1H), 7.56-7.64 (m, 1H), 7.10-7.22 (m, 3H), 6.83-6.96 (m, 3H), 4.67 (s, 2H), 4.67 (s, 3H), 3.47-3.56 (m, 2H), 3.02-3.09 (m, 2H); MS (ESI) m/z 433, 435 [M−1]⁻.

a) 4-[2-(4-Chloro-2-methoxy-phenyl)-ethanesulfonylamino]-3-sulfamoyl-benzoic acid methyl ester

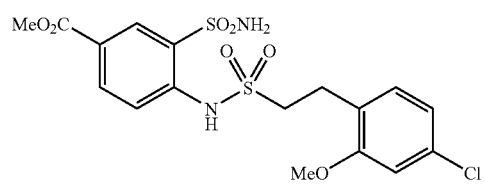 [SMILES: COC(=O)c1ccc(NS(=O)(=O)CCc2ccc(Cl)cc2OC)c(S(N)(=O)=O)c1]

To a solution of 4-[2-(4-chloro-2-methoxy-phenyl)-ethanesulfonylamino]-3-sulfamoyl-benzoic acid (0.18 g, 0.40 mmol) in anhydrous methanol (15 mL), thionyl chloride (1 mL) was added and the mixture was heated at reflux for 18 hours. The volatiles were removed under reduced pressure to give 0.18 g (97% yield) of the title compound.

¹H NMR (400 MHz, CD₃OD) δ ppm 8.56 (br. s., 1H), 8.15 (m, 1H), 7.82 (m, 1H), 7.06-7.12 (m, 1H), 6.86 (dd, 1H), 6.82 (dd, 1H), 3.92 (s, 3H), 3.67 (s, 3H), 3.38-3.46 (m, 2H), 3.00-3.10 (m, 2H); MS (ESI) m/z 461, 463 [M−1]⁻.

b) 4-[2-(4-Chloro-2-methoxy-phenyl)-ethanesulfonylamino]-3-sulfamoyl-benzoic acid

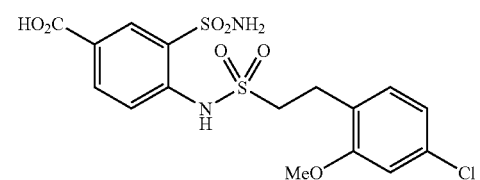 [SMILES: COc1cc(Cl)ccc1CCS(=O)(=O)Nc1ccc(C(=O)O)cc1S(N)(=O)=O]

The title compound was synthesized as described for Example 211 b) in 34% yield, starting from 2-[2-(4-chloro-2-methoxy-phenyl)-ethanesulfonylamino]-5-methyl-benzenesulfonamide.

¹H NMR (400 MHz, DMSO-d₆) δ ppm 9.16 (br s., 1H), 8.82 (s., 1H), 8.43 (d, 1H), 8.12 (dd, 1H), 8.08 (br s., 2H), 7.17 (d, 2H), 6.98 (dd, 1H), 6.90 (dd, 1H), 3.67 (s, 3H), 3.47-3.41 (m, 2H), 3.00-2.85 (m, 2H); MS (ESI) m/z 447, 449 [M−1]⁻.

c) 2-[2-(4-Chloro-2-methoxy-phenyl)-ethanesulfonylamino]-5-methyl-benzenesulfonamide

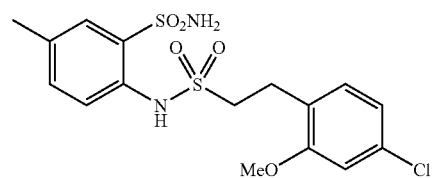 [SMILES: COc1cc(Cl)ccc1CCS(=O)(=O)Nc1ccc(C)cc1S(N)(=O)=O]

Palladium on carbon (5 wt. %, 0.4 g) was added to a solution of 2-[2-(4-chloro-2-methoxy-phenyl)-ethenesulfonylamino]-5-methyl-benzenesulfonamide (0.55 g, 1.32 mmol) in ethyl acetate (20 mL) and the reaction mixture was shaken under a hydrogen atmosphere (30 psi) for 4 hours. The solution was filtered through a pad of Celite and concentrated under reduced pressure to give 0.31 g (57% yield) of the title compound.

$^1$H NMR (400 MHz, CD$_3$OD) δ ppm 7.77 (d, 1H), 7.63 (d, 1H), 7.41 (d, 1H), 7.08 (d, 1H), 6.88 (d, 1H), 6.83 (dd, 1H), 3.64 (s, 3H), 3.36-3.46 (m, 2H), 2.92-3.05 (m, 2 h), 2.37 (s, 3H); MS (ESI) m/z 417, 419 [M−1]$^−$.

d) 2-[2-(4-Chloro-2-methoxy-phenyl)-ethenesulfonylamino]-5-methyl-benzenesulfonamide (2)

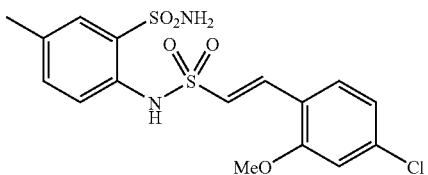 [SMILES: COc1cc(Cl)ccc1/C=C/S(=O)(=O)Nc1ccc(C)cc1S(N)(=O)=O]

2-(4-Chloro-2-methoxy-phenyl)-ethenesulfonyl chloride (0.50 g, 1.87 mmol) was added slowly to a solution of 2-amino-5-methyl-benzenesulfonamide (0.38 g, 2.05 mmol) in anhydrous pyridine (10 mL) and the reaction mixture was stirred for 18 hours at room temperature. The solvent was removed in vacuo and the residue was dissolved in ethyl acetate (30 mL). The organic phase was washed with 1 M hydrochloric acid and brine, dried over anhydrous sodium sulfate and concentrated under reduced pressure. Purification by column chromatography gave 0.42 g (54% yield) of the title compound.

$^1$H NMR (400 MHz, CD$_3$OD) δ ppm 7.70 (s, 1H), 7.52-7.61 (m, 2H), 7.42 (d, 1H), 7.36 (d, 1H), 7.14 (d, 1H), 7.06 (s, 1H), 6.94 (d, 1H), 3.72 (s, 3H).

g) 2-(3,4-Dichloro-phenyl)-ethanesulfonyl chloride

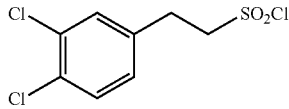 [SMILES: O=S(=O)(Cl)CCc1ccc(Cl)c(Cl)c1]

Thionyl chloride (1.15 mL, 15.83 mmol) was added dropwise to a suspension of sodium 2-(3,4-dichloro-phenyl)-ethanesulfonate (3.17 g, 11.47 mmol) in a mixture of anhydrous benzene (50 mL) and anhydrous N,N-dimethylformamide (1 mL) at 0° C. The reaction mixture was allowed to warm slowly to room temperature and was then heated at 80° C. for 18 hours. The reaction mixture was cooled to room temperature and filtered through a pad of Celite. The solids were washed with benzene and the combined filtrates were concentrated in vacuo. The residue was taken up in hexane and the resulting suspension was heated at 50° C. for 30 min. After cooling to room temperature, a solid was collected by filtration to give 2.20 g (70% yield) of the title compound.

$^1$H NMR (400 MHz, CDCl$_3$) δ ppm 7.44 (d, 1H), 7.36 (d, 1H), 7.10 (d, 1H), 3.84-3.93 (m, 2H), 3.27-3.34 (m, 2H); MS (ESI) m/z 253 [M−1]$^−$ (corresponding sulfonic acid Mw=255).

Example 214

3-{2-[4-(3,3-Dimethyl-but-1-ynyl)-phenyl]-ethanesulfonylamino}-thiophene-2-sulfonic acid amide

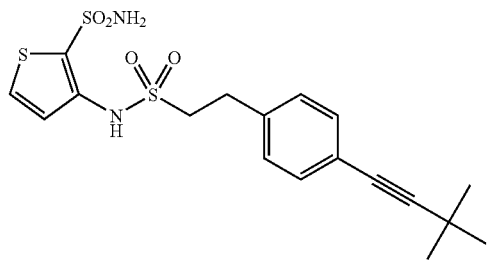 [SMILES: CC(C)(C)C#Cc1ccc(CCS(=O)(=O)Nc2ccsc2S(N)(=O)=O)cc1]

The title compound was synthesized as described for Example 210 in 18% yield, starting from 3-[2-(4-bromo-phenyl)-ethanesulfonylamino]-thiophene-2-sulfonic acid amide and 3,3-dimethyl-1-butyne. Purification by column chromatography, using 50% ethyl acetate in hexanes as the eluent, followed by purification by preparative HPLC.

$^1$H NMR (400 MHz, CD$_3$OD) δ ppm 7.66 (d, 1H), 7.30 (d, 1H), 7.22 (d, 2H), 7.12 (d, 2H), 3.40 (m, 2H), 3.04 (m, 2H), 1.29 (s, 9H); MS (ESI) m/z 425 [M−1]$^+$.

a) 3-[2-(4-Bromo-phenyl)-ethanesulfonylamino]-thiophene-2-sulfonic acid amide

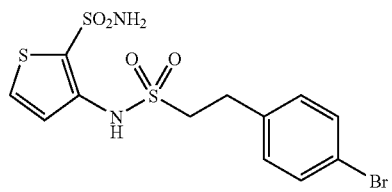 [SMILES: NS(=O)(=O)c1sccc1NS(=O)(=O)CCc1ccc(Br)cc1]

A mixture of 3-amino-thiophene-2-sulfonnamide (0.10 g, 0.56 mmol) and 2-(4-bromo-phenyl)-ethanesulfonyl chloride (0.18 g, 0.62 mmol) in anhydrous pyridine (3 mL) was stirred at room temperature overnight. The reaction mixture was diluted with ethyl acetate (25 mL) and the organic phase was washed with 1 M hydrochloric acid (25 mL), saturated sodium bicarbonate (25 mL) and brine, dried over magnesium sulfate and concentrated under reduced pressure to give 0.16 g (67% yield) of the title compound.

$^1$H NMR (400 MHz, CD$_3$OD) δ ppm 7.65 (d, 1H), 7.41 (d, 2H), 7.32 (d, 1H), 7.12 (d, 2H), 3.43 (m, 2H), 3.04 (m, 2H)

b) 3-Amino-thiophene-2-sulfonamide

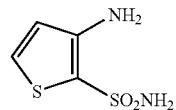

A 57% aqueous solution of hydriodic acid (15 mL) was added to neat 3-nitro-thiophene-2-sulfonamide (1.02 g, 4.90 mmol) at room temperature. The reaction mixture was heated at 90° C. for 1 hour, cooled to room temperature and diluted with ethyl acetate (50 mL). The mixture was washed with a solution of sodium thiosulfate and the pH was adjusted to pH~8 with sodium bicarbonate. The mixture was extracted with 10% methanol in ethyl acetate and the organic phase was dried over magnesium sulfate and concentrated in vacuo. Purification by column chromatography, using a gradient of 30-70% ethyl acetate in hexanes as the eluent, gave 65% yield of the title compound.

$^1$H NMR (400 MHz, DMSO-$d_6$) δ ppm 7.54 (d, 1H), 7.29 (s, 2H), 6.62 (d, 1H), 5.85 (s, 2H); MS (ESI) m/z 179 [M+1]$^+$.

c) 3-Nitro-thiophene-2-sulfonamide

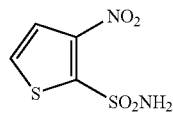

Ammonium hydroxide (28% aqueous, 2.4 mL, 17.57 mmol) was added to a stirred solution of 3-nitro-thiophene-2-sulfonyl chloride (1.00 g, 4.39 mmol) in tetrahydrofuran (50 mL) at room temperature. After 15 min the reaction mixture was concentrated under reduced pressure. The residue was triturated in methanol and dichloromethane. The solid was collected by filtration and dried to give 1.02 g (quantitative yield) of the title compound.

$^1$H NMR (400 MHz, DMSO-$d_6$) δ ppm 7.93 (d, 1H) 7.74 (d, 1H) 7.58 (br. s., 2H); MS (ESI) m/z 207 [M−1]$^-$.

d) 3-Nitro-thiophene-2-sulfonyl chloride

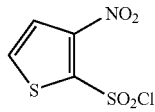

Water (35 mL) and formic acid (35 mL) were added to a solution of 2-benzylsulfanyl-3-nitro-thiophene (1.00 g, 3.98 mmol) in dichloromethane (70 mL). The reaction mixture was cooled to −5° C. and chlorine gas was bubbled through the heterogeneous mixture with vigorous stirring for 15 min. The reaction mixture was warmed to room temperature and stirred for 30 min under a nitrogen flow to remove excess chlorine gas. Dichloromethane (50 mL) was added and the phases were separated. The organic phase was washed with brine, dried over magnesium sulfate and concentrated in vacou. Purification by column chromatography, using a gradient of 15-30% ethyl acetate in hexanes as the eluent, gave 59% yield of the title compound.

$^1$H NMR (400 MHz, CDCl$_3$) δ ppm 7.78 (q, 2H); MS (ESI) m/z 208 [M−1]$^-$ (corresponding sulfonic acid, MW=209)

e) 2-Benzylsulfanyl-3-nitro-thiophene

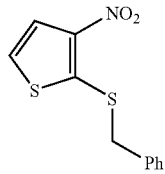 [SMILES: O=[N+]([O-])c1ccsc1SCc1ccccc1]

A mixture of 2-chloro-3-nitrothiophene (1.00 g, 6.11 mmol), N,N-diisopropylethylamine (2.1 mL, 12.22 mmol) and benzyl mercaptan (0.8 mL, 6.72 mmol) in dimethyl sulfoxide (5 mL) was placed in a sealed tube. The reaction mixture was heated at 80° C. for 1 hour, cooled to room temperature and water (10 mL) was added. The mixture was diluted with ethyl acetate (50 mL) and the organic phase was washed with brine, dried over magnesium sulfate, concentrated in vacuo and dried in vacuo to give 97% yield of the title compound.

$^1$H NMR (400 MHz, CDCl$_3$) δ ppm 7.61 (d, 1H), 7.40-7.48 (m, 2H), 7.29-2.41 (m, 5H), 7.07 (d, 1H), 4.27 (s, 2H); MS (ESI) m/z 252 [M+1]$^+$.

Example 215

3-[3-(5-Chloro-6-methoxy-pyridin-3-yl)-benzene-sulfonylamino]-thiophene-2-sulfonic acid amide

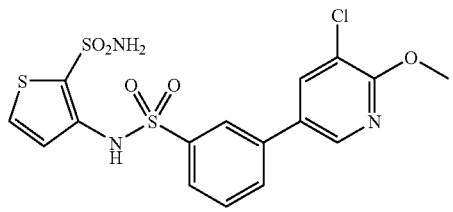 [SMILES: COc1ncc(-c2cccc(S(=O)(=O)Nc3ccsc3S(N)(=O)=O)c2)cc1Cl]

Bis(triphenylphosphine)palladium(II) chloride (4.65 mg, 6.62 µmol) was added to a degassed mixture of 3-chloro-2-methoxy-pyridine-5-boronic acid (62.02 mg, 0.33 mmol), sulfonamide 3-(3-bromo-benzenesulfonylamino)-thiophene-2-sulfonic acid amide (146.10 mg, 0.37 mmol), triethylamine (0.10 mL, 0.73 mmol) in anhydrous ethanol (5 mL). The resulting mixture was heated in a microwave reactor at 140° C. for 10 min, cooled to room temperature, diluted with ethyl acetate (10 mL), filtered through a pad of Celite and concentrated in vacuo. Purification by preparative HPLC, using 0.1% aqueous trifluoroacetic acid/acetonitrile as the eluent, gave 83.3 mg (55% yield) of the title compound.

$^1$H NMR (400 MHz, CD$_3$OD) δ ppm 8.31 (d, 1H), 7.96-8.06 (m, 2H), 7.79-7.86 (m, 2H), 7.56-7.64 (m, 2H), 7.33 (d, 1H), 4.04 (s, 3H); MS (ESI) m/z 460, 462 [M+1]$^+$.

a) 3-(3-Bromo-benzenesulfonylamino)-thiophene-2-sulfonic acid amide

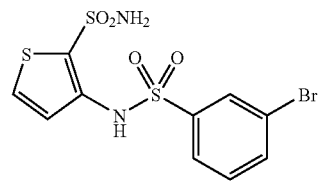 [SMILES: NS(=O)(=O)c1sccc1NS(=O)(=O)c1cccc(Br)c1]

A mixture of 3-amino-thiophene-2-sulfonic acid amide (100 mg, 0.56 mmol) and 3-bromo-benzenesulfonyl chloride (97 µL, 0.67 mmol) in anhydrous pyridine (3 mL) was stirred at room temperature for 17 hours. The solvent was removed in vacuo and the residue was taken up in dichloromethane (25 mL). The organic phase was washed with 1 M hydrochloric acid, saturated sodium bicarbonate and brine, dried over sodium sulfate and concentrated under reduced pressure. Purification by column chromatography, using 4-6% methanol in dichloromethane as the eluent, gave 147.6 mg (66% yield) of the title compound.

$^1$H NMR (400 MHz, CD$_3$OD) δ ppm 7.87 (d, 1H), 7.68 (m, 2H), 7.53 (d, 1H), 7.34 (t, 1H), 7.16 (d, 1H); MS (ESI) m/z 395, 397 [M−1]$^−$ (corresponding sulfonic acid Mw=397).

General Procedure for Synthesis of Styrenyl Sulfonyl Chlorides

Method C

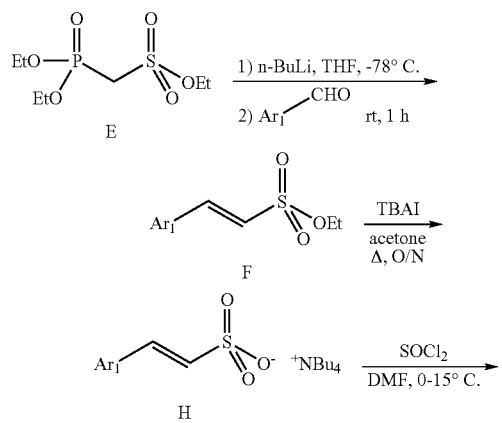

Method C.1 Synthesis of Arylethenesulfonic Acid Ethyl Esters (F)

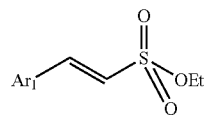

n-Butyllithium (11 mmol, 2.5 M solution in hexanes) was added dropwise to a stirred solution of diethoxy(phosphoryl)methanesulfonic acid ethyl ester E (11 mmol) in 150 mL of tetrahydrofurane at −78° C. The reaction mixture was stirred at −78° C. for 15 min and a solution of the corresponding aldehyde (10 mmol) in 5 mL tetrahydrofuran was added dropwise. After the addition was complete the reaction mixture was warmed to room temperature, stirred for 1 hour and quenched with brine. Most of the tetrahydrofuran was removed in vacuo and dichloromethane (200 mL) was added. The organic phase was separated, washed with brine, dried over magnesium sulfate and the solvent was evaporated. Purification by column chromatography, using hexane/ethyl acetate (2:1) as the eluent, gave ester F.

Compounds listed in Table 4 were synthesized following this procedure.

TABLE 4

| Structure | Yield | Analytical data |
|---|---|---|
| 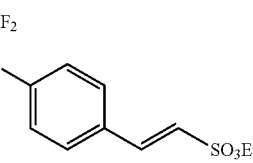 | 50% | $^1$H NMR (400 MHz, CDCl$_3$) δ ppm 7.48-7.65 (m, 3 H), 7.22-7.36 (m, 2 H), 6.73 (d, 1 H), 5.94 (t, 1 H), 4.25 (q, 2 H), 1.41 (t, 3 H) |
| 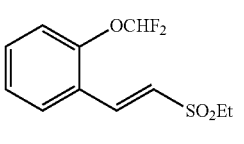 | 90% | $^1$H NMR (400 MHz, CDCl$_3$) δ ppm 7.79 (dd, 1 H), 7.40-7.48 (m, 1 H), 7.35 (d, 1 H), 7.24-7.31 (m, 1 H), 7.16 (d, 1H), 6.56 (t, 1 H), 6.48 (d, 1 H), 4.15 (q, 2 H), 1.25 (t, 3 H) |
| 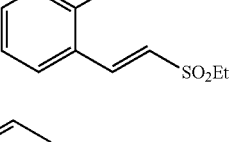 | 90% | $^1$H NMR (400 MHz, CDCl$_3$) δ ppm 7.77 (d, 1 H), 7.34-7.46 (m, 2 H), 6.91-7.01 (m, 3 H), 4.67 (m, 1 H), 4.22 (q, 2 H), 1.37-1.46 (m, 9 H) |
| 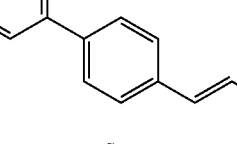 | 90% | $^1$H NMR (400 MHz, CDCl$_3$) δ ppm 7.61-7.73 (m, 9 H), 6.81 (d, 1 H), 4.26 (q, 2 H), 1.42 (t, 3 H) |
| 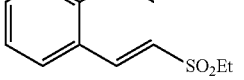 | 65% | $^1$H NMR not available |

TABLE 4-continued

| Structure | Yield | Analytical data |
|---|---|---|
| 2-OCF₃-C₆H₄-CH=CH-SO₂Et | 71% | ¹H NMR (400 MHz, CDCl₃) δ ppm 7.81 (d, 1 H), 7.62 (d, 1 H), 7.45-7.56 (m, 1 H), 7.32-7.43 (m, 2 H), 6.85 (d, 1 H), 4.25 (q, 2 H), 1.42 (t, 3 H) |
| 2-OEt-C₆H₄-CH=CH-SO₂Et | 79% | ¹H NMR (400 MHz, CDCl₃) □ ppm 7.77 (d, 1 H), 7.33-7.46 (m, 2 H), 6.88-7.07 (m, 3 H), 4.19-4.30 (m, 2 H), 4.06-4.19 (m, 2 H), 1.45-1.55 (m, 3 H), 1.32-1.44 (m, 3 H) |

Method C.2 Synthesis of Arylethenesulfonyl Chlorides (I)

a) Arylethenesulfonatetetrabutyl-ammonium (H)

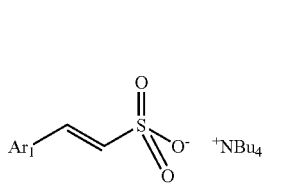

Tetrabutyl-ammonium iodide (12 mmol) was added to a solution of arylethenesulfonic acid ethyl ester F in acetone (500 mL) and the reaction mixture was heated at reflux overnight. The reaction mixture was cooled to room temperature and concentrated under reduced pressure. Purification by column chromatography, using dichloromethane/methanol (95:5) as the eluent. The residue was triturated with diethyl ether to afford H (contaminated with tetrabutylammonium iodide) used in the next step without further purification.

b) Arylethenesulfonyl Chlorides (I)

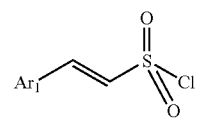

Thionyl chloride (45 mmol) was added dropwise at 0° C. to a solution of H (15 mmol) in N,N-dimethylformamide (30 mL). The reaction mixture was stirred at 10-15° C. for 15-45 min, poured onto crushed ice and ethyl acetate (100 mL) was added. The organic phase was separated, washed with brine, dried over magnesium sulfate, and concentrated under reduced pressure. Purification by column chromatography, using 10% ethyl acetate in hexanes as the eluent, followed by recrystallization from pentane/diethyl ether gave the desired sulfonyl chloride I.

Compounds listed in Table 5 were synthesized following this method.

TABLE 5

| Structure | Yield (over two steps) | Analytical data |
|---|---|---|
| 4-(OCF₂CHF₂)-C₆H₄-CH=CH-SO₂Cl | 19% | ¹H NMR (400 MHz, CDCl₃) δ ppm 7.72 (d, 1 H), 7.61 (m, 2 H), 7.34 (m, 2 H), 7.22 (d, 1 H), 5.94 (t, 1 H) MS (ESI) m/z 299 [M − 1]⁻ (corresponding sulfonic acid MW = 300) CHN Calc.: C, 38.25; H, 2.39. Found: C, 38.18; H, 2.59 (1/22 hexane) |
| 2-OCHMe₂-C₆H₄-CH=CH-SO₂Cl | 43% | ¹H NMR (400 MHz, CDCl₃) δ ppm 7.86 (d, 1 H), 7.54 (d, 1 H), 7.38-7.49 (m, 2 H), 6.93-7.05 (m, 2 H), 4.63-4.78 (m, 1 H), 1.44 (d, 6 H). MS (ESI) m/z 241 [M − 1]⁻ (corresponding sulfonic acid MW = 242). CHN Calc.: C, 50.67; H, 5.03. Found: C, 50.84; H, 4.43. |
| 2-OCHF₂-C₆H₄-CH=CH-SO₂Cl | 53% | ¹H NMR (400 MHz, CDCl₃) δ ppm 7.93 (d, 1 H), 7.49-7.64 (m, 2 H), 7.27-7.43 (m, 2 H), 7.24 (s, 1H), 6.64 (t, 1 H). MS (ESI) m/z 249 [M − 1]⁻ (corresponding sulfonic acid MW = 250). CHN Calc.: C, 40.23; H, 2.63. Found: C, 40.55; H, 2.82. |

TABLE 5-continued

| Structure | Yield (over two steps) | Analytical data |
|---|---|---|
| F₃C-[biphenyl]-CH=CH-SO₂Cl | 57% | ¹H NMR (400 MHz, CDCl₃) δ ppm 7.65-7.82 (m, 9 H), 7.29 (d, 1 H) MS (ESI) m/z 327 [M − 1]⁻ (corresponding sulfonic acid MW = 328). CHN Calc.: C, 51.96; H, 2.91. Found: C, 51.99; H, 3.02. |
| 2-(methylthio)phenyl-CH=CH-SO₂Cl | 68% | ¹H NMR (400 MHz, CDCl₃) δ ppm 8.26 (d, 1 H), 7.52 (d, 1 H), 7.38-7.49 (m, 2 H) 7.22-7.29 (m, 2 H), 2.53 (s, 3 H) MS (ESI) m/z 229 [M − 1]⁻ (corresponding sulfonic acid MW = 230). CHN Calc.: C, 43.46; H, 3.65. Found: C, 43.44; H, 4.04 |
| 2-(OCF₃)phenyl-CH=CH-SO₂Cl | 31% | ¹H NMR (400 MHz, CDCl₃) δ ppm 7.93 (d, 1 H), 7.64 (dd, 1 H), 7.54-7.61 (m, 1 H), 7.37-7.45 (m, 2 H), 7.34 (d, 1 H) MS (ESI) m/z 267 [M − 1]⁻ (corresponding sulfonic acid MW = 268) CHN Calc.: C, 37.71; H, 2.11. Found: C, 37.78; H, 2.21 |
| 2-(OEt)phenyl-CH=CH-SO₂Cl | 24% | ¹H NMR (400 MHz, CDCl₃) δ ppm 7.86 (d, 1 H), 7.57 (d, 1 H), 7.40-7.52 (m, 2 H), 6.91-7.11 (m, 2 H), 4.19 (q, 2 H), 1.42-1.63 (m, 4 H) MS (ESI) m/z 227 [M − 1]⁻ (corresponding sulfonic acid MW = 228). CHN Calc.: C, 48.68; H, 4.49. Found: C, 48.84; H, 4.63 |

General Method for Synthesis of Styrenyl Sulfonamides
Method D

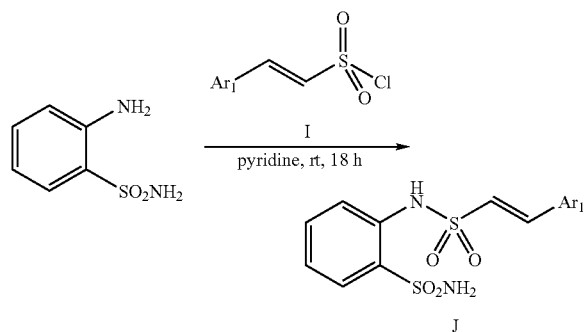

A solution of 2-amino-benzenesulfonamide (1 mmol) and styrenyl sulfonyl chloride J (1 mmol) in anhydrous pyridine (2 mL) was stirred at room temperature for 18 hours. The solvent was removed under reduced pressure and the residue was dissolved in dichloromethane. The organic phase was washed with 1 M hydrochloric acid, saturated aqueous sodium bicarbonate and brine, dried over sodium sulfate and concentrated in vacuo. Purification by column chromatography, using 5% methanol in dichloromethane as the eluent, or by preparative HPLC gave the title compound J.

Compounds listed in Table 6 were synthesized following this procedure.

TABLE 6

| Example | Structure | Yield | Analytical data |
|---|---|---|---|
| 216 | 2-(SO₂NH₂)phenyl-NH-SO₂-CH=CH-C₆H₄-OCF₂CHF₂ | 77% | ¹H NMR (400 MHz, DMSO-d₆) δ ppm 9.12 (s, 1H), 7.72-7.89 (m, 5 H), 7.52-7.66 (m, 3 H), 7.39-7.48 (m, 1 H), 7.31 (d, 2 H), 7.26 (t, 1 H), 6.80 (t, 1H) MS (ESI) m/z 455 [M + 1]⁺ |

TABLE 6-continued

| Example | Structure | Yield | Analytical data |
|---|---|---|---|
| 217 | 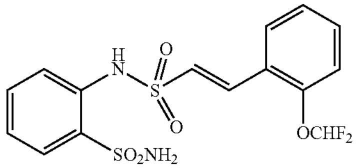 [SMILES: NS(=O)(=O)c1ccccc1NS(=O)(=O)/C=C/c1ccccc1OC(F)F] | 55% | $^1$H NMR (400 MHz, DMSO-$d_6$) δ ppm 9.12 (s, 1 H), 7.75-7.85 (m, 4 H), 7.38-7.67 (m, 6 H), 7.24-7.31 (m, 3 H) MS (ESI) m/z 403 [M − ]$^-$ |
| 218 | 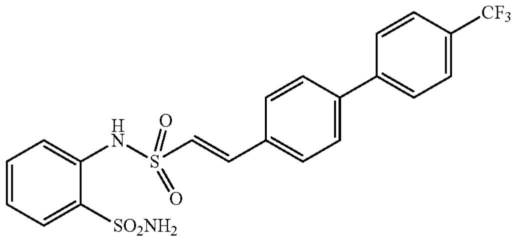 [SMILES: NS(=O)(=O)c1ccccc1NS(=O)(=O)/C=C/c1ccc(-c2ccc(C(F)(F)F)cc2)cc1] | 25% | $^1$H NMR (400 MHz, DMSO-$d_6$) δ ppm 9.15 (s, 1 H), 7.94 (d, 2 H), 7.78-7.88 (m, 9 H), 7.56-7.69 (m, 3 H), 7.51 (d, 1 H), 7.28 (t, 1 H) MS (ESI) m/z 481 [M − 1]$^-$ |
| 219 | 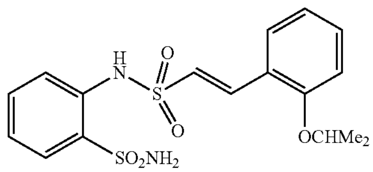 | 42% | $^1$H NMR (400 MHz, CDCl$_3$) δ ppm 8.43 (s, 1 H), 7.91-7.97 (m, 1 H), 7.78 (m, 1 H), 7.68 (d, 1 H), 7.50-7.57 (m, 1 H), 7.32-7.42 (m, 2 H), 7.14-7.25 (m, 2 H), 6.89-6.97 (m, 2 H), 5.26 (s, 2 H), 4.64 (m, 1 H), 1.37 (d, 6 H) MS (ESI) m/z 395 [M − 1]$^-$ |
| 220 | 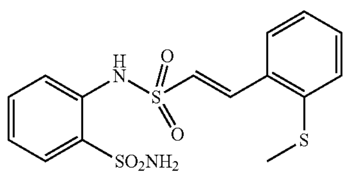 [SMILES: CSc1ccccc1/C=C/S(=O)(=O)Nc1ccccc1S(N)(=O)=O] | 30% | MS (ESI) m/z 383 [M − 1]$^-$ CHN Calc.: C, 48.86; H, 4.19. Found: C, 47.02; H, 4.21 |
| 221 | 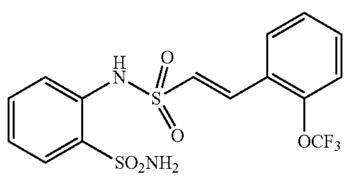 [SMILES: NS(=O)(=O)c1ccccc1NS(=O)(=O)/C=C/c1ccccc1OC(F)(F)F] | 25% | $^1$H NMR (400 MHz, CD$_3$OD) δ ppm 7.90 (dd, 1 H), 7.69-7.76 (m, 2 H), 7.63 (d, 1 H), 7.48-7.57 (m, 2 H), 7.32-7.41 (m, 2 H), 7.18-7.28 (m, 2 H) MS (ESI) m/z 421 [M − 1]$^-$ |
| 222 | 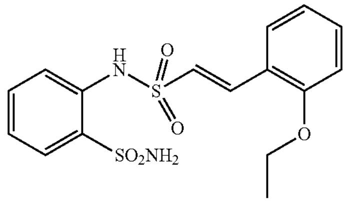 [SMILES: CCOc1ccccc1/C=C/S(=O)(=O)Nc1ccccc1S(N)(=O)=O] | 64% | $^1$H NMR (400 MHz, CD$_3$OD) δ ppm 7.85-7.95 (m, 1 H), 7.63-7.77 (m, 2 H), 7.48-7.59 (m, 1 H), 7.44 (dd, 1 H), 7.29-7.40 (m, 1 H), 7.17-7.26 (m, 2 H), 6.99 (d, 1 H), 6.92 (t, 1 H), 4.09 (q, 2 H), 1.41 (t, 3 H) MS (ESI) m/z 381 [M − 1]$^-$ |

General Method for Synthesis of (aryl-ethanesulfonyl-amino)-benzenesulfonamides

Method E

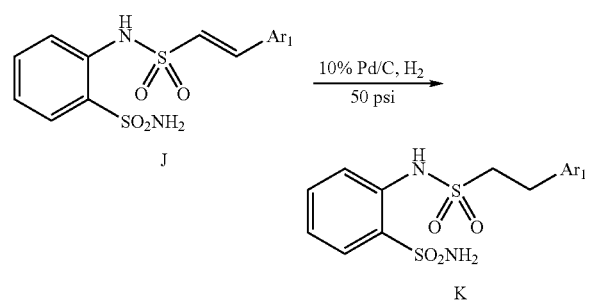

Palladium on carbon (10 wt. %) was added to a solution of styrenyl sulfonamides J (0.2 mmol) in absolute alcohol (10 mL) or in a mixture of absolute alcohol (10 mL) and ethyl acetate (5 mL) and the resulting mixture was shaken on a Parr Shaker under a hydrogen atmosphere (50 psi) for 4 to 16 hours. The reaction mixture was filtered through a pad of Celite and the filtrate was concentrated under reduced pressure. Purification by preparative HPLC gave title compound K.

Compounds listed in Table 7 were synthesized following this procedure.

TABLE 7

| Example | Structure | Yield | Analytical data |
|---|---|---|---|
| 223 | ![structure] | 27% | $^1$H NMR (400 MHz, (CD$_3$)$_2$O) δ ppm 7.97 (dd, 1H), 7.81 (d, 1 H), 7.63 (m, 1 H), 7.34-7.40 (m, 2 H), 7.31 (t, 1 H), 7.19 (d, 2 H), 6.47 (m, 1 H), 3.59-3.70 (m, 2 H), 3.09-3.23 (m, 2 H) ESMS m/z [M − 1] 455 |
| 224 | ![structure] | 26% | $^1$H NMR (400 MHz, (CD$_3$)$_2$O) δ ppm 7.97 (d, 1 H), 7.75-7.89 (m, 4 H), 7.61-7.68 (m, 4 H), 7.40 (d, 2 H), 7.30 (t, 1 H), 3.63-3.73 (m, 2 H), 3.15-3.24 (m, 2 H) ESMS m/z [M − 1] 483 |

Example 225

2-[2-(2-Hydroxy-phenyl)-ethenesulfonylamino]-benzenesulfonamide

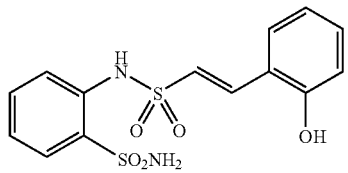 [SMILES: NS(=O)(=O)c1ccccc1NS(=O)(=O)/C=C/c1ccccc1O]

Boron tribromide (1 M in dichloromethane, 5.4 mL, 5.44 mmol) was added dropwise over 5 min to a suspension of 2-[2-(2-ethoxy-phenyl)-ethenesulfonylamino]-benzene-sulfonamide (example 222) (0.21 g, 0.54 mmol) in dichloromethane (10 mL) at −78° C. The reaction mixture was allowed to warm to room temperature and stirred overnight. Cooled to −20° C. and methanol (5 mL) was added slowly. The resulting solution was warmed up to room temperature and heated at 50° C. for 1 hour. The volatiles were removed under reduced pressure and the residue was taken up in methanol (5 mL). The mixture was concentrated in vacuo and the process was repeated once more. The residue was taken up in water (5 mL) and ethyl acetate (15 mL). The organic phase was separated, dried over magnesium sulfate and concentrated in vacuo. Purification by preparative HPLC gave 31 mg (16% yield) of the title compound.

$^1$H NMR (400 MHz, CD$_3$OD) δ ppm 7.87 (dd, 1H) 7.65-7.71 (m, 2H) 7.46-7.54 (m, 1H) 7.37 (d, 1H) 7.09-7.24 (m, 3H) 6.79-6.85 (m, 2H); MS (ESI) m/z 355 [M+1]$^+$.

General Method for the Synthesis of Amino Sulfonamide Building Blocks

Method F a) General Method for Synthesis of 1,2,4-benzothiadiazine Derivatives

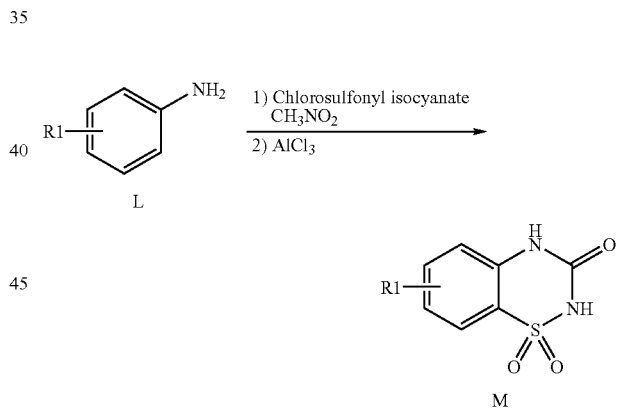

A solution of aniline L (50 mmol) in anhydrous nitromethane (50 mL) was added slowly to a vigorously stirred mixture of chlorosulfonyl isocyanate (58 mmol) in anhydrous nitromethane (150 mL) at −5° C. Anhydrous aluminium chloride (62.5 mmol) was added in small portions to the resulting suspension and the mixture was heated at reflux for 30 min. The hot solution was poured onto ice (800 g) and stirred for 30 min. The precipitate was collected by filtration, washed with water (75 mL) and suspended in aqueous sodium bicarbonate (10 g/200 mL of water). The suspension was heated until most of the precipitate dissolved, treated with charcoal and filtered. The pH of the filtrate was adjusted to pH~1 using 6 M hydrochloric acid and the solid was collected by filtration, washed with water, air-dried and used in the next step without further purification.

b) General Procedure for the Synthesis of Amino Sulfonamide Building Blocks

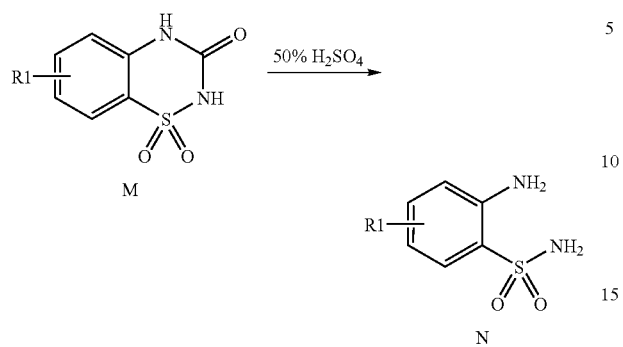

A suspension of 1,2,4-benzothiadiazine derivative M (20.64 mmol) in aqueous sulfuric acid (50% w/v) was heated at reflux for 17-24 hours until a clear solution was obtained. The reaction mixture was then cooled to 0° C. and the pH was adjusted to pH~7 using aqueous sodium hydroxide (30% w/v). The crude product was collected by filtration, washed with water, air-dried and purified by column chromatography, using 20-50% ethyl acetate in hexanes as the eluent, or by preparative HPLC.

Compounds listed in Table 8 were synthesized following this method.

TABLE 8

| Structure | Yield | Spectral data |
|---|---|---|
| 2,4-difluoro-6-amino benzenesulfonamide | 19% | $^1$H NMR (400 MHz, DMSO-d6) δ ppm 7.60 (br. s., 2 H), 6.64 (br. s., 2 H), 6.34-6.44 (m, 2 H)<br>MS (ESI) m/z 207 [M − 1]$^-$ |
| 3,5-difluoro-2-amino benzenesulfonamide | 21% | $^1$H NMR (400 MHz, DMSO-d6) δ ppm 7.61 (br. s., 2 H), 7.42 (ddd, 1 H), 7.17-7.26 (m, 1 H), 5.69 (br. s., 2 H)<br>MS (ESI) m/z 209 [M + 1]$^+$ |
| 4,5-difluoro-2-amino benzenesulfonamide | 29% | $^1$H NMR (400 MHz, DMSO-d6) δ ppm 7.49 (dd, 1 H), 7.40 (br. s., 2 H), 6.77 (dd, 1 H), 5.97 (br. s., 2 H)<br>MS (ESI) m/z 209 [M + 1]$^+$ |
| 5-fluoro-4-methoxy-2-amino benzenesulfonamide | 34% | $^1$H NMR (400 MHz, DMSO-d6) δ ppm 7.26 (d, 1 H), 7.19 (br.s., 2 H), 6.51 (d, 1 H), 5.76 (br.s., 2 H), 3.80 (s, 3 H)<br>MS (ESI) m/z 221 [M + 1]$^+$ |
| 3-fluoro-2-amino benzenesulfonamide | 23% | $^1$H NMR (400 MHz, DMSO-d$_6$) δ ppm 7.45 (s, 2 H), 7.40 (d, 1 H), 7.19-7.30 (m, 1 H), 6.62 (m, 1 H), 5.79 (s, 2 H)<br>MS (ESI) m/z 198 [M − 1]$^-$ |
| 4-iodo-2-amino benzenesulfonamide | 27% | $^1$H NMR (400 MHz, CD3OD) δ ppm 7.34 (d, 1 H), 7.24 (d, 1 H), 6.99 (dd, 1 H)<br>MS (ESI) m/z 299 [M + 1]$^+$ |

TABLE 8-continued

| Structure | Yield | Spectral data |
|---|---|---|
| 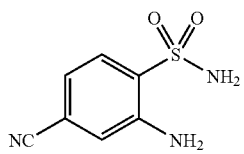 | 22% | ¹H NMR (400 MHz, DMSO-d6) δ ppm 7.79 (d, 1 H), 7.48 (dd, 1 H), 7.34 (br. s., 2 H), 6.64 (d, 1 H), 6.02 (br. s., 2 H) MS (ESI) m/z 299 [M + 1]⁺ |

General Method for the Synthesis Cyano-benzenesulfonamides:

Method G

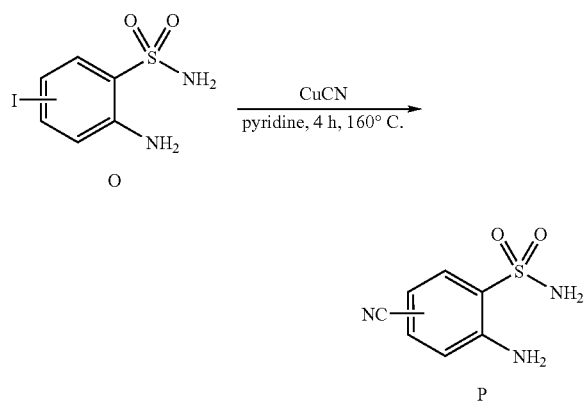

Copper(I) cyanide (10 mmol) was added to a solution of iodo-benzenesulfonamide O (5 mmol) in anhydrous pyridine (15 mL) at room temperature and the resulting mixture was heated in a sealed tube at 160° C. for 4 hours. Most of the pyridine was removed in vacuo and the residue was taken up in ethyl acetate (100 mL). The organic phase was washed with water and brine, dried over sodium sulfate and concentrated under reduced pressure.

Purification by column chromatography, using 50% ethyl acetate in pentane as the eluent, gave the title compound P.

a) 2-Amino-4-cyanobenzenesulfonamide

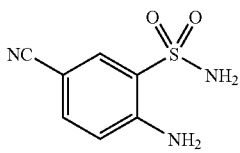

The title compound was synthesized as described for method G in 31% yield, starting from 2-amino-4-iodo-benzenesulfonamide.

¹H NMR (400 MHz, (CD₃)₂O)) δ ppm 7.80 (d, 1H), 7.26 (d, 1H), 7.03 (dd, 1H), 6.77 (br. s., 2H), 6.01 (br. s., 2H); MS (ESI) m/z 196 [M−1]⁻.

b) 2-Amino-5-cyanobenzenesulfonamide

The title compound was synthesized as described for method G in 42% yield, starting from 2-amino-5-iodo-benzenesulfonamide.

¹H NMR (400 MHz, CD₃OD) δ ppm 7.96 (d, 1H), 7.50 (dd, 1H), 6.88 (d, 1H); MS (ESI) m/z 196 [M−1]⁻

Example 226

4-Chloro-2-(2-(4-(difluoromethoxy)phenyl)ethylsulfonamido)benzenesulfonamide

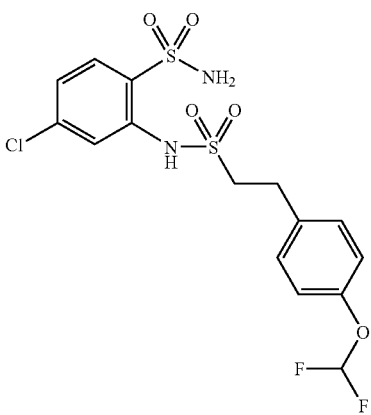 [SMILES: NS(=O)(=O)c1ccc(Cl)cc1NS(=O)(=O)CCc1ccc(OC(F)F)cc1]

(E)-4-Chloro-2-(2-(4-(difluoromethoxy)phenyl)vinylsulfonamido)benzenesulfonamide (0.426 g, 0.97 mmol) was dissolved in anhydrous tetrahydrofuran (2 mL). Sodium acetate (0.318 g, 3.88 mmol) and p-toluenesulfonic acid hydrazide (0.723 g, 3.88 mmol) were added and the reaction was heated in a microwave at 180° C. for 60 min. The mixture was filtered and the solvent was evaporated under vacuum. Purification by preparative HPLC, gave 41 mg (10% yield) of the title compound.

$^{1}$H NMR (DMSO-d$_{6}$) δ ppm 9.03 (br. s., 1H) 7.93 (br. s., 2H) 7.86 (d, 1H) 7.67 (d, 1H) 7.41 (d, 1H) 7.33-7.26 (m, 2H) 7.07 (d, 2H) 3.73-3.60 (m, 2H) 3.07-2.91 (m, 2H); MS (ESI) m/z 439 [M−1]$^{−}$ a) (E)-4-Chloro-2-(2-(4-(difluoromethoxy)phenyl)vinylsulfonamido) benzenesulfonamide

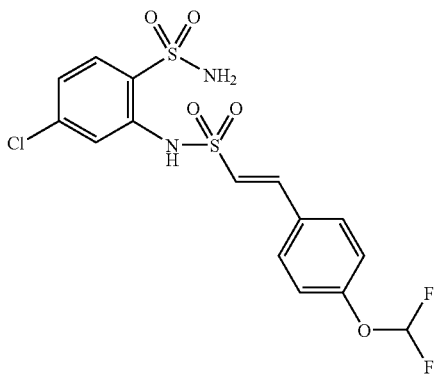 [SMILES: NS(=O)(=O)c1ccc(Cl)cc1NS(=O)(=O)/C=C/c1ccc(OC(F)F)cc1]

2-Amino-4-chlorobenzenesulfonamide (200 mg, 0.97 mmol) and (E)-2-(4-(difluoromethoxy)phenyl)ethenesulfonyl chloride (260 mg, 0.97 mmol) were dissolved in anhydrous dichloromethane (5 mL) and flushed with argon. Anhydrous pyridine (0.391 mL, 4.84 mmol) was added and the reaction was stirred at room temperature under an inert atmosphere over night. The reaction was quenched using 2 M hydrochloric acid (20 mL) and extracted with dichloromethane. The combined organic phase was washed with water, dried over magnesium sulfate and concentrated under vacuum to give 426 mg (100% yield) of the title compound.

MS (ESI) m/z 437 [M−1]$^{−}$

Example 227

4-Chloro-2-(2-(2-methoxyphenyl)ethylsulfonamido)benzenesulfonamide

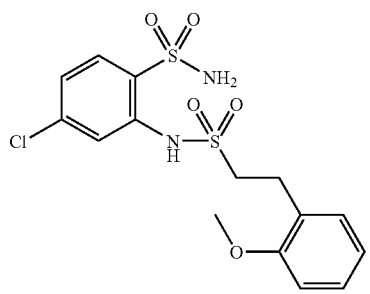 [SMILES: COc1ccccc1CCS(=O)(=O)Nc1cc(Cl)ccc1S(N)(=O)=O]

The title compound was synthesized as described for Example 226 in 21% yield, starting from (E)-4-chloro-2-(2-(2-methoxyphenyl)vinylsulfonamido)benzenesulfonamide.

$^{1}$H NMR (DMSO-d$_{6}$) δ ppm 9.03 (s, 1H) 7.94 (br. s., 2H) 7.88 (d, 1H) 7.66 (d, 1H) 7.42 (d, 1H) 7.23-7.13 (m, 2H) 6.92 (d, 1H) 6.84 (t, 1H) 3.59-3.52 (m, 2H) 3.66 (s, 3H) 3.00-2.93 (m, 2H); MS (ESI) m/z 403 [M−1]$^{−}$ a) (E)-4-chloro-2-(2-(2-methoxyphenyl)vinylsulfonamido)benzenesulfonamide

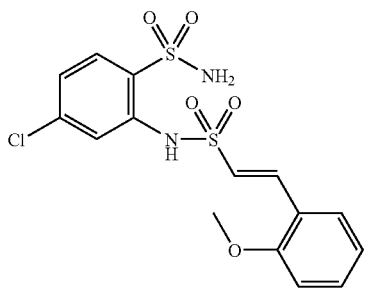 [SMILES: COc1ccccc1/C=C/S(=O)(=O)Nc1cc(Cl)ccc1S(N)(=O)=O]

The title compound was synthesized as described for Example 226 a) starting from 2-amino-4-chlorobenzenesulfonamide and (E)-2-(2-methoxyphenyl)ethenesulfonyl chloride.

MS (ESI) m/z 401 [M−1]$^{−}$

Example 228

4-Chloro-2-(2-(4-chloro-2-methoxyphenyl)ethylsulfonamido)benzenesulfonamide

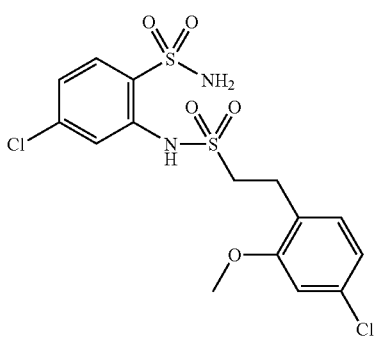 [SMILES: COc1cc(Cl)ccc1CCS(=O)(=O)Nc1cc(Cl)ccc1S(N)(=O)=O]

The title compound was synthesized as described for Example 226 in 41% yield, starting from (E)-4-chloro-2-(2-(4-chloro-2-methoxyphenyl)vinylsulfonamido)benzenesulfonamide.

$^{1}$H NMR (DMSO-d$_{6}$) δ ppm 9.03 (br. s., 1H) 7.92 (br. s., 2H) 7.86 (d, 1H) 7.63 (d, 1H) 7.41 (d, 1H) 7.19 (d, 1H) 6.99 (d, 1H) 6.90 (dd, 1H) 3.68 (s, 3H) 3.60-3.51 (m, 2H) 2.98-2.90 (m, 2H); MS (ESI) m/z 437 [M−1]$^{−}$ a) (E)-4-Chloro-2-(2-(4-chloro-2-methoxyphenyl)vinylsulfonamido)benzenesulfonamide

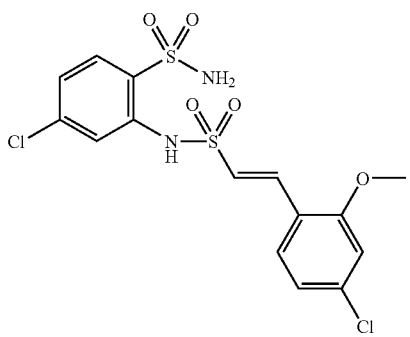 [SMILES: COc1cc(Cl)ccc1/C=C/S(=O)(=O)Nc1cc(Cl)ccc1S(N)(=O)=O]

The title compound was synthesized as described for Example 226 a) in 100% yield, starting from 2-amino-4-chlorobenzenesulfonamide and (E)-2-(4-chloro-2-methoxyphenyl)ethenesulfonyl chloride.

MS (ESI) m/z 435 [M−1]⁻

Example 229

2-(2-(3,4-Dichlorophenyl)ethylsulfonamido)-3,5-difluorobenzenesulfonamide

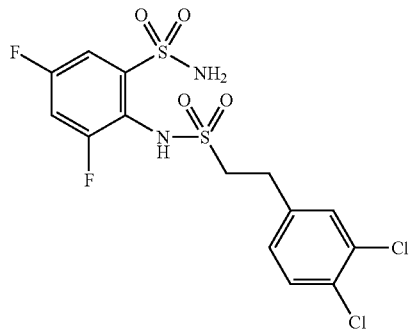 [SMILES: NS(=O)(=O)c1cc(F)cc(F)c1NS(=O)(=O)CCc1ccc(Cl)c(Cl)c1]

The title compound was synthesized as described for Example 226 in 3% yield, starting from (E)-2-(2-(3,4-dichlorophenyl)vinylsulfonamido)-3,5-difluorobenzenesulfonamide.

$^1$H NMR (DMSO-d$_6$) δ ppm 9.28 (br. s., 1H) 7.81-7.67 (m, 3H) 7.64-7.49 (m, 3H) 7.32 (dd, 1H) 3.62-3.52 (m, 2H) 3.20-3.07 (m, 2H); MS (ESI) m/z 443 [M−1]⁻ a) (E)-2-(2-(3,4-Dichlorophenyl)vinylsulfonamido)-3,5-difluoro benzenesulfonamide

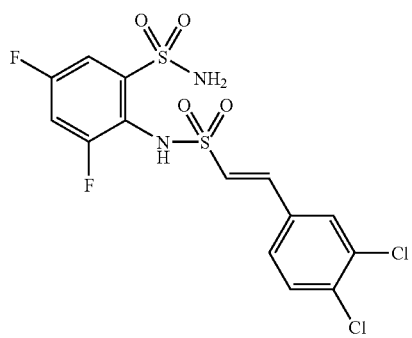 [SMILES: NS(=O)(=O)c1cc(F)cc(F)c1NS(=O)(=O)/C=C/c1ccc(Cl)c(Cl)c1]

The title compound was synthesized as described for Example 226 a) in 100% yield, starting from 2-amino-4-chlorobenzenesulfonamide and (E)-2-(3,4-dichlorophenyl)ethenesulfonyl chloride.

MS (ESI) m/z 442 [M−]⁻

Example 230

2,3-Dichloro-N-(4-fluoro-5-methoxy-2-sulfamoylphenyl)benzenesulfonamide

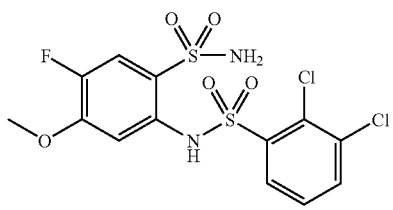 [SMILES: COc1cc(NS(=O)(=O)c2cccc(Cl)c2Cl)c(S(N)(=O)=O)cc1F]

2-Amino-5-fluoro-4-methoxybenzenesulfonamide (200 mg, 0.91 mmol) and 2,3-dichlorobenzene-1-sulfonyl chloride (290 mg, 1.18 mmol) were dissolved in anhydrous dichloromethane (5 mL). Anhydrous triethylamine (0.290 mL, 2.09 mmol) was added and the reaction was stirred at room temperature for 48 hours under an inert atmosphere. The reaction was quenched using 2 M hydrochloric acid (20 mL) and was extracted with dichloromethane. The combined organic phase were washed with water, dried over magnesium sulfate and concentrated under vacuum. Purification by preparative HPLC gave 23 mg (6% yield) of the title compound.

$^1$H NMR (CD$_3$OD) δ ppm 8.05 (dd, 1H) 7.53 (dd, 1H) 7.35-7.21 (m, 2H) 6.95 (d, 1H) 3.61 (s, 3H); MS (ESI) m/z 427 [M−1]⁻

Example 231

4-Chloro-2-(2-(3,4-dichlorophenyl)ethylsulfonamido)benzenesulfonamid

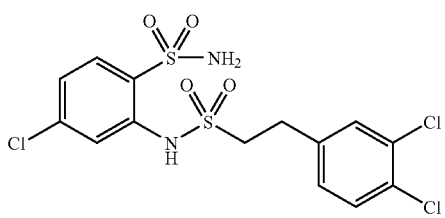 [SMILES: NS(=O)(=O)c1ccc(Cl)cc1NS(=O)(=O)CCc1ccc(Cl)c(Cl)c1]

The title compound was synthesized as described for Example 226 in 3% yield, starting from (E)-4-chloro-2-(2-(3,4-dichlorophenyl)vinylsulfonamido)benzenesulfonamide.

$^1$H NMR (CD$_3$OD) δ ppm 7.80 (d, 1H) 7.65 (d, 1H) 7.32-7.27 (m, 2H) 7.16 (dd, 1H) 7.05 (dd, 1H) 3.51-3.42 (m, 2H) 3.02-2.95 (m, 2H); MS (ESI) m/z 443 [M−1]⁻ a) (E)-4-Chloro-2-(2-(3,4-dichlorophenyl)vinylsulfonamido)benzenesulfonamide

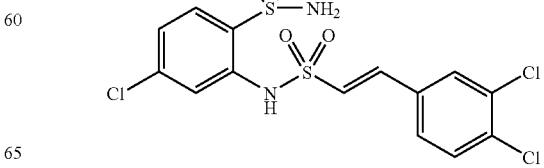

2-Amino-4-chlorobenzenesulfonamide (100 mg, 0.48 mmol) and (E)-2-(3,4-dichlorophenyl)ethenesulfonyl chloride (171 mg, 0.63 mmol) were dissolved in anhydrous dichloromethane (5 mL) and were flushed with argon. Anhydrous triethylamine (0.155 mL, 1.11 mmol) was added and the reaction was stirred at room temperature under an inert atmosphere over night. The reaction was quenched using 2 M hydrochloric acid (20 mL) and extracted with dichloromethane. The combined organic phases were washed with water, dried over magnesium sulfate and concentrated under vacuum to give 194 mg (91% yield) of the title compound.

MS (ESI) m/z 441 [M−1]⁻

Example 232

5-Chloro-2-(2-(4-chlorophenyl)ethylsulfonamido)-4-fluorobenzenesulfonamide

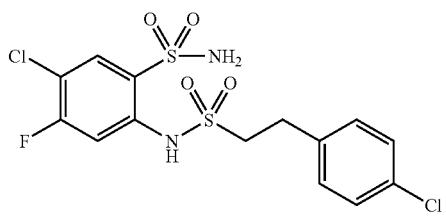 [SMILES: NS(=O)(=O)c1cc(Cl)c(F)cc1NS(=O)(=O)CCc1ccc(Cl)cc1]

The title compound was synthesized as described for Example 226 in 24% yield, starting from (E)-5-chloro-2-(2-(4-chlorophenyl)vinylsulfonamido)-4-fluorobenzenesulfonamide.

¹H NMR (CD₃OD) δ ppm 7.92 (d, 1H) 7.54 (d, 1H) 7.16-7.04 (m, 4H) 3.51-3.42 (m, 2H) 3.03-2.90 (m, 2H); MS (ESI) m/z 425 [M−1]⁻ a) (E)-5-Chloro-2-(2-(4-chlorophenyl)vinylsulfonamido)-4-fluorobenzene sulfonamide

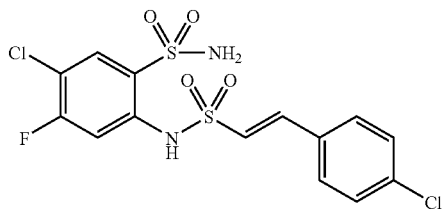 [SMILES: NS(=O)(=O)c1cc(Cl)c(F)cc1NS(=O)(=O)/C=C/c1ccc(Cl)cc1]

The title compound was synthesized as described for 226 a) in 61% yield, starting from 2-amino-5-chloro-4-fluorobenzenesulfonamide and (E)-2-(4-chlorophenyl)ethenesulfonyl chloride.

MS (ESI) m/z 423 [M−1]⁻

Example 233

5-Chloro-2-(2-(3,4-dichlorophenyl)ethylsulfonamido)-4-fluorobenzenesulfonamide

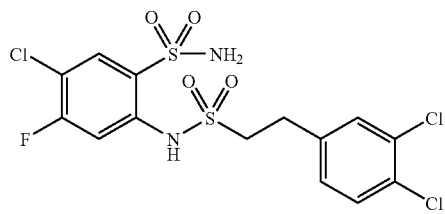 [SMILES: NS(=O)(=O)c1cc(Cl)c(F)cc1NS(=O)(=O)CCc1ccc(Cl)c(Cl)c1]

The title compound was synthesized as described for Example 226 in 15% yield, starting from (E)-5-chloro-2-(2-(3,4-dichlorophenyl)vinylsulfonamido)-4-fluorobenzenesulfonamide.

¹H NMR (CD₃OD) δ ppm 7.90 (d, 1H) 7.52 (d, 1H) 7.33-7.26 (m, 2H) 7.06 (dd, 1H) 3.51-3.44 (m, 2H) 3.02-2.96 (m, 2H); MS (ESI) m/z 461 [M−1]⁻ a) (E)-5-Chloro-2-(2-(3,4-dichlorophenyl)vinylsulfonamido)-4-fluoro benzenesulfonamide

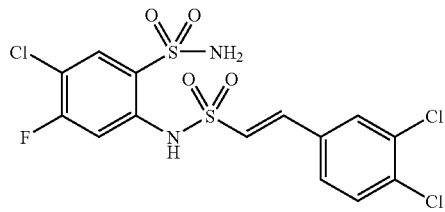 [SMILES: NS(=O)(=O)c1cc(Cl)c(F)cc1NS(=O)(=O)/C=C/c1ccc(Cl)c(Cl)c1]

The title compound was synthesized as described for Example 226 a) in 40% yield, starting from 2-amino-5-chloro-4-fluorobenzenesulfonamide and (E)-2-(3,4-dichlorophenyl)ethenesulfonyl chloride.

MS (ESI) m/z 459 [M−1]⁻

Example 234

5-(2-(4-(Furan-2-yl)phenyl)ethylsulfonamido)-2,3-dihydro-1H-indene-4-sulfonamide

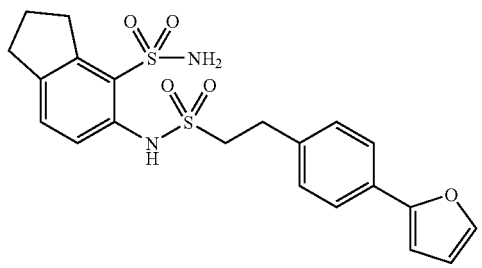 [SMILES: NS(=O)(=O)c1c(NS(=O)(=O)CCc2ccc(-c3ccco3)cc2)ccc2c1CCC2]

The title compound was synthesized as described for Example 226 in 40% yield, starting from (E)-5-(2-(4-(Furan-2-yl)phenyl)vinylsulfonamido)-2,3-dihydro-1H-indene-4-sulfonamide.

¹H NMR (CDCl₃) δ ppm 7.61 (d, 2H) 7.46 (dd, 1H) 7.42 (d, 2H) 7.22 (d, 2H) 6.63 (dd, 1H) 6.47 (dd, 1H) 3.53-3.47 (m, 2H) 3.31-3.19 (m, 4H) 2.94 (t, 2H) 2.19-2.09 (m, 2H); MS (ESI) m/z 445 [M−1]⁻ a) (E)-6-(2-(4-(furan-2-yl)phenyl)vinylsulfonamido)-2,3-dihydro-1H-indene-5-sulfonamide

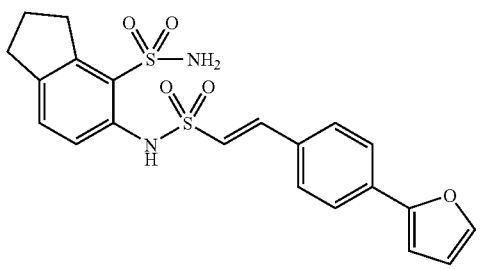 [SMILES: NS(=O)(=O)c1c(NS(=O)(=O)/C=C/c2ccc(-c3ccco3)cc2)ccc2c1CCC2]

The title compound was synthesized as described for Example 226 a) in 18% yield, starting from a mixture of 5-amino-2,3-dihydro-1H-indene-4-sulfonamide compound and 6-amino-2,3-dihydro-1H-indene-5-sulfonamide (1:1). The two isomers were separated by preparative HPLC.

MS (ESI) m/z 443 [M−1]⁻ b) 5-Amino-2,3-dihydro-1H-indene-4-sulfonamide compound with 6-amino-2,3-dihydro-1H-indene-5-sulfonamide (1:1)

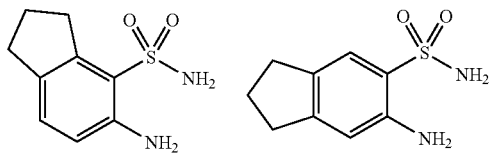 [SMILES: Nc1ccc2c(c1S(N)(=O)=O)CCC2 ; Nc1cc2c(cc1S(N)(=O)=O)CCC2]

Sulfurisocyanatidic chloride (0.752 mL, 8.63 mmol) and anhydrous nitroethane (10 mL) were mixed, cooled to −5° C. (ice/salt-bath) and a solution of 2,3-dihydro-1H-inden-5-amine (1 g, 7.51 mmol) in anhydrous nitroethane (10 mL) was added dropwise under vigorous stirring. When the addition was completed, anhydrous aluminum chloride (1.251 g, 9.39 mmol) was added and the suspension was heated at 110° C. for 60 min. The solution was cooled to room temperature and diluted with water (50 mL) and ethyl acetate (50 mL). The mixture was filtered and the layers were separated. The organic phase was dried over magnesium sulfate and concentrated under vacuum. The residue was dissolved in sulfuric acid and water (1:1 30 mL) and heated at 140° C. for 90 min before it was allowed to reach room temperature and stirred over night. The mixture was neutralized using 15% sodium hydroxide and extracted with ethyl acetate. The combined organic phases were dried over magnesium sulfate and concentrated under vacuum to give 0.664 g (21% yield) of the title mixture.

MS (ESI) m/z 211 [M−1]⁻

Example 235

6-(2-(4-(Furan-2-yl)phenyl)ethylsulfonamido)-2,3-dihydro-1H-indene-5-sulfonamid

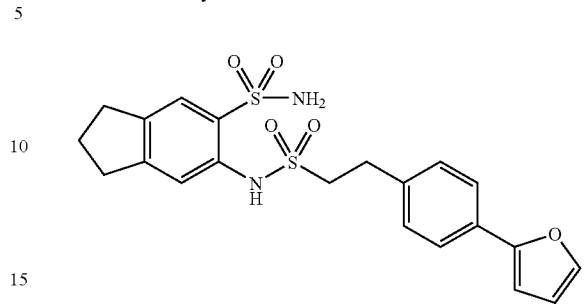

The title compound was synthesized as described for Example 226 in 47% yield, starting from (E)-6-(2-(4-(furan-2-yl)phenyl)vinylsulfonamido)-2,3-dihydro-1H-indene-5-sulfonamide. Heated in a microwave at 180° C. for 15 min. The mixture was filtered and the solvent was evaporated under vacuum.

¹H NMR (CDCl₃) δ ppm 7.80 (s, 1H) 7.61 (d, 2H) 7.49-7.43 (m, 2H) 7.23 (d, 2H, 6.63 (dd, 1H) 6.47 (dd, 1H) 3.61-3.47 (m, 2H) 3.27-3.18 (m, 2H) 3.02-2.89 (m, 4H) 2.23-2.04 (m, 2H); MS (ESI) m/z 445 [M−1]⁻ a) (E)-6-(2-(4-(furan-2-yl)phenyl)vinylsulfonamido)-2,3-dihydro-1H-indene-5-sulfonamide

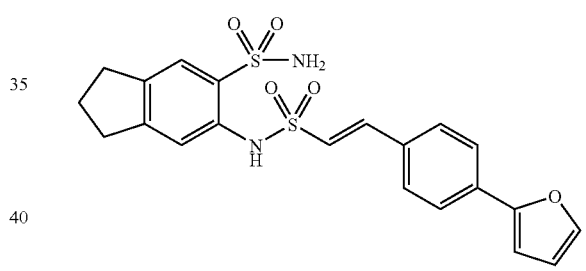

The title compound was synthesized as described for Example 226 a) in 18% yield, starting from a mixture of 5-amino-2,3-dihydro-1H-indene-4-sulfonamide compound and 6-amino-2,3-dihydro-1H-indene-5-sulfonamide (1:1) The two isomers were separated by preparative HPLC.

MS (ESI) m/z 443 [M−1]⁻

Example 236

5-(2-(3,4-Dichlorophenyl)ethylsulfonamido)-2,3-dihydro-1H-indene-4-sulfonamide

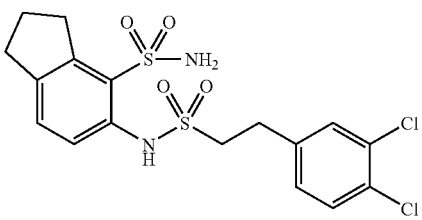

The title compound was synthesized as described for Example 226 in 20% yield, starting from a mixture of (E)-5-

(2-(3,4-dichlorophenyl)vinylsulfonamido)-2,3-dihydro-1H-indene-4-sulfonamide compound and (E)-6-(2-(3,4-dichlorophenyl)vinylsulfonamido)-2,3-dihydro-1H-indene-5-sulfonamide (1:1). Purification by preparative HPLC.

$^1$H NMR (CD$_3$OD) δ ppm 7.50 (d, 1H) 7.39-7.29 (m, 3H) 7.08 (dd, 1H) 3.51-3.42 (m, 2H) 3.30-3.21 (m, 2H) 3.05-2.99 (m, 2H) 2.90 (t, 2H) 2.02-2.16 (m, 2H); MS (ESI) m/z 447 [M−1]$^−$ a) (E)-5-(2-(3,4-Dichlorophenyl)vinylsulfonamido)-2,3-dihydro-1H-indene-4-sulfonamide compound and (E)-6-(2-(3,4-dichlorophenyl)vinylsulfonamido)-2,3-dihydro-1H-indene-5-sulfonamide (1:1)

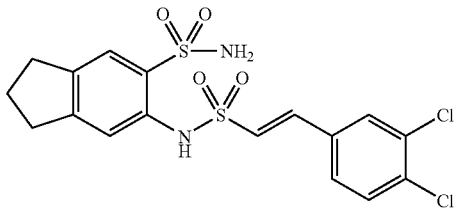

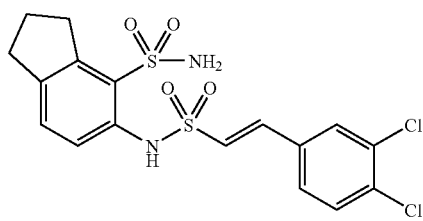 [SMILES: NS(=O)(=O)c1c(NS(=O)(=O)CCc2ccc(Cl)c(Cl)c2)ccc2c1CCC2]

The title compound was synthesized as described for Example 226 a) in 38% yield, starting from a mixture of 5-amino-2,3-dihydro-1H-indene-4-sulfonamide compound and 6-amino-2,3-dihydro-1H-indene-5-sulfonamide (1:1).

MS (ESI) m/z 445 [M−1]$^−$

Example 237

(E)-5-(2-(4-Chlorophenyl)vinylsulfonamido)-2,3-dihydro-1H-indene-4-sulfonamide

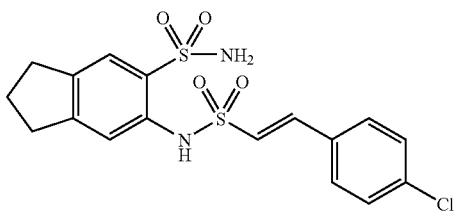 [SMILES: NS(=O)(=O)c1cc2c(cc1NS(=O)(=O)/C=C/c1ccc(Cl)cc1)CCC2]

The title compound was synthesized as described for Example 226 a) in 41% yield, starting from a mixture of 5-amino-2,3-dihydro-1H-indene-4-sulfonamide compound with 6-amino-2,3-dihydro-1H-indene-5-sulfonamide (1:1). Purification by preparative HPLC.

$^1$H NMR (CDCl$_3$) δ ppm 7.79 (s, 1H) 7.55 (d, 1H) 7.48 (s, 1H) 7.46-7.37 (m, 3H) 6.94 (d, 1H) 5.05 (s, 1H) 2.94 (ddd, 4H) 2.22-2.07 (m, 2H); MS (ESI) m/z 411 [M−]$^−$ Example 238

(E)-6-(2-(4-Chlorophenyl)vinylsulfonamido)-2,3-dihydro-1H-indene-5-sulfonamide

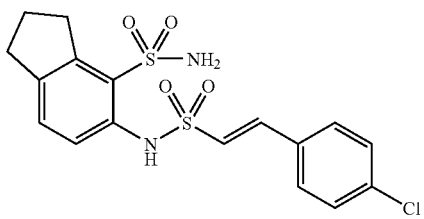 [SMILES: NS(=O)(=O)c1c(NS(=O)(=O)/C=C/c2ccc(Cl)cc2)ccc2c1CCC2]

The title compound was synthesized as described for Example 226 a) in 60% yield, starting from a mixture of 5-amino-2,3-dihydro-1H-indene-4-sulfonamide compound with 6-amino-2,3-dihydro-1H-indene-5-sulfonamide (1:1). Purification by preparative HPLC.

$^1$H NMR (CDCl$_3$) δ ppm 8.72 (s, 1H) 7.43 (d, 1H) 7.37-7.27 (m, 4H) 6.82 (d, 1H) 5.00 (s, 1H) 3.19 (t, 2H) 2.84 (t, 2H) 2.09-2.00 (m, 2H); MS (ESI) m/z 411 [M−1]$^−$ Example 239

2-[[3-(3,4-Dichlorophenyl)phenyl]sulfonylamino]-N-methyl-benzenesulfonamide

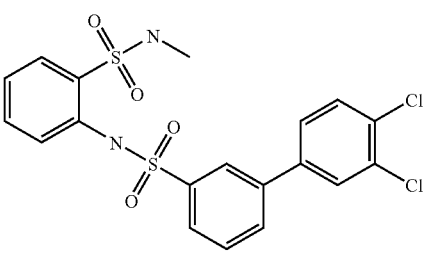 [SMILES: CNS(=O)(=O)c1ccccc1NS(=O)(=O)c1cccc(-c2ccc(Cl)c(Cl)c2)c1]

The title compound was synthesized by the analogous preparation of Example 148 in 47% yield, starting from 3-(3, 4-dichlorophenyl)benzenesulfonyl chloride.

$^1$H NMR (400 MHz, DMSO-d$_6$) δ ppm 9.30 (br. s., 1H), 8.19 (br. s., 1H), 8.03 (d, 1H), 7.90-7.98 (m, 3H), 7.77 (d, 1H), 7.66-7.74 (m, 3H), 7.58-7.66 (m, 2H), 7.29 (t, 1H), 2.30 (d, 3H); MS m/z 469, 471 [M−1]$^−$

Example 240

2-(2-(6-((4-(Trifluoromethyl)phenyl)ethynyl)pyridin-3-yl)ethylsulfonamido)benzenesulfonamide

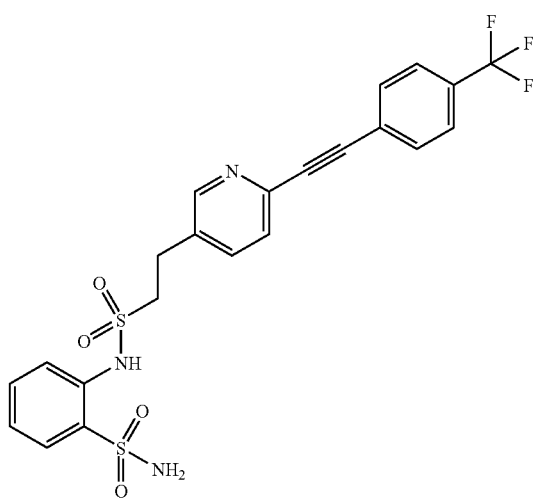 [SMILES: NS(=O)(=O)c1ccccc1NS(=O)(=O)CCc1ccc(C#Cc2ccc(C(F)(F)F)cc2)nc1]

The title compound was synthesized as described for Example 179 a) in 28% yield, starting from 2-(2-(6-bromopyridin-3-yl)ethylsulfonamido)benzenesulfonamide and 4-ethynyl-alpha,alpha,alpha-trifluorotoluene. Purification by preparative HPLC.

$^1$H NMR (400 MHz, DMSO-d$_6$) δ ppm 8.98 (s, 1H) 8.51 (d, 1H) 7.89 (dd, 1H) 7.81-7.86 (m, 6H) 7.77 (dd, 1H) 7.59-7.69 (m, 3H) 7.32-7.37 (m, 1H) 3.67-3.74 (m, 2H) 3.06-3.12 (m, 2H); MS (ESI) m/z 508 [M−1]$^-$.

Assays for Determining Biological Activity
Inhibition of Prostaglandin E Synthase Activity Compounds were tested as inhibitors of microsomal prostaglandin E synthase activity in microsomal prostaglandin E synthase assays and whole cell assays. These assays measure prostaglandin E2 (PGE2) synthesis which is taken as a measure of prostaglandin E synthase activity. Microsomal prostaglandin E synthase biochemical assays used microsomal prostaglandin E synthase-1 in microsomal preparations. The source of the microsomes can be for example interleukin-1β-stimulated human A549 cells (which express human mPGES-1) or Sf9 cells transfected with plasmids encoding human mPGES-1 cDNA.

The whole blood assay [described by Patrignani, P. et al, Journal of Pharmacology and Experimental Therapeutics, 1994, vol. 271, pp 1705-1712] was used as the whole cell assay for testing the compounds. Whole blood provides a protein and cell rich milieu for the study of biochemical efficacy of anti-inflammatory compounds such as prostaglandin synthase inhibitors. To study the inhibitory activities of these compounds, human blood was stimulated with lipopolysaccharide (LPS) for typically 16 hours to induce mPGES-1 expression, after which the concentration of produced PGE2 was measured by competitive-immuno assay (homogeneous time-resolved fluorescence, HTRF) as read out for effectiveness against mPGES-1-dependent PGE2 production.

Microsomal Prostaglandin E Synthase Biochemical Assay

A solution of test compound was added to a diluted microsome preparation containing human mPGES-1 and pre-incubated for 15 minutes in potassium phosphate buffer pH 6.8 with cofactor glutathione (GSH). Corresponding solutions without test compound were used as positive controls, and corresponding solutions without test compound and without microsomes were used as negative controls. The enzymatic reaction was then started by addition of the substrate PGH2 in an organic solution (dry acetonitrile).

The typical reaction conditions of the enzymatic reaction were thus: Test compound: ranging from 60 μM to 0.002 μM, or zero in positive and negative controls; potassium phosphate buffer pH 6.8: 50 mM; GSH: 2.5 mM; mPGES-1-containing microsomes: 2 μg/mL (sample and positive controls) or 0 μg/mL (negative control); PGH2: 10.8 μM; Acetonitrile: 7.7% (v/v); DMSO: 0.6% (v/v). The reaction was stopped after one minute by adding an acidic solution (pH 1.9) of ferric chloride and citrate (final concentrations 7 mM and 47 mM respectively), by which the PGH2 was sequestered (the PGH2 is reduced to mainly 12-hydroxy heptadecatrineoic acid (12-HHT) which is not detected by the subsequent PGE2 detection step). The resulting solution was then pH neutralized by addition of potassium phosphate buffer, prior to diluting an aliquot of the resulting solution in a weak potassium phosphate buffer (50 mM, pH 6.8) containing 0.2% BSA (w/v). [Adapted from Jacobsson et al., Proc. Natl. Acad. Sci. USA, 1999, vol. 96, pp. 7220-7225] The PGE2 formed was quantified by use of a commercial HTRF based kit (catalogue #62PG2PEC or #62P2APEC from Cisbio International). 100% activity was defined as the PGE2 production in positive controls subtracted by the PGE2 production in the negative controls. IC50 values were then determined using standard procedures.

Data from this assay for representative compounds is shown in the Table below. The potency is expressed as IC50 and the value indicated is an average of at least n=2. The data indicate that the compounds of the invention are expected to possess useful therapeutic properties.

| Example No. | IC$_{50}$ (μM) |
|---|---|
| 1 | 0.13 |
| 2 | 0.27 |
| 3 | 0.14 |
| 4 | 0.079 |
| 5 | 0.04 |
| 6 | 0.074 |
| 7 | 0.28 |
| 8 | 2.2 |
| 9 | 0.61 |
| 10 | 0.45 |
| 11 | 0.59 |
| 12 | 1 |
| 13 | 0.52 |
| 14 | 3.1 |
| 15 | 7.6 |
| 16 | 0.19 |
| 17 | 5.3 |
| 18 | 0.044 |
| 19 | 1.4 |
| 20 | 0.7 |
| 21 | 0.32 |
| 22 | 0.43 |
| 23 | 0.27 |
| 24 | 0.3 |
| 25 | 0.077 |
| 26 | 0.42 |
| 27 | 0.27 |
| 28 | 0.29 |
| 29 | 0.28 |
| 30 | 5.9 |
| 31 | 5.7 |
| 32 | 5.1 |
| 33 | 1.1 |
| 34 | 0.12 |

| Example No. | IC$_{50}$ (μM) |
|---|---|
| 35 | 0.17 |
| 36 | 0.057 |
| 37 | 0.16 |
| 38 | 0.22 |
| 39 | 1.4 |
| 40 | 1.2 |
| 41 | 1.1 |
| 42 | 1.6 |
| 43 | 0.11 |
| 44 | 0.75 |
| 45 | 1.3 |
| 46 | 1.1 |
| 47 | 1.6 |
| 48 | 0.59 |
| 49 | 0.036 |
| 50 | 0.13 |
| 51 | 4.9 |
| 52 | 0.084 |
| 53 | 0.16 |
| 54 | 0.27 |
| 55 | 0.36 |
| 56 | 0.53 |
| 57 | 0.62 |
| 58 | 0.3 |
| 59 | 2.3 |
| 60 | 2.4 |
| 61 | 2.4 |
| 62 | 2.5 |
| 63 | 3 |
| 64 | 3.1 |
| 65 | 3.8 |
| 66 | 6.2 |
| 67 | 6.4 |
| 68 | 9.1 |
| 69 | 0.27 |
| 70 | 0.22 |
| 71 | 0.3 |
| 72 | 0.49 |
| 73 | 0.29 |
| 74 | 9.8 |
| 75 | 2.6 |
| 76 | 1.2 |
| 77 | 3.1 |
| 78 | 0.35 |
| 79 | 9.9 |
| 80 | 0.57 |
| 81 | 2.9 |
| 82 | 7.3 |
| 83 | 0.43 |
| 84 | 0.19 |
| 85 | 0.8 |
| 86 | 0.7 |
| 87 | 2.4 |
| 88 | 1.3 |
| 89 | 2.8 |
| 90 | 0.87 |
| 91 | 0.31 |
| 92 | 0.091 |
| 93 | 0.65 |
| 94 | 0.65 |
| 95 | 0.31 |
| 96 | 4.8 |
| 97 | 3.4 |
| 98 | 0.68 |
| 99 | 0.29 |
| 100 | 4 |
| 101 | 1.6 |
| 102 | 0.85 |
| 103 | 9.2 |
| 104 | 4.6 |
| 105 | 0.67 |
| 106 | 0.074 |
| 107 | 0.14 |
| 108 | 4.9 |
| 109 | 6.1 |
| 110 | 0.49 |
| 111 | 0.76 |
| 112 | 6.1 |
| 113 | 0.48 |
| 114 | 0.83 |
| 115 | 2.6 |
| 116 | 1.7 |
| 117 | 1.3 |
| 118 | 4.7 |
| 119 | 4.5 |
| 120 | 3.3 |
| 121 | 0.22 |
| 122 | 6.7 |
| 123 | 9.3 |
| 124 | 1.3 |
| 125 | 7.2 |
| 126 | 1.2 |
| 127 | 5.1 |
| 128 | 1.7 |
| 129 | 2.5 |
| 130 | 5.2 |
| 131 | 6.6 |
| 132 | 4.5 |
| 133 | 2.2 |
| 134 | 3.7 |
| 135 | 8.3 |
| 136 | 3.8 |
| 137 | 2.1 |
| 138 | 0.57 |
| 139 | 1.8 |
| 140 | 2.9 |
| 141 | 3.1 |
| 142 | 4.9 |
| 143 | 1.1 |
| 144 | 1.1 |
| 145 | 4.1 |
| 146 | 4.7 |
| 147 | 3.9 |
| 148 | 0.38 |
| 149 | 0.65 |
| 150 | 4.2 |
| 151 | 3.7 |
| 152 | 3.9 |
| 153 | 3.2 |
| 154 | 9.3 |
| 155 | 9.8 |
| 156 | 5.4 |
| 157 | 1.1 |
| 158 | 8.7 |
| 159 | 3.5 |
| 160 | 1.2 |
| 161 | 1.3 |
| 162 | 5.7 |
| 163 | 0.46 |
| 164 | 0.19 |
| 165 | 2.3 |
| 166 | 4.8 |
| 167 | 3.8 |
| 168 | 0.63 |
| 169 | 0.022 |
| 170 | 0.29 |
| 171 | 1.7 |
| 172 | 7.3 |
| 173 | 1.5 |
| 174 | 0.22 |
| 175 | 3.7 |
| 176 | 0.9 |
| 177 | 2.2 |
| 178 | 2.7 |
| 179 | 6.2 |
| 180 | 1.4 |
| 181 | 0.37 |
| 182 | 0.52 |
| 183 | 0.081 |
| 184 | 9.6 |
| 185 | 2.5 |
| 186 | 0.25 |
| 187 | 0.68 |
| 188 | 0.27 |

-continued

| Example No. | IC$_{50}$ (µM) |
|---|---|
| 189 | 1.4 |
| 190 | 0.68 |
| 191 | 8.3 |
| 192 | 3.2 |
| 193 | 7.9 |
| 194 | 1 |
| 195 | 5.5 |
| 196 | 1.9 |
| 197 | 0.64 |
| 198 | 0.29 |
| 199 | 2.5 |
| 200 | 1.4 |
| 201 | 0.72 |
| 202 | 2.9 |
| 203 | 2.1 |
| 204 | 0.62 |
| 205 | 0.56 |
| 206 | 9.1 |
| 207 | 0.097 |
| 208 | 0.055 |
| 209 | 0.22 |
| 210 | 0.36 |
| 211 | 0.075 |
| 212 | 0.041 |
| 213 | 0.33 |
| 214 | 1.4 |
| 215 | 0.74 |
| 216 | 0.13 |
| 217 | 0.11 |
| 218 | 0.18 |
| 219 | 0.95 |
| 220 | 0.27 |
| 221 | 0.42 |
| 222 | 0.38 |
| 223 | 0.42 |
| 224 | 0.1 |
| 225 | 6.3 |
| 226 | 1.3 |
| 227 | 1.9 |
| 228 | 0.13 |
| 229 | 5.5 |
| 230 | 6.1 |
| 231 | 0.13 |
| 232 | 0.87 |
| 233 | 0.15 |
| 234 | 6.2 |
| 235 | 6.2 |
| 236 | 4.6 |
| 237 | 8.9 |
| 238 | 2.1 |
| 239 | 6.06 |
| 240 | 0.031 |

Whole Blood Assay

Human blood collected from human volunteers in heparinized tubes was incubated with 100 µM acetyl salicylic acid, in order to inhibit the constitutively expressed cyclooxygenase (COX)-1/COX-2 enzymes, and then stimulated with 0.1 µg/ml LPS to induce the expression of enzymes along the COX-2 pathway, e.g. COX-2 and mPGES-1. 100 µL of this blood was added to the wells of a 384-well plate containing 1 µL DMSO solutions of compounds typically in the final concentration range 316 µM to 0.01 µM. Naproxen was used as reference compound. The mix was incubated at 37° C. for 16 hours. Plasma was harvested by centrifugation and stored at −70° C. until further analysis of PGE2 levels. For the calculations, the 0%-activity value was represented by blood treated with acetyl salicylic acid, LPS and the reference compound (1 mM Naproxen). The 100%-activity value was represented by blood treated with aspirin, LPS and DMSO. [Reference: Patrignani, P. et al, Journal of Pharmacology and Experimental Therapeutics, 1994, vol. 271, pp 1705-1712]. The PGE2 formed was quantified, after dilution in a weak potassium phosphate buffer (50 mM, pH 6.8) containing 0.2% BSA (w/v), by use of a commercial HTRF based kit (catalogue #62PG2PEC or #62P2APEC from Cisbio International). IC50 values were then determined using standard procedures.

The invention claimed is:

1. A compound of formula (I) or a pharmaceutically acceptable salt thereof

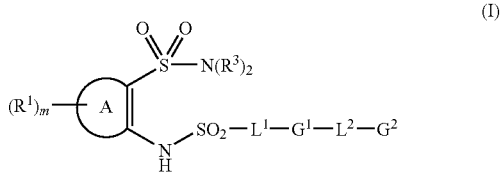

(I)

wherein:
A is phenyl;
each $R^1$ is independently halogen, CN, OH, CONR$^5$R$^6$, NR$^5$R$^6$, C$_{1-4}$alkyl, C$_{2-4}$alkynyl, or C$_{1-4}$alkoxy; said C$_{1-4}$alkyl or C$_{2-4}$alkynyl being optionally substituted by OH or C$_{1-4}$alkyl;
m is an integer that is 0, 1, or 2;
each $R^3$ is hydrogen;
$L^1$ is a direct bond, C$_{1-3}$alkylene or C$_{2-3}$alkenylene;
$L^2$ is a direct bond, —O—, —OCH$_2$—, —C≡C— or —NHCONH—;
$G^1$ is phenyl;
$G^2$ is phenyl, 5- or 6-membered heteroaryl, C$_{3-10}$carbocyclyl or C$_{5-8}$heterocyclyl;
any phenyl, heteroaryl, carbocyclyl or heterocyclyl moieties in G$^1$ and G$^2$ being optionally substituted by one or more substituents that are independently selected from the group consisting of halogen, OH, CN, NO$_2$, CO$_2$R$^9$, C$_{1-6}$alkyl, C$_{1-6}$alkoxy, C$_{1-4}$thioalkoxy, SO$_2$NR$^{10}$R$^{11}$, NR$^{12}$R$^{13}$, —NHCOC(OH)(CH$_3$)CF$_3$, and —CH$_2$OCH$_2$CF$_2$CHF$_2$; said C$_{1-6}$alkyl or C$_{1-6}$alkoxy being optionally substituted by OH or by one or more F atoms;
$R^9$ is C$_{1-6}$alkyl; and
each $R^4$, $R^5$, $R^6$, $R^7$, $R^8$, $R^{10}$, $R^{11}$, $R^{12}$ and $R^{13}$ is independently selected from the group consisting of H or C$_{1-4}$alkyl;
with the proviso that the following compounds are excluded:
2-amino-N-(2-sulfamoylphenyl)benzenesulfonamide;
3-amino-4-hydroxy-N-(2-sulfamoylphenyl)benzenesulfonamide;
4-bromo-N-(2-sulfamoylphenyl)benzenesulfonamide;
4-fluoro-N-(2-sulfamoylphenyl)benzenesulfonamide;
4-nitro-N-(2-sulfamoylphenyl)benzenesulfonamide;
2-[(phenylsulfonyl)amino]-4-(trifluoromethyl)benzenesulfonamide;
2,5-dibromo-N-(2-(N-ethylsulfamoyl)phenyl)benzenesulfonamide; and
2,3,4,5,6-pentafluoro-N-(2-sulfamoylphenyl)benzenesulfonamide.

2. A compound according to claim 1 wherein m is an integer that is 0 or 1.

3. A compound according to claim 1 wherein $L^1$ is C$_{1-3}$alkylene.

4. The compound according to any claim 1 wherein G$^2$ is phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl or dibenzofuranyl.

5. The compound according to claim 1 wherein $R^5$ and $R^6$ is hydrogen.

6. The compound according to claim 1 wherein $R^{10}$ is hydrogen.

7. The compound according to claim 1 wherein $R^{11}$, $R^{12}$ and $R^{13}$ are each methyl.

8. The compound according to claim 1 wherein any phenyl, heteroaryl, carbocyclyl or heterocyclyl moieties in $G^1$ and $G^2$ are optionally substituted by one or more substituents independently selected from the group consisting of halogen, CN, OH, $C_{1-4}$alkyl, $C_1$thioalkoxy, $NR^{12}R^{13}$, —NHCOC(OH)(CH$_3$)CF$_3$, SO$_2$NR$^{10}$R$^{11}$, and $C_1$alkoxy; said $C_{1-4}$alkyl or $C_1$alkoxy being optionally substituted by OH or by one or more F atoms.

9. The compound according to claim 1 wherein
each $R^1$ is independently selected from the group consisting of halogen, CN, OH, CONR$^5$R$^6$, NR$^5$R$^6$, $C_{1-4}$alkyl, $C_{2-4}$alkynyl, and $C_{1-4}$alkoxy; said $C_{1-4}$alkyl or $C_{2-4}$alkynyl being optionally substituted by one or more substituents selected from the group consisting of OH and $C_{1-4}$alkyl; and
m is an integer that is 0 or 1;
$R^3$, $R^5$, $R^6$ and $R^{10}$ are each hydrogen;
$L^1$ is a direct bond, $C_{1-3}$alkylene or $C_{2-3}$alkenylene;
$L^2$ is a direct bond, —O—, —OCH$_2$—, —NHCONH— or —C≡C—;
$G^1$ is phenyl;
$G^2$ is phenyl, 5- or 6-membered heteroaryl, $C_{3-10}$carbocyclyl or $C_{5-8}$heterocyclyl;
any phenyl, heteroaryl, carbocyclyl or heterocyclyl moieties in $G^1$ and $G^2$ being optionally substituted by one or more substituents independently selected from the group consisting of halogen, CN, OH, $C_{1-4}$alkyl, $C_1$thioalkoxy, NR$^{12}$R$^{13}$, —NHCOC(OH)(CH$_3$)CF$_3$, SO$_2$NR$^{10}$R$^{11}$, and $C_1$alkoxy; said $C_{1-4}$alkyl or $C_1$alkoxy being optionally substituted by OH or by one or more F atoms; and
$R^{11}$, $R^{12}$ and $R^{13}$ are each methyl.

10. The compound according to claim 1 wherein
each $R^1$ is independently selected from the group consisting of chloro, fluoro, bromo, CN, OH, CONR$^5$R$^6$, methyl, 1-butynyl, and methoxy; said methyl and 1-butynyl being optionally substituted by OH or methyl; and
m is an integer that is 0 or 1;
$R^3$, $R^5$, $R^6$ and $R^{10}$ are each hydrogen;
$L^1$ is a direct bond, ethylene, 1-methylethylene, 2-methylethylene, ethenylene, —C(CH$_3$)CH—, —CHC(CH$_3$)— or —CH$_2$C(CH$_2$)—;
$L^2$ is a direct bond, —O—, —OCH$_2$—, —NHCONH—, or —C≡C—;
$G^1$ is phenyl;
$G^2$ is phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl, or dibenzofuranyl;
any methyl, ethyl, tert-butyl, iso-propyl phenyl, pyridyl, pyrimidyl, cyclopentyl, cyclopentenyl, cyclohexyl, furanyl, tetrahydrofuranyl, thienyl, thiazolyl, pyrazolyl, bensofuranyl, 2,3-dihydro-bensofuranyl, indolyl, tetrahydronaphtyl or dibenzofuranyl in $G^1$ and $G^2$ being optionally substituted by one or more substituents independently selected from the group consisting of bromo, chloro, fluoro, CN, OH, methyl, tert-butyl, methylthio, NR$^{12}$R$^{13}$, —NHCOC(OH)(CH$_3$)CF$_3$, SO$_2$NR$^{10}$R$^{11}$, and methoxy; said methyl or methoxy being optionally substituted by OH or by one or more F atoms; and
$R^{11}$, $R^{12}$ and $R^{13}$ are each methyl.

11. A compound according to claim 1 selected from the group consisting of:
2-[2-(4-Benzofuran-2-ylphenyl)ethylsulfonylamino]benzenesulfonamide;
2-[2-[4-(2,3-Dihydrobenzofuran-2-yl)phenyl]ethylsulfonylamino]benzenesulfonamide;
2-[[(E)-2-(4-Benzofuran-2-ylphenyl)ethenyl]sulfonylamino]benzenesulfonamide;
2-[[(E)-2-(4-Benzofuran-2-ylphenyl)ethenyl]sulfonylamino]-5-fluoro-benzenesulfonamide;
2-[[(E)-2-(4-Benzofuran-2-ylphenyl)ethenyl]sulfonylamino]-4-fluoro-benzenesulfonamide;
2-[[(E)-2-(4-Benzofuran-2-ylphenyl)ethenyl]sulfonylamino]-6-fluoro-benzenesulfonamide;
2-[2-[4-(2-Furyl)phenyl]ethylsulfonylamino]benzenesulfonamide;
2-[2-[4-(Oxolan-2-yl)phenyl]ethylsulfonylamino]benzenesulfonamide;
2-[[(E)-2-[4-(2-Furyl)phenyl]ethenyl]sulfonylamino]benzenesulfonamide;
2-[2-[4-(Difluoromethoxy)phenyl]ethylsulfonylamino] benzenesulfonamide;
4-Fluoro-2-[[(E)-2-[4-(2-furyl)phenyl]ethenyl]sulfonylamino]benzenesulfonamide;
5-Fluoro-2-[[(E)-2-[4-(2-furyl)phenyl]ethenyl]sulfonylamino]benzenesulfonamide;
2-Fluoro-6-[[(E)-2-[4-(2-furyl)phenyl]ethenyl]sulfonylamino]benzenesulfonamide;
2-Fluoro-6-[[(E)-2-(4-phenylphenyl)ethenyl]sulfonylamino]benzenesulfonamide;
5-Fluoro-2-[[(E)-2-(4-phenylphenyl)ethenyl]sulfonylamino]benzenesulfonamide;
4-Fluoro-2-[[(E)-2-(4-phenylphenyl)ethenyl]sulfonylamino]benzenesulfonamide;
3-Fluoro-2-[[(E)-2-(4-phenylphenyl)ethenyl]sulfonylamino]benzenesulfonamide;
2-[2-(4-Cyclopentylphenyl)ethylsulfonylamino]benzenesulfonamide;
2-[[3-(2,3-Dichlorophenyl)phenyl]sulfonylamino]benzenesulfonamide;
2-[[3-(3,5-difluorophenyl)phenyl]sulfonylamino]benzenesulfonamide;
3-(5-Chloro-2-methoxy-phenyl)-N-(2-sulfamoylphenyl) benzenesulfonamide;
2-[[3-(3-Cyanophenyl)phenyl]sulfonylamino]benzenesulfonamide;
2-[[3-(4-Cyanophenyl)phenyl]sulfonylamino]benzenesulfonamide;
3-(2,4-Dimethoxypyrimidin-5-yl)-N-(2-sulfamoylphenyl)benzenesulfonamide;
2-[[3-(3-Furyl)phenyl]sulfonylamino]benzenesulfonamide;
2-[[3-(1H-Indol-5-yl)phenyl]sulfonylamino]benzenesulfonamide;
2-[[3-[3-(Trifluoromethoxy)phenyl]phenyl]sulfonylamino]benzenesulfonamide;
2-(3,4-Dichlorophenyl)-N-(2-sulfamoylphenyl)benzenesulfonamide;
2-[[4-[3-Chloro-5-(trifluoromethyl)pyridin-2-yl]oxyphenyl]sulfonylamino]benzenesulfonamide;
4-Phenylmethoxy-N-(2-sulfamoylphenyl)benzenesulfonamide;
2-[(4-Cyclohexylphenyl)sulfonylamino]benzenesulfonamide;

3-Phenyl-N-(2-sulfamoylphenyl)benzenesulfonamide;
2-[[3-(2,5-Dichlorophenyl)phenyl]sulfonylamino]benzenesulfonamide;
3-Dibenzofuran-4-yl-N-(2-sulfamoylphenyl)benzenesulfonamide;
2-[[3-[4-(Trifluoromethyl)phenyl]phenyl]sulfonylamino]benzenesulfonamide;
3-(3-Methoxyphenyl)-N-(2-sulfamoylphenyl)benzenesulfonamide;
3-Benzofuran-2-yl-N-(2-sulfamoylphenyl)benzenesulfonamide;
2-[[3-(2,3-Dihydrobenzofuran-5-yl)phenyl]sulfonylamino]benzenesulfonamide;
3-(6-Methoxypyridin-3-yl)-N-(2-sulfamoylphenyl)benzenesulfonamide;
2-[[3-(2,4-Dichlorophenyl)phenyl]sulfonylamino]benzenesulfonamide;
3-(1-Methylindol-2-yl)-N-(2-sulfamoylphenyl)benzenesulfonamide;
2-[[3-[3-(Trifluoromethyl)phenyl]phenyl]sulfonylamino]benzenesulfonamide;
4-Benzofuran-2-yl-N-(2-sulfamoylphenyl)benzenesulfonamide;
2-[[3-(2,4-Difluorophenyl)phenyl]sulfonylamino]benzenesulfonamide;
5-Bromo-2-[[3-(3,4-dichlorophenyl)phenyl]sulfonylamino]benzenesulfonamide;
2-[[3-(3,4-Dichlorophenyl)phenyl]sulfonylamino]-5-methyl-benzenesulfonamide;
4-[[3-(3,4-Dichlorophenyl)phenyl]sulfonylamino]-3-sulfamoyl-benzamide;
5-Methyl-2-[[3-[3-(trifluoromethoxy)phenyl]phenyl]sulfonylamino]-benzenesulfonamide;
3-(6-Methoxypyridin-2-yl)-N-(2-sulfamoylphenyl)benzenesulfonamide;
2-[[4-[(2-Chloro1,3-thiazol-5-yl)methoxy]phenyl]sulfonylamino]-benzenesulfonamide;
3-(5-Fluoro-6-methoxy-pyridin-3-yl)-N-(2-sulfamoylphenyl)benzenesulfonamide;
3-(2-Methoxypyrimidin-5-yl)-N-(2-sulfamoylphenyl)benzenesulfonamide;
3-(4-Methylpyridin-3-yl)-N-(2-sulfamoylphenyl)benzenesulfonamide;
3-(2-Methoxypyridin-3-yl)-N-(2-sulfamoylphenyl)benzenesulfonamide;
2-[[3-(5-Chloropyridin-3 yl)phenyl]sulfonylamino]benzenesulfonamide;
3-(5-Chloro-6-methoxy-pyridin-3-yl)-N-(2-sulfamoylphenyl)benzenesulfonamide;
3-(6-Dimethylaminopyridin-3-yl)-N-(2-sulfamoylphenyl)benzenesulfonamide;
2-[[3-[3-(Hydroxymethyl)phenyl]phenyl]sulfonylamino]benzenesulfonamide;
2-[[3-[4-(Hydroxymethyl)phenyl]phenyl]sulfonylamino]benzenesulfonamide;
2-[[4-(3,4-Dichlorophenyl)phenyl]sulfonylamino]benzenesulfonamide;
2-[[3-(3,4-Dichlorophenyl)phenyl]sulfonylamino]benzenesulfonamide;
2-[[4-(4-Chlorophenoxyl)phenyl]sulfonylamino]benzenesulfonamide;
3-(4-Chlorophenyl)-1-[3-methyl-4-[(2-sulfamoylphenyl)sulfamoyl]phenyl]urea;
3-(2-Methylthiazol-4-yl)-N-(2-sulfamoylphenyl)benzenesulfonamide;
(E)-2-(2-(4-Cyclopentenylphenyl)vinylsulfonamido)benzenesulfonamide;
2-[2-(4-Cyclopentylethynyl-phenyl)-ethanesulfonylamino]-5-hydroxymethyl-benzenesulfonamide;
(E)-2-(2-(4'-(trifluoromethyl)biphenyl-4-yl)vinylsulfonamido)benzenesulfonamide; and
2-(2-(4'-(trifluoromethyl)biphenyl-4-yl)ethylsulfonamido)benzenesulfonamide;
and pharmaceutically acceptable salts of any one thereof.

12. A pharmaceutical composition comprising a compound of formula (I) or a pharmaceutically acceptable salt thereof as claimed in claim 1 in association with a pharmaceutically acceptable adjuvant, diluent or carrier.

13. A process for the preparation of a pharmaceutical composition as claimed in claim 12 which comprises mixing a compound of formula (I) or a pharmaceutically acceptable salt thereof as claimed in claim 1 with a pharmaceutically acceptable adjuvant, diluent or carrier.

14. A method of treating pain associated with osteoarthritis, pain associated with rheumatoid arthritis, acute pain, chronic pain, or neuropathic pain comprising administering to a patient in need thereof a therapeutically effective amount of a compound of formula (I) or a pharmaceutically acceptable salt thereof

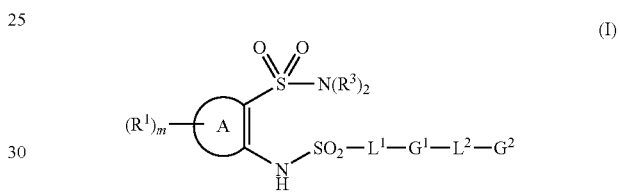

wherein:
A is phenyl;
each $R^1$ is independently selected from the group consisting of halogen, CN, OH, $CONR^5R^6$, $NR^5R^6$, $C_{1-4}$alkyl, $C_{2-4}$alkynyl, and $C_{1-4}$alkoxy; said $C_{1-4}$alkyl or $C_{2-4}$alkynyl being optionally substituted by OH or $C_{1-4}$alkyl;
m is an integer that is 0, 1 or 2;
each $R^3$ is hydrogen;
$L^1$ is a direct bond, $C_{1-3}$alkylene or $C_{2-3}$alkenylene;
$L^2$ is a direct bond, —O—, —OCH$_2$—, —NHCONH—, or —C≡C—;
$G^1$ is phenyl;
$G^2$ is H, $C_{1-6}$alkyl, phenyl, 5- or 6-membered heteroaryl, $C_{3-10}$carbocyclyl, or $C_{5-8}$heterocyclyl; said $C_{1-6}$alkyl being optionally further substituted by one or more groups selected from the group consisting of OH, $C_{1-6}$alkoxy, and halogen;
any phenyl, heteroaryl, carbocyclyl or heterocyclyl moieties in $G^1$ and $G^2$ being optionally substituted by one or more substituents independently selected from the group consisting of halogen, OH, CN, $NO_2$, $CO_2R^9$, $C_{1-6}$alkyl, $C_{1-6}$alkoxy, $C_{1-4}$thioalkoxy, $SO_2NR^{10}R^{11}$, $NR^{12}R^{13}$, —NHCOC(OH)(CH$_3$)CF$_3$, and —CH$_2$OCH$_2$CF$_2$CHF$_2$; said $C_{1-6}$alkyl or $C_{1-6}$alkoxy being optionally substituted by OH or by one or more F atoms;
$R^9$ is $C_{1-6}$alkyl; and
each $R^4$, $R^5$, $R^6$, $R^7$, $R^8$, $R^{10}$, $R^{11}$, $R^{12}$ and $R^{13}$ is independently H or $C_{1-4}$alkyl;
with the proviso that the following compounds are excluded:
2-amino-N-(2-sulfamoylphenyl)benzenesulfonamide;
4-amino-N-(2-sulfamoylphenyl)benzenesulfonamide.

* * * * *